United States Patent [19]
Nugent et al.

[11] Patent Number: 6,043,248
[45] Date of Patent: Mar. 28, 2000

[54] ALPHA-SUBSTITUTED PYRIMIDINE-THIOALKYL AND ALKYLETHER COMPOUNDS AS INHIBITORS OF VIRAL REVERSE TRANSCRIPTASE

[75] Inventors: Richard A. Nugent, Galesburg, Mich.; Stephen T. Schlachter, Boulder, Colo.; Michael J. Murphy, Kalamazoo, Mich.; Joel Morris, Kalamazoo, Mich.; Richard C. Thomas, Kalamazoo, Mich.; Donn G. Wishka, Kalamazoo, Mich.; Gary J. Cleek, Kalamazoo, Mich.; David R. Graber, Kalamazoo, Mich.

[73] Assignee: Pharmacia & Upjohn Company, Kalamazoo, Mich.

[21] Appl. No.: 08/945,153

[22] PCT Filed: May 3, 1996

[86] PCT No.: PCT/US96/06119

§ 371 Date: Oct. 17, 1997

§ 102(e) Date: Oct. 17, 1997

[87] PCT Pub. No.: WO96/35678

PCT Pub. Date: Nov. 14, 1996

Related U.S. Application Data

[63] Continuation-in-part of application No. 08/436,708, May 8, 1995, abandoned.

[51] Int. Cl.⁷ ...................... C07D 239/46; C07D 239/56; C07D 239/48; A61K 31/505
[52] U.S. Cl. ..................... 514/256; 514/269; 514/274; 544/310; 544/311; 544/313; 544/314; 544/316; 544/317; 544/318; 544/326; 544/327; 544/328
[58] Field of Search ................................. 514/256, 269, 514/274; 544/311, 313, 317, 310, 314, 316, 318, 326, 327, 328

[56] References Cited

U.S. PATENT DOCUMENTS

| | | |
|---|---|---|
| 2,295,560 | 9/1942 | D'Alello et al. .................. 260/251 |
| 3,940,394 | 2/1976 | Santilli et al. .................. 260/256.5 |
| 4,724,232 | 2/1988 | Rideout et al. .................. 514/50 |
| 5,025,016 | 6/1991 | Ahrens et al. .................. 514/274 |

FOREIGN PATENT DOCUMENTS

| | | |
|---|---|---|
| 0 124 630 | 11/1984 | European Pat. Off. . |
| 0 276 825 | 1/1988 | European Pat. Off. ...... C07D 239/95 |
| 0 391 254 | 3/1990 | European Pat. Off. ...... C07D 239/56 |
| 0 477 778 | 4/1992 | European Pat. Off. . |
| 62-209062 | 9/1987 | Japan . |
| 6-080647 | 3/1994 | Japan . |
| 744 867 | 2/1956 | United Kingdom . |
| 2 266 716 | 11/1993 | United Kingdom ......... C07D 401/12 |
| WO 89/11279 | 11/1989 | WIPO ............................. A61K 31/50 |
| WO 91/09849 | 7/1991 | WIPO . |
| WO 93/01181 | 1/1993 | WIPO . |
| WO 95/07901 | 3/1995 | WIPO ........................... C07D 307/60 |
| 95/13267 | 5/1995 | WIPO .................................. 514/274 |
| WO 95/13267 | 5/1995 | WIPO ........................... C07D 239/46 |
| WO 95/29897 | 11/1995 | WIPO ........................... C07D 235/28 |
| WO 96/02505 | 2/1996 | WIPO ........................... C07D 213/70 |

OTHER PUBLICATIONS

Althaus, Irene W; Chou, Kuo–Chen; Lemay, Richelle J; Franks, Kellie M; Deibel, Martin R; Kezdy, Ferenc J; Resnick, Lionel; Busso, Mariano E; So, Antero G; Downey, Kathleen M; Romero, Donna L; Thomas, Richard C; Aristoff, Paul A; Tarpley, W. Gary; Reusser, Fritz; The Benzylthio–Pyrimidine U–31,355, a Potent Inhibitor of HIV–1 Reverse Transcriptase, Biochemical Pharmacology, vol. 51, pp 743–750, 1996.

Goldman, Mark E; Nunberg, Jack H; O'Brien, Julie A; Quintero, Julio C; Schleif, William A; Freund, Kurt F; Gaul, S. Lee; Saari, Walfred S; Wai, John S; Hoffman, Jacob M; Anderson, Paul S; Hupe, Donald J; Emini, Emilio A; Stern, Andrew M; Pyridinone derivatives: Specific human immunodeficiency virus type 1 reverse transcriptase inhibitors with antiviral activity, Proc. Natl. Acad. Sci USA, vol. 88, pp. 6863–6867, Aug. 1991 Medical Sciences.

Jiang, JB; Hesson, DP; Dusak, BA; Dexter, DL; Kang, GJ; Hamel, E; Synthesis and Biological Evaluation of 2–Styrylquinazolin–4(3H)–ones, a New Class of Antimitotic Anticancer Agents Which Inhibit Tubulin Polymerization, J. Med. Chem. 1990, 33, 1721–1728.

Montgomery, John A; Holum, Lee B; Johnston, Thomas P; Synthesis of Potential Anticancer Agents. XIX. 2–Substituted N⁶–Alkyladenines, J. Am. Chem. Soc., vol. 81, 1959, pp 3962–3969.

(List continued on next page.)

*Primary Examiner*—Mukund J. Shah
*Assistant Examiner*—Deepak Rao
*Attorney, Agent, or Firm*—Andrew M. Solomon

[57] ABSTRACT

The subject invention relates to pyrimidine-thioalkyl and alkylether compounds of Formula (I) and pyrimidine-thioalkyl and alkylethers of Formula (IA), namely the compounds of Formula (I) where $R_4$ is selected from the group consisitng of —H or —$NR_{15}R_{16}$ where $R_{15}$ is —H and $R_{16}$ is —H, $C_1$–$C_6$ alkyl, $NH_2$ or $R_{15}$ and $R_{16}$ taken together with the —N form 1-pyrrolidino, 1-morpholino or 1-piperidino; and $R_6$ is selected from the group consisting of —H, or halo (preferably —Cl); with the overall proviso that $R_4$ and $R_6$ are not both —H. The compounds of Formula (IA) are useful in the treatment of individuals who are HIV positive being inhibitors of viral reverse transcriptase.

(I)

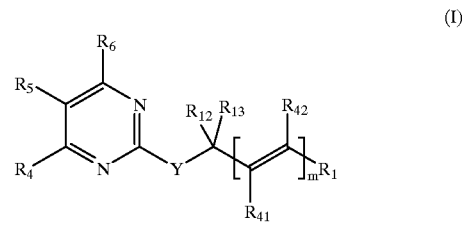

24 Claims, No Drawings

OTHER PUBLICATIONS

Ota, M. et al, Chemical Abstracts, vol. 108, No. 21, May 23, 1988—Abstract No. 186590u.

Saari, Walfred S., et al, 2–Pyridinone Derivatives: A New Class of Nonnucleoside, HIV–1–Specific Reverse Transcriptase Inhibitors, J. Med. Chem. 1991, 34, 2922–2925.

Saida, M., et al, Preparation of Quinazolines for Neoplasm Inhibitors or Skin Preparations, Chemical Abstracts, vol. 121, No. 9, Aug. 29, 1994—Abstract No. 108827f.

Cloned Viral Protein Vaccine for Foot–and–Mouth Disease: Responses n Cattle and Swine, Science, vol. 214, 1125–1129 (Dec. 4, 1981).

Baker, BR, Joseph JP, Williams, JH, Puromycin. Synthetic Studies. VI. Analogs of 6–Dimethylaminopurine, J. Org. Chem, 19, 1793–1801 (1954).

Norman et al., News and Comment, Science, 661–662 (Nov. 7, 1986).

Budesinsky, Z., Bruna, L., Svab, A. and Capek, A., 5–(3–Iodopropargyloxy)pyrimidines as Effective Fungistatics, Collection Czechoslov. Chem. Commun (vol. 40) 1078–1088 (1975).

Curran, James W., Morgan, W. Meade, Hardy, Ann M. Jaffe, Harold W., Darrow, William W., Dowdle, Walter R., The Epideiology of AIDS: Current Status and Future Prospects, Science, vol. 229 1352–1357 (1985).

Dueweke, Thomas J., Pushkarskaya Tatyana, Poppe, Susan M., Swaney, Steven M., Zhao, Jia Q., Chen, Irvin S.Y., Stevenson, Mario, Tarpley, W. Gary, A mutation in reverse transcriptase of bis(heteroaryl)piperazine–resistant human immunodeficiency virus type 1 that confers increased sensitivity to other nonnucleoside inhibitors, Proc. Natl. Acad. Sci., vol. 90, 4713–4717, (May 1993).

Koppel, Henry C., Springer, Robert Henre, Cheng, C.C., Pyrimidines. IV. Aziridinylpyrimidines[1]J. Org. Chem., 26, 1884–1890 (1961).

Koppel, Henry C., Springer, Robert Henre, Robbins, Roland K., Cheng, C.C., Pyrimidines. V. Analogs of 2–(o–Chlorobenzylthio)–4–dimethylamino–5–methylpyriidine (Bayer DG–428)[1] J. Org. Chem., Jan. 1962, 27, 181–185.

Kropf, Heinz, Amirabadi, Hedayat Mirzai, 4–t–Butylperoxypyrimidine, 2,4–Di–t–butylperoxy–und 4,6–Di–t–butylperoxypyrimidine[1], Synthesis Communications 397–400 (1981).

Larder, Brendan, Purifoy, Dorothy, Powell, Kenneth and Darby, Graham, AIDS virus reverse transcriptase defined by high level expression in *Escherichia coli*, The EMBO Journal vol. 6, No. 10 3133–3137 (1987).

Merluzzi, Vincent J., Hargrave, Karl D. Labadia, Mark, Grozinger, Karl, Skoog, Mark, Wu, Joseph C., Shih, Cheng–Kon, Eckner, Kristine, Hattox Susan, Adams, Julian, Rosehthal, Alan S., Faanes, Ronald, Eckner, Robert J., Koup, Richard A., Sullivan, John L., Inhibition of HIV–1 Replication by a Nonnucleoside Reverse Transcriptase Inhibitor, Science, vol. 250, 1411–1413 (Dec. 7, 1990).

Pauwels, Rudi, Andries, Koen, Desmyter, Jan, Schols, Dominique, Kukla, Michael J., Breslin, Henry J., Raeymaeckers, Alfons, Van Gelder, Jozef, Woestenborghs, Robert, Heykants, Jozef, Schellekens, Karel, Janssen, Marcel A.C., Clercq, Erik De, Janssen, Paul A.J., Potent and selective inhibition of HIV–1 replication in vitro by a novel series of TIBO derivatives, Nature, vol. 343 470–473 (Feb. 1, 1990).

Schickaneder, Helmut, Engler, Heidrun, Szelenyi Istvan, 2–[3–Pyridinylmethyl)thio]pyrimidine Derivatives: New Bronchosecretolytic Agents, J. Med. Chem. 30, 547–551 (1987).

Tjarks, Werner, Gabel, Detlef, Boron–Containing Thiouracil Derivatives for Neutron–Capture Therapy of Melanoma, J. Med. Chem. 34, 315–319 (1991).

Ward, A. David, Baker, B.R., Irreversible Enzyme Inhibitors. 200.[1] Active–Site–Directed Inhibitors of Deoxycytidine Kinase, Jouranl of Medicinal Chemistry, vol. 20, No. 1, 88–92 (1977).

CA 121 : 108827f, 1994.

CA 108 : 186590u, 1988.

ALPHA-SUBSTITUTED PYRIMIDINE-THIOALKYL AND ALKYLETHER COMPOUNDS AS INHIBITORS OF VIRAL REVERSE TRANSCRIPTASE

This application is the national phase of international application PCT/U96/06119, filed May 3, 1996, which is a continuation-in-part application of U.S. Ser. No. 08/436,708, filed May 8, 1995 now abandoned.

BACKGROUND OF THE INVENTION

1. Field of Invention

The pyrimidine-thioalkyl and alkylether derivatives of Formula IA are useful in the treatment of individuals who are HIV positive, whether or not they show AIDS symptoms at the present time. The pyrimidine-thioalkyl and alkylether derivatives of Formula IB are useful in the preparation of the pyrimidine-thioalkyl and alkylether derivatives of Formula IA.

2. Description of the Related Art

U.S. Pat. No. 5,025,016 (and EP 124 630) pyrimidine-thioalkyl pyridine derivatives corresponding to the general formula

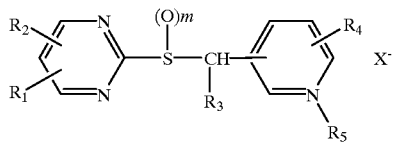

in which $R_1$ to $R_4$, independently of one another, represent hydrogen, lower alkyl, halogen, amino or hydroxy groups, $R_5$ represents a free electron pair or a lower alkvl group, a halogen atom, m has the value 0 or 1, the pyrimidine-thioalkyl group being bonded in the 2-, 3- or 4-position of the pyridine ring, and to therapeutically compatible acid addition salts thereof. The compounds allegedly exhibit surprisingly improved bronchosecretolytic and myucolytic activity as well as having been found to show antiphlogistic activity.

J. Med Chem. 1987, 30, 547–551 describes various 2-[(pyridinylmethyl)thio]-pyrimidine derivatives and the influence thereof on bronchosecretolytic properties in the phenol red screening model of the mouse in comparison to the known drug ambroxol.

EP 477 778 (Derwent 92-106190/14) describes various benzene, pyridine and pyrimidine derivatives as ACAT enzyme inhibitors, for treating arteriosclerosis. and cerebrovascular disease.

J. Org. Chem, 1954, 19, 1793–1801 describes pyrimidine derivatives, including 2-benzylmercapto-4-amino-6-pyrimidinol, 2-benzylmercapto-4-amino-6-chloropyrimidine, 2-benzylmercapto-4-amino-6-diethylaminopyrimidine as well as analogs of 6-dimethylaminopurine.

British Patent 744,867 (CA 51:2063i) describes various 2-R'-S-6-RR'N-substituted 4-aminopyrimidines.

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousand people will develop AIDS in the next five years, see Science, 1352–1357 (1985). On Mar. 20, 1987, the FDA approved the use of the compound, AZT (zidovudine), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm$^3$ in the peripheral blood. AZT is a known inhibitor of viral reverse transcriptase, an enzyme necessary for human immunodeficiency virus replication.

U.S. Pat. No. 4,724,232 claims a method of treating humans having acquired immunodeficiency syndrome utilizing 3'-azido-3'-deoxy-thymidine (azidothymidine, AZT).

It is known in the art that certain antibiotics and polyanionic dyes inhibit retrovirus reverse transcriptase.

Many publications have reported the ability of various sulfated compounds to inhibit virus replication, including HIV.

Nature 343, 470 (1990) and Science 250, 1411 (1990) disclose potent benzodiazepin type reverse transcriptase inhibitors. The compounds of the present invention are not benzodiazepin type compounds.

J. Org. Chem. 1962, 27, 181–185 describes various 2-benzylthio pyrimidine derivatives, including 4-chloro-5-methyl-2-[(phenylmethyl)thio]-pyrimidine, 4-chloro-5-methyl-2-[[(2,4-dichloro-phenyl)methyl]thio]-pyrimidine, 4-chloro-5-methyl-2-[[(2-chloro-phenyl)methyl]thio]-pyrimidine, and 4-chloro-5-methyl-2-[[(4-chloro-phenyl)methyl]thio]-pyrimidine and their activity as antitumor compounds in screens against SA-180, CA 755, and L-1210 tumor systems.

J. Med. Chem. 1977, 20, 88–92 describes 2-alkoxy and 2-alkylthio-4-amino pyrimidines, including 2-[(phenylmethyl)thio]4-pyrimidinamine, 2-[[(4-chlorophenyl)methyl]thio]-4-pyrimidinamine, 2-[(3-pyridinylmethyl)thio]4-pyrimidinamine, and 2-(phenylmethoxy)-4-pyrimidinamine, and their activity as inhibitors of deoxycytidine kinase.

Collect. Czech. Chem. Comm. 1975, 40, 1078–1088 (CA 83:114326e) describes 5-(3-iodopropargyloxy)pyrimidines as effective fungistatics.

Synthesis 1981, 397–400 describes peroxypyrimidines

J. Org. Chem. 1961, 26, 1884 describes the synthesis of aziridinyl pyrimidines as analogs of methioprim.

J. Med. Chem. 1991, 34, 315–319 describes derivatives of thiouracil which have dihydroxyboryl group at the C-5 position. These compounds are useful for B neutron-capture therapy of malignant melanoma.

SUMMARY OF INVENTION

Disclosed are pyrimidine-thioalkyl and alkylether compounds of Formula I

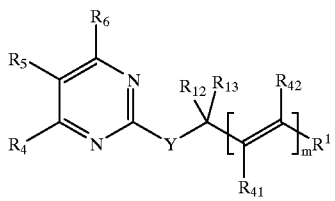

and therapeutically/pharmaceutically compatible acid addition salts thereof.

The compounds corresponding to Formula I may exist in various tautomeric formulas, and are included within the scope of Formula I as well as Formula IA and IB.

DETAILED DESCRIPTION OF THE INVENTION

Disclosed are pyrimidine-thioalkyl and alkylether compounds of Formula I

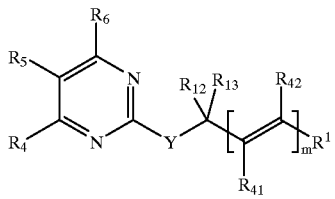

where m is 0 or 1;

$R^1$ is selected from the group consisting of —C≡CH, —$CO_2R_{53}$, —$CONR_{54}R_{55}$,

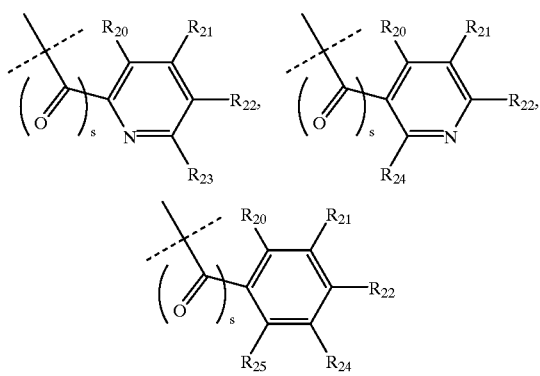

where s is 0 or 1 (preferably 0) and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, —halo, —OH, —CN, phenyl, phenylthio, —styryl, —$CO_2(R_{31})$, —$CON(R_{31})$ ($R_{32}$), —$CO(R_{31})$, —$(CH_2)_n$—$N(R_{31})(R_{32})$, —$C(OH)(R_{31})(R_{33})$, —$(CH_2)_nN(R_{31})$ $(CO(R_{33}))$, $(CH_2)_nN(R_{31})(SO_2(R_{33}))$, or where $R_{20}$ and $R_{21}$, or $R_{21}$, and $R_{22}$ or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —$CH_2OH$, —$(CH_2)_n$—$N(R_{31})(R_{32})$, —$C_3$–$C_8$ cycloalkyl, —$CF_3$, —halo, $CO_2(R_{31})$, —$CON(R_{31})$ $(R_{32})$, —$CO(R_{31})$, —$(CH_2)_nN(R_{31})(CO(R_{33}))$, —$(CH_2)_nN(R_{31})(SO_2(R_{33}))$, —CN, —$CH_2CF_3$ or —$CH(CF_3)_2$, or phenyl, and the saturated ring may be optionally substituted with 1, 2 or 3, —$C_1$–$C_6$ alkyl, —$C_1$–$C_6$ alkoxy, —OH, —$CH_2OH$ or —$(CH_2)_n$—N $(R_{31})(R_{32})$ or one oxo (=O);

where n is 0–3 and $R_{31}$, $R_{32}$, and $R_{33}$ are the same or different and are selected from
—H,
$C_1$–$C_6$ alkyl,
phenyl optionally substituted with 1, 2, or 3 -halo, $C_1$–$C_6$ alkyl, $C_1$–$C_6$ alkoxy, —$CF_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl,
or a member selected from the group consisting of:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl; where $R_{53}$ is selected from the group consisting of —H, $C_1$–$C_6$alkyl, $C_3$–$C_6$cycloalkyl, phenyl (optionally substituted with 1, 2, or 3 -halo, $C_1$–$C_6$ alkyl, $C_1$–$C_6$ alkoxy, —$CF_3$, —OH, —CN), or a five or six-membered unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2OH$, or —$(CH_2)_n$—$N(R_{31})$ $(R_{32})$;

where $R_{54}$ and $R_{55}$ being the same or different are selected from —H, $C_1$–$C_6$ alkyl, allyl, or phenyl (optionally substituted with 1, 2, or 3 -halo, $C_1$–$C_6$ alkyl, $C_1$–$C_6$ alkoxy or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl;

$R_{41}$ and $R_{42}$, being the same or different, are selected from the group consisting of —H and $C_1$–$C_4$ alkyl;

$R_{12}$ is selected from the group consisting of —H, $C_1$–$C_6$ alkyl, —$C_3$–$C_6$ cycloalkyl, —CN, —$C(O)NH_2$, —$C(O)N(C_1$–$C_6$alkyl$)(C_{C6}$alkyl$)$, —$CO_2H$, —$CO_2$ $(C_1$–$C_6$alkyl$)$, —$CH_2OH$, —$CH_2NH_2$ or —$CF_3$;

$R_{13}$ is selected from the group consisting of —H, $C_1$–$C_6$ alkyl or —$CF_3$;

Y is selected from —S—, —S(O)—, —$S(O)_2$, or —O—;

$R_4$ is selected from the group consisting of —H, —OH, halo or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 4-morpholino or 1-piperidino;

$R_5$ is selected from the group consisting of —H, —$C_2H_4OH$, —$C_2H_4$—O—TBDMS, halo, —$C_3$–$C_6$ cycloalkyl, $C_1$–$C_3$ alkoxy, —$CH_2CH_2Cl$ or $C_1$–$C_4$ alkyl, with the proviso that $R_5$ is not isobutyl;

or $R_4$ and $R_5$ are taken together to form a five or six-membered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo[3,4-d]pyrimidine, 1H-purine, pyrimido[4,5-d]pyrimidine, pteridine, pyrido[2,3-d]pyrimidine, or quinazoline, where the unsaturated ring may be optionally substituted with 1, 2 or 3, $C_1$–$C_6$ alkyl, $C_1$–$C_6$ alkoxy, —OH, —$CH_2OH$, or —$(CH_2)_nN(R_{31})(R_{32})$, —$C_3$–$C_8$ cycloalkyl, —$CF_3$, -halo, —$CO_2(R_{31})$, —$CON(R_{31})(R_{32})$, —$CO(R_3)$, —$(CH_2)_nN(R_{31})(CO(R_{33}))$, —$(CH_2)_nN(R_{31})(SO_2(R_{33}))$, and the saturated ring may be optionally substituted with 1, 2 or 3, —$C_1$–$C_6$ alkyl, —$C_1$–$C_6$ alkoxy, —OH, —$CH_2OH$, or —$(CH_2)_nN(R_{31})(R_{32})$ or one oxo (=O); and $R_6$ is selected from the group consisting of —H, —OH, halo (preferably —Cl), —CN, —$CF_3$, —$CO_2(R_{61})$, —$C(O)R_{61}$ or —$C(O)N(R_{61})(R_{62})$ where $R_{61}$ and $R_{62}$ are the same or different and are selected from
—H,
$C_1$–$C_6$ alkyl,
phenyl optionally substituted with 1, 2, or 3 -halo, $C_1$–$C_6$ alkyl, $C_1$–$C_6$ alkoxy, —$CF_3$, —OH, —CN,
or where $R_{61}$ and $R_{62}$ taken together with the attached nitrogen to form a ring selected from -pyrrolidinyl, -piperidinyl, -4-morpholinyl, -4-thiomorpholinyl, -4-piperazinyl, or -4-($C_1$–$C_6$ alkyl)piperazinyl;

with the overall proviso that $R_4$ and $R_6$ are not both —H; and with the further proviso that and $R_{12}$ and $R_{13}$ are not both —H except when $R_6$ is selected from —CN, —$CF_3$, —$CO_2(R_{61})$, —$C(O)R_{61}$ or —$C(O)N(R_{61})(R_{62})$, or $R_1$ is selected from —$CO_2R_{53}$ or —$C(O)N(R_{54})(R_{55})$;

pharmaceutically acceptable salts, hydrates, N-oxides and solvates thereof; other than 4-amino-6-chloro-2-(1-(4-(4-morpholinylcarbinyl)-2-pyridinyl)ethyl)thiopyrimidine 4-Amino-6-chloro-2-(1-(4-methyl-2-pyridyl)pentyl)thio-pyrimidine An embodiment of the present invention are compounds of Formula IA where $R_{12}$ and $R_{13}$ are not both —H.

An embodiment of the present invention are pyrimidine-thioalkyl and arlkyether anti-AIDS compounds of Formula IA, namely the compounds of Formula I where $R_4$ is selected from the group consisting of —H or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 4-morpholino or 1-piperidino; and $R_6$ is selected from the group consisting of —H, halo (preferably —Cl), —CN, —$CF_3$, —$CO_2(R_{61})$, —$C(O)R_{61}$ or —$C(O)N(R_{61})(R_{62})$.

Compounds of Formula IB, namely the compounds of Formula I where:

i) $R_4$ and/or $R_6$ are —OH; or ii) $R_4$ and $R_6$ are both halo, are useful as intermediates to produce the pyrimidine-thioalkyl and alkylether anti-AIDS compounds of Formula IA.

An embodiment of the present invention are compounds of Formula I (as well as Formula IA and IB) where Y is —O—.

A preferred embodiment of the present invention are compounds of Formula I (as well as Formula IA and IB) where s is 0 and Y is selected from the group consisting of —S—, —S(O)— or —S(O)$_2$; more preferably Y is —S—.

A preferred embodiment of the present invention are compounds of Formula I (as well as Formula IA and IB) where s is 0 and Y is selected from the group consisting of —S—, —S(O)— or —S(O)$_2$ (more preferably Y is —S—); and with the proviso that $R_{12}$ and $R_{13}$ are not both —H.

A preferred embodiment of the present invention are novel compounds of Formula I (as well as Formula IA and IB) where s is 0 and Y is selected from the group consisting of —S—, —S(O)— or —S(O)$_2$ (more preferably Y is —S—); and with the proviso that $R_{12}$ and $R_{13}$ are not both —H and with the further proviso that when $R_4$ is halo or amino and $R_6$ is halo, $R_1$ is not

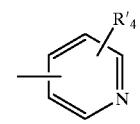

in which R'$_4$ represent hydrogen, lower alkyl, halogen, amino or hydroxy groups.

$R_4$ is preferably —$NH_2$.

m is preferably 0.

$R_6$ is preferably —Cl, —$CF_3$ or —CN.

$R_{41}$ and $R_{42}$ are preferably —H.

$R_{12}$ is preferably —$CH_3$.

$R_{13}$ is preferably —H.

$R^1$ is preferably selected from

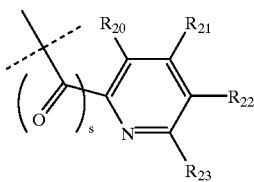

more preferably a member selected from the group consisting of:
3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-b]pyridinyl, 6-(2,3-dihydro)-furo[2,3-b]pyridinyl, 5-(2,3-dihydro)-furo

[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)- 1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, or 8-(3,4-dihydro)-2H-1-benzothiopyranyl; wherein such member is optionally substituted as described above;

most preferably a member selected from the group consisting of: 3-isoquinolinyl, 1-isoquinolinyl, 2-quinolinyl, 3-quinolnyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4- dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, or 6-(3,4-dihydro)-2H-pyrano[3,2-b]pyridinyl; wherein such member is optionally substituted as described above.

Illustrative $R_1$ members include:

phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; 2- or 3-pyridinyl optionally substituted with $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, -halo, —OH, —CN, phenyl, phenylthio, -styryl, —$CO_2(R_{31})$, —$CON(R_{31})(R_{32})$, —$CO(R_{31})$, —$(CH_2)_n$—$N(R_{31})(R_{32})$, —$C(OH)(R_{31})(R_{33})$, —$(CH_2)_nN(R_{31})(COR_{33}))$, —$(CH_2)_nN(R_{31})(SO_2(R_{33}))$; naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio or nitro; —C≡CH; as well as 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2- benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, 8-(3,4-dihydro)-2H-1-benzothiopyranyl;

or a member selected from the group consisting of: 4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 2,3-dihydrobenzofuran-2-yl, 1-methylimidazol-2-yl, quinoxalin-2-yl, isoquinolin-3-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenyl-cylcohexen-1-yl and 4-dihydronaphth-2-yl.

Novel alpha-substituted pyrimidine-thioalkyl compounds of Formula I include compounds where $R_1$ is not 2- or 3-pyridinyl optionally substituted with $C_1$–$C_4$alkyl, a halogen atom, $NH_2$ or —OH, when m is 0, Y is S, $R_{13}$ is —H, $R_{12}$ is —H or $C_1$–$C_4$alkyl $R_4$ is —H, —OH, halo or $NH_2$, $R_5$ is —H, halo or $C_1$–$C_4$ alkyl and $R_6$ is from the group consisting of —H, halo or —OH.

Preferred novel alpha-substituted pyrimidine-thioalkyl and alkylether anti-AIDS compounds of Formula IA include compounds where Y is S, and m is 0.

Additional preferred novel alpha-substituted pyrimidine-thioalkyl and alkylether anti-AIDS compounds of Formula IA include compounds where Y is S, m is 0, $R_{12}$ is $CH_3$ and $R_{13}$ is —H.

Additional preferred novel alpha-substituted pyrimidine-thioalkyl and alkylether anti-AIDS compounds of Formula IA include compounds where Y is S, m is 0, $R_{12}$ is $CH_3$, $R_{13}$ is —H, $R_4$ is $NH_2$, $R_5$ is —H and $R_6$ is —Cl, $CF_3$ or CN.

More preferred novel alpha-substituted pyrimidine-thioalkyl and alkylether anti-AIDS compounds of Formula IA include compounds where Y is S, m is 0, s is 0, $R_{12}$ is $CH_3$, $R_{13}$ is —H, $R_4$ is $NH_2$, $R_5$ is —H, $R_6$ is —Cl, $CF_3$ or CN, and $R_1$ is selected from the group consisting of

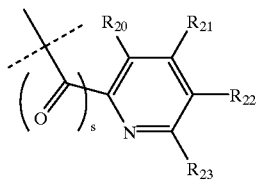

Most preferred novel alpha-substituted pyrimidine-thioalkyl and alkylether anti-AIDS compounds of Formula IA include compounds where Y is S, m is 0, s is 0, $R_{12}$ is $CH_3$, $R_{13}$ is —H, $R_4$ is $NH_2$, $R_5$ is —H, $R_6$ is —Cl, $CF_3$ or CN, and $R_1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1- benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl,5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl,5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, 8-(3,4-dihydro)-2H-1-benzothiopyranyl;

most preferably a member selected from the group consisting of: 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl.

The pyrimidine-thioalkyl compounds of Formula I are generally and most often prepared by contacting a 2-mercaptopyrimidine with an appropriate alkylating agent, e.g. mesylate or halide. See e.g. Chart A.

When $R_{12}$ and $R_{13}$ are different, the compounds of Formula I (as well as IA and IB) are drawn as the racemic mixture and include the R and S isomers, which can be resolved from the racemic mixture by HPLC using a chiral column, such as Chiralcel OD-H, eluting with an appropriate solvent mixture, such as isopropanol/hexane. The R and S isomers of Formula I (when $R_{12}$ and $R_{13}$ are different) can be prepared from an appropriate chiral halide (or mesylate) II (see Chart B). The appropriate chiral halide (or mesylate) II is prepared from a chiral alcohol IV. The appropriate chiral alcohol IV can be prepared from the appropriate ketone V using a chiral reducing agent, such as (+) or (−)-diisopinocampheylchloroborane or other chiral reducing agents known in the art. The appropriate chiral alcohol IV is also obtained from the resolution of the racemic alcohol VII via the enzymatic hydrolysis of the appropriate racemic acetate VI with the appropriate enzyme, such as PS-30 amano lipase or L1754 Type VII from candidae cylindracea or other enzymes known in the art. The appropriate chiral alcohol IV is also obtained from the resolution of the racemic alcohol VII via the enzymatic esterification (such as acetylation or butyration) of the racemic alcohol VII (to give chiral VIII) using the appropriate enzyme, such as porcine pancreatic lipase type II, or other enzymes known in the art.

The alpha-substituted pyrimidine-thioalkyl and alkylether compounds of Formula I include the compounds of EXAMPLES 193–291. Preferred are the anti-AIDS compounds of EXAMPLES 230, 231, 233, 234, 237, 238, 239, 240, 241, 242, 243, 246, 247, 248, 249, 250, 251, 252, 256, 269, 270, 271, 272, 273, 277, 194, 199, 203, 207, 282, 283, 284, 285, 286, 287, 289, 290, 297, 299 and preferrably 237, 238, 239, 246, 289, 290, 297, 299 and more preferably 290, 297, 299 and salts thereof (e.g. 302, 306 and 301).

The pyrimidine-thioalkyl and alkylether compounds of Formula I form acid addition salts; such as mesylate, hydrochloride, hydrobromide, hydroiodide, sulfate, phosphate, acetate, propionate, lactate, maleate, malate, succinate, tartrate, and the like. Some of the variable substituents are acids and as such form base addition salts when reacted with bases of sufficient strength. The pharmaceutically acceptable salts include both inorganic and organic bases. The preferred pharmaceutically acceptable salts include salts of the following bases, for example, hydroxide, ammonia, tromethamine (THAM), 2-amino-2-(hydroxymethyl)-1,3-propanediol. Suitable cations include, for example, sodium, potassium, calcium and magnesium.

The pyrimidine-thioalkyl and alkylether anti-AIDS compounds of Formula IA are useful as inhibitors of viral reverse transcriptase, an enzyme necessary for human immunodeficiency virus replication and therefore would be useful in the treatment of such diseases as AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than 200/mm$^3$ in the peripheral blood.

The compounds of Formula IA can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on the particular compound of Formula IA used, the particular condition being treated, the severity of the condition being treated, the age, weight, general physical condition of the particular patient, other medication the individual may be taking as is well known to those skilled in the art and can be more accurately determined by measuring the blood level or concentration of the compounds of Formula IA in the patient's blood and/or the patient's response to the particular condition being treated.

Patients who are HIV positive but asymptomatic would typically be treated with lower oral doses (about 0.2 to about 100 mg/kg/day. ARC (AIDS-related complex) and AIDS patients would typically be treated with higher oral doses (about 1 to about 500 mg/kg/day).

The pyrimidine-thioalkyl and alkylether anti-AIDS compounds of Formula IA of this invention can be used in conjunction with (or sequentially with) other antiviral agents such as AZT, ddI, ddC, with non-nucleoside anti-AIDS agents such as those disclosed in Ser. No. 08/400,095 Case 4788.1 CP, filed Mar. 7, 1995, International Publication No. WO91/09849, published Jul. 11, 1991, and International Publication No. WO93/01181, published Jan. 21, 1993, and with protease inhibitors.

The utility of the pyrimidine-thioalkyl and alkylether anti-AIDS compounds of Formula IA of this invention can be determined by their ability to inhibit viral reverse transcriptase, an enzyme essential for human immunodeficiency virus replication. This enzyme has characteristics which differentiate it from other known cellular polymerases and it is a unique enzyme which is not found in uninfected cells. Viral reverse transcriptase (Wild Type) is found in extracts from bacterial clones prepared according to the procedure described in AIDS Virus Reverse Transcriptase defined by high level expression in *Escherichia coli*, EMBO J. 6:3133–3137 (1987). P236L viral reverse transcriptase is obtained by PNAS 90: 4713–4717 (1993). Inhibition of this enzyme is determined in a cell free assay which measures the level of radioactive precursors incorporated into DNA. Extracts prepared according to the procedure of Science, 1125–1129 (1981) are incubated in a mixture of inhibitor, 20 mM dithiothreitol, 60 mM sodium chloride, 0.05% NP-40, 10 mM magnesium chloride, 50 mM Tris pH 8.3, 10 $\mu$M [$^{35}$S]-labeled deoxynuleoside-5'-triphosphate, 10 $\mu$g/ml RNA template (poly rC or poly rG) and 5 $\mu$g/ml DNA primer (oligo dG or oligo dT) for 30 minutes at 37° C. Incorporation of radio-labeled percursor is determined by spotting aliquots of the reaction mixture on DE81 paper, washing the papers to remove unincorporated percursor, drying and determining counts. The results (IC$_{50}$ means the concentration, in $\mu$M of drug, required to inhibit the reverse transcriptase activity (P236L and Wild Type) to the extent of 50%) of various assay(s) are combined and reported as % inhibition and/or IC$_{50}$ (calculated) in Table I (P236L) and Table II (Wild Type).

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C *$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C(X$_1$)(X2)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent (X$_1$) which is "below" another substituent (X$_2$) will be identified as being in the alpha ($\alpha$) configuration and is identified by a broken, dashed or dotted line attachment to the carbon atom, i.e., by the symbol "———" or "...". The corresponding substituent attached "above" (X$_2$) the other (X$_1$) is identified as being in the beta ($\beta$) configuration and is indicated by an unbroken line attachment to the carbon atom.

When a variable substituent is bivalent, the valences may be taken together or separately or both in the definition of the variable. For example, a variable R$_i$ attached to a carbon atom as —C(=R$_i$)— might be bivalent and be defined as oxo or keto (thus forming a carbonyl group (—CO—) or as two separately attached monovalent variable substituents $\alpha$-R$_{i-j}$ and $\beta$R$_{i-k}$. When a bivalent variable, R$_i$, is defined to consist of two monovalent variable substituents, the convention used to define the bivalent variable is of the form "$\alpha$-R$_{i-j}$:$\beta$-R$_{i-k}$" or some variant thereof. In such a case both $\alpha$-R$_{i-j}$ and $\beta$-R$_{i-k}$ are attached to the carbon atom to give —C($\alpha$-R$_{i-j}$)($\beta$-R$_{i-k}$)—. For example, when the bivalent variable R$_6$, —C(=R$_6$)— is defined to consist of two monovalent variable substituents, the two monovalent variable substituents are $\alpha$-R$_{6-1}$:$\beta$-R$_{6-2}$, . . . $\alpha$-R$_{6-9}$:$\beta$R$_{6-10}$, etc, giving —C($\alpha$-R$_{6-1}$)($\beta$-R$_{6-2}$)—, . . . —C($\alpha$-R$_{6-9}$)($\beta$-R$_{6-10}$)—, etc. Likewise, for the bivalent variable R$_{11}$, —C(=R$_{11}$)—, two monovalent variable substituents are $\alpha$-R$_{11-1}$:$\beta$-R$_{11-2}$. For a ring substituent for which separate $\alpha$ and $\beta$ orientations do not exist (e.g., due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —C$_1$(R$_i$)H—C$_2$(R$_j$)H—(C$_1$ and C$_2$ define arbitrarily a first and second carbon atom, respectively) R$_i$ and R$_j$ may be defined to be taken together to form (1) a second bond between C$_1$ and C$_2$ or (2) a bivalent group such as oxa (—O—) and the formula thereby describes an epoxide. When R$_i$ and R$_j$ are taken together to form a more complex entity, such as the group —X—Y—, then the orientation of the entity is such that C$_1$ in the above formula is bonded to X and C$_2$ is bonded to Y. Thus, by convention the designation ". . . R$_i$ and R$_j$ are taken together to form —CH$_2$—CH$_2$—O—CO—. . ." means a lactone in which the carbonyl is bonded to C$_2$. However, when designated ". . ." R$_j$ and R$_i$ are taken together to form —CO—O—CH$_2$—CH$_2$— the convention means a lactone in which the carbonyl is bonded to C$_1$.

The carbon atom content of variable substituents is indicated in one of two ways. The first method uses a prefix to the entire name of the variable such as "C$_1$–C$_4$", where both "1" and "4" are integers representing the minimum and maximum number of carbon atoms in the variable. The prefix is separated from the variable by a space. For example, "C$_1$–C$_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus C$_2$–C$_4$ alkoxycarbonyl describes a group CH$_3$—(CH$_2$)$_n$—O—CO— where n is zero, one or two. By the second method the carbon atom content of only each portion of the definition is indicated separately by enclosing the "C$_{i-Cj}$" designation in parentheses and placing it immediately (no intervening space) before the portion of the definition being defined. By this optional convention (C$_1$–C$_3$)alkoxycarbonyl has the same meaning as C$_2$–C$_4$ alkoxycarbonyl because the "C$_1$–C$_3$" refers only to the carbon atom content of the alkoxy group. Similarly while both C$_2$–C$_6$ alkoxyalkyl and (C$_1$–C$_3$) alkoxy(C$_1$–C$_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

Chromatography refers to medium pressure chromatography on silica gel.

THF refers to tetrahydrofuran.

TBDMS refers to tert-butyldimethylsilyl.

Saline refers to an aqueous saturated sodium chloride solution.

NMR refers to nuclear (proton) magnetic resonance spectroscopy, chemical shifts are reported in ppm ($\delta$) downfield from tetramethylsilane.

IR refers to infrared spectroscopy.

—$\Phi$ refers to phenyl (C$_6$H$_5$).

MS refers to mass spectrometry expressed as m/e or mass/charge unit. [M+H]$^+$ refers to the positive ion of a parent plus a hydrogen atom. EI refers to electron impact. CI refers to chemical ionization. FAB refers to fast atom bombardment.

Ether refers to diethyl ether.

Halo refers to a halogen atom (—Cl, —Br, —F or —I).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pyridinyl refers to the pyridyl radical as defined by IUPAC nomenclature. For example, 2-pyridyl (pyridine ring substituted in the 2-position).

When solvent pairs are used, the ratios of solvents used are volume/volume (v/v).

HIV refers to HIV-1 (wild type and/or drug resistant mutants thereof e.g. M41L, K65N, K67L, K70R, L74V, V75T, A98G, L100I, K103E, K103N, K103Q, V106A, V108I, E138K, V179D, V179E, Y181C, Y188H, Y188L, G190A, T215Y, T215F, K219Q, K219E, P236L and K238T).

Treatment refers to inhibition of the HIV virus and will differ depending on the infected individual. For individuals who are HIV positive (infected) but who are asymptomatic, the pyrimidine-thioalkyl derivatives of Formula IA will delay, or prevent, the onset of symptoms. For individuals who are HIV positive, symptomatic and are pre-AIDS or ARC patients, the pyrimidine-thioalkyl derivatives of Formula IA will delay, or prevent, the onset of "full blown AIDS". For individuals who have "full blown AIDS", the pyrimidine-thioalkyl and alkylether derivatives of Formula IA will extend survival time of these individuals.

Pyrimidine-thioalkyl and alkylether compounds of Formula I (as well as Formula IA and/or IB) include alpha-substituted pyrimidine-thioalkyl and alkylether compounds. All references to "pyrimidine-thioalkyl and alkylether compounds" and "pyrimidine-thioalkyl and alkylether anti-AIDS compounds" include "alpha-substituted pyrimidine-thioalkyl and alkylether compounds" and "alpha-substituted pyrimidine-thioalkyl and alkylether anti-AIDS compounds" unless specifically indicated otherwise.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Preparation of 4-amino-6-hydroxy-2-(2,6-difluorophenylmethylthio)-pyrimidine; (Cpd #1)

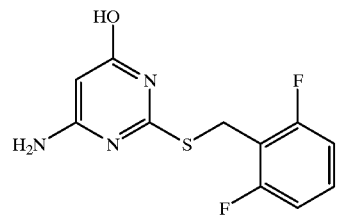

4-Amino-6-hydroxy-2-mercaptopyrimidine monohydrate (1.61 g, 10.0 mmol) is suspended in 50% ethanol (10 ml), then treated with solid sodium hydroxide (440 mg, 11.0 mmol) and stirred until the solid dissolved. 2,6-Difluorobenzyl bromide (2.17 g, 10.5 mmol) is added and the reaction heated to reflux for 1.5 hrs. After cooling to 22° C., the solid is collected, washed with water, then air dried. The title compound is recrystallized from ethanol, mp 245–246° C.

Following the general procedure of Example 1 and making noncritical changes, but using the appropriate halide, the following compounds are synthesized:

|   |   | mp (° C.) |
|---|---|---|
| Ex./Cpd #2 | 4-amino-2-(benzylthio)-6-hydroxypyrimidine | 236–239 |
| Ex./Cpd #3 | 4-amino-2-(2-methylphenylmethylthio)-6-hydroxypyrimidine | 250–251 |
| Ex./Cpd #4 | 4-amino-2-(3-methylphenylmethylthio)-6-hydroxypyrimidine | 230–231 |
| Ex./Cpd #5 | 4-amino-2-(4-methylphenylmethylthio)-6-hydroxypyrimidine | 266–267 |
| Ex./Cpd #6 | 4-amino-2-(3-trifluoromethylphenylmethylthio)-6-hydroxypyrimidine | 222–223 |
| Ex./Cpd #7 | 4-amino-2-(3-methoxyphenylmethylthio)-6-hydroxypyrimidine | 206–207 |
| Ex./Cpd #8 | 4-amino-2-(4-methoxyphenylmethylthio)-6-hydroxypyrimidine | 231–234 |
| Ex./Cpd #9 | 4-amino-2-(3-fluorophenylmethylthio)-6-hydroxypyrimidine | 92–93 |
| Ex./Cpd #10 | 4-amino-2-(3-chlorophenylmethylthio)-6-hydroxypyrimidine | 84–85 |
| Ex./Cpd #11 | 4-amino-2-(3-bromophenylmethylthio)-6-hydroxypyrimidine | 194–196 |
| Ex./Cpd #12 | 4-amino-2-(3-iodophenylmethylthio)-6-hydroxypyrimidine | 208–209 |
| Ex./Cpd #13 | 4-amino-2-(3-nitrophenylmethylthio)-6-hydroxypyrimidine | 263–264 |
| Ex./Cpd #14 | 4-amino-2-(3-carbomethoxyphenylmethylthio)-6-hydroxypyrimidine NMR: (DMSO-$d_6$)8.01(s, 1H), 7.83(d, J=7.8, 1H), 7.74 (d, J=7.8, 1H), 7.45(t, J=7.8, 1H), 6.55(s, 2H), 4.95 (s, 1H), 4.40(s, 2H), 3.84(s, 3H) |   |
| Ex./Cpd #15 | 4-amino-2-(4-t-butylphenylmethylthio)-6-hydroxypyrimidine | 263–264 |
| Ex./Cpd #16 | 4-amino-2-(3,4-difluorophenylmethylthio)-6-hydroxypyrimidine | 222–224 |
| Ex./Cpd #17 | 4-amino-2-(3,4-dichlorophenylmethylthio)-6-hydroxypyrimidine | 255 |
| Ex./Cpd #18 | 4-amino-2-(3,5-dichlorophenylmethylthio)-6-hydroxypyrimidine | 276–277 |
| Ex./Cpd #19 | 4-amino-2-(2,4-dichlorophenylmethylthio)-6-hydroxypyrimidine | 278–279 |
| Ex./Cpd #20 | 4-amino-2-(3,5-dibromophenylmethylthio)-6-hydroxypyrimidine | 288–289 |
| Ex./Cpd #21 | 4-amino-5-cyclohexyl-2-(benzylthio)-6-hydroxypyrimidine | 195–196 |
| Ex./Cpd #22 | 4-amino-5-isopropyl-2-(benzylthio)-6-hydroxypyrimidine | 170–171 |
| Ex./Cpd #23 | 4-amino-2-(2-pyridylmethylthio)-6-hydroxypyrimidine | 219–220 |

-continued

| | | mp (° C.) |
|---|---|---|
| Ex./Cpd #24 | 4-amino-2-[2-(3-ethoxy)pyridylmethylthio]-6-hydroxypyrimidine | 214–216 |
| Ex./Cpd #25 | 4-amino-2-(3-pyridylmethylthio)-6-hydroxypyrimidine | 210–212 |
| Ex./Cpd #26 | 4-amino-2-(1-naphthylmethylthio)-6-hydroxypyrimidine | 240–242 |
| Ex./Cpd #27 | 4-amino-2-(2-naphthylmethylthio)-6-hydroxypyrimidine | 247–249 |
| Ex./Cpd #28 | 4-amino-2-(6,7-difluoro-2-naphthylmethylthio)-6-hydroxy-pyrimidine | 281–283(d) |
| Ex./Cpd #29 | 4-amino-2-(2-quinolinylmethylthio)-6-hydroxypyrimidine NMR: (DMSO-$d_6$)8.33(d, J=8.4, 1H), 7.99(m, 2H), 7.76 (dt, $J_d$=1.2, $J_t$=7.6, 1H), 7.68(d, J=8.4, 1H), 7.59 (dt, $J_d$=1.2, $J_t$=7.6, 1H), 6.58(s, 2H), 4.97 (s, 1H), 4.63(s, 2H) | |
| Ex./Cpd #30 | 4-amino-2-(6-chloro-5-piperonylmethylthio)-6-hydroxy-pyrimidine | 254–255 |
| Ex./Cpd #32 | 4-amino-2-(E-styrylmethylthio)-6-hydroxypyrimidine | 253–254 |
| Ex./Cpd #33 | 4-amino-2-(propargylthio)-6-hydroxypyrimidine | 193–198 |

Example 34

Preparation of 4-amino-6-chloro-2-(2,6-difluorophenylmethylthio)-pyrimidine; (Cpd #34)

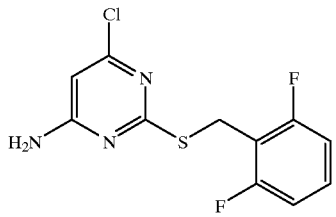

4-amino-6-hydroxy-2-(2,6-difluorophenylmethylthio) pyrimidine (1.33 g, 4.94 mmol; Cpd #1) and 2-picoline (0.5 ml) are heated in refluxing $POCl_3$ (6 ml) overnight. After removing excess solvent in vacuo, the residue is treated with ice, then refluxed for 30 min. The aqueous layer is decanted, then the residue treated with excess $NH_4OH$ and refluxed for 30 min. After cooling, the solid is collected and washed with water then recrystallized from toluene, mp 154° C.

Following the general procedure of Example 34 and making noncritical changes, but beginning with the appropriate hydroxy pyrimidine, the following compounds are synthesized:

| | | mp (° C.) |
|---|---|---|
| Ex./Cpd #34A | 4-amino-6-chloro-2-(benzylthio)-pyrimidine | 112–114.6 |
| Ex./Cpd #35 | 4-amino-6-chloro-2-(2-methylphenylmethylthio)-pyrimidine | 129–131 |
| Ex./Cpd #36 | 4-amino-6-chloro-2-(3-methylphenylmethylthio)-pyrimidine | 97–99 |
| Ex./Cpd #37 | 4-amino-6-chloro-2-(4-methylphenylmethylthio)-pyrimidine | 95–96 |
| Ex./Cpd #38 | 4-amino-6-chloro-2-(3-trifluoromethylphenylmethylthio)-pyrimidine | 95–96 |
| Ex./Cpd #39 | 4-amino-6-chloro-2-(3-methoxyphenylmethylthio)-pyrimidine | 100 |
| Ex./Cpd #40 | 4-amino-6-chloro-2-(4-methoxyphenylmethylthio)-pyrimidine | 118–120 |
| Ex./Cpd #41 | 4-amino-6-chloro-2-(3-fluorophenylmethylthio)-pyrimidine | 97–99 |
| Ex./Cpd #42 | 4-amino-6-chloro-2-(3-chlorophenylmethylthio)-pyrimidine | 103–105 |
| Ex./Cpd #43 | 4-amino-6-chloro-2-(3-bromophenylmethylthio)-pyrimidine | 91–93 |
| Ex./Cpd #44 | 4-amino-6-chloro-2-(3-iodophenylmethylthio)-pyrimidine | 109 |
| Ex./Cpd #45 | 4-amino-6-chloro-2-(3-nitrophenylmethylthio)-pyrimidine | 117–119 |
| Ex./Cpd #46 | 4-amino-6-chloro-2-(3-carbomethoxyphenylmethylthio)-pyrimidine | 169–171 |
| Ex./Cpd #47 | 4-amino-6-chloro-2-(4-t-butylphenylmethylthio)-pyrimidine | 124–126 |
| Ex./Cpd #48 | 4-amino-6-chloro-2-(3,4-difluorophenylmethylthio)-pyrimidine | 123–125 |
| Ex./Cpd #49 | 4-amino-6-chloro-2-(3,4-dichlorophenylmethylthio)-pyrimidine | 172 |
| Ex./Cpd #50 | 4-amino-6-chloro-2-(3,5-dichlorophenylmethylthio)-pyrimidine | 166–168 |
| Ex./Cpd #51 | 4-amino-6-chloro-2-(2,4-dichlorophenylmethylthio)-pyrimidine | 144–147 |
| Ex./Cpd #52 | 4-amino-6-chloro-2-(3,5-dibromophenylmethylthio)-pyrimidine | 184–186 |
| Ex./Cpd #53 | 4-amino-6-chloro-5-cyclohexyl-2-(benzylthio)-pyrimidine | 149–151 |
| Ex./Cpd #54 | 4-amino-6-chloro-5-isopropyl-2-(benzylthio)-pyrimidine | 83–85 |
| Ex./Cpd #55 | 4-amino-6-chloro-2-(2-pyridylmethylthio)-pyrimidine | 185–187 |
| Ex./Cpd #56 | 4-amino-6-chloro-2-[2-(3-ethoxy)pyridylmethylthio]-pyrimidine | 151.5–154 |
| Ex./Cpd #57 | 4-amino-6-chloro-2-(3-pyridylmethylthio)-pyrimidine | 159–161 |
| Ex./Cpd #58 | 4-amino-6-chloro-2-(1-naphthylmethylthio)-pyrimidine | 114–117 |
| Ex./Cpd #59 | 4-amino-6-chloro-2-(2-naphthylmethylthio)-pyrimidine | 98–101 |
| Ex./Cpd #60 | 4-amino-6-chloro-2-(6,7-difluoro-2-naphthylmethylthio)- | 125–127 |

-continued

| | | mp (° C.) |
|---|---|---|
| | pyrimidine | |
| Ex./Cpd #61 | 4-amino-6-chloro-2-(2-quinolinylmethylthio)-pyrimidine | 150–152 |
| Ex./Cpd #62 | 4-amino-6-chloro-2-(6-chloro-5-piperonylmethylthio)-pyrimidine | 157–159 |
| Ex./Cpd #64 | 4-amino-6-chloro-2-(E-styrylmethylthio)-pyrimidine | 117–120 |
| Ex./Cpd #65 | 4-chloro-2-(2-naphthylmethylthio)-pyrimidine | 76–78 |
| Ex./Cpd #66 | 4-amino-6-chloro-2-(propargylthio)-pyrimidine | 137–140 |

Example 67

Preparation of 4-amino-6-chloro-2-(3-bromophenylmethylsulfinyl)pyrimidine; (Cpd #67)

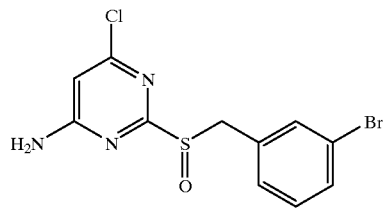

4-amino-6-chloro-2-(3-bromophenylmethylthio)-pyrimidine (165 mg, 0.5 mmol; Cpd #43) in methylene chloride (10 ml) is treated with 50% mCPBA (172 mg, 0.50 mmol) and stirred for 17 hours. The solid is collected by filtration, washed with ether, and dried, mp 216–217° C.

Following the procedure of Example 67 and making noncritical changes, but starting with 4-amino-6-chloro-2-(2-naphthylmethylthio)-pyrimidine (Cpd #59), the compound 4-amino-6-chloro-2-(2-naphthylmethylsulfinyl)-pyrimidine (Cpd #68) is prepared (mp 222–223° C.).

Example 69

Preparation of 4-amino-6-chloro-2-(3-bromophenylmethylsulfonyl)pyrimidine (Cpd #69)

4-amino-6-chloro-2-(3-bromophenylmethylthio)-pyrimidine (660 mg, 2.0 mmol; Cpd #43) in acetic acid (5 ml) is treated with 30% $H_2O_2$ (1 ml) and stirred at rt for 72 hours. The crude product is diluted with ethyl acetate, washed with water, sat'd $NaHCO_3$ and brine, dried with $MgSO_4$, then concentrated in vacuo. The material is purified by chromatography using 1:1 ethyl acetate/hexanes, mp 191–192° C.

Example 70

Preparation of 4-amino-5-bromo-6-chloro-2-(2-naphthylmethylthio)pyrimidine; (Cpd #70)

4-amino-6-chloro-2-(2-naphthylmethylthio)-pyrimidine (302 mg, 1.0 mmol; Cpd #59) and $NaHCO_3$ (100 mg, 1.2 mmol) are dissolved in 50% methanol (3 ml) and treated dropwise with a solution of bromine in methanol (0.92 M, 1.2 ml, 1.1 mmol). The reaction is decolorized with sat'd $NaHSO_3$ and extracted with ethyl acetate. The organic fraction is washed with water, dried with $MgSO_4$, then concentrated in vacuo. The material is purified by chromatography using 15:85 ethyl acetate/hexanes, mp 158° C.

Following the general procedure of Example 70 and making noncritical changes, 4-amino-5-bromo-6-chloro-2-(2-pyridylmethylthio)-pyrimidine (Cpd #71; mp 119–120° C.) is prepared from 4-amino-6-chloro-2-(2-pyridylmethylthio)-pyrimidine (Cpd #55).

Example 72

Preparation of 4,6 dihydroxy-2-(phenylmethylthio)-pyrimidine

Thiobarbituric acid (5.22 g, 36.2 mmol) in ethanol (52 ml) is treated with 3.25 M NaOH (11.1 ml, 36.2 mmol) and the mixture heated to reflux for 30 minutes. After cooling the reaction mixture briefly, benzyl bromide (4.3 ml, 36.2 mmol) is added and the solution is heated to reflux for one hour. The reaction mixture was cooled and concentrated in vacuo, and the resultant white solid is filtered and washed with cold $H_2O$ followed by cold ethanol, mp >320° C.

Following the general procedure of Example 72 and making noncritical changes, but beginning with the appropriate dihydroxy pyrimidine thione, the following compounds are synthesized:

| | | mp (° C.) |
|---|---|---|
| Ex./Cpd #73 | 4,6-dihydroxy-5-methoxy-2-(2-naphthylmethylthio)-pyrimidine | 248–249 |
| Ex./Cpd #74 | 4,6-dihydroxy-5-fluoro-2-(2-naphthylmethylthio)-pyrimidine | >325 |
| Ex./Cpd #75 | 4,6-dihydroxy-5-methyl-2-(2-naphthylmethylthio)-pyrimidine | 285–286 |
| Ex./Cpd #76 | 4,6-dihydroxy-5-fluoro-2-(2-pyridylmethylthio)-pyrimidine | 195(d) |
| Ex./Cpd #77 | 4,6-dihydroxy-2-(4-methoxyphenylmethylthio)-pyrimidine | 207–208 |

Example 78

Preparation of 4,6-dichloro-2-(benzylthio)-pyrimidine (Cpd #78)

2-(Benzylthio)-4,6-dihydroxypyrimidine (5.95 g, 25.4 mmol; Cpd #72) is treated with $POCl_3$ (26 ml) and heated to reflux for 2 hours. The reaction is cooled and excess $POCl_3$ is removed by distillation in vacuo. The hot residue is poured onto ice and the aqueous layer is neutralized with solid NaOH to pH 7–8. The aqueous solution is extracted with ethyl acetate three times and the combined organics are washed dilute NaOH and brine, then dried with MgSO$_4$. The solution is filtered and concentrated in vacuo then purified by distillation, BP (0.2 mmHg) 155–160° C. to yield the title compound.

NMR: (CDCl$_3$) 7.43 (m, 2H), 7.29 (m, 3H), 7.02 (s, 1H), 4.37 (s, 2H).

Following the general procedure of Example 78 and making noncritical changes, but beginning with the appropriate dihydroxy pyrimidine, the following compounds are synthesized:

|  |  | mp (° C.) |
|---|---|---|
| Ex./Cpd #79 | 4,6-dichloro-5-methoxy-2-(2-naphthylmethylthio)-pyrimidine | 93–94 |
| Ex./Cpd #80 | 4,6-dichloro-5-fluoro-2-(2-naphthylmethylthio)-pyrimidine | 80–81 |
| Ex./Cpd #81 | 4,6-dichloro-5-methyl-2-(2-naphthylmethylthio)-pyrimidine | 109–110 |
| Ex./Cpd #82 | 4,6-dichloro-5-fluoro-2-(2-pyridylmethylthio)-pyrimidine | NMR |
| Ex./Cpd #83 | 4,6-dichloro-2-(4-methoxyphenylmethylthio)-pyrimidine | 39–42 |

Cpd #82: NMR: (CDCl$_3$) 8.58 (d, J=4.1, 1H), 7.67 (m, 1H), 7.50 (m, 1H), 7.24 (m, 1H), 4.51 (s, 2H).

Example 84

Preparation of 4-piperido-6-chloro-2-(benzylthio)-pyrimidine; Cpd #84

4,6-dichloro-2-(benzylthio)-pyrimidine (261 mg, 0.96 mmol; Cpd 78) is dissolved in methylene chloride (3 ml), treated with triethyl amine (0.17 ml, 1.20 mmol) and piperidine (0.10 ml, 1.06 mmol) and stirred at rt for 60 hours. The reaction is quenched with sat'd NH$_4$Cl, washed with sat'd NaHCO$_3$, dried with MgSO$_4$ and concentrated in vacuo. The sample is purified by chromatography using 1:3 ethyl acetate/hexanes, mp 85–86° C.

Following the general procedure of Example 84 and making noncritical changes, but beginning with the appropriately substituted amine, the following compounds are synthesized:

|  |  | mp (° C.) |
|---|---|---|
| Ex./Cpd #85 | 4-pyrrolidino-6-chloro-2-(benzylthio)-pyrimidine | 80–81 |
| Ex./Cpd #86 | 4-morpholino-6-chloro-2-(benzylthio)-pyrimidine | 119–120 |
| Ex./Cpd #87 | 4-propylamino-6-chloro-2-(benzylthio)-pyrimidine | 67–68 |
| Ex./Cpd #88 | 4-hydrazino-6-chloro-2-(benzylthio)-pyrimidine | 136–138 |

Example 89

Preparation of 4-amino-5-methoxy-6-chloro-2-(2-naphthylmethylthio)-pyrimidine (Cpd #89)

4,6-dichloro-5-methoxy-2-(2-naphthylmethylthio)-pyrimidine (1.40 g, 4.0 mmol; Cpd #79) is dissolved in acetonitrile (10 ml), treated with concentrated ammonium hydroxide (2 ml), then heated to 120° C. in a sealed tube for 2.5 hrs. After cooling, the product is filtered, washed with water, and dried, mp 115–117° C.

Following the general procedure of Example 89 and making noncritical changes, but beginning with the appropriate dichloropyrimidine, the following compounds are synthesized:

|  |  | mp (° C.) |
|---|---|---|
| Ex./Cpd #90 | 4-amino-5-methyl-6-chloro-2-(2-naphthylmethylthio)-pyrimidine | 156 |
| Ex./Cpd #91 | 4-amino-5-fluoro-6-chloro-2-(2-naphthylmethylthio)-pyrimidine | 160 |
| Ex./Cpd #92 | 4-amino-5-fluoro-6-chloro-2-(2-pyridylmethylthio)-pyrimidine | 171–172 |
| Ex./Cpd #93 | 4-amino-6-chloro-2-(4-methoxyphenylmethylthio)-pyrimidine | 118.5–119.5 |

Example 94

Preparation of 4-amino-2-(2-pyridylmethylthio)-pyrimidine; Cpd #94

4-Amino-2-mercaptopyrimidine (0.40 g, 3.15 mmol) is slurried in ethanol (2 ml) and 3.25 M NaOH (2.0 ml, 6.5 mmol) is added. The solution is heated to reflux for 10 minutes and after cooling to 22° C., 2-picolyl chloride*HCl (0.49 g, 2.98 mmol) is added. The solution is heated to reflux for an additional 15 minutes. The solution is cooled and concentrated in vacuo. The residue is dissolved in 1 N HCl and diluted with ethyl acetate. The mixture is neutralized with NaOH to pH 8 and the aqueous layer is separated and washed twice with ethyl acetate. The combined organic layers are washed with saturated NaHCO$_3$, saturated NaCl, dried with MgSO$_4$ and concentrated in uacuo, mp 133–134° C.

Following the general procedure of Example 94 and making noncritical changes, but beginning with the appropriate thiol, the following compounds are synthesized:

|  |  | mp (° C.) |
|---|---|---|
| Ex./Cpd #95 | 4-amino-2-(3-bromophenylmethylthio)-pyrimidine | 111–112 |
| Ex./Cpd #96 | 4-amino-2-(3-methylphenylmethylthio)-pyrimidine | 88–89 |
| Ex./Cpd #97 | 4-amino-2-(3-pyridylmethylthio)-pyrimidine | 118–119 |
| Ex./Cpd #98 | 4-amino-2-(2-naphthylmethylthio)-pyrimidine | 115–116 |
| Ex./Cpd #99 | 4-amino-6-chloro-2-(2-benzothiazolomethylthio)-pyrimidine | 202–203 |
| Ex./Cpd #100 | 4-amino-6-chloro-2-[2-(1-phenyl-1-ethanon)thio]-pyrimidine | 194–195 |
| Ex./Cpd #101 | 4-amino-6-chloro-2-(cyclohex-1-enylmethylthio)-pyrimidine | 122–123 |
| Ex./Cpd #102 | 4-amino-6-chloro-2-(Z-styrylthio)-pyrimidine |  |

Example 103

Preparation of 4-amino-6-chloro-2-(1-naphthylmethyloxy)-pyrimidine;

1-Naphthalenemethanol (227 mg, 1.44 mmol) is added to a slurry of 50% sodium hydride (69 mg, 1.44 mmol) in dry THF (4 ml) at 0° C. After stirring for 30 minutes, 4-amino-2,6-dichloropyrimidine (157 mg, 0.96 mmol) is added and stirred at 22° C. for 72 hours. The solution is quenched with saturated NH$_4$Cl and concentrated in vacuo. The residue is dissolved in methylene chloride and washed 3× saturated NaHCO$_3$, dried with MgSO$_4$, filtered, and concentrated in vacuo. The sample is purified by chromatography using 1:2 ethyl acetate/hexanes and recrystallization from heptane/toluene, mp 160–161° C.

Following the general procedure of Example 103 and making noncritical changes, but beginning with the appropriate alcohol, the following compounds are synthesized:

|  |  | mp (° C.) |
|---|---|---|
| Ex./Cpd #104 | 4-amino-6-chloro-2-(benzyloxy)-pyrimidine | 114–115 |
| Ex./Cpd #105 | 4-amino-6-chloro-2-(2-naphthylmethyloxy)-pyrimidine | 130–131 |
| Ex./Cpd #106 | 4-amino-6-chloro-2-(3-methylphenylmethyloxy)-pyrimidine | 85–87 |
| Ex./Cpd #107 | 4-amino-6-chloro-2-(3-bromophenylmethyloxy)-pyrimidine | 96–98 |

Example 108

Preparation of 4-amino-6-chloro-2-(3-hydroxyphenylmethylthio)-pyrimidine 4-amino-6-chloro-2-(3-methoxyphenylmethylthio)-pyrimidine (36 mg, 0.128 mmol; Cpd #39) is dissolved in methylene chloride (0.25 ml), cooled to 0° C. and treated with a solution of BBr$_3$ (0.32 ml, 0.32 mmol, 1M in methylene chloride). The reaction is stirred at 0° C. for 20 min, then refluxed for 2 hrs. After cooling, the reaction is quenched with water, and refluxed for an additional 30 min. Upon cooling the solid is collected and purified by recrystallization from ethanol/water, mp 147.5–148.5° C.

Example 109

Preparation of 4-amino-6-chloro-2-(3-isopropoxyphenylmethylthio)-pyrimidine (Cpd #108)

4-amino-6-chloro-2-(3-hydroxyphenylmethylthio)-pyrimidine (135 mg, 0.50 mmol; Cpd 108) is added to a solution of KOH (280 mg, 5 mmol) in DMSO (2.5 ml) at room temperature. 2-Bromopropane (615 mg, 5 mmol) is added and the reaction stirred overnight, then poured onto water. The aqueous solution is extracted with ethyl acetate, dried with $MgSO_4$, filtered, and concentrated in vacuo. The sample is purified by chromatography using 1:3 ethyl acetate/hexanes, mp 71° C.

Example 110

Preparation of 4-amino-6-chloro-2-thio-pyrimidine (Cpd #110)

4-amino-6-chloro-2-(4-methoxyphenylmethylthio)-pyrimidine (11.0 g, 39.15 mmol; Cpd #93) and trifluoroacetic acid (84 ml) are heated to reflux for 20 hours, then the excess solvent is removed in vacuo. The sample is triturated with chloroform then stirred with ether and filtered. The solid is washed with ether then air dried, mp >320° C.

Example 110A

Preparation of 4-amino-6-chloro-2-thio-pyrimidine mesylate salt Cpd #110A 4-Amino-6-chloro-2-mercaptopyrimidine mesylate A suspension of 4-amino-6-chloro-2-(4-methoxyphenylmethylthio)pyrimidine (10.0 g, 33.22 mmol) in 160 ml of methylene chloride at room temperature is treated with methanesulfonic acid (31.89 g, 332.2 mmol, 10 eq) at once. After TLC analysis indicaates the absence of starting material (ca. 50 min), 1280 ml of diethyl ether is added dropwise initially. As the volume of white solid becomes quite copious the remaining $Et_2O$ is added quite rapidly. The suspension is stirred overnight and the material is collected by filtration and washed with diethyl ether to afford 8.62 g of the title compound (Melting Point: 166–167° C.). Analysis: Calculated for $C_5H_8ClN_3O_3S_2$.4.94% $H_2O$: C, 23.22; H, 3.16; N, 16.25. Found: C, 23.48; H, 3.25; N, 15.70.

Example 111

Preparation of 4-amino-6-chloro-2-[2-(4-chloro)-5 pyridylmethylthio]-pyrimidine (Cpd #111)

4-Amino-6-chloro-2-thio-pyrimidine (Cpd #110; 614 mg, 2.38 mmol) in ethanol (1.5 ml) is treated with 3.25 M NaOH (1.47 ml, 4.8 mmol) and the mixture is warmed to 50° C. 4-chloro-2-chloromethyl pyridine is added and the solution is stirred warm for 1 hour. The reaction mixture is cooled and concentrated in vacuo, and the resultant solid is filtered and washed with water followed by cold ethanol, mp 195° C.

Following the general procedure of Example 111 and making noncritical changes, but beginning with the appropriate chloromethylarene, the following compounds are synthesized:

|  |  | mp (° C.) |
|---|---|---|
| Ex./Cpd #112 | 4-amino-6-chloro-2-[2-(6-chloro)pyridylmethylthio]-pyrimidine | 135–136 |
| Ex./Cpd #113 | 4-amino-6-chloro-2-[2-(6-methyl)pyridylmethylthio]-pyrimidine | 156–157 |
| Ex./Cpd #114 | 4-amino-6-chloro-2-[2-(4-methyl)pyridylmethylthio]-pyrimidine | 192–193 |
| Ex./Cpd #115 | 4-amino-6-chloro-2-[2-(4-ethoxy)pyridylmethylthio]-pyrimidine | 181–185 |
| Ex./Cpd #116 | 4-amino-6-chloro-2-[2-(4-thiophenyl)pyridylmethylthio]-pyrimidine | 136–137 |
| Ex./Cpd #117 | 4-amino-6-chloro-2-[2-(3-methyl)pyridylmethylthio]-pyrimidine | 148–149 |
| Ex./Cpd #118 | 4-amino-6-chloro-2-[2-(5-methyl)pyridylmethylthio]-pyrimidine | 191–192 |
| Ex./Cpd #119 | 4-amino-6-chloro-2-[2-(4-bromo)pyridylmethylthio]-pyrimidine | 188d |
| Ex./Cpd #120 | 4-amino-6-chloro-2-[2-(4-methoxy-6-methyl)-pyridylmethylthio]-pyrimidine | 171–172 |
| Ex./Cpd #121 | 4-amino-6-chloro-2-[2-(4,6-dimethyl)pyridylmethylthio]-pyrimidine | 160–16 1 |
| Ex./Cpd #122 | 4-amino-6-chloro-2-[2-(4-ethyl)pyridylmethylthio]-pyrimidine | 173–174 |
| Ex./Cpd #123 | 4-amino-6-chloro-2-[2-(4-methoxy)pyridylmethylthio]-pyrimidine | 191–192 |
| Ex./Cpd #124 | 4-amino-6-chloro-2-[2-(4-(2-methylpropyl))pyridylmethylthio]-pyrimidine | 156–157 |
| Ex./Cpd #125 | 4-amino-6-chloro-2-[2-(6-chloro-4-methyl)pyridylmethylthio]-pyrimidine | 171–172 |
| Ex./Cpd #126 | 4-amino-6-chloro-2-[2-(4-isopropoxy)pyridylmethylthio]-pyrimidine | 168–169 |
| Ex./Cpd #127 | 4-amino-6-chloro-2-[2-(4,6-dimethyl)pyrimidinylmethylthio]-pyrimidine | 180–181 |
| Ex./Cpd #128 | 4-amino-6-chloro-2-[2-(4-cyano)pyridylmethylthio]-pyrimidine | 214–215 |
| Ex./Cpd #130 | 4-amino-6-chloro-2-[4-(6-methyl)pyrimidinylmethylthio]-pyrimidine | 165–166 |
| Ex./Cpd #131 | 4-amino-6-chloro-2-[2-(4-propyl)pyridylmethylthio]-pyrimidine | 161–162 |
| Ex./Cpd #132 | 4-amino-6-chloro-2-[2-(4-isopropyl)pyridylmethylthio]-pyrimidine | 139 |
| Ex./Cpd #133 | 4-amino-6-chloro-2-[2-(5-phenyl)pyridylmethylthio]-pyrimidine | 191 |
| Ex./Cpd #134 | 4-amino-6-chloro-2-[2-(4-ethyl)pyridylmethylthio]-pyrimidine | 180 |
| Ex./Cpd #135 | 4-amino-6-chloro-2-[2-(4-(α-hydroxy, α(-methyl)ethyl)pyridyl-methylthio]-pyrimidine | 140–143 |
| Ex./Cpd #137 | 4-amino-6-chloro-2-[2-(4-cyclopropyl)pyridylmethylthio]-pyrimidine | 162–163 |
| Ex./Cpd #138 | 4-amino-6-chloro-2-[2-(4-cyclopentyl)pyridylmethylthio]-pyrimidine | 138–139 |
| Ex./Cpd #140 | 4-amino-6-chloro-2-[2-(4,5-dimethyl)pyridylmethylthio]-pyrimidine | 210–211 |
| Ex./Cpd #142 | 4-amino-6-chloro-2-[4-(2,6-dimethyl)pyrimidinylmethylthio]-pyrimidine | 132–138 |
| Ex./Cpd #143 | 4-amino-6-chloro-2-[2-(4-pyrrolidino)pyridylmethylthio]-pyrimidine | 205d |
| Ex./Cpd #144 | 4-Amino-6-chloro-2-[(5-chlorothiophen-2-ylmethyl)thio]pyrimidine | 100–102 |
| Ex./Cpd #145 | 4-amino-6-chloro-2-[2-(4-(2-butyl))pyridylmethylthio]-pyrimidine | 115–117 |
| Ex./Cpd #146 | 4-amino-6-chloro-2-[2-(4-dimethylamino)pyridylmethylthio]-pyrimidine | 207–208 |

-continued

|  |  | mp (° C.) |
|---|---|---|
| Ex./Cpd #147 | 2-[2-(4-amino-6-chloro)pyrimidinylthiomethyl]-pyridine–1-oxide | 199–200d |
| Ex./Cpd #148 | 4-Amino-6-chloro-2-[(furan-3-ylmethyl)thio]pyrimidine | 83–84 |
| Ex./Cpd #149 | 4-amino-6-chloro-5-fluoro-2-[2-(4-chloro)pyridylmethylthio]pyrimidine | 172 |
| Ex./Cpd #151 | 4-amino-6-chloro-2-[2-(4-(3-pentyl))pyridylmethylthio]-pyrimidine | 144–145 |
| Ex./Cpd #152 | 4-amino-6-chlbro-2-[2-(4-acetyl)pyridylmethylthio]-pyrimidine NMR: (CF$_3$OD)8.67(d, J=5.2, 1H), 8.12(s, 1H), 7.74(d, J=5.1, 1H), 6.22(s, 1H), 4.53(s, 2H), 2.64(s, 3H) |  |
| Ex./Cpd #153 | 4-Amino-6-chloro-2-[(benzofuran-2-ylmethyl)thio]pyrimidine | 118–119 |
| Ex./Cpd #154 | 4-amino-6-chloro-2-[2-(6-dimethylamino-4-methyl)pyridylmethylthio]-pyrimidine | 166–168 |
| Ex./Cpd #155 | 4-amino-6-chloro-2-[(1H-inden-3-ylmethyl)thio]pyrimidine NMR: (CDCl$_3$)7.47, 7.26, 6.54, 6.15, 4.99, 4.34, 3.37 |  |
| Ex./Cpd #156 | 4-amino-6-chloro-2-[2-(4-carbomethoxy)pyridylmethylthio]-pyrimidine | 168–169 |
| Ex./Cpd #157 | 4-Amino-6-chloro-2-[((S)-(—)perillyl)thio]pyrimidine | 115–116 |
| Ex./Cpd #158 | 4-Amino-6-chloro-2-[(benzothiophen-2-ylmethyl)thio]pyrimidine | 155–156 |
| Ex./Cpd #159 | 4-Amino-6-chloro-2-[(2H–1-benzopyran-8-ylmethyl)thio]pyrimidine | 110–118 |

Example #163

Preparation of 4-amino-6-chloro-2-[2-(4-carboxamido)-pyridylmethylthio]-pyrimidine (Cpd #163)

4-amino-6-chloro-2-[2-(4-carbomethoxy) pyridylmethylthio]-pyrimidine (100 mg, 0.32 mmol) and freshly distilled formamide (48 mg, 1.06 mmol) are dissolved in THF (0.5 ml) and the solution is heated to reflux. Sodium methoxide (25%, 24 μl, 0.107 mmol) is added and the mixture is refluxed for 1 hour. The reaction is cooled and filtered through celite then concentrated in vacuo. The resultant solid is triturated with acetone. mp 191–192° C.

Example #164

Preparation of 4-amino-6-chloro-2-[2-(4-hydroxymethyl)-pyridylmethylthio]-pyrimidine (Cpd #164)

Lithium aluminum hydride (12 mg, 0.32 mmol) is suspended in THF (1 ml) and cooled to 0° C. The slurry is then treated with a solution of 4-amino-6-chloro-2-[2-(4-carbomethoxy)pyridylmethylthio]-pyrimidine (100 mg, 0.32 mmol) in THF (0.5 ml). The solution is allowed to warm to room temperature and stirred for 1 hour. The reaction is quenched with water (1 drop), 1 N NaOH (1 drop), and water (3 drops) and diluted with ethyl acetate. The reaction is dried with MgSO$_4$ and concentrated in vacuo. The resultant solid is triturated with ethyl acetate. mp 117–118° C.

Following the general procedure of Example 70 and making noncritical changes, but beginning with the appropriate 4-amino-6-chloro-2-[2-(4-substituted)-pyridylmethylthio]-pyrimidine, the following compounds are synthesized:

|  |  | mp (° C.) |
|---|---|---|
| Ex./Cpd #165 | 4-amino-5-bromo-6-chloro-2-[2-(4-methyl)pyridylmethylthio]-pyrimidine | 138–139 |
| Ex./Cpd #166 | 4-amino-5-bromo-6-chloro-2-[2-(4-isopropyl)pyridylmethylthio]-pyrimidine | 146–147 |

Following the general procedure of Example 111 and making noncritical changes, but beginning with the appropriate chloromethylarene, the following compounds are synthesized:

|  |  |  |
|---|---|---|
| Ex./Cpd #167 | 4-amino-6-chloro-2-(2,6-dichlorophenyl)methylthio-pyrimidine | 173–174 |
| Ex./Cpd #168 | 4-Amino-6-chloro-2-[(2,3-dihydrobenzofuran-5-ylmethyl)thio]pyrimidine | 153 |
| Ex./Cpd #169 | 4-Amino-6-chloro-2-[(5-phenylisoxazol-3-ylmethyl)thio]pyrimidine | 217–219 |
| Ex./Cpd #170 | 4-Amino-6-chloro-2-[(2,3-dihydrobenzofuran-2-ylmethyl)thio]pyrimidine | 105–107 |

-continued

| Ex./Cpd #171 | 4-Amino-6-chloro-2-[[(3,4-dihydro-1-naphthalen-2-yl)methyl]thio]-pyrimidine | 104–105 |
|---|---|---|
| Ex./Cpd #172 | 4-Amino-6-chloro-2-[[(5-chloroimidazo[1,2-a]pyridin-2-yl)methyl]thio]-pyrimidine | >240 |
| Ex./Cpd #173 | 4-Amino-6-chloro-2-[(6-methylpyrazin-2-ylmethyl)thio]pyrimidine | 162 |
| Ex./Cpd #174 | 4-Amino-6-chloro-2-[(5-methylisoxazol-3-ylmethyl)thio]pyrimidine | 177–180 |
| Ex./Cpd #175 | 4-Amino-6-chloro-2-[(5-methylpyrazin-2-ylmethyl)thio]pyrimidine | 154–155 |
| Ex./Cpd #176 | 4-Amino-6-chloro-2-[(1-methylimidazol-2-ylmethyl)thio]pyrimidine | 178–180 |
| Ex./Cpd #177 | 4-Amino-6-chloro-2-[(3-methylpyrazin-2-ylmethyl)thio]pyrimidine | 162–163 |
| Ex./Cpd #178 | 4-Amino-6-chloro-2-[(quinolin-6-ylmethyl)thio]pyrimidine | 186–188(d) |
| Ex./Cpd #179 | 4-Amino-6-chloro-2-[(quinoxalin-2-ylmethyl)thio]pyrimidine | 195(d) |
| Ex./Cpd #180 | 4-Amino-6-chloro-2-[(quinolin-8-ylmethyl)thio]pyrimidine | 174–175 |
| Ex./Cpd #181 | 4-Amino-6-chloro-2-[(quinolin-4-ylmethyl)thio]pyrimidine | 195(d) |
| Ex./Cpd #182 | 4-Amino-6-chloro-2-[(isoquinolin-3-ylmethyl)thio]pyrimidine | >210 |
| Ex./Cpd #183 | 4-Amino-6-chloro-2-[(quinolin-5-ylmethyl)thio]pyrimidine | 190(d) |
| Ex./Cpd #184 | 4-Amino-6-chloro-2-[(quinolin-7-ylmethyl)thio]pyrimidine | 195(d) |
| Ex./Cpd #186 | 4-Amino-6-chloro-2-[(piperon-5-ylmethyl)thio]pyrimidine | 148–150 |
| Ex./Cpd #187 | 4-Amino-6-chloro-2-[[(3,4-dihydro-1-naphthalenyl)methyl]thio]pyrimidine | 127–130 |
| Ex./Cpd #188 | 4-amino-6-chloro-2[2-(5-carbomethyoxy)pyridylmethylthio]pyrimidine | 200 |
| Ex./Cpd #189 | 4-amino-6-chloro-2[2-(4-cyclohexyl)pyridylmethylthio]pyrimidine | 134 |

Following the general procedure of Example 72 and making noncritical changes, but beginning with the appropriate dihydroxy pyrimidine thione, the following compound is synthesized:

Ex./Cpd #190 4,6-dihydroxy-5-fluoro-2-[2-(4-chloro)pyridylmethylthio]pyrimidine

NMR: (DMSO) 8.48 (d,J=5.5,1H), 7.71 (s, 1H), 7.44 (s, 1H), 4.44 (s, 2H)

Following the general procedure of Example 78 and making noncritical changes, but beginning with the appropriate dihydroxy pyrimidine, the following compound is synthesized:

Ex./Cpd #191 4,6-dichloro-5-fluoro-2-[2-(4-chloro)pyridylmethylthio]pyrimidine

NMR: (CDCl$_3$) 8.54 (d,J=5.5,1H), 7.77 (s, 1H), 7.39 (d,J=5.4, 1H), 4.59 (s, 2H)

Example 193

(E)-4-[(4-Amino-6-chloro-2-pyrimidinyl)thio]-2-butenoic acid methyl ester (Cpd #193)

4-Amino-6-chloro-2-mercaptopyrimidine mesylate (0.30 g, 1.16 mmol) is dissolved in 3.25N sodium hydroxide (2 ml) and ethanol (1 ml) at ambient temperature followed by the addition of methyl 4-bromocrotonate (0.16 ml, 1.40 mmol). The reaction is stirred for 2 to 15 hours, quenched with excess water, extracted with methylene chloride (2×25 ml). The extracts are combined, washed with saline (25 ml), dried over sodium sulfate, concentrated in vacuo and recrystallized from hexane/ethyl acetate to give Cpd #193. mp 146–149° C.

Example 194

(E)-N,N-Diethyl-4-[(4-amino-6-chloro-2-pyrimidinyl)thio]-2-butenamide (Cpd #194)

4-Chlorocrotonyl chloride (1.36 g, 9.80 mmol) in ether (20 ml) is combined with diethylamine in ether (5 ml) at −15° C. in a flame dried flask. The reaction is warmed to ambient temperature, stirred for 1 to 2 hours, quenched with water (30 ml), extracted with ethyl acetate (2×30 ml), washed with saline (30 ml), dried over sodium sulfate, and concentrated in vacuo to yield the crude 4-chloro-N,N-diethylcrotonamide.

Following the general procedure of EXAMPLE 193 and making noncritical variations but substituting crude 4-chloro-N,N-diethylcrotonamide (1.72 g, 9.80 mmol) for cis/trans-1,3-dichloro-2-butene, the title compound is obtained, mp 143–145° C.

Example 195

(E)-4-methyl-1-[4-[(4-amino-6-chloro-2-pyrimidinyl)thio]-1-oxo-2-butenyl]piperazine (Cpd #195)

Following the general procedure of EXAMPLE 194 and making noncritical variations but substituting 1-methylpiperazine (2.15 g, 21.50 mmol) for diethylamine, the title compound is obtained, mp 155–156° C.

Example 196

(E)-N-ethyl-4-[(4-amino-6-chloro-2-pyrimidinyl)thio]-2-butenamide (Cpd #196)

Following the general procedure of EXAMPLE 194 and making noncritical variations but substituting ethylamine (0.73 g, 16.17 mmol) for diethylamine, the title compound is obtained, mp 160–161° C.

Example 197

(E)-1-[4-[(4-amino-6-chloro-2-pyrimidinyl)thio]-1-oxo- 2-butenyl]piperidine (Cpd #197)

Following the general procedure of EXAMPLE 194 and making noncritical variations but substituting piperidine (1.38 g, 16.17 mmol) for diethylamine, the title compound is obtained, mp 159–163° C.

Example 198

(E)-4-[4-[(4-amino-6-chloro-2-pyrimidinyl)thio]-1-oxo-2-butenyl]morpholine (Cpd #198)

Following the general procedure of EXAMPLE 194 and making noncritical variations but substituting morpholine

Example 199

(E)-1-[4-[(4-amino-6-chloro-2-pyrimidinyl)thio]-1-oxo-2-butenyl]pyrrolidine (Cpd #199)

Following the general procedure of EXAMPLE 194 and making noncritical variations but substituting pyrrolidine (1.15 g, 16.17 mmol) for diethylamine, the title compound is obtained, mp 178–180° C.

Example 200

(E)-N-methyl-N-phenyl-4-[(4-amino-6-chloro-2-pyrimidinyl)thio]-2-butenamide (Cpd #200)

Following the general procedure of EXAMPLE 194 and making noncritical variations but substituting N-methylaniline (2.31 g, 21.56 mmol) for diethylamine, the title compound is obtained, mp 152–154° C.

Example 201

(E)-N-allyl-N-methyl-4-[(4-amino-6-chloro-2-pyrimidinyl)thio]-2-butenamide (Cpd #201)

Following the general procedure of EXAMPLE 194 and making noncritical variations but substituting N-methylallylamine (1.15 g, 16.17 mmol) for diethylamine, the title compound is obtained, mp 140–142° C.

Example 202

(E)-N,N-Dipropyl-4-[(4-amino-6-chloro-2-pyrimidinyl)thio]-2-butenamide (Cpd #202)

4-Chlorocrotonyl chloride (1.02 g, 7.35 mmol) in ether (10 ml) is combined with dipropylamine (1.64 g, 16.17 mmol) in ether (5 ml) at −15° C. in a flame dried flask. The reaction is warmed to ambient temperature, stirred for 1 to 2 hours, quenched with water (30 ml), extracted with ethyl acetate (2×30 ml), washed with saline (30 ml), dried over sodium sulfate, concentrated in vacuo, and chromatographed on silica gel (230–400 mesh, 100 ml), eluting with hexane/ethyl acetate (60/40). The appropriate fractions are combined ($R_f$=0.53, TLC, hexane/ethyl acetate, 25/75) and concentrated in vacuo to give 4-chloro-N,N-dipropylcrotonamide. 4-Amino-6-chloro-2-mercaptopyrimidine mesylate (0.30 g, 1.16 mmol) is dissolved in DMF (5 ml) and sodium hydride (0.06 g, 2.55 mmol) at ambient temperature followed by the addition of 4-chloro-N,N-dipropylcrotonamide (0.23 g, 1.13 mmol). The reaction is stirred for 2 to 15 hours, quenched with excess water, extracted with ethyl acetate (3×20 ml). The extracts are combined, washed with saline (20 ml), dried over sodium sulfate, concentrated in vacuo and chromatographed on silica gel (230–400 mesh, 100 ml), eluting with hexane/ethyl acetate (60/40). The appropriate fractions are combined ($R_f$=0.40, TLC, hexane/ethyl acetate, 25/75) and concentrated in vacuo to give the title compound, mp 139–142° C.

Example 203

(E)-N-ethyl-N-methyl-4-[(4-amino-6-chloro-2-pyrimidinyl)thio]-2-butenamide (Cpd #203)

Following the general procedure of EXAMPLE 202 and making noncritical variations but substituting N-ethylmethylamine (0.87 g, 14.70 mmol) for dipropylamine, the title compound is obtained, mp 170–172° C.

Example 204

(E)-N,N-Dimethyl-4-[(4-amino-6-chloro-2-pyrimidinyl)thio]-2-butenamide (Cpd #204)

Following the general procedure of EXAMPLE 202 and making noncritical variations but substituting dimethylamine (0.50 g, 11.03 mmol) for dipropylamine, the title compound is obtained, mp 173–176° C.

Example 205

(E)-N,N-Diethyl-4-oxo-2-pentenamide

To flame dried flask containing (E)-4-oxo-2-pentenoyl chloride (1.16 g, 8.76 mmol) in ether cooled to −15° C. is added diethylamine (1.41 g, 19.28 mmol) in ether (5 ml) and stirred for 2 hours while being warmed to ambient temperature. The solvents are removed in vacuo, and chromatographed on silica gel (230–400 mesh, 100 ml), eluting with hexane/ethyl acetate (75/25). The appropriate fractions are combined ($R_f$=0.31, TLC, hexane/ethyl acetate, 25/75) and concentrated in vacuo to give the title compound, NMR (CDCl$_3$) 7.15, 7.04, 3.45, 3.40, 2.33, 1.20, 1.15.

Example 206

(E)-N,N-Diethyl-4-hydroxy-2-pentenamide

To (E)-N,N-diethyl-4-oxo-2-pentenamide (0.73 g, 4.31 mmol) in methanol (10 ml) cooled to 0° C. is added sodium borohydride (0.18 g, 4.75 mmol) under nitrogen stirred for minutes, quenched with excess water, and extracted with ethyl acetate (3×50 ml). The organic extracts are combined, washed with saline (50 ml), dried over sodium sulfate, concentrated in vacuo to give the title compound, NMR (CDCl$_3$) 6.89, 6.42, 4.49, 3.41, 2.51, 1.33, 1.17.

Example 207

(E)-N,N-Diethyl-4-[(4-amino-6-chloro-2-pyrimidinyl)thio]-2-pentenamide (Cpd #207)

To (E)-N,N-Diethyl-4-hydroxy-2-pentenamide (0.67 g, 3.93 mmol) in methylene chloride cooled to -15° C. in a flame dried flask is added dichlorotriphenylphosphorane (1.40 g, 4.33 mmol). The reaction is warmed to ambient temperature, quenched by addition of ice (10 ml), extracted with methylene chloride (3×20 ml), washed with saline (30 ml), dried over sodium sulfate, concentrated in vacuo, and chromatographed on silica gel (230–400 mesh, 100 ml), eluting with hexane/ethyl acetate (75/25). The appropriate fractions are combined ($R_f$=0.48, TLC, hexane/ethyl acetate, 25/75) and concentrated in vacuo to give (E)-4-chloro-N,N-diethyl-2-pentenamide. 4-Amino-6-chloro-2-mercaptopyrimidine mesylate (0.56 g, 2.19 mmol) is dissolved in DMF (4 ml) and sodium hydride (0.12 g, 4.82 mmol) at ambient temperature followed by the addition of (E)-4-chloro-N,N-diethyl-2-pentenamide (0.41 g, 2.19 mmol). The reaction is stirred for 15 hours, quenched with excess water, extracted with ethyl acetate (3×25 ml). The extracts are combined, washed with saline (25 ml), dried over sodium sulfate, concentrated in vacuo and chromatographed on silica gel (230–400 mesh, 100 ml), eluting with a gradient of hexane/ethyl acetate (80/20–60/40). The appropriate fractions are combined ($R_f$=0.27, TLC, hexane/ethyl acetate, 25/75) and concentrated in vacuo to give the title compound, mp 152–153° C.

Example 208

(E)-4-[(4-Amino-6-chloro-2-pyrimidinyl)thio]-3-methyl-2-butenoic acid methyl ester (Cpd #208)

To (E)-4-hydroxy-3-methyl-2-butenoic acid methyl ester (0.75 g, 5.76 mmol) in methylene chloride cooled to −15° C. in a flame dried flask is added dibromotriphenylphosphorane (2.68 g, 6.34 mmol). The reaction is stirred at −15° C.–0° C. for two hours, quenched by addition of ice (10 ml), extracted with methylene chloride (2×10 ml), washed with saline (10 ml), dried over sodium sulfate, concentrated in vacuo, and chromatographed on silica gel (230–400 mesh, 100 ml), eluting with hexane/ethyl acetate (95/5). The appropriate fractions are combined and concentrated in vacuo to give (E)-4-chloro-3-methyl-2-butenoic acid methyl ester. 4-Amino-6-chloro-2-mercaptopyrimidine mesylate (0.30 g, 1.16 mmol) is dissolved in DMF (4 ml) and sodium hydride (0.06 g, 2.56 mmol) at ambient temperature followed by the addition of (E)-4-bromo-3-methyl-2-butenoic acid methyl ester (0.22 g, 1.16 mmol). The reaction is stirred for 15 hours, quenched with excess water, extracted with ethyl acetate (3×20 ml). The extracts are combined, washed with saline (20 ml), dried over sodium sulfate, concentrated in uacuo and chromatographed on silica gel (230–400 mesh, 100 ml), eluting with hexane/ethyl acetate (80/20). The appropriate fractions are combined ($R_f$=0.43, TLC, hexane/ethyl acetate, 50/50) and concentrated in vacuo to give the title compound, mp 134–136° C.

Example 209

(E)-4-[(4-Amino-6-chloro-2-pyrimidinyl)thio]-3-methyl-2-pentenoic acid methyl ester (Cpd #209)

To (E)-4-hydroxy-3-methyl-2-pentenoic acid methyl ester (1.00 g, 6.94 mmol) in methylene chloride cooled to −15° C. in a flame dried flask is added dichlorotriphenylphosphorane (2.47 g, 7.63 mmol). The reaction is warmed to ambient temperature, quenched by addition of ice (10 ml), extracted with methylene chloride (2×10 ml), washed with saline (10 ml), dried over sodium sulfate, concentrated in vacuo, and chromatographed on silica gel (230–400 mesh, 75 ml), eluting with hexane/ethyl acetate (95/5). The appropriate fractions are combined ($R_f$=0.55, TLC, hexane/ethyl acetate, 75/25) and concentrated in vacuo to give (E)-4-chloro-3-methyl-2-pentenoic acid methyl ester. 4-Amino-6-chloro-2-mercaptopyrimidine mesylate (0.30 g, 1.16 mmol) is dissolved in DMF (4 ml) and sodium hydride (0.06 g, 2.56 mmol) at ambient temperature followed by the addition of (E)-4-chloro-3-methyl-2-pentenoic acid methyl ester (0.19 g, 1.16 mmol). The reaction is stirred for 15 hours, quenched with excess water, extracted with ethyl acetate (3×15 ml). The extracts are combined, washed with saline (15 ml), dried over sodium sulfate, concentrated in vacuo and chromatographed on silica gel (230–400 mesh, 100 ml), eluting with hexane/ethyl acetate (85/15). The appropriate fractions are combined ($R_f$=0.18, TLC, hexane/ethyl acetate, 50/50) and concentrated in vacuo to give the title compound, mp 124–126° C.

Example 210

4-Amino-6-chloro-2-(1-(4-(1,1-dimethyl)ethyl-2-pyridyl)ethyl)thio-pyrimidine (Cpd #210)

Part A: 4-t-Butyl-pyridine N-oxide 4-t-Butyl-pyridine (14.8 ml, 100 mmole) is dissolved in 35 ml glacial acetic acid in a 200 ml one neck round bottom flask under nitrogen. The solution is warmed to 95–100° C., is treated with 30% hydrogen peroxide (28 ml, 274 mmole), and is stirred 6 h. The reaction is treated portionwise with paraformaldehyde until a negative reaction is obtained with starch iodide paper. The volatiles are removed in vacuo and the residue is azeotroped with 2×100 ml toluene. The residue is partitioned between 1×100 ml dichloromethane and 2×75 ml saturated sodium bicarbonate. The aqueous layer is backwashed with 3×50 ml dichloromethane. The combined organics are dried over magnesium sulfate and are concentrated in vacuo to give 14.5 g (96%) of 4-t-Butyl-pyridine N-oxide as a pale yellow solid.

$^1$H-NMR (CDCl$_3$, TMS): δ 1.32 (s, 9), 7.27 (m, 2), 8.15 (m, 2) ppm. $^{13}$C-NMR (CDCl$_3$): δ 30.3; 34.4; 122.9; 138.3; 150.7 ppm. TLC (silica gel-60, F-254): $R_f$=0.42, 10% methanol/dichloromethane. Melting Point: 93–95° C. Infrared (ν max, mineral oil): 3098, 2924, 1685, 1488, 1466, 1250, 1183, 825 cm$^{-1}$. Mass Spectrum: Calculated for C$_9$H$_{13}$NO: 151.0997. Found: 151.0993. Analysis: Calculated for C$_9$H$_{13}$NO: C, 71.49; H,8.67; N,9.26. Found: C, 71.10; H,9.17; N,9.20.

Part B:

4-t-Butyl-pyridine N-oxide (11.0 g, 72.9 mmole) is dissolved in 200 ml dichloromethane in a 500 ml one neck round bottom flask under nitrogen. The solution is treated with trimethyloxonium tetrafluoroborate (10.8 g, 72.9 mmole), is stirred 1h at room temperature, and the volatiles are removed in vacuo. The solid residue is dissolved in 200 ml methanol in a 500 ml one neck round bottom flask. The solution is heated to reflux, is treated with ammonium persulfate (3.3 g, 14.5 mmole) in 15 ml water, and the reaction mixture is vigorously refluxed for 30 min. The reaction is treated with a second lot of ammonium persulfate (1.65 g, 7.2 mmole) in 7 ml water and is refluxed for an additional 1 h. The reaction is cooled and the bulk of the methanol is removed in vacuo. The residue is diluted with 300 ml conc ammonium hydroxide and the mixture is extracted with 4×100 ml dichloromethane. The combined organics are dried over potassium carbonate and are concentrated in vacuo to a yellow oil. The crude material is chromatographed over 400 g silica gel (230–400 mesh), eluting with 40% acetone/hexane, while collecting 50 ml fractions. Fractions 26–52 are combined and concentrated to afford 8.79 g (73%) of 4-t-Butyl-2-hydroxymethyl-pyridine as a yellow oil.

$^1$H-NMR (CDCl$_3$, TMS): δ 1.31 (s, 9), 3.99 (bs, 1), 4.75 (s, 2), 7.18 (m, 1), 8.43 (m, 1) ppm. $^{13}$C-NMR (CDCl$_3$): δ 30.5; 34.7; 64.5; 117.6; 119.5; 148.3; 159.2; 161.0 ppm. TLC (silica gel-60, F-254): $R_f$=0.31, 40% acetone/hexane. Infrared (ν max, mineral oil): 3233, 2966, 1606, 1552, 1479, 1405, 1066 cm$^{-1}$. Mass Spectrum: Calculated for C$_{10}$H$_{15}$NO: 165.1154. Found: 165.1147.

Part C:

4-t-Butyl-2-hydroxymethyl-pyridine (4.13 g, 25 mmole) is dissolved in 75 ml dioxane in a 200 ml one neck round bottom flask under nitrogen. The solution is treated with selenium dioxide (1.53 g, 13.75 mmole) and the reaction is warmed to 80–85° C. for 1 h. The mixture is cooled, diluted with dichloromethane, and is filtered through celite. The filter cake is washed well with dichloromethane and the filtrate is concentrated to an amber oil. The crude oil is passed through a 50 g plug of silica gel (230–400 mesh), eluting with 20% acetone/hexane, while collecting 100 ml fractions. Fractions 1–3 are combined and concentrated to give 3.91 g (96%) of 4-t-Butyl-2-pyridine-carboxaldehyde as a light amber oil.

$^1$H-NMR (CDCl$_3$, TMS): δ 1.36 (s, 9), 7.53 (m, 1), 7.99 (m, 1), 8.70 (m, 1), 10.10 (s, 1) ppm. $^{13}$C-NMR (CDCl$_3$): δ 30.3; 35.0; 118.7; 124.9; 150.1; 152.7; 161.5; 193.8 ppm. TLC (silica gel-60, F-254): R$_f$=0.62, 40% acetone/hexane. Infrared (ν max, liquid): 2968, 1712, 1597, 1481, 1367, 1210, 822 cm$^{-1}$. Mass Spectrum, [M/Z](relative intensity): [324](71).

Part D:

Methylmagnesium bromide (9.7 ml, 29 mmole) is added to 20 ml dry tetrahydrofuran in an oven dried 100 ml two neck round bottom flask under nitrogen at 0° C. The solution is treated with 4-t-Butyl-2-pyridine-carboxaldehyde (3.8 g, 23.3 mmole) in 2×5 ml diethyl ether followed by 10 ml diethyl ether. The reaction is warmed to room temperature and then to reflux for 1 h. The mixture is cooled to 0° C., is quenched with 1×20 ml 10% hydrochloric acid, and the pH is adjusted to 9 with 2 N sodium hydroxide. The layers are separated, the aqueous layer is extracted with 4×25 ml dichloromethane, and the combined organics are dried over potassium carbonate. The dried organics are concentrated in vacuo to give 3.9 g (93%) of 4-t-Butyl-2-(1-hydroxyethyl)-pyridine as a tan solid. Analytical material is obtained via recrystallization from hexane.

$^1$H-NMR (CDCl$_3$, TMS): δ 1.31 (s, 9), 1.50 (d, J=6.5 Hz, 3), 4.10 (bs, 1), 4.87 (q, J=6.5, 13 Hz, 1), 7.18 (m, 1), 7.26 (m, 1), 8.41 (m, 1) ppm. $^{13}$C-NMR (CDCl$_3$): δ 24.3; 30.4; 34.7; 69.1; 116.4; 119.4; 147.8; 160.9; 162.9 ppm. TLC (silica gel-60, F-254): R$_f$=0.37, 40% acetone/hexane. Melting Point: 85–86° C. Infrared (ν max, mineral oil): 3158, 2925, 1608, 1551, 1409, 1341, 1093, 1069 cm$^{-1}$. Mass Spectrum, [M/Z](relative intensity): [179](10), [164](100). Analysis: Calculated for C$_{11}$H$_{17}$NO: C, 73.70; H,9.56; N,7.82. Found: C, 73.79; H,9.91; N,7.74.

Part E:

4-t-Butyl-2-(1-hydroxyethyl)-pyridine (3.6 g, 20.1 mmole) is dissolved in 60 ml dichloromethane in a 200 ml one neck round bottom flask under nitrogen. The solution is cooled to 0° C., is treated with thionyl chloride (2.2 ml, 30 mmole) in 10 ml dichloromethane, and the reaction is stirred 1 h at 0° C. followed by 2 h at room temperature. The reaction is quenched with 1×75 ml saturated sodium bicarbonate, the layers are separated and the aqueous layer is extracted with 3×25 ml dichloromethane. The combined organics are dried over potassium carbonate and are concentrated in vacuo to give 3.9 g (98%) of 4-t-Butyl-2-(1-chloroethyl)-pyridine as a yellow oil.

$^1$H-NMR (CDCl$_3$, TMS): δ 1.33 (s, 9), 1.89 (d, J=6.5 Hz, 3), 5.14 (q, J=6.5, 13 Hz, 1), 7.21 (m, 1), 7.44 (m, 1), 8.47 (m, 1) ppm. $^{13}$C-NMR (CDCl$_3$): δ 24.7; 30.2; 34.6; 59.0; 117.8; 119.9; 148.7; 160.2; 161.0 ppm. TLC (silica gel-60, F-254): R$_f$=0.61, 40% acetone/hexane. Mass Spectrum: Calculated for C$_{11}$H$_{16}$ClN—CH$_3$: 182.0747. Found: 182.0736.

Part F:

4-Amino-6-chloro-2-thio-pyrimidine mesylate salt (1.29 g, 5 mmole) is dissolved in 8 ml of dry dimethylformamide in a 50 ml one neck round bottom flask under nitrogen. The solution is treated with 60% sodium hydride (400 mg, 10 mmole) (exotherm) and the mixture is stirred 1 h. 1-(1-Chloroethyl)-5,6,7,8-tetrahydroisoquinoline (978 mg, 5 mmole) in 2×2 ml dry dimethylformamide, is added to the reaction and the mixture is stirred overnight at room temperature. The reaction mixture is poured into 100 ml 50% saturated sodium chloride and is extracted with 4×25 ml ethyl acetate. The combined organics are backwashed with 4×50 ml 50% saturated sodium chloride. The organics are dried over potassium carbonate and were concentrated in vacuo to a yellow oil. The crude material is chromatographed over 120 g silica gel (230–400 mesh), eluting with 25% acetone/hexane while collecting 22 ml fractions. Fractions 16–27 were combined and concentrated to afford a white foam. Crystallization from diethyl ether provided 888 mg (55%) of 1-amino-4-chloro-2-(1-(4-(1,1-dimethyl)ethyl-2-pyridyl)ethyl)thio-pyrimidine as a white solid.

$^1$H-NMR (CDCl$_3$, TMS): δ 1.30 (s, 9), 1.76 (d, J=6.5 Hz, 3), 5.10 (q, J=6.5, 13 Hz, 1), 5.53 (bs, 1), 6.10 (s, 1), 7.14 (m, 1), 7.45 (m, 1), 8.46 (m, 1) ppm. $^{13}$C-NMR (CDCl$_3$): δ 21.0; 30.4; 34.7; 45.5; 99.1; 119.2; 119.5; 148.9; 159.2; 160.7; 161.4; 163.3; 171.4 ppm. TLC (silica gel-60, F-254): R$_f$=0.49, 40% acetone/hexane. Melting Point: 153–154° C.,d. Ultraviolet (k max, Ethanol), nm(E): 230(22,700); 255(12,200); 268(8,790); 286(7,000). Infrared (ν max, mineral oil): 3177, 3140, 2925, 1642, 1565, 1527, 1368, 1280, 825 cm$^{-1}$. Mass Spectrum, [M/Z](relative intensity): [322] (8), [289](100). Analysis: Calculated for C$_{15}$H$_{19}$ClN$_4$S: C, 55.80; H,5.93; N,17.35. Found: C, 55.74; H,5.90; N,17.16.

Example 211

4-Amino-6-chloro-2-(1-(2-pyridyl)ethyl)thio-pyrimidine (Cpd #211)

Part A:

To a suspension of 4,6-dihydroxy-2-(2-pyridylmethyl)thio-pyrimidine (7.0 g, 0.0298 mol) in 105 ml of dimethylformamide at room temperature is added imidazole (5.06 g, 0.0744 mol, 2.5 equiv.) followed by t-butyl dimethylsilyl chloride (9.48 g, 0.0626 mol, 2.10 equiv.). The reaction mixture is stirred for 2.5 h, poured into 350 ml of water and extracted twice with ether. The combined organic extracts are dried with anhydrous Na$_2$SO$_4$ and concentrated at reduced pressure. The crude product is dissolved in an ethyl acetate-methylene chloride-methanol mixture, treated with 37 g of silica gel and concentrated to a free flowing powder. This is applied to the top of a column of silica gel (350 g), packed and eluted with ethyl acetate-hexane (1:10), to obtain 7.81 g (56%) of 4,6-di-(tert-butyldimethylsilyloxy)-2-(2-pyridylmethyl)thio-pyrimidine.

TLC (silica gel GF): R$_f$=0.38 ethyl acetate-hexane (1:9). $^1$H NMR (CDCl$_3$,TMS): δ 8.55 (d, 1 H, J=5.01 Hz), 7.64 (dt, 1 H, J=1.8, 7.72 Hz), 7.47 (d, 1 H, J=7.86 Hz), 7.20 (t, 1 H, J=16.72 Hz), 5.70 (s, 1 H), 4.52 (s, 2 H), 0.930 (s, 18 H), 0.265 (s, 12 H) ppm.

Part B:

A solution of n-butyllithium (11.02 ml, 17.63 mmol, 1.2 equiv., 1.6 M in hexanes) in 60 ml of tetrahydrofuran cooled at −78° C. is treated dropwise with diisopropylamine (1.93 g, 19.10 mmol, 1.3 equiv.) over a two minute period. After stirring for another 10 min, a solution of 4,6-di-(tert-butyldimethylsilyloxy)-2-(2-pyridylmethyl)thio-pyrimidine (6.80 g, 14.69 mmol) in 16 ml of tetrahydrofuran is added dropwise over a 10 min period. The reaction mixture is stirred for 30 min longer and treated dropwise with methyl iodide (2.29 g, 16.16 mmol, 1.1 equiv.) in 6 ml of tetrahydrofuran over a 3 min period. Stirring is facilitated by adding an additional 30 ml of tetrahydrofuran. One hour after the addition of the methyl iodide, the cooling bath is removed and the mixture allowed to warm to room temperature. The contents are then cast into ice water and extracted once with ethyl acetate. The organic layer washed with saturated brine, dried with anhydrous $Na_2SO_4$ and concentrated at reduced pressure. A methylene chloride solution of the crude product was treated with silica gel (36 g), concentrated to a free flowing powder and applied to the top of a 350 g silica gel column, packed and eluted with ethyl acetate-hexane (5:95), to obtain 2.23 g (32%) 4,6-di-(tert-butyldimethylsilyloxy)-2-(1-(2-pyridyl)ethyl)thio-pyrimidine.

TLC (silica gel GF): $R_f$=0.50 ethyl acetate-hexane (1:9). $^1$H NMR ($CDCl_3$,TMS): δ 8.49 (d, 1 H, J=4.80 Hz), 7.54 (dt, 1 H, J=1.81, 7.68 Hz), 7.31 (d, 1 H, J=7.84 Hz), 7.06 (t, 1 H, J=4.93 Hz), 5.59 (s, 1 H), J=5.0 (q, 1 H, J=7.04 Hz), 1.71 (d, 3 H, J=7.02 Hz), 0.90–0.82 (m, 18 H), 0.28–0.17 (m, 12 H) ppm. Mass Spectrum: M/Z (relative intensity %): 477 (5), 462 (6), 444 (79), 420 (100), 315 (34), 257 (16).

Part C:

A solution of 4,6-di-(tert-butyldimethylsilyloxy)-2-(1-(2-pyridyl)ethyl)thio-pyrimidine (1.23 g, 2.58 mmol) in 8 ml of tetrahydrofuran is treated with 2 N HCl (5.2 ml, 10.31 mmol, 4.0 equiv.) at room temperature. After 30 min, the reaction mixture is concentrated directly at reduced pressure, diluted with toluene and reconcentrated again. The resulting white solid is triturated with methylene chloride, collected and dried to obtain 0.819 g of crude 4,6-dihydroxy-2-(1-(2-pyridyl)ethyl)thio-pyrimidine hydrochloride.

TLC (silica gel GF): $R_f$=0.32 chloroform:methanol (4:1). $^1$H NMR ($d_6$-DMSO, TMS): δ 8.55 (brs, 1 H), 7.80 (m, 1 H), 7.53 (d, 1 H, J=7.72 Hz), 7.31 (m, 1 H), 5.15 (q, 1 H, J=7.04 Hz), 4.35 (s, 1 H), 3.72–3.26 (brs, 1 H), 166 (d, 3 H, J=6.95 Hz) ppm.

Part D:

The crude diol hydrochloride (0.735g, 2.58 mmol) is treated with 2-picoline (0.446 g, 4.80 mmol, 1.86 equiv.) followed by phosphorous oxychloride (4.39 g, 28.7 mmol, 11.1 equiv.). The contents are stirred at 90° C. in an oil bath for 2.25 h, and at ambient temperature for another 1.75 h. The reaction mixture is quenched with crushed ice followed by a saturated solution of $NaHCO_3$ until basic, then extracted twice with ethyl acetate. The combined organic extracts are dried with $Na_2SO_4$ and concentrated at reduced pressure. Chromatography is accomplished using 125 g of silica gel packed and eluted with ethyl acetate-hexane (1:6) to afford 0.569 mg (73%) of 4,6-dichloro-2-(1-(2-pyridyl)ethyl)thio-pyrimidine.

TLC (silica gel GF): $R_f$=0.50 ethyl acetate-hexane (1:4). $^1$H NMR ($CDCl_3$,TMS): δ 8.56 (d, 1 H, J=3.11 Hz), 7.61 (t, 1 H, J=7.60 Hz), 7.41 (d, 1 H, J=7.86 Hz), 7.14 (m, 1 H), 6.96 (s, 1 H), 5.08 (q, 1 H, J=7.12 Hz), 1.76 (d, 3 H, J=7.07 Hz) ppm. Mass Spectrum: M/Z (relative intensity %): HRMS calculated: 284.9894. Found: 284.9905.

Part E:

A flask is charged with 4,6-dichloro-2-(1-(2-pyridyl)ethyl)thio-pyrimidine (0.560 g, 1.96 mmol), acetonitrile (6.5 ml) and 13 ml of 29 % $NH_4OH$. The contents are stirred at 35° C. for 15 h, poured into 50 ml of water, extracted once with ethyl acetate. The organic layer is washed with a saturated solution of brine (1×30 ml), dried with anhydrous $Na_2SO_4$ and concentrated in vacuo. Chromatography is accomplished with 100 g of silica gel, packed and eluted with ethyl acetate-hexane (2:3), to yield 0.491 g (94%) of 4-amino-6-chloro-2-(1-(2-pyridyl)ethyl)thio-pyrimidine.

TLC (silica gel GF): $R_f$=0.23 ethyl acetate-hexane (1:1). Melting Point: 125–126 ° C. $^1$H NMR ($CDCl_3$,TMS): δ 8.56 (m, 1 H), 7.64 (t, 1 H, J=7.71 Hz), 7.46 (d, 1 H, J=7.82 Hz), 7.17 (m, 1 H), 6.09 (s, 1 H), 5.48 (brs, 2 H), 5.12 (q, 1 H, J=7.16), 1.74 (d, 3 H, J=7.16 Hz) ppm. UV (λ max, ethanol): 230 (22,000), 255 (12,500), 269sh (8580), 287 (6920). Infrared (ν max, mineral oil): $cm^{-1}$. 1572, 1531, 2925, 1275, 2954, 1594, 1117, 1293, 3089, 2855, 1665, 1359, 1372, 833, 3133, 1467, 2868, 1436, 1477, 1255, 988, 3269, 3011, 1454, 1443. Mass Spectrum: M/Z (relative intensity %): 266 (6), 233 (100), 171 (6), 138 (26), 126 (12), 106 (98), 78 (61). Analysis: Calculated for $C_{11}H_{11}ClN_4S$: C, 49.62; H, 4.13; N, 21.05. Found: C, 49.46; H, 4.18; N, 20.45.

Example 212

4-Amino-6-chloro-2-(1-(2-pyridyl)-1-methylethyl)thio-pyrimidine (Cpd #212)

Following the procedure for the preparation of 4-amino-6-chloro-2-(1-(2-pyridyl)ethyl)thio-pyrimidine but employing an additional alkylation of 4,6-di-(tert-butyldimethylsilyloxy)-2-(1-(2-pyridyl)ethyl)thio-pyrimidine with methyl iodide, this compound is prepared. Melting Pt. 183–184.5° C.

Example 213

4-Amino-6-chloro-2-(1-(2-(4-methyl)pyridyl)-1-methylethyl)thio-pyridine (Cpd #213)

Following the procedure for the preparation of 4-amino-6-chloro-2-(1-(2-pyridyl)-1-methylethyl)thio-pyrimidine and starting with 4,6-dihydroxy-2-(2-(4-methyl)-pyridylmethyl)thio-pyrimidine, this compound is prepared. Melting Pt. 149–151° C.

Example 214

4-Amino-6-chloro-2-(1-(4-cyano-2-pyridyl)ethyl)thio-pyrimidine (Cpd #214)

Part A:

A solution of 4-cyanopyridine (5.20 g, 50.0 mmol) in 90 ml of methanol is treated with a mixture of $H_2SO_4$ (6.42 g, 65.5 mmol, 1.31 equiv.) and water (45 ml) at once followed by the addition of $(NH_4)_2S_2O_8$ (22.8 g, 100 mmol, 2.0 equiv.). The contents were heated to reflux at which point vigorous refluxing ensued for several minutes. After refluxing for 24 h, the reaction mixture is partially concentrated to remove most of the methanol, treated with ice-water mixture and basified with ammonium hydroxide (20 ml, 29% aq). The residue is extracted four times with chloroform, the combined extracts are dried with anhyrous $Na_2SO_4$ and concentrated at reduced pressure. Chromatography is accomplished using 300 g of silica gel packed and eluted with acetone-methylene chloride (1:6) to provide 2.65 g (39.5%) of 4-Cyano-2-hydroxymethylpyridine.

TLC (silica gel GF): $R_f$=0.30 acetone-methylene chloride (1:4). $^1$H NMR ($CDCl_3$,TMS):δ 8.78 (d, 1H,J=5.07 Hz), 7.66 (s, 1H), 7.49 (d, 1H, J=5.12 Hz), 4.88 (d, 2H, J=4.96 Hz), 3.64 (t, 1H, J=5.21 Hz). UV (λ max, ethanol): 216 sh (7,710), 220 sh (6,590), 280 (3,510), 287 sh (3,020). Analysis: Calculated for $C_7H_6N_2O$: C, 62.69; H, 4.48; N, 20.89. Found: C, 62.66; H, 4.46; N, 21.00. Mass Spectrum: M/Z (relative intensity %): 134 (73), 133 (100), 105 (79), 104 (39), 77 (38), 50 (30).

Part B:

A flask is charged with 4-cyano-2-hydroxymethylpyridine (2.60 g, 19.40 mmol) and selenium dioxide (1.19 g, 10.75 mmol, 0.554 molar equiv.) in 40 ml of p-dioxane and the mixture heated in an oil bath at 80–85° for 3.5 h. The contents were diluted with 150 ml of methylene chloride, treated with celite and after stirring at ambient temperature for ca. 15 min, is filtered through a pad of celite. The filtrate, upon concentration in vacuo, gave 2.77 g of yellow solid which is chromatographed with 125 g of silica gel packed and eluted with acetone-methylene chloride-hexane (0.5: 1.5: 8) to yield 2.32 g (90%) of 4-cyano-2-pyridinecarboxaldehyde as a white solid.

TLC (silica gel GF): $R_f$=0.17 acetone-methylene chloride-hexane (0.5:1.5:8). $^1$H NMR ($CDCl_3$,TMS):δ 9.93 (s, 1H), 8.82 (d, 1H, J=4.28 Hz), 8.00 (s, 1H) 7.60 (d of d, 1H, J=4.84, 1.48 Hz). Melting Point: 95–97° C. UV (λ max, ethanol): 219 sh (7,130), 276 (3,460), 283 sh (2,990). Analysis: Calculated for $C_7H_4N_2O$: C, 63.64; H, 3.03; N, 21.21. Found: C, 63.42; H, 2.95; N, 21.26. Mass Spectrum: M/Z (relative intensity %): (FAB) [M+H]$^+$ 133 (100), 104 (22), 77 (67).

Part C:

To a flask charged with 70 ml of ether and 40 ml of tetrahydrofuran cooled in an ice bath at 0–5° is added methylmagnesium bromide (8.71 ml, 26.14 mmol, 1.50 equiv.) at once. To this is added a solution of 4-cyano-2-pyridinecarboxaldehyde (2.30 g, 17.42 mmol), dissolved in 60 ml of ether and 5 ml of tetrahydrofuran, dropwise over a 20 min period. The resulting tan slurry is refluxed for 1.5 h, cooled and poured into ice water containing 55 ml of 3N HCl and stirred at ambient temperature for 5 min. The contents are basified with 23 ml of 29% ammonium hydroxide and extracted 5 times with chloroform. The combined organic extracts are dried over $Na_2SO_4$ and concentrated at reduced pressure. Chromatography with 160 g of silica gel, packed and eluted with acetone-methylene chloride (1:6), afforded 1.60 g (62%) of 4-cyano-2-(2-hydroxy)-ethylpyridine.

TLC (silica gel GF): $R_f$=0.27 acetone-methylene chloride (1:6). $^1$H NMR ($CDCl_3$,TMS):δ 8.46 (d, 1H, J=4.33 Hz), 7.41 (s, 1H), 7.20 (dd, 1H, J=4.87, 0.82 Hz), 4.72 (q, 1H, J=6.08 Hz), 3.75 (s, 1H), 1.28 (d, 3H, J=6.55 UV (λ max, ethanol): 216 sh (7,760), 220 sh (6,530), 278 (3,560), 287 sh (2,960). Analysis: Calculated for $C_8H_8N_2O$: C, 64.86; H, 5.41; N, 18.92. Found: C, 64.77; H, 5.51; N, 18.90. Mass Spectrum: M/Z (relative intensity %): (FAB) [M+H]$^+$ 149 (100), 131 (30), 105 (8).

Part D:

To a solution of 4-cyano-2-(2-hydroxy)ethylpyridine (1.44 g, 9.73 mmol) in 55 ml of methylene chloride at room temperature is added methanesulfonyl chloride (1.16 g, 10.22 mmol, 1.05 equiv.) followed by triethylamine (1.08 g, 10.70 mmol, 1.1 equiv.). After stirring for 1 h, the contents were concentrated directly at reduced pressure and the resulting solid, 4-cyano-2-(2-methanesulfonyl)ethylpyridine is used directly in the subsequent coupling reaction.

TLC (silica gel GF): $R_f$ 0.69 acetone-methylene chloride (1:6).

Part E:

To a stirred suspension of NaH (0.817 g, 20.43 mmol, 2.1 equiv., 60% oil dispersion) in 35 ml of dimethylformamide at room temperature is added the 4-Amino-6-chloro-2-thio-pyrimidine mesylate salt (2.50 g, 9.73 mmol) at once as a solid. After 50 min, a slurry of 4-cyano-2-(2-methanesulfonyl)ethylpyridine (2.20 g, 9.73 mmol, 1.0 equiv.) in 15 ml of dimethylformamide is added at once with 2×5 ml rinses with same solvent. After 24 h, the reaction mixture is cast into 200 ml of ice water plus 50 ml of saturated brine, extracted twice with ethylacetate, and the combined organic extracts dried with anhydrous $Na_2SO_4$. The filtrate is concentrated in vacuo, chromatographed with 200 g of silica gel packed and eluted with acetone-methylene (1:9) to afford 2.32 g of product as a golden oil contaminated with dimethylformamide. Rechromatography using 150 g of silica gel packed and eluted with ethylacetate-hexane (2:3) yielded 1.75 g (62%) of Cpd #214 as a colorless oil. Crystallization is accomplished using ethylacetate-ether-hexane solvent mixture.

TLC (silica gel GF): $R_f$=0.50 acetone-methylene chloride (1:4). $^1$H NMR ($CDCl_3$,TMS):δ 8.61 (d, 1H, J=5.04 Hz), 7.63 (s, 1H), 7.23 (d, 1H, J=5.03 Hz), 6.00 (s, 1H), 4.97 (m, 3H), 1.61 (d, 3H, J=7.30 Hz). Melting Point: 119–120° C. UV (λ max, ethanol): 214 sh (19,100), 222 (23,600), 228 sh (22,300), 249 sh (11,700), 286 (9,860). Infrared (υ max, mineral oil): 1572, 1646, 2927, 1531, 2954, 1366, 1278, 2855, 1546, 1119, 2869, 1469, 3188, 3314, 834, 1457, 825, 1596, 3144, 3216, 1444, 855, 2979, 988, 3378 cm$^{-1}$. Analysis: Calculated for $C_{12}H_{10}ClN_5S$: C, 49.48; H, 3.44; N, 24.05. Found: C, 49.31; H, 3.69; N, 23.89. Mass Spectrum: M/Z (relative intensity %): 291 (3), 293 (1), 258 (100), 196 (5), 162 (17), 131 (33), 103 (18), 67 (22).

Example 215

4-Amino-6-chloro-2-(1-(4-methyl-2-pyridyl)ethyl) thio-pyrimidine hydrochloride (Cpd #215)

A solution of 4-picoline-N-oxide (3.0 g, 27.52 mmol) in 90 ml of methylene chloride at room temperature is reacted with trimethyloxonium tetrafluoroborate (4.07 g, 27.52 mmol, 1.0 equiv.) for 1.5 h. The reaction mixture is concentrated directly at reduced pressure, the white solid dissolved in 60 ml of refluxing methanol and treated with ammonium persulfate (1.25 g, 5.50 mmol, 0.20 equiv.) in 5.5 ml of water with another addition of ammonium persulfate (0.625 g, 0.10 equiv.) in 2.5 ml of water 30 min later. After refluxing for an additional 40 min, the contents are concentrated at reduced pressure, treated with 75 ml of saturated brine plus 75 ml of water and finally 50 ml of 3N HCl. After stirring at room temperature for 1 h, the mixture is basified with 20 ml of 29% ammonium hydroxide, extracted 4 times with chloroform, dried the combined organic extracts with anhydrous $Na_2SO_4$ and concentrated in vacuo. Chromatography with 250 g of silica gel, packed and eluted with acetone-chloroform-methanol (1:2:2%), yielded 2.65 g (78%) of 2-hydroxymethyl-4-methylpyridine.

TLC (silica gel GF): $R_f$=0.32 acetone-chloroform-methanol (1:2:2%). $^1$H NMR ($CDCl_3$,TMS):δ 8.38 (d, 1H, J=5.05 Hz), 7.18 (s, 1H), 7.03 (d, 1H, J=4.86 Hz), 5.02 (s, 1H), 4.75 (s, 2H), 2.37 (s, 3H). UV (λ max, ethanol): 254 sh (2,240), 259 (2,690), 266 (2,180). Analysis: Calculated for $C_7H_9NO$: C, 68.29; H, 7.32; N, 11.38. Found: C, 67.35; H, 7.37; N, 11.22. Mass Spectrum: M/Z (relative intensity %): 123 (48), 122 (100), 94 (43), 93 (30), 92 (27), 39 (17).

In a manner similar to that described for the preparation of 4-cyano- 2-pyridinecarboxaldehyde, 2-hydroxymethyl-4-methylpyridine (2.60 g, 21.14 mmol) provided 2.0 g (78%) of the 4-methyl-2-pyridinecarboxaldehyde.

TLC (silica gel GF): $R_f$=0.23 acetone-methylene-hexane (0.5:1.5:8.0). $^1$H NMR ($CDCl_3$,TMS):δ 10.09 (s, 1H), 8.67 (d, 1H, J=4.93 Hz), 7.81 (s, 1H):δ 7.38 (d, 1H, J=3.78 Hz), 2.48 (s, 3H).

In a manner similar to that described for the preparation of 4-cyano-2-(2-hydroxy)ethylpyridine, 4-methyl-2-pyridinecarboxaldehyde (2.0 g, 16.53 mmol) and methylmagnesium bromide (8.30 ml, 24.8 mmol, 3 M in ether) gave 1.95 g (86%) of 2-(1-hydroxy)ethyl-4-methylpyridine.

TLC (silica gel GF): $R_f$=0.30 acetone-methylene chloride (1:2). $^1$H NMR ($CDCl_3$,TMS):δ 8.27 (d, 1H, J=5.03 Hz), 6.99 (s, 1H), 6.90 (d, 1H, J=4.83 Hz), 4.74 (q, 1H, J=6.52 Hz), 4.28 (brs, 1H), 2.26 (s, 3H), 1.38 (d, 3H, J=6.58 Hz). Melting Point: 76–78° C. UV (λ max, ethanol): 253 sh (2,320), 259 (2,810), 265 (2,270). Analysis: Calculated for $C_8H_{11}NO$: C, 70.07; H, 8.03; N, 10.22. Found: C, 70.04; H, 8.14; N, 10.08. Mass Spectrum: M/Z (relative intensity %): 137 (7), 136 (14), 122 (100), 120 (46), 93 (38).

2-(2-hydroxy)ethyl-4-methylpyridine (0.796 g 5.81 mmol), methanesulfonyl chloride (0.695 g, 6.10 mmol, 1.05 equiv.) and triethylamine (0.649 g, 6.39 mmol, 1.1 equiv.) provided 2-(2-methanesulfonyl)ethyl-4-methylpyridine upon concentration at reduced pressure which is used directly in the subsequent alkylation.

TLC (silica gel GF): $R_f$=0.70 acetone-methylene chloride (1:2).

In a manner similar to the procedure described for the preparation of Cpd # 214, 4-amino-6-chloro-2-thio-pyrimidine mesylate salt (1.49 g, 5.81 mmol) is reacted with 2-(2-methanesulfonyl)ethyl-4-methylpyridine (1.25 g, 5.81 mmol, 1.0 equiv.) and NaH (0.488 g, 12.20 mmol, 2.1 equiv., 60% oil dispersion) to yield 0.869 g (53%) of 4-Amino-6-chloro-2-(1-(4-methyl-2-pyridyl)ethyl)thio-pyrimidine as a colorless oil. Preparation of the HCl salt is carried out by adding acetyl chloride (0.281 g, 2.93 mmol, 1.0 equiv.) dropwise to 5 ml of methanol cooled in an ice bath. After stirring for 25 min at ambient temperature the solution is diluted with 100 ml of ether and added dropwise to 4-Amino-6-chloro-2-(1-(4-methyl-2-pyridyl)ethyl)thio-pyrimidine (0.820 g, 2.93 mmol, 1.0 equiv.) in 100 ml of ether over a 20 min period. After stirring the suspension for 4 h, 100 ml of hexane is added, the stirring is continued for another 2 h, the white solid collected and dried in vacuum oven to give 0.845 g (91%) of Cpd #215. Residual ether is removed by dissolution/reprecipitation from a methylene chloride-hexane solvent mixture followed by drying @90° C. in a vacuum oven overnight.

Free base: TLC (silica gel GF): $R_f$=0.26 acetone-methylene chloride (1:4). HCl salt: $^1$H NMR (CDCl,TMS):δ 8.49 (d, 1H, J=5.96 Hz), 7.75 (s, 1H), 7.50 (d, 1H, J=5.57 Hz), 6.12 (s, 1H), 5.23 (q, 1H, J=7.42 Hz), 2.56 (s, 3H), 1.6 7.46 Hz). Melting Point: 149–151° C. UV (λ max, ethanol): 229 (22,000), 254 (12,200), 267 sh (8,570), 287 (6,820).

Infrared (υ max, mineral oil): 2925, 1567, 2954, 2854, 1633, 1528, 2869, 1374, 828, 1466, 3163, 3296, 1283, 1254, 3203, 1116, 3093, 3057, 2692, 985, 2538, 657, 1070, 1330, 960 $cm^{-1}$. Analysis: Calculated for $C_{12}H_{14}Cl_2N_4S$: C, 45.43; H, 4.42; N, 17.67. Found: C, 45.79; H, 4.87; N, 17.28. Mass Spectrum: MJZ (relative intensity %): 280 (8), 247 (100), 211 (2), 185 (5), 152 (33), 120 (93), 92 (36).

Example 216

4-Amino-6-chloro-2-(1-(4-ethyl-2-pyridyl)ethyl) thio-pyrimidine (Cpd #216)

A solution of 4-ethylpyridine (10.7 g, 0.10 mol) in 35 ml of acetic acid heated at 95–100° C. is treated dropwise over a 18 min period with 30% hydrogen peroxide (28 ml). After 4 h, the excess hydrogen peroxide is decomposed by the portionwise addition of paraformaldehyde (10.0 g) at the previously maintained temperature until a negative starch iodide test is obtained. The reaction mixture is cooled and concentrated at reduced pressure. The residue is chromatographed with 325 g of silica gel packed and eluted initially with acetone-chloroform-methanol (3:6.7:0.3) and thereafter with an increasing methanol gradient to obtain 10.55 g (83%) of 4-Ethylpyridine-1-oxide.

TLC (silica gel GF): $R_f$=0.20 acetone-chloroform-methanol (3:6.5:0.5) $^1$H NMR ($CDCl_3$,TMS):δ 7.94 (d, 2H, J=7.00 Hz), 6.93 (d, 2H, J=6.99 Hz), 2.44 (q, 2H, J=7.61 Hz), 1.06 (t, 3H, J=7.53 Hz).

In a procedure similar to that described for the preparation of 4-hydroxymethyl-4-methylpyridine, 4-ethylpyridine-1-oxide (3.5 g, 27.56 mmol) led to 1.64 g (43%) of 4-ethyl-2-hydroxymethylpyridine.

TLC (silica gel GF): $R_f$=0.09 acetone-methylene chloride (1:2). $^1$H NMR ($CDCl_3$,TMS):δ 8.50 (d, 1H, J=5.11 Hz), 7.32 (s, 1H), 7.15 (d, 1H, J=4.88 Hz), 5.30 (brs, 1H), 4.87 (s, 2H), 2.77 (q, 2H, J=7.60 Hz), 1.37 (t, 3H, J=7.63 Hz). UV (λ max, ethanol): 254 sh (2,260), 259 (2,710), 264 (2220). Infrared (υ max, mineral oil): 1610, 2969, 3221, 1055, 2935, 1067, 1561, 2877, 839, 1459, 1417, 3059, 2841, 1005, 3020, 1116, 994, 1364, 1481, 746, 2735, 890, 1327, 1264, 902 $cm^{-1}$. Mass Spectrum: M/Z (relative intensity %): (FAB) 138 (100), 120 (28), 106 (4).

In a manner similar to that described for the preparation of 4-methyl-2-pyridine-carboxaldehyde, 4-ethyl-2-hydroxymethylpyridine (1.60 g, 11.68 mmol) yielded 1.33 g (84%) of 4-ethyl-2-pyridinecarboxaldehyde.

TLC (silica gel GF): $R_f$=0.23 acetone-methylene chloride-hexane (0.5:1.5:8). $^1$H NMR ($CDCl_3$,TMS):δ 8.74 (d, 1H, J=4.95 Hz), 7.89 (s, 1H), 7.44 (d, 1H, J=5.08 Hz), 2.82 (q, 2H, J=7.58 Hz), 1.37 (t, 3H, J=7.65 Hz).

In a manner analagous to that described for the synthesis of 4-cyano-2-(2-hydroxy) ethylpyridine, 4-ethyl-2-pyridinecarboxaldehyde (1.33 g, 9.85 mmol) and methylmagnesium bromide (4.93 ml, 14.78 mmol, 3 M in ether) provided 1.29 g (86%) of 4-ethyl-2-(2-hydroxy) ethylpyridine as a colorless oil.

TLC (silica gel GF): $R_f$=0.37 acetone-methylene chloride (1:2). $^1$H NMR (CDCl$_3$,TMS):δ 8.19 (d, 1H, J=5.08 Hz), 6.91 (s, 1H), 6.83 (d, 1H, J=5.11 Hz), 4.65 (q, 1H, J=6.51 Hz), 4.24 (brs, 1H), 2.45 (q, 2H, J=7.64 Hz), 129 (d, 3H, J=5.11 Hz), 4.65 (q, 1H, J=6.51 Hz), 4.24 (brs, 1H), 2.45 (q, 2H, J=7.64 Hz), 1.29 (d, 3H, J=6.57 Hz), 1.06 (t, 3H, J=7.66).

Mesylation of 4-ethyl-2-(2-hydroxy)ethylpyridine (1.29 g, 8.54 mmol) with methanesulfonyl chloride (1.02 g, 8.97 mmol, 1.05 equiv.) and triethylamine (0.949 g, 9.39 mmol, 1.1 equiv.) gave 4-ethyl-2-(2-methanesulfonyl)ethylpyridine upon concentration of reaction mixture in vacuo which is subsequently used in the alkylation reaction.

TLC (silica gel GF): $R_f$=0.73 acetone-methylene chloride (1:2).

In a manner analagous to that described for the preparation of Cpd #214, 4-amino-6-chloro-2-thio-pyrimidine mesylate salt (2.19 g, 8.54 mmol), NaH (0.717 g, 17.93 mmol, 2.1 equiv. 60% oil dispersion) and 4-ethyl-2-(2-methanesulfonyl)ethylpyridine (1.95 g, 8.54 mmol, 1.0 equiv.) yielded 1.27 g (51%) of Cpd #216.

TLC (silica gel GF): $R_f$=0.22 ethyl acetate-hexane (1:1). $^1$H NMR (CDCl$_3$,TMS):δ 8.29 (d, 1H, J=5.06 Hz), 7.15 (s, 1H), 6.84 (d, 1H, J=5.06 Hz), 5.95 (s, 1H), 5.04 (brs, 2H), 4.94 (q, 1H, J=7.11 Hz), 2.48 (q, 2H, J=7.60 Hz), 1.61 (d, 3H, J=7.13 Hz), 1.09 (s, 3H, J=7.59 Hz). Melting Point: 113–115° C. UV (λ max, ethanol): 230 (22,500), 254 (12,400), 267 sh (8,620), 286 (6,940). Infrared (λ max, mineral oil): 1574, 2926, 1281, 1663, 2954, 1529, 1359, 2855, 1363, 1114, 1560, 3147, 2870, 1608, 1467, 818, 3293, 1257, 988, 823, 836, 1484, 3051, 1209, 1059 cm$^{-1}$. Analysis: Calculated for $C_{13}H_{15}ClN_4S$: C, 53.06; H, 5.10; N, 19.05. Found: C, 52.61; H, 5.17; N, 18.84. Mass Spectrum: M/Z (relative intensity %): 294 (6), 261 (87), 166 (40), 134 (100), 119 (67).

Example 217

4-Amino-6-chloro-2-(1-(4-methyl-2-pyridyl)-1-cyanomethyl)thio-pyrimidine (Cpd #217)

To 4-methyl-2-pyridinecarboxaldehyde (2.10 g, 17.35 mmol) cooled at −10° C., is added 2N HCl until pH 3.5 is reached. Then a saturated aqueous solution of KCN cooled at −10° C., is added dropwise until pH 7 is reached. The precipitate is collected after 10 min, washed three times with water and dried to obtain 1.88 g (73%) of 2-(α-Cyano-4-methyl)pyridyl carbinol.

TLC (silica gel GF): $R_f$=0.17 ethyl acetate-hexane (1:2). $^1$H NMR (CDCl$_3$,TMS):δ 8.47 (d, 1H, J=5.09 Hz), 7.38 (s, 1H), 7.22 (d, 1H, J=5.09 Hz), 6.31–5.65 (brs, 1H), 5.58 (s, 1H), 2.45 (s, 3H). Melting Point: 99–102° C. UV (λ max, ethanol): 243 (3,230), 256 (2,620), 264 (2,260), 275 sh (939), 374 (369). Infrared (υ max, mineral oil) 2924, 1056, 1613, 2854, 2954, 2867, 1013, 839, 3055, 2727, 3026, 1466, 963, 783, 1378, 1284, 1481, 1324, 1302, 604, 1169, 2626, 824, 669, 1411 cm$^{-1}$. Mass Spectrum: M/Z (relative intensity %): 148 (15), 119 (5), 93 (100), 65 (52), 51 (14), 38 (58). The mesylation of the 2-(α-cyano-4-methyl)pyridyl carbinol (1.00 g, 6.76 mmol) with methanesulfonyl chloride (0.892 g, 7.83 mmol, 1.16 equiv.) and triethylamine (0.819 g, 8.11 mmol, 1.2 equiv.) gave 2-(1-cyano-1-methanesulfonyloxy) methyl-4-methylpyridine as a dark red solid upon concentration of the reaction mixture at reduced pressure.

TLC (silica gel GF): $R_f$ 0.76 acetone-methylene chloride (1:6).

In a manner to that described for the synthesis of Compound #214, 4-amino-6-chloro-2-thio-pyrimidine mesylate salt (Cpd #110A; 1.74 g, 6.76 mmol), NaH (0.568 g, 14.20 mmol, 2.1 equiv., 60% oil dispersion) and 2-(1-cyano-1-methanesulfonyloxymethyl)-4-methylpyridine (1.53 g, 6.76 mmol, 1.0 equiv.) provided 0.927 g (47%) of 4-Amino-6-chloro-2-(1-(4-methyl-2-pyridyl)-1-cyanomethyl)thio-pyrimidine.

TLC (silica gel GF): $R_f$=0.33 acetone-methylene chloride (1:9). $^1$H NMR (CDCl$_3$,TMS):δ 8.33 (d, 1H, J=5.00 Hz), 7.28 (s, 1H), 6.97 (d, 1H, J=5.03 Hz), 6.08 (s, 1H), 5.80 (s, 1H), 5.15 (brs, 2H), 2.24 (s, 3H). Melting Point: 145–146.5° C. UV (λ max, ethanol): 225 (27,700), 246 sh (12,000), 266 sh (6,640), 285 (6,860), 312 sh (1,730). Infrared (λ max, mineral oil): 2925, 1573, 1637, 1531, 2954, 2965, 2855, 1288, 1373, 1607, 1272, 1464, 2869, 832, 3445, 1128, 3322, 3192, 986, 3216, 841, 3161, 850, 605, 3062 cm$^{-1}$. Analysis: Calculated for $C_{12}H_{10}ClN_5S$: C, 49.48; H, 3.44; N, 24.05. Found: C, 49.25; H, 3.41; N, 23.87. Mass Spectrum: M/Z (relative intensity %): 291 (32), 260 (33), 258 (100), 233 (8), 163 (15), 136 (16).

Example 218

4-Amino-6-chloro-2-(1-(4-methyl-2-pyridyl)propyl) thio-pyrimidine (Cpd #218)

4-Methyl-2-pyridinecarboxaldehyde (1.21 g, 10.0 mmol) and ethylmagnesium bromide (15.0 ml, 15.0 mmol, 1.5 equiv. 1 M in THF) led to 0.776 g (51%) of 2-(1-hydroxypropyl)-4-methyl-pyridine.

TLC (silica gel GF): $R_f$=0.28 acetone-methylene chloride (1:4). $^1$H NMR (CDCl$_3$,TMS):δ 8.48 (d, 1H, J=5.06 Hz), 7.20 (s, 1H), 7.11 (d, 1H, J=5.05 Hz), 4.75 (t, 1H, J=7.12 Hz), 4.55 (brs, 1H), 2.48 (s, 3H), 2.07–1.91 (m, 1H), 1.91–1.74 (m, 1H), 1.06 (t, 3H, J=5.09 Hz). UV (λ max, ethanol): 254 sh (2,320), 259 (2,800), 265 (2,280). Infrared (υ max, mineral oil): 1610, 2965, 2934, 825, 3374, 3258, 984, 2876, 1454, 1462, 1127, 1052, 1564, 1095, 3056, 1428, 1407, 1003, 3019, 1379, 1477, 1328, 1348, 659, 680 cm$^{-1}$. Mass Spectrum: M/Z (relative intensity %): FAB 152 (88), 134 (24), 123(14), 109 (41), 95 (39), 81 (48), 69 (83), 55 (100), 43 (81).

Treatment of 2-(1-hydroxypropyl)-4-methyl-pyridine (0.775 g, 5.13 mmol) with methanesulfonyl chloride (0.659 g, 5.78 mmol, 1.13 equiv.) and triethylamine (0.570 g, 5.64 mmol, 1.1 equiv.) gave 2-(1-methanesulfonyloxy)propyl-4-methylpyridine upon concentration in vacuo which is used directly in the subsequent alkylation reaction.

TLC (silica gel GF): $R_f$ 0.62 acetone-methylene chloride (1:4).

Alkylation of 4-amino-6-chloro-2-thio-pyrimidine mesylate salt (1.32 g, 5.13 mmol) with 2-(1-methanesulfonyloxy) propyl-4-methylpyridine (1.17 g, 5.13 mmol, 1.0 equiv.) and NaH (0.431 g, 10.77 mmol, 2.1 equiv., 60% oil dispersion) gave 0.726 g (48%) of 4-Amino-6-chloro-2-(1-(4-methyl-2-pyridyl)propyl)thio-pyrimidine. Treatment of Cpd #218 (0.294 g, 1.0 mmol) with methanesulfonic acid (0.096 g, 1.0 mmol, 1.0 equiv.) in ether afforded an analytically pure mesylate salt of Cpd #218 (0.372 g, 95%).

TLC (silica gel GF): $R_f$=0.20 ethyl acetate-hexane (1:2). HCl salt: $^1$H NMR (CDCl$_3$,TMS):δ 8.66 (d, 1H, J=6.07 Hz), 7.87 (s, 1H), 7.63 (d, 1H, J=6.04 Hz), 6.22 (s, 1H), 5.25 (t,1H, J=8.17 Hz), 2.73 (s, 3H), 2.30–2.01 (m, 2H), 1.19 (t, 3H, J=7.35 Hz). Melting Point: 116–120° C. UV (λ max, ethanol): 230 (22,500), 254 (12,500), 267 sh (8,760), 287 (6,940). Infrared (υ max, mineral oil): 2924, 1567, 2955, 2855, 1528, 1633, 2870, 1374, 1461, 828, 3164, 3295, 1279, 1249, 3203, 1116, 3091, 3058, 2692, 2633, 986, 3453, 603, 1084, 1207 cm$^{-1}$. Analysis: (free base) Calculated for C$_{13}$H$_{15}$ClN$_4$S: C, 53.06; H, 5.10; N, 19.05. Found: C, 52.68; H, 5.29; N, 18.59. Mass Spectrum: M/Z (relative intensity %): 294 (14), 279 (13), 261 (100), 233 (24), 166 (14), 134 (90).

Mesylate Salt of Cpd #218: Melting Point: 172–175° C. Analysis: Calculated for C$_{14}$H$_{19}$ClN$_4$O$_3$S$_2$: C, 43.08; H, 4.87; N, 14.36. Found: C, 42.97; H, 5.04; N, 14.03.

Example 219

4-Amino-6-chloro-2-(1-(4-acetyl-2-pyridyl)ethyl) thio-pyrimidine (Cpd #219)

4-Cyano-2-pyridinecarboxaldehyde (1.0 g, 7.57 mmol) and methylmagnesium bromide (6.31 ml, 18.92 mmol, 2.5 equiv., 3.0 M in ether) led to 0.729 g (58%) of 4-acetyl-2-(1-hydroxy)ethylpyridine.

TLC (silica gel GF): $R_f$=0.27 acetone-methylene chloride (1:4). $^1$H NMR (CDCl$_3$,TMS): δ 8 8.68 (d, 1H, J=5.1 Hz), 7.76 (s, 1H), 7.61 (dd, 1H, J=1.49, 5.05 Hz), 4.97 (q, 1H, J=6.42 Hz), 4.20 (brs, 1H), 2.62 (s, 3H), 1.52 (d, 3H, J=6.52 Hz). Mass Spectrum: M/Z (relative intensity %): 165 (7), 164 (9), 150 (100), 122 (24).

4-Acetyl-2-(1-hydroxy)ethylpyridine (0.729 g, 4.42 mmol), methanesulfonyl chloride (0.554 g, 4.86 mmol, 1.1 equiv.) and triethylamine (0.536 g, 5.30 mmol, 1.2 equiv.) afforded 4-acetyl-2-(1-methanesulfonyloxy)ethylpyridine upon concentration at reduced pressure.

TLC (silica gel GF): $R_f$0.59 acetone-methylene chloride (1:4).

4-Amino-6-chloro-2-thio-pyrimidine mesylate salt (1.13 g, 4.42 mmol), NaH (0.371 g, 9.28 mmol, 2.1 equiv., 60% oil dispersion) and 4-acetyl-2-(1-methanesulfonyloxy) ethylpyridine (1.07 g, 4.42 mmol, 1.0 equiv.) gave 0.774 g (57%) of 4-Amino-6-chloro-2-(1-(4-acetyl-2-pyridyl)ethyl) thio-pyrimidine (Cpd #219).

TLC (silica gel GF): $R_f$=0.17 acetone-methylene chloride (1:9). $^1$H NMR (CDCl$_3$,TMS): δ 8.75 (d, 1H, J=3.79 Hz), 7.96 (s, 1H), 7.58 (dd, 1H, J =1.24, 3.79 Hz), 6.11 (s, 1H), 5.17 (q, 1H, J=5.40 Hz), 5.08 (brs, 2H), 2.63 (s, 3H), 1.79 (d, 3H, J=5.41). Melting Point: 149–150° C. UV (λ max, ethanol): 227 (27,400), 249 sh (11,400), 288 (9,370). Infrared (v max, mineral oil): 1568, 2925, 2954, 1692, 1555, 1526, 1653, 1275, 2855, 3208, 1369, 1115, 3372, 3329, 1284, 3224, 601, 815, 1460, 982, 1105, 1259, 621, 849, 1445 cm-1. Analysis: Calculated for C$_{13}$H$_{13}$ClN$_4$OS: C, 50.65; H, 4.22; N, 18.18. Found: C, 50.40; H, 4.28; N, 18.16. Mass Spectrum: M/Z (relative intensity %): 308 (4), 275 (100), 148 (33), 105 (13).

Example 220

4-Amino-6-chloro-2-(1-(4-methyl-2-pyridyl)-1-carbomethoxy-methyl)thio-pyrimidine (Cpd #220)

A flask is charged with 2-(1-cyano-1-hydroxy)methyl-4-methyl-pyridine (0.863 g, 5.83 mmol) in 3.5 ml of methanol,
treated with 1.8 ml of concentrated H$_2$SO$_4$, followed by 0.30 ml of water and the mixture heated to reflux for 1.25 h. The contents are cooled, poured into 50 ml of saturated NaHCO$_3$, extracted twice with ethyl acetate, the combined organic extracts dried over anhydrous Na$_2$SO$_4$ and the filtrate concentrated at reduced pressure. Chromatographic purification is accomplished using 75 g of silca gel, packed and eluted with acetone-methylene chloride (1:6), to obtain 0.739 g (70%) of 2-(1-carbomethoxy-1-hydroxy)methyl-4-methyl-pyridine.

TLC (silica gel GF): $R_f$=0.35 acetone-methylene chloride (1:4). $^1$H NMR (CDCl$_3$,TMS): δ 8.41 (s, 1H), 7.30 (s, 1H), 7.09 (d, 1H, J=3.75 Hz), 5.25 (s, 1H), 3.76 (s, 3H), 2.37 (s, 3H). Mass Spectrum: M/Z (relative intensity %): 181 (0.4), 150 (0.3), 122 (100), 92 (32).

2-(1-Carbomethoxy-1-hydroxy)methyl-4-methyl-pyridine (0.735 g, 4.06 mmol), methanesulfonyl chloride (0.509 g, 4.47 mmol, 1.1 equiv.) and triethylamine (0.492 g, 4.87 mmol, 1.2equiv.) provided the 2-(1-carbomethoxy-1-methanesulfonyloxy)methyl-4-methylpyridine upon direct concentration in vacuo.

TLC (silica gel GF): $R_f$0.70 acetone-methylene chloride (1:9).

Alkylation of 4-amino-6-chloro-2-thio-pyrimidine mesylate salt (1.04 g, 4.06 mmol) with NaH (0.341 g, 8.53 mmol, 2.1 equiv., 60% oil dispersion) and 2-(1-carbomethoxy-1-methanesulfonyloxy)methyl-4-methyl-pyridine (1.05 g, 4.06 mmol, 1.0 equiv.) yielded 0.765 g (58%) of 4-Amino-6-chloro-2-(1-(4-methyl-2-pyridyl)-1-carbomethoxymethyl)thio-pyrimidine.

TLC (silica gel GF): $R_f$=0.26 acetone-methylene chloride (1:6). $^1$H NMR (CDCl$_3$,TMS): δ 8.44 (d, 1H, J=4.99 Hz), 7.36 (s, 1H), 7.06 (d, 1H, J =5.06 Hz), 6.15 (s, 1H), 5.77 (s, 1H), 5.40 (brs, 2H), 3.79 (s, 3H), 2.37 (s, 3H). Melting Point: 137.5–139° C. UV (λ max, ethanol): 228 (25,77), 250 sh (12,300), 267 sh (7,650), 286 (6,880). Infrared (v max, mineral oil): 1573, 2925, 1645, 1736, 1532, 2955, 2964, 1188, 1167, 2855, 1282, 1292, 1603, 1368, 1124, 828, 1158, 835, 1430, 2869, 3461, 1467, 3188, 3315, 3163 cm$^{-1}$. Analysis: Calculated for C$_{13}$H$_{13}$ClN$_4$O$_2$S: C, 48.15; H, 4.01; N, 17.28. Found: C, 47.99; H, 4.10; N, 17.11. Mass Spectrum: M/Z (relative intensity %): 324 (11), 293 (42), 291 (100), 265 (37), 229 (9), 196 (7), 171 (20), 136 (39).

Example 221

4-Amino-6-chloro-2-(1-(4-(1-methylethenyl)-2-pyridyl)ethyl)thio-pyrimidine (Cpd #221)

A suspension of methyltriphenylphosphonium bromide (14.90 g, 0.0417 mol, 2.2 equiv.) in 170 ml of THF, cooled at 0–5° C., was treated dropwise with n-butyllithium (26.1 ml, 0.0417 mol, 2.2 equiv., 1.6 M in hexane) over a period of 20 min. After stirring for an additional 35 min, 4-acetyl-2-(2-hydroxy)ethylpyridine (3.13 g, 0.0190 mol, 1.0 equiv.) dissolved in 25 ml of THF, is added dropwise to the reaction mixture over a 20 min period. After 3.5 h, the contents are cast into 500 ml of ice water, extracted 4 times with ethylacetate and the combined organic extracts dried with anhydrous Na$_2$SO$_4$. The concentrated filtrate is chromatographed over 500 g of silica gel, packed and eluted with ethylacetate-hexane (1:1) to give 2.55 g (82%) of 4-(1-methylethenyl)-2-(1-hydroxy)ethylpyridine.

TLC (silica gel GF): $R_f$=0.23 ethyl acetate-hexane (1:1). $^1$H NMR (CDCl$_3$,TMS): δ 8.47 (d, 1H, J=5.30 Hz), 7.33 (s, 1H), 7.24 (dd, 1H, J=1.75, 5.21 Hz), 5.58 (s, 1H), 5.28 (s, 1H), 4.90 (q, 1H, J=6.53 Hz), 4.40 (brs, 1H), 2.15 (s, 3H), 1.52 (d, 3H, J=6.57 Hz). Mass Spectrum: M/Z (relative intensity %): 163 (11), 162 (13), 148 (100), 146 (40), 120 (23).

4-(1-Methylethenyl)-2-(1-hydroxy)ethylpyridine (0.775 g, 4.75 mmol), methanesulfonyl chloride (0.670 g, 5.88 mmol, 1.24 equiv.) and triethylamine (0.576 g, 5.70 mmol, 1.2 equiv.) gave 4-(1-methylethenyl)-2-(1-methanesulfonyloxy) ethylpyridine upon concentration at reduced pressure.

TLC (silica gel GF): $R_f$ 0.31 ethylacetate-hexane (1:1). 4-(1-Methylethenyl)-2-(1-methanesulfonyloxy) ethylpyridine (1.14 g, 4.75 mmol), NaH (0.399 g, 9.98 mmol, 2.1 equiv., 60% oil dispersion) and 4-amino-6-chloro-2-thio-pyrimidine mesylate salt (1.22 g, 4.75 mmol, 1.0 equiv.) provided 0.801g (55%) of 4-Amino-6-chloro-2-(1-(4-(1-methylethenyl)-2-pyridyl)ethyl)thio-pyrimidine.

TLC (silica gel GF): $R_f$=0.22 ethylacetate-hexane (1:1). $^1$H NMR (CDCl$_3$,TMS): δ 8.51 (d, 1H, J=5.28 Hz), 7.53 (s, 1H), 7.19 (dd, 1H, J =1.80, 5.20 Hz), 6.10 (s, 1H), 5.58 (s, 1H), 5.30–5.09 (m, 4H), 2.14 (s, 3H), 1.77 (d, 3H, J=7.19 Hz).

Melting Point: 133–135° C. UV (λ max, ethanol): 231 (28,200), 250 sh (19,900), 285 (9,270). Infrared (ν max, mineral oil): 1569, 1529, 2925, 1642, 1281, 2953, 1359, 1119, 1600, 1367, 2855, 1467, 3184, 828, 3314, 3364, 1378, 902, 1052, 986, 3217, 2982, 1263, 603, 911 cm$^{-1}$. Analysis: Calculated for C$_{14}$H$_{15}$ClN$_4$S: C, 54.90; H, 4.90; N, 18.30. Found: C, 54.61; H, 5.11; N, 17.99. Mass Spectrum: M/Z (relative intensity %): 306 (7), 291 (1), 273 (100), 211 (4), 178 (22), 146 (53).

Example 223

4-Amino-6-chloro-2-(1-(4-(1-methylethyl)-2-pyridyl)ethyl)thio-pyrimidine (Cpd #223)

A flask equipped with separate inlet and outlet valves is charged with 4-(1-methylethyl)-2-(1-hydroxy) ethenylpyridine (1.00 g, 6.13 mmol) in 50 ml of 95% ethanol, 10% palladium on carbon (100 mg) and exposed to a hydrogen atmosphere via a balloon at room temperature. After 1 h the reaction mixture is filtered through a pad of celite using methylene chloride to wash the pad. The filtrate is concentrated in vacuo and chromatographed with 100 g of silica gel packed and eluted with ethylacetate-hexane (1:1) to give a 91% yield of 4-(1-methylethyl)-2-(1-hydroxy) ethylpyridine.

TLC (silica gel GF): $R_f$=0.25 acetone-hexane (1:2). $^1$H NMR (CDCl$_3$,TMS): δ 8.19 (d, 1H, J=5.15 Hz), 6.92 (s, 1H), 6.84 (dd, 1H, J =1.51, 5.17 Hz), 4.65 (q, 1H, J=6.51 Hz), 4.22 (brs, 1H), 2.69 (m, 1H),1.29 (d, 3H, J=6.45 Hz), 1.04 (d, 6H, J=6.91 Hz). Mass Spectrum: M/Z (relative intensity %): 165 (9), 164 (14), 150 (100), 148 (45), 135 (20), 122 (21), 106 (15).

The mesylation of 4-(1-methylethyl)-2-(1-hydroxy) ethylpyridine (1.07 g, 6.48 mmol) with methanesulfonyl chloride (0.887 g, 7.78 mmol, 1.2 equiv.) and triethylamine (0.851 g, 8.42 mmol, 1.3 equiv.) afforded 4-(1-methylethyl)-2-(1-methanesulfonyloxy)ethylpyridine. TLC (silica gel GF): $R_f$ 0.34 ethylacetate-hexane (1:1). Alkylation of 4-amino-6-chloro-2-thio-pyrimidine mesylate salt (1.66 g, 6.48 mmol) with NaH (0.544 g, 13.61 mmol, 2.1 equiv., 60% oil dispersion) and 4-(1-methylethyl)-2-(1-methanesulfonyloxy)ethylpyridine (1.57 g, 6.48 mmol, 1.0 equiv.) gave 1.02 g (51%) of 4-Amino-6-chloro-2-(1-(4-(1-methylethyl)-2-pyridyl)ethyl)thio-pyrimidine.

TLC (silica gel GF): $R_f$=0.23 acetone-methylene chloride (1:6). Analysis: Calculated for C$_{14}$H$_{17}$ClN$_4$S: C, 54.54; H, 5.52; N, 18.18. Found: C, 54.06; H, 5.62; N, 17.77.

Mesylate Salt:

$^1$H NMR (CDCl$_3$,TMS): δ 8.83 (d, 1H, J=6.14 Hz), 7.90 (s, 1H), 7.63 (d, 1H, J =6.16 Hz), 6.29 (s, 1H), 5.33 (q, 1H, J=7.55 Hz), 3.19 (m, 1H), 2.98 (s, 3H, J=7.50 Hz), 1.41 (dd, 6H, J=1.37, 6.91 Hz). Melting Point: 155–159° C. UV (λ max, ethanol): 229 (21,300), 253 (11,600), 267 sh (8,250), 286 (6,530). Infrared (ν max, mineral oil): 2925, 1571, 2955, 2855, 1633, 1162, 2870, 1217, 1041, 1528, 1376, 1465, 1117, 828, 3192, 3323, 3219, 1282, 3089, 3060, 1479, 3370, 986, 774, 2719 cm$^{-1}$. Mass Spectrum: M/Z (relative intensity %): 308 (8), 293 (2), 275 (100), 180 (34), 148 (67), 132 (55).

Example 224

4-Amino-6-chloro-2-(1-(4-methyl-2-pyridyl)pentyl) thio-pyrimidine (Cpd #224)

A solution of n-butyllithium (6.71 ml, 10.74 mmol, 1.3 equiv., 1.6 M in hexanes) in 60 ml of ether at 0–5° C., is treated dropwise with 4-methyl-2-pyridinecarboxaldehyde (1.0 g, 8.26 mmol, 1.0 equiv.) in 40 ml of ether over a period of 10 min. After 30 min the contents are poured into 45 ml of 3 N HCl containing 60 ml of crushed ice. The cold mixture is warmed to room temperature, stirred for 20 min, basified with 15 ml of 29% aqueous ammonium hydroxide and extracted once with ethylacetate. The organic layer is dried over anhydrous Na$_2$SO$_4$ and concentrated at reduced pressure. Chromatography with 150 g of silica gel packed and eluted with ethylacetate-hexane (1:2) provided 0.364 g (24%) of 2-(1-hydroxy)pentyl-4-methylpyridine.

TLC (silica gel GF): $R_f$=0.18 ethylacetate-hexane (1:2). $^1$H NMR (CDCl$_3$,TMS): δ 8.24 (d, 1H, J=5.05 Hz), 6.92 (s, 1H), 6.87 (d, 1H, J=4.93 Hz), 4.55 (m, 1H), 4.01 (brs, 1H), 2.23 (s, 3H), 1.75–1.45 (m, 2H), 1.34–1.12 (m, 2H), 1.34–1.12 (m, 4H), 0.76 (t, 3H, J=7.19 Hz).

A solution of 2-(1-hydroxy)pentyl-4-methylpyridine (0.364 g, 2.03 mmol) in 10 ml of methylene chloride is treated with thionyl chloride (0.525 g, 4.41 mmol, 2.17 equiv.) and triethylamine (0.226 g, 2.23 mmol, 1.1 equiv.). After 1 h the reaction mixture is poured into 100 ml of saturated NaHCO$_3$, extracted twice with methylene chloride and dried the combined organic extracts with anhydrous Na$_2$SO$_4$. The filtrate is concentrated in vacuo to afford 2-(1-chloro)pentyl-4-methylpyridine.

TLC (silica gel GF): $R_f$=0.78 acetone-methylene chloride (1:6). $^1$H NMR (CDCl$_3$,TMS): δ 8.25 (d, 1H, J=5.06 Hz), 7.10 (s, 1H), 6.86 (d, 1H, J=5.15 Hz), 4.75 (t, 1H, J=7.11 Hz), 2.21 (s, 3H), 2.02–1.91 (m, 2H), 1.43–1.09 (m, 4H), 0.73 (t, 3H, J=6.73 Hz).

Alkylation of 4-amino-6-chloro-2-thio-pyrimidine mesylate salt (0.514 g, 2.0 mmol) with NaH (0.176 g, 4.4 mmol, 2.2 equiv., 60% oil dispersion) and 2-(1-chloro)pentyl-4-methylpyridine (0.394 g, 2.0 mmol), 1.0 equiv.) afforded 0.400 g (62%) of 4-Amino-6-chloro-2-(1-(4-methyl-2-pyridyl)pentyl)thio-pyrimidine.

TLC (silica gel GF): $R_f$=0.25 acetone-methylene chloride (1:6). $^1$H NMR (CDCl$_3$,TMS): δ 8.35 (d, 1H, J=5.00 Hz), 7.20 (s, 1H), 6.90 (d, 1H, J =4.54 Hz), 6.02 (s, 1H), 5.12 (brs, 2H), 4.88 (t, 1H, J=7.20), 2.27 (s, 3H), 2.13–1.92 (m, 2H), 1.39–1.12 (m, 4H), 0.81 (t, 3H, J=6.90 Hz). Melting Point: 139.5–141° C. UV (λ max, ethanol): 230 (22,600), 254 (12,600), 267 sh (8,830), 287 (7,040). Infrared (λ max, mineral oil): 1573, 2928, 2961, 1281, 1659, 1534, 1123, 3143, 2854, 1605, 1466, 990, 1367, 1271, 1362, 1264, 3314, 2872, 829, 1296, 1453, 1381, 824, 1097, 3231 cm$^{-1}$. Analysis: KF H$_2$O 0.20%. Analysis: Calculated for C$_{15}$H$_{19}$ClN$_4$S-0.20% H$_2$O: C, 55.80; H, 5.93; N, 17.37. Found: C, 55.25; H, 5.83; N, 17.62. Mass Spectrum: M/Z (relative intensity %): 322 (11), 289 (38), 279 (25), 266 (24), 233 (54), 162 (100).

Example 225

4-Amino-5-bromo-6-chloro-2-(1-(4-methylethyl)-2-pyridyl)ethyl)thio-pyrimidine (Cpd #225)

The mesylate salt of 4-amino-6-chloro-2-(1-(4-(1-methylethyl)-2-pyridyl)ethyl)thio-pyrimidine (0.404 g, 1.0 mmol) is dissolved in 10 ml of methanol cooled at 0–5° C. and treated dropwise with bromine (0.160 g, 1.0 mmol, 1.0 equiv.) over a 1 min period. After 10 min the reaction mixture is poured into a mixture of 50 ml of saturated NaHCO$_3$ plus 75 ml of water and extracted once with ethylacetate. The organic extract is dried over Na$_2$SO$_4$ and concentrated in vacuo. Chromatography with 75 g of silica gel packed and eluted with acetone-methylene chloride (1:8) afforded 0.308 g (80%) of 4-Amino-5-bromo-6-chloro-2-(1-(4-methyl-2-pyridyl)pentyl)thio-pyrimidine (Cpd #225). Crystallization is effected from methylene chloride-hexane solvent mixture.

TLC (silica gel GF): R$_f$=0.33 acetone-methylene chloride (1:6). $^1$H NMR (CDCl$_3$,TMS): δ 8.35 (d, 1H, J=5.04 Hz), 7.19 (s, 1H), 6.90 (dd, 1H, J =1.70, 5.15 Hz), 5.54 (brs, 2H), 4.91 (q, 1H, J=7.12 Hz), 2.85–2.69 (m, 1H), 1.65 (d, 3H, J=7.17 Hz), 1.14 (d, 6H, J=6.91 Hz). Melting Point: 124–125° C. UV (λ max, ethanol): 230 (19,600), 261 (15,100), 297 (8,440). Infrared (ν max, mineral oil): 1535, 2927, 1518, 2958, 1634, 1332, 2855, 1462, 3474, 2870, 1267, 838, 3132, 993, 1600, 3287, 758, 3178, 1245, 1248, 3062, 1480, 1443, 1364. Analysis: Calculated for C$_{14}$H$_{16}$BrClN$_4$S: C, 43.41; H, 4.13; N, 14.47. Found: C, 43.43; H, 4.31; N, 14.15. Mass Spectrum: M/Z (relative intensity %): 388 (15), 387 (3), 386 (11), 206 (3), 180 (47), 148 (78), 132 (47).

Example 226

4-Amino-6-chloro-2-(1-(4-methyl-2-pyridyl)-1-cyclopropyl-methyl)thio-pyrimidine mesylate (Cpd #226)

The Grignard reaction of 4-methyl-2-pyridinecarboxaldehyde (1.21 g, 10.0 mmol) and cyclopropylmagnesium bromide (24 ml, 15.0 mmol, 1.5 equiv., 1.6 ml/mmol) provided 1.42 g (87%) of 2-(1-hydroxy-1-cyclopropylmethyl)-4-methyl-pyridine. TLC (silica gel GF): R$_f$=0.21 acetone-methylene chloride (1:6). $^1$H NMR (CDCl$_3$,TMS): δ 8.47 (d, 1H, J=5.08 Hz), 7.30 (s, 1H), 7.12 (d, 1H, J=5.14 Hz), 4.70 (brs, 1H), 4.16 (d, 1H, J=7.92 Hz), 2.47 (s, 3H), 1.26–1.12 (m, 1H), 0.74–0.57 (m, 4H). Mass Spectrum: M/Z (relative intensity %): 163 (34), 162 (51), 146 (51), 135 (70), 122 (100), 107 (57), 92 (98).

To a solution of 2-(1-chloro-1-cyclopropylmethyl)-4-methyl-pyridine (1.42 g, 8.71 mmol) in 40 ml of chloroform at room temperature is added thionyl chloride (1.35 g, 11.32 mmol, 1.3 equiv.). After 1.5 h, the contents are cast into 150 ml of saturated NaHCO$_3$, extracted twice with methylene chloride and the combined organic extracts dried with anhydrous Na$_2$SO$_4$. The filtrate is concentrated at reduced pressure and chromatographed using 160 g of silica gel packed and eluted with ethylacetate-hexane (1:6) to provide 0.894 g (56%) of 2-(1-chloro-1-cyclopropylmethyl)-4-methyl-pyridine.

TLC (silica gel GF): R$_f$=0.19 ethylacetate-hexane (1:6). $^1$H NMR (CDCl$_3$,TMS): δ 8.21 (d, 1H, J=5.03 Hz), 7.08 (s, 1H), 6.83 (d, 1H, J=4.13 Hz), 4.10 (d, 1H, J=9.48 Hz), 2.16 (s, 3H), 1.52–1.39 (m, 1H), 0.68–0.55 (m, 1H), 0.51–0.25 (m, 3H).

Alkylation of 4-amino-6-chloro-2-thio-pyrimidine mesylate salt (1.27 g, 4.94 mmol) with NaH (0.435 g, 10.87 mmol, 2.2 equiv., 60% oil dispersion) and 2-(1-chloro-1-cyclopropylmethyl)-4-methyl-pyridine (0.894, 4.94 mmol, 1.0 equiv.) gave 0.762 g (50%) of 4-Amino-6-chloro-2-(1-(4-methyl-2-pyridyl)-1-cyclopropylmethyl)thio-pyrimidine. Treatment with one equivalent of methanesulfonic acid in ether afforded the analytically pure title compound as a white crystalline solid.

TLC (silica gel GF): (Free base) R$_f$=0.31 acetone-methylene chloride (1:4). $^1$H NMR (CDCl$_3$,TMS): δ 8.51 (d, 1H, J=6.08 Hz), 7.75 (s, 1H), 7.31 (d, 1H, J =5.89 Hz), 5.90 (s, 1H), 4.22 (d, 1H, J=10.75 Hz), 2.72 (s, 3H), 2.45 (s, 3H), 1.08–0.91(m, 1H), 0.76–0.60 (m, 2H), 0.60–0.42 (m, 2H). Melting Point: 192–193° C. UV (λ max, ethanol): 229 (22,500), 254 (12,400), 268 sh (8,460), 287 (6,840). Infrared (ν max, mineral oil): 2924, 1576, 1217, 1228, 1527, 1035, 2954, 1377, 2854, 827, 1242, 2869, 1653, 1638, 3187, 1160, 1169, 1116, 1256, 3348, 3323, 1182, 1461, 1466, 773 cm$^{-1}$. Analysis: Calculated for C$_{15}$H$_{19}$ClN$_4$O$_3$S$_2$: C, 44.78; H, 4.73; N, 13.93. Found: C, 44.58; H, 4.85; N, 13.86. Mass Spectrum: M/Z (relative intensity %): 306 (7), 273 (13), 178 (17), 164 (19), 146 (100), 131 (40).

Example 227

4-Amino-6-chloro-2-(1-(4-(4-morpholinyl)methyl-2-pyridyl)ethyl)thio-pyrimidine (Cpd #227)

A suspension of 4-picolyl chloride hydrochloride (10.0 g, 60.98 mmol) in 100 ml of methylene chloride at room temperature is treated with morpholine (26.52 g, 304.9 mmol, 5.0 equiv.) at once. After stirring for 50 h, the reaction mixture is poured into 250 ml of water, extracted six times with ethylacetate, three times with ethylacetate-methanol (9:1) and the combined organic extracts are dried over Na$_2$SO$_4$. The concentrated filtrate is chromatographed with 350 g of silica gel, packed and eluted with acetone-methylene chloride (1:2), to give 9.17 g (84%) of 4-(4-morpholinyl)methylpyridine as a yellow liquid.

TLC (silica gel GF): R$_f$=0.28 acetone-methylene chloride (1:2). $^1$H NMR (CDCl$_3$,TMS): δ 8.59 (d, 2H, J=6.04 Hz), 7.33 (d, 2H, J=6.01 Hz), 3.77 (t, 4H, J=4.55 Hz), 3.55 (s, 2H), 2.50 (t, 4H, J=4.66 Hz). Mass Spectrum: M/Z (relative intensity %): 178 (77), 147 (38), 134 (16), 119 (80), 100 (100).

In a manner similar to the procedure described for the preparation of 4-cyano-2-hydroxymethylpyridine, 4-(4- morpholinyl)methylpyridine (9.15 g, 51.40 mmol), ammonium persulfate (23.44 g, 102.81 mmol, 2.0 equiv.), methanol (92 ml), water (46 ml) and concentrated $H_2SO_4$ (11.59 g, 118.2 mmol, 2.3 equiv.) provided 2.29 g (21%) of 2-hydroxymethyl-4-(4-morpholinyl)methylpyridine.

TLC (silica gel GF): $R_f$=0.25 acetone-methylene chloride (2:1). $^1$H NMR (CDCl$_3$,TMS): δ 8.45 (d, 1H, J=5.05 Hz), 7.27 (s, 1H), 7.18 (d, 1H, J =4.90 Hz), 4.73 (s, 2H), 4.12 (brs, 1H), 3.70 (t, 4H, J=4.76 Hz), 3.48 (s, 2H), 2.43 (t, 4H, J=4.63 Hz). Mass Spectrum: M/Z (relative intensity %): 208 (55), 177 (28), 149 (52), 123 (100), 100 (99), 86 (51).

In a manner similar to that reported for the preparation of 4-cyano-2-pyridine-carboxaldehyde, 2-hydroxymethyl-4-(4-morpholinyl)methylpyridine (2.29 g, 11.01 mmol) gave 1.03 g (45%) of 4-(4-morpholinyl)methyl-2-pyridine carboxaldehyde.

TLC (silica gel GF): $R_f$=0.42 acetone-methylene chloride (1:4). $^1$H NMR (CDCl$_3$,TMS): δ 9.89 (s, 1H), 8.54 (d, 1H, J=4.87 Hz), 7.76 (s, 1H), 7.36 (d, 1H, J=4.86 Hz), 3.53 (t, 4H, J=4.54 Hz), 3.39 (s, 2H), 2.27 (t, 4H, J=4.65 Hz).

Grignard reaction between 4-(4-morpholinyl)methyl-2-pyridine carboxaldehyde (1.03 g, 5.00 mmol) and methylmagnesium bromide (2.50 ml, 7.50 mmol, 1.5 equiv., 3.0 M in ether) yielded 1.05 g (94%) of 2-(1-hydroxyethyl)-4-(4-morpholinyl)methylpyridine.

TLC (silica gel GF): $R_f$=0.37 acetone-methylene chloride (2:1). $^1$H NMR (CDCl$_3$,TMS): δ 8.52 (d, 1H, J=5.04 Hz), 7.34 (s, 1H), 7.27 (d,1H, J=5.04 Hz), 4.95 (q, 1H, J=6.54 Hz), 3.79 (t, 4H, J=4.50 Hz), 3.58 (s, 2H), 2.52 (q, 4H, J=4.62 Hz), 1.57 (d, 3H, J=6.50 Hz). Mass Spectrum: M/Z (relative intensity %): 222 (100), 207 (11), 191 (30), 177 (13), 163 (10), 149 (76), 147 (64), 137 (74), 121 (53), 100 (92).

Treatment of 2-(1-hydroxyethyl)-4-(4-morpholinyl) methylpyridine (1.05 g 4.73 mmol) with thionyl chloride (0.732 g, 6.15 mmol, 1.3 equiv.) gave 1.08 g (96%o) of 2-(1-chloroethyl)-4-(4-morpholinyl)methylpyridine.

TLC (silica gel GF): $R_f$=0.39 acetone-methylene chloride (2:1). $^1$H NMR (CDCl$_3$,TMS): δ 8.46 (d, 1H, J=4.90 Hz), 7.42 (s, 1H), 7.19 (d, 1H, J =5.08 Hz),5.09 (q, 1H, J=6.86 Hz), 3.69 (t, 4H, J=4.54 Hz), 3.47 (s, 2H), 2.42 (t, 4H, J=4.64 Hz), 1.84 (d, 3H, J=6.88 Hz).

Alkylation of 4-amino-6-chloro-2-thio-pyrimidine mesylate salt (1.16 g, 4.50 mmol) with NaH (0.396 g, 9.90 mmol, 2.2 equiv., 60% oil dispersion) and 2-(1-chloroethyl)-4-(4-morpholinyl)methylpyridine (1.08 g, 4.50 mmol, 1.0 equiv.) gave 0.900 g (68%) of 4-Amino-6-chloro-2-(1-(4-(4-morpholinyl)methyl-2-pyridyl)ethyl)thio-pyrimidine.

TLC (silica gel GF): $R_f$=0.33 acetone-methylene chloride (1:2). $^1$H NMR (CDCl$_3$,TMS): δ 8.31 (d, 1H, J=4.90 Hz), 7.26 (s, 1H), 6.97 (d, 1H, J=4.96 Hz), 5.92 (s, 1H), 5.01 (brs, 2H), 4.92 (q, 1H, J=7.13), 3.53 (t, 4H, J=4.49 Hz), 3.30 (s, 2H), 2.25 (t, 4H, J=4.60 Hz), 1.58 (d, 3H, J=7.20 Hz). Melting Point: 146–147.5 ° C. UV (λ max, ethanol): 230 (22,400), 250 (12,200), 270 sh (8,290), 287 (7,010). Infrared (ν max, mineral oil): 2924, 1566, 1559, 1533, 1109, 2957, 1374, 2855, 2865, 1639, 825, 865, 1464, 1454, 1255, 1604, 1291, 1117, 1272, 3400, 858, 1045, 604, 3301, 3155 cm$^{-1}$. Analysis: Calculated for $C_{16}H_{20}ClN_5OS$: C, 52.60; H, 5.48; N, 19.18. Found: C, 52.74; H, 5.68; N, 19.00. Mass Spectrum: M/Z (relative intensity %): 365 (0.1), 332 (9), 280 (100), 247 (9), (20).

Example 228

4-Amino-6-chloro-2-(1-(4-dimethylaminomethyl-2-pyridyl)ethyl)thio-pyrimidine (Cpd #228)

In a manner similar to the procedure described for the synthesis of 4-(4-morpholinyl)methylpyridine, 4-picolylchloride hydrochloride (6.00 g, 0.0366 mol) and diethylamine (10.68 g, 0.146 mol, 4.0 equiv.) provided 5.28 g (88%) of 4-(N,N-diethylaminomethyl)pyridine.

TLC (silica gel GF): $R_f$=0.32 acetone-methylene chloride (1:2). $^1$H NMR (CDCl$_3$,TMS): δ 8.44 (d, 2H, J=4.48 Hz), 7.20 (d, 2H, J=5.89 Hz), 3.48 (s, 2H), 2.45 (q, 4H, J=7.14 Hz), 0.960 (t, 6H, J=7.13 Hz). Mass Spectrum: M/Z (relative intensity %): 164 (12), 149 (100), 92 (87).

Treatment of 4-(N,N-diethylaminomethyl)pyridine (2.0 g, 12.20 mmol) with ammonium persulfate (5.56 g, 24.4 g, 2.0 equiv.), methanol (22 ml), water (11 ml) and concentrated $H_2SO_4$ (2.76 g, 28.18 mmol, 2.31 equiv.) as described for Cpd #214 gave 0.697 g (29%) of 4-(N,N-diethylaminomethyl)-2-hydroxymethylpyridine.

TLC (silica gel GF): $R_f$=0.28 acetone-methylene chloride (2:1). $^1$H NMR (CDCl$_3$,TMS): δ 8.34 (d, 1H, J=5.05 Hz), 7.15 (s, 1H), 7.10 (d, 1H, J=5.13 Hz), 4.63 (s, 2H), 3.45 (s, 2H), 2.41 (q, 4H, J=7.12 Hz), ).924 (t, 6H, J=7.16 Hz). Mass Spectrum: M/Z (relative intensity %): 194 (10), 179 (100), 122 (15), 86 (30).

Oxidation of 4-(N,N-diethylaminomethyl-2-hydroxymethylpyridine (0.695 g, 3.58 mmol), SeO$_2$ (0.220 g, 1.98 mmol, 0.554 equiv.) as described for Cpd #214 gave 0.395 g (57%) of 4-(N,N-diethylaminomethyl)-2-pyridinecarboxaldehyde.

TLC (silica gel GF): $R_f$=0.27 acetone-methylene chloride (2:1). $^1$H NMR (CDCl$_3$,TMS): δ 10.02 (s, 1H), 8.64 (d, 1H, J=4.88 Hz), 7.89 (s, 1H), 7.51 (d, 1H, J=5.04 Hz), 3.58 (s, 2H), 2.47 (q, 4H, J=7.18 Hz), 0.976 (t, 6H, J=7.16 Hz). Mass Spectrum: M/Z (relative intensity %): 192 (9), 177 (100), 149 (9), 134 (8), 120 (31), 86 (32).

Grignard reaction of 4-(N,N-diethylaminomethyl)-2-pyridinecarboxaldehyde (0.840 g, 4.37 mmol) with methylmagnesium bromide (2.19 ml, 6.56 mmol, 1.5 equiv., 3.0 M in ether) provided 0.668 g (73%) of 4-(N,N-diethylaminomethyl)-2-(1-hydroxy)ethylpyridine.

TLC (silica gel GF): $R_f$=0.36 acetone-methylene chloride (2:1). $^1$H NMR (CDCl$_3$,TMS): δ 8.43 (d, 1H, J=5.04), 7.30 (s, 1H), 7.20 (d, 1H, J=5.03 Hz), 4.88 (q, 1H, J=6.56 Hz), 4.52 (brs, 1H), 3.57 (s, 2H), 2.52 (q, 4H, J=7.11 Hz), 1.50 (d, 3H, J=6.54 Hz), 1.04 (t, 6H, J=7.08 Hz). Mass Spectrum: M/Z (relative intensity %): 208 (23), 193 (100), 177 (0.8), 149 (3), 136 (9), 121 (53), 86 (50).

Treatment of 4-(N,N-diethylaminomethyl)-2-(1-hydroxy) ethylpyridine (0.668 g, 3.21 mmol) with thionyl chloride (0.497 g, 4.17 mmol, 1.3 equiv.) yielded 0.687 g (95%) of 2-( 1-chloro)ethyl-4-(N,N-diethylaminomethyl)pyridine.

TLC (silica gel GF): $R_f$=0.42 acetone-methylene chloride (1:4). $^1$H NMR (CDCl$_3$,TMS): δ 8.45 (d, 1H, J=4.97 Hz), 7.44 (s, 1H), 7.21 (d, 1H, J=5.01 Hz), 5.11 (q, 1H, J=6.81), 3.55 (s, 2H), 2.50 (q, 4H, 7.15 Hz), 1.85 (d, 3H, J=6.84 Hz), 1.02 (t, 6H, J=7.12 Hz).

Alkylation of 4-amino-6-chloro-2-thio-pyrimidine mesylate salt (0.781 g, 3.04 mmol) with NaH (0.268 g, 6.69 mmol, 2.20 equiv., 60% oil dispersion) and 2-(1-chloro)ethyl-4-(N, N-diethylaminomethyl)pyridine (0.687 g, 3.04 mmol, 1.0 equiv.) gave 4-Amino-6-chloro-2-(1(4-dimethylaminomethyl-2-pyridyl)ethyl)thio-pyrimidine.

TLC (silica gel GF): $R_f$=0.26 acetone-methylene chloride (1:2). $^1$H NMR (CDCl$_3$,TMS): δ 8.26 (d, 1H, J=5.04 Hz), 7.26 (s, 1H), 6.94 (d, 1H, 5.08 Hz), 5.88 (s, 1H), 5.17 (brs, 2H), 4.88 (q, 1H, J=7.15 Hz), 3.34 (s, 2H), 2.30 (q, 4H, J=7.12 Hz), 1.55 (d, 3H, J=7.19 Hz), 0.816 (t, 6H, J=7.15 Hz). Melting Point: 92–94° C. UV (λ max, ethanol): 230 (22,900), 253 (12,600), 286 (7,190).

Infrared (ν max, mineral oil): 2925, 1570, 2955, 1561, 1278, 1529, 2855, 1117, 2871, 1366, 1658, 1462, 3144, 1604, 1453, 3297, 989, 1259, 1378, 825, 3228, 3058, 2826, 1099, 3013 cm$^{-1}$.
Analysis: Calculated for $C_{16}H_{22}ClN_5S$: C, 54.70; H, 6.27; N, 19.94. Found: C, 54.52; H, 6.35; N, 19.76. Mass Spectrum: M/Z (relative intensity %): 351 (0.2), 336 (47), 318 (5), 280 (100), 246 (12), 190 (33), 175 (24), 119 (82), 86 (76).

Example 229

4-Amino-6-chloro-2-(1-(2-naphthalenyl)ethyl)thio-pyrimidine (Cpd #229)

Alkylation of 4-amino-6-chloro-2-thio-pyrimidine mesylate salt (1.49 g. 5.81 mmol) with NaH (0.490 g, 12.20 mmol, 2.1 equiv., 60% in oil dispersion) and the mesylate derived from the commercially available a-methyl-2-naphthalenemethanol (1.45 g, 5.81 mmol, 1.0 equiv.) yielded 0.363 g (20%) of 4-Amino-6-chloro-2-(1-(2-naphthalenyl)-ethyl)thio-pyrimidine.

TLC (silica gel GF): $R_f$=0.27 ethylacetate-hexane (1:3). $^1$H NMR (CDCl$_3$,TMS): δ ppm. 7.82 (s, 1H), 7.71 (m, 3H), 7.48 (dd, 1H, J=1.81, 8.53 Hz), 7.36 (m, 2H), 6.00 (s, 1H), 5.09 (q, 1H, J=7.14 Hz), 5.04 (brs, 2H), 7.10 Hz). Melting Point: 55–58 ° C. UV (λ max, ethanol): 225 (81,200), 256 (18,300), 277 (11,500), 286 (11,400). Infrared (ν max, mineral oil): 1564, 1531, 2925, 2954, 1367, 1359, 1285, 2856, 1631, 1612, 820, 2867, 1118, 1457, 3311, 1241, 748, 3180, 3390, 3209, 1508, 3462, 3054, 3016, 857 cm$^{-1}$. Analysis: Calculated for $C_{16}H_4ClN_3S$: C, 60.95; H, 4.44; N, 13.33. Found: C, 60.66; H, 4.49; N, 13.06. Mass Spectrum: M(Z (relative intensity %): 315 (13), 282 (20), 171 (2), 155 (100), 128 (10), 115 (6).

Example 230

4-Amino-6-chloro-2-(1-(3-isoquinolyl)ethyl)thio-pyrimidine (Cpd #230)

Isoquinoline-3-carbonitrile (1.76 g, 11.4 mmole) is dissolved in 10 ml tetrahydrofuran in an oven dried 100 ml two neck round bottom flask under nitrogen. The solution is cooled to 0° C., is diluted with 5 ml diethyl ether, and is treated with methyl magnesium bromide in ether (5.7 ml, 17.1 mmole). The reaction is warmed to reflux for one hour, is cooled to 0° C., and is quenched with 15 ml 6 M hydrochloric acid. The reaction mixture is warmed to 50° C. for one hour, is cooled, and is poured into 75 ml 2N sodium hydroxide. The mixture is extracted with 3×50 ml ethyl acetate and the combined organics are dried over potassium carbonate. The dried organics are concentrated in vacuo to a crude orange solid. The crude material is chromatographed over 60 g silica gel (230–400 mesh), eluting with 20% acetone/hexane, while collecting 22 ml fractions. Fractions 7–11 are combined and concentrated to provide 1.7 g (87%) of 3-acetyl-isoquinoline.

H-NMR (CDCl$_3$, TMS): δ 2.83 (s, 3), 7.70–7.78 (m, 2), 7.97–8.06 (m, 2), 8.47 (s, 1), 9.28 (s, 1) ppm. $^{13}$C-NMR (CDCl$_3$): δ 26.6; 120.2; 127.6; 128.6; 129.4; 130.1; 131.0; 135.5; 124.7; 151.9; 200.3 ppm. TLC (silica gel-60, F-254): $R_f$=0.37, 20% acetone/hexane. Melting Point: 90–91° C. Infrared (ν max, mineral oil): 2925, 1689, 1418, 1386, 1220, 944, 764 cm$^{-1}$. Mass Spectrum, [M/Z](relative intensity): [171](88). Analysis: Calculated for $C_{11}H_9N_1O_1$: C, 77.17; H,5.30; N,8.18. Found: C, 76.98; H,5.41; N,8.29

3-Acetyl-isoquinoline (1.53 g, 8.9 mmole) is dissolved in 42 ml methanol in a 100 ml one neck round bottom flask at 0° C. The solution is treated portionwise with sodium borohydride (388 mg, 10.3 mmole) and the reaction mixture is stirred 30 min at 0° C. The volatiles are removed in vacuo and the residue is partitioned between 1×100 ml 1N sodium hydroxide and 3×25 ml dichloromethane. The combined organics are dried over potassium carbonate and are concentrated in vacuo to a pale yellow solid. The crude material is chromatographed over 60 g silica gel (230–400 mesh), eluting with 40% acetone/hexane, while collecting 9 ml fractions. Fractions 26–45 are combined and concentrated to afford 1.23 g (80%) of 3-(1-hydroxyethyl)-isoquinoline.

H-NMR (CDCl$_3$, TMS): δ 1.61 (d, J=6.5 Hz, 3), 3.91 (bs, 1), 5.07 (q, J=6.5, 12.9 Hz, 1), 7.54–7.60 (m, 1), 7.65–7.71 (m, 2), 7.80 (d, J=8 Hz, 1), 7.95 (d, J=8 Hz, 1), 9.20 (s, 1) ppm. $^{13}$C-NMR (CDCl$_3$): δ 24.2; 69.6; 115.6; 126.6; 127.0; 127.6; 127.9; 130.6; 136.5; 151.6; 156.9 ppm TLC (silica gel-60, F-254): $R_f$=0.46, 50% acetone/hexane. Melting Point: 104–106° C. Infrared (ν max, mineral oil): 3215, 2925, 1631, 1363, 1130, 1098, 959, 761 cm$^{-1}$. Mass Spectrum: Calculated for $C_{11}H_{11}N_1O_1$+H: 174.0919. Found: 174.0923.

3-(1-Hydroxyethyl)-isoquinoline (1.32 g, 7.6 mmole) is dissolved in 20 ml dichloromethane in a 100 ml one neck round bottom flask under nitrogen. The solution is cooled to 0° C., is treated dropwise with thionyl chloride (835 μl, 11.4 mmole), and is stirred 3 h at 0° C. followed by 1 h at room temperature. The mixture is recooled to 0° C., is quenched with 50 ml saturated sodium bicarbonate, and the layers are separated. The aqueous layer is extracted with 3×25 ml dichloromethane and the combined organics are dried over potassium carbonate. The dried organics are concentrated in vacuo to a pale amber oil. The crude material is chromatographed over 60 g silica gel (230–400 mesh), eluting with 20% acetone/hexane, while collecting 9 ml fractions. Fractions 17–26 are combined and concentrated to afford 1.39 g (95%) of 3-(1-chloroethyl)-isoquinoline as a yellow oil.

H-NMR (CDCl$_3$, TMS): δ 1.99 (d, J=6.8 Hz, 3), 5.33 (q, J=6.8, 13 Hz, 1), 7.58–7.63 (m, 1), 7.67–7.72 (m, 1), 7.78 (s, 1), 7.82 (d, J=8 Hz, 1), 7.97 (d, J=8 Hz, 1), 9.24 (s, 1) ppm. $^{13}$C-NMR (CDCl$_3$): δ 24.9; 59.1; 117.2; 126.7; 127.4; 127.5; 127.9; 130.6; 136.1; 152.3; 154.0 ppm. TLC (silica gel-60, F-254): $R_f$=0.40, 20% acetone/hexane. Infrared (ν max, liquid): 2979, 1629, 1584, 1493, 1045, 947, 887, 752 cm$^{-1}$. Mass Spectrum, [M/Z](relative intensity): [191](9), [156](100). Analysis: Calculated for $C_{11}H_{10}ClN$: C, 68.94; H,5.26; N,7.31. Found: C, 68.69; H,5.39; N,7.21.

4-Amino-6-chloro-2-mercapto-pyrimidine mesylate salt (1.79 g, 6.94 mmole) is dissolved in 12 ml dry dimethylformamide in a 50 ml one neck round bottom flask under nitrogen. The solution is treated with 60% sodium hydride (605 mg, 15.1 mmole) (exotherm) and the mixture is stirred one hour. 3-(1-chloroethyl)-isoquinoline (1.33 g, 6.94 mmole) in 2×3 ml dry dimethylformamide, is added to the reaction and the mixture is stirred 6 hours at room temperature. The reaction mixture is poured into 300 ml water and is extracted with 3×100 ml ethyl acetate. The combined organics are backwashed with 4×50 ml 50% saturated sodium chloride. The organics are dried over potassium carbonate and are concentrated in vacuo to a yellow oil. The crude material is chromatographed over 75 g silica gel (230–400 mesh), eluting with 40% acetone/hexane while collecting 9 ml fractions. Fractions 26–39 are combined and concentrated to afford 1.26 g (57%) of 4-Amino-6-chloro-2-(1-(3-isoquinolyl)ethyl)thio-pyrimidine as a white solid.

H-NMR ($d_6$DMSO): δ 1.78 (d, J=7 Hz, 3), 5.19 (q, J=7, 14, Hz, 1), 6.18 (s, 1), 7.38 (bs, 1), 7.63–7.69 (m, 1), 7.75–7.80 (m, 1), 7.94 (d, J=8 Hz, 1), 7.95 (s, 1), 8.10 (d, J=8 Hz, 1), 9.31 (s, 1) ppm. $^{13}$C-NMR ($d_6$DMSO): δ 21.2; 45.0; 98.5; 117.6; 126.40; 127.1; 127.2; 127.4; 130.7; 135.5; 152.2; 154.2; 157.3; 164.1; 170.2 ppm. TLC (silica gel-60, F-254): $R_f$=0.50, 50% acetone/hexane. Melting Point: 179–180° C. Ultraviolet (λ max, Ethanol), nm(ε): 220(73,300); 237(31,500); 252(16,500); 282(9640); 325(3,100); 312 (3,000). Infrared (ν max, mineral oil): 3306, 2925, 1642, 1572, 1533, 1465, 1366, 1288, 1121 cm$^{-1}$. Mass Spectrum, [M/Z](relative intensity): [316](18), [283](680. Analysis: Calculated for $C_{15}H_{13}ClN_4S$: C, 56.87; H,4.14; N,17.68. Found: C, 56.93; H,4.33; N,17.25.

Example 231

4-Amino-5-bromo-6-chloro-2-(1-(3-isoquinolyl)ethyl)thio-pyrimidine (Cpd #231)

4-Amino-6-chloro-2-(1-(3-isoquinolyl)ethyl)thio-pyrimidine (475 mg, 1.5 mmole) is suspended in 15 ml methanol in a 50 ml one neck round bottom flask under nitrogen at 0° C. The suspension is treated slowly dropwise with bromine (85 μl, 1.65 mmole) and the reaction mixture is stirred 20 min at 0° C. The volatiles are removed in vacuo and the residue is partitioned between 1×50 ml dichloromethane and 1×50 ml saturated sodium carbonate followed by 1×50 ml saturated sodium thiosulfate. The organic layer is dried over potassium carbonate and is concentrated in vacuo to a white foam. Crystallization from 1:9 diethyl ether/hexane afforded 513 mg (86%) of 4-Amino-5-bromo-6-chloro-2-(1-(3-isoquinolyl)ethyl)thio-pyrimidine as a white solid.

H-NMR ($d_6$DMSO): δ 1.87 (d, J=7 Hz, 3), 5.23 (q, J=7, 14 Hz, 1), 7.39 (bs, 1), 7.71–7.77 (m, 1), 7.83–7.89 (m, 1), 8.03 (d, J=8 Hz, 1), 8.06 (s, 1), 8.18 (d, J=8 Hz, 1), 8.21 (bs, 1), 9.40 (s, 1) ppm. $^{13}$C-NMR ($d_6$DMSO): δ 21.2; 45.7; 95.4; 117.9; 126.6; 127.4; 127.4; 127.6; 130.9; 135.7; 152.5; 154.1; 157.0; 161.5; 168.0 ppm. TLC (silica gel-60, F-254): $R_f$=0.42, 40% acetone/hexane. Melting Point: 173–174° C. Ultraviolet (λ max, Ethanol), nm(ε): 207(35,100); 220(71,100); 261(18,600); 298(10,400); 325(3,300). Infrared (ν max, mineral oil): 3472, 3291, 2925, 1640, 1538, 1464, 1334, 1273, 757 cm$^{-1}$. Mass Spectrum, [M/Z](relative intensity): [394](8). Analysis: Calculated for $C_{15}H_{12}BrClN_4S$: C, 45.53; H,3.06; N,14.16. Found: C, 45.65; H,3.38; N,13.87.

Example 232

4-Amino-6-chloro-2-(1-(1-isoquinolyl)ethyl)thio-pyrimidine (Cpd #232)

Methyl magnesium bromide in ether (8.1 ml, 24.3 mmole) is dissolved in 16 ml tetrahydrofuran in an oven dried 100 ml two neck round bottom flask under nitrogen. The solution is cooled to 0° C., is diluted with 8 ml diethyl ether, and is treated with 1-isoquinoline carbonitrile (3.0 g, 19.5 mmole). The reaction is warmed to reflux for one hour, is cooled to 0° C., and is quenched with 20 ml 6 M hydrochloric acid. The reaction mixture is warmed to 50° C. for two hours, is cooled, and is poured into 75 ml 2N sodium hydroxide. The mixture is extracted with 3×80 ml ethyl acetate and the combined organics are dried over potassium carbonate. The dried organics are concentrated in vacuo to a crude amber oil. The crude material is chromatographed over 150 g silica gel (230–400 mesh), eluting with 10% acetone/hexane, while collecting 22 ml fractions. Fractions 16–26 are combined and concentrated to provide 2.1 g (62%) of 1-acetylisoquinoline.

H-NMR (CDCl$_3$, TMS): δ 2.87 (s, 3), 7.64–7.73 (m, 2), 7.80 (d, J=5.5 Hz, 1), 7.83–7.88 (m, 1), 8.58 (d, J=5.5 Hz, 1), 8.94–8.98 (m, 1) ppm. $^{13}$C-NMR (CDCl$_3$): δ 28.6; 124.6; 125.7; 126.9; 127.0; 129.1; 130.3; 137.0; 141.0; 152.8; 202.7 ppm. TLC (silica gel-60, F-254): $R_f$=0.45, 20% acetone/hexane. Infrared (ν max, liquid): 3054, 1694, 1582, 1358, 1239, 1133, 940, 833, 750 cm$^{-1}$. Mass Spectrum, [M/Z](relative intensity): [171](63). Analysis: Calculated for $C_{11}H_9NO$: C, 77.17; H,5.30; N,8.18. Found: C, 77.09; H,5.33; N,8.10.

1-Acetyl-isoquinoline (2.0 g, 11.7 mmole) is dissolved in 50 ml methanol in a 100 ml one neck round bottom flask at 0° C. The solution is treated portionwise with sodium borohydride (495 mg, 13.1 mmole) and the reaction mixture is stirred for 1 h at 0° C. The volatiles are removed in vacuo and the residue is partitioned between 1×50 ml 1N sodium hydroxide and 4×25 ml dichloromethane. The combined organics are dried over potassium carbonate and are concentrated in vacuo to a pale oil. The crude material is chromatographed over 100 g silica gel (230–400 mesh), eluting with 15% acetone/hexane, while collecting 22 ml fractions. Fractions 23–37 are combined and concentrated to afford 1.99 g (98%) of 1-(1-hydroxyethyl)-isoquinoline.

H-NMR (CDCl$_3$, TMS): δ 1.62 (d, J=6.5 Hz, 3), 5.29 (bs, 1), 5.59 (q, J=6.5 Hz, 13 Hz, 1), 7.58–7.73 (m, 3), 7.85 (d, J=8 Hz, 1), 8.04 (d, J=8 Hz, 1), 8.44 (d, J=5.7 Hz, 1) ppm. $^{13}$C-NMR (CDCl$_3$): δ 25.4; 66.0; 120.5; 124.2; 124.6; 127.3; 127.5; 130.2; 136.5; 140.4; 162.2 ppm. Melting Point: 60–62° C. Infrared (ν max, mineral oil): 3179, 2925, 1592, 1444, 1367, 1077, 751 cm$^{-1}$. Mass Spectrum, [M/Z](relative intensity): [173](24), [158](100). Analysis: Calculated for $C_{11}H_{11}NO$: C, 76.28; H,6.40; N,8.09. Found: C, 76.15; H,6.38; N,8.00.

1-(1-Hydroxyethyl)-isoquinoline (1.9 g, 11 mmole) is dissolved in 30 ml dichloromethane in a 100 ml one neck round bottom flask under nitrogen. The solution is cooled to 0° C., is treated dropwise with thionyl chloride (1.2 ml, 16.4 mmole), and is stirred 2 h at 0° C. followed by 1 h at room temperature. The mixture is recooled to 0° C., is quenched with 50 ml saturated sodium bicarbonate, and the layers are separated. The aqueous layer is extracted with 3×25 ml dichloromethane and the combined organics are dried over potassium carbonate. The dried organics are concentrated in vacuo to a brown oil. The crude material is chromatographed over 100 g silica gel (230–400 mesh), eluting with 15% acetone/hexane, while collecting 22 ml fractions. Fractions 17–26 are combined and concentrated to afford 1.99 g (94%) of 1-(1-chloroethyl)-isoquinolinel.

H-NMR (CDCl$_3$, TMS): δ 2.10 (d, J=6.7 Hz, 3), 5.93 (q, J=6.7, 13 Hz, 1), 7.61–7.72 (m, 3), 7.84 (m, 1), 8.30 (m, 1), 8.52 (d, J=5.5 Hz, 1) ppm. $^{13}$C-NMR (CDCl$_3$): δ 22.8; 54.3; 121.4; 124.5; 125.8; 127.6; 130.1; 136.7; 141.6; 158.1 ppm. TLC (silica gel-60, F-254): $R_f$=0.63, 50% acetone/hexane.

Infrared (ν max, liquid): 3054, 1624, 1584, 1563, 1376, 1224, 828, 747, 620 cm$^{-1}$. Mass Spectrum, [M/Z](relative intensity): [191](2), [156](100). Analysis: Calculated for $C_{11}H_{10}ClN$: C, 68.94; H,5.26; N,7.31. Found: C, 68.65; H,5.32; N,7.21.

4-Amino-6-chloro-2-mercapto-pyrimidine mesylate salt (1.29 g, 5 mmole) is dissolved in 8 ml dry dimethylformamide in a 50 ml one neck round bottom flask under nitrogen. The solution is treated with 60% sodium hydride (400 mg, 10 mmole) (exotherm) and the mixture is stirred 45 min. 1-(1-chloroethyl)-isoquinoline (958 mg, 5 mmole) in 2×2 ml dry dimethylformamide, is added to the reaction and the mixture is stirred overnight at room temperature. The reaction mixture is poured into 200 ml water and is extracted with 4×50 ml ethyl acetate. The combined organics are backwashed with 4×50 ml 50% saturated sodium chloride. The organics are dried over potassium carbonate and are concentrated in vacuo to a yellow oil. The crude material is chromatographed over 100 g silica gel (230–400 mesh), eluting with 25% acetone/hexane while collecting 22 ml fractions. Fractions 27–39 are combined and concentrated to given a pale yellow foam. Crystallization from diethyl ether afforded 847 mg (54%) of 4-Amino-6-chloro-2-(1-(1-isoquinolyl)ethyl)thio-pyrimidine (Cpd #232) as an off-white solid.

H-NMR (d$_6$DMSO): δ 1.79 (d, J=7 Hz, 1), 5.97 (q, J=7, 14 Hz, 1), 6.19 (s, 1), 7.39 (bs, 2), 7.64–7.76 (m, 3), 7.94 (d, J=8 Hz, 1), 8.28 (d, J=8 Hz, 1), 8.44 (d, J=5.5 Hz, 1) ppm. $^{13}$C-NMR (d$_6$DMSO): δ 21.6; 40.7; 98.8; 120.2; 124.3; 124.8; 127.5; 127.8; 130.3; 135.9; 141.5; 157.5; 159.9; 164.3; 170.1 ppm. Melting Point: 179–180° C.

Ultraviolet (λ max, Ethanol), nm(ε): 203(25,400); (27,100); 219(70,300); 236(23,800); 250(13,600); 277(10,400); 286(11,100); 295(8,430); 311(4,950); 323(5,240). Infrared (ν max, mineral oil): 3295, 3193, 2925, 1655, 1571, 1531, 1368, 1276, 1117, 825 cm$^{-1}$. Mass Spectrum, [M/Z](relative intensity) [316](14). Analysis: Calculated for $C_{15}H_{13}ClN_4S$: C, 56.87; H,4.14; N,17.68. Found: C, 56.74; H,4.22; N, 17.59.

Example 233

4-Amino-6-chloro-2-(1-(3-(5,6,7,8-tetrahydroisoquinolyl))ethyl)thiopyrimidine (Cpd #233)

3-Methyl-5,6,7,8-tetrahydroisoquinoline N-oxide (4.3 g, 26.3 mmole) is dissolved in 10 ml acetic anhydride and is added slowly dropwise to 40 ml acetic anhydride in a 100 ml one neck round bottom flask under nitrogen at 140° C. At the conclusion of the addition (20 min) the black reaction mixture is stirred for 1 h at 140° C. and the volatiles are removed under reduced pressure.

The residue is chromatographed over 150 g silica gel (230–400 mesh), eluting with 40% ethyl acetate/hexane, while collecting 22 ml fractions. Fractions 24–37 are combined and concentrated to give 2.33 g of a pale oil. The oil is dissolved 60 ml methanol in a 200 ml one neck round bottom flask. The solution is treated with potassium carbonate (3.14 g, 22.7 mmole), is stirred 1.5 h, and the volatiles are removed in vacuo. The residue is taken up in 50 ml dichloromethane, the insoluble material are removed by filtration and the filtrate is concentrated in vacuo to a yellow oil. The crude material is chromatographed over silica gel (230–400 mesh) eluting with 5.5% methanol/ dichloromethane, while collecting 9 ml fractions. Fractions 35–66 are combined and concentrated to afford 1.37 g (32%) of 3-hydroxymethyl-5,6,7,8-tetrahydroisoquinoline.

H-NMR (CDCl$_3$, TMS): δ 1.80 (m, 4), 2.73 (m, 4), 3.48 (bs, 1), 4.67 (s, 2), 6.95 (s, 1), 8.22 (s, 1) ppm. TLC (silica gel-60, F-254): R$_f$=0.16, 33% acetone/chloroform+0.6% ammonium hydroxide. $^{13}$C-NMR (CDCl$_3$): δ 22.4; 22.6; 26.0; 28.8; 64.0; 120.6; 131.8; 147.1; 149.0; 155.6 ppm. Infrared (ν max, mineral oil): 3228, 2925, 1608, 1437, 1069 cm$^{-1}$. Mass Spectrum: Calculated for $C_{10}H_{13}NO$+H: 164.1075. Found: 164.1074. Analysis, Calculated for $C_{10}H_{13}NO$: C, 73.59; H,8.03; N,8.58. Found: C, 73.53; H,8.14; N,8.52.

3-Hydroxymethyl-5,6,7,8-tetrahydroisoquinoline (1.73 g, 10.6 mmole) is dissolved in 30 ml dioxane in a 100 ml one neck round bottom flask under nitrogen. The solution is treated with selenium dioxide (647 mg, 5.8 mmole) and the reaction mixture is warmed to 80–85° C. for 1.5 h. The mixture is cooled to room temperature, is diluted with 30 ml dichloromethane and is filtered through celite. The filter cake is washed well with fresh dichloromethane and the filtrate is concentrated in vacuo to a dark amber oil. The crude material is chromatographed through a 25 g plug of silica gel (230–400 mesh), eluting with 20% acetone/hexane while collecting 50 ml fractions. Fractions 1–3 are combined and concentrated to give 1.20 g (70%) of 5,6,7,8,-tetrahydroisoquinoline-3-carbaldehyde.

H-NMR (CDCl$_3$, TMS): δ 1.86 (m, 4), 2.83 (m, 4), 7.67 (s, 1), 8.46 (s, 1), 10.02 (s, 1) ppm. $^{13}$C-NMR (CDCl$_3$): δ 8 22.1; 22.2; 26.7; 28.8; 122.2; 138.6; 147.3; 150.3; 150.9; 193.6 ppm. TLC (silica gel-60, F-254): R$_f$=0.46, 40% acetone/hexane. Melting Point: 35–36° C. Infrared (ν max, mineral oil):2925, 1709, 1592, 1434, 1217, 1128, 931, 748 cm$^{-1}$. Analysis: Calculated for $C_{10}H_{11}NO$: C, 74.51; H,6.88; N,8.69. Found: C, 74.60; H,7.03; N,8.66.

5,6,7,8,-Tetrahydroisoquinoline-3-carbaldehyde (1.2 g, 7.44 mmole) is dissolved in 15 ml tetrahydrofuran at 0° C. in an oven dried 100 ml two neck round bottom flask under nitrogen. The solution is treated with methylmagnesium bromide in diethyl ether (3.7 ml, 11.2 mmole) followed by 10 ml diethyl ether. The reaction mixture is warmed to room temperature and then to reflux for 1 h. The mixture was cooled, is quenched with 20 ml 10% hydrochloric acid, and the pH is adjusted to 9 with 2N sodium hydroxide. The layers are separated, the aqueous layer is washed with 4×25 ml dichloromethane, and the combined organics are dried over potassium carbonate. The dried organics are concentrated in vacuo to give 1.30 g (99%) of the 3-(1-hydroxyethyl)-5,6,7,8-tetrahydroisoquinoline.

H-NMR (CDCl$_3$, TMS): δ 1.47 (d, J=6.5 Hz, 3), 1.81 (m, 4), 2.72 (m, 4), 4.15 (bs, 1), 4.81 (q, J=6.5, 13 Hz, 1), 6.95 (s, 1), 8.22 (s, 1) ppm. $^1$C-NMR (CDCl$_3$): δ 22.4; 22.6; 24.3; 26.0; 28.9; 68.5; 119.7; 131.7; 147.2; 159.6 ppm. TLC (silica gel-60, F-254): R$_f$=0.12, 10% acetone/chloroform. Melting Point: 44–45° C. Infrared (ν max, mineral oil): 3341, 3098, 2925, 1604, 1434, 1142, 1108, 1077 cm$^{-1}$. Mass Spectrum, [M/Z](relative intensity): [177](2), [162](100). Analysis: Calculated for $C_{11}H_{15}NO$: C, 74.54; H,8.53; N,7.90. Found: C, 74.41; H,8.83; N,7.84.

3-(1-Hydroxyethyl)-5,6,7,8-tetrahydroisoquinoline (360 mg, 2.0 mmole) was dissolved in 4 ml dichloromethane in a 25 ml one neck round bottom flask under nitrogen. The solution is cooled to 0° C., is treated dropwise with thionyl chloride (218 μl, 3.0 mmole) in 3 ml dichloromethane, and is stirred 2 h at 0° C. followed by 1.5 h at room temperature.

The mixture is recooled to 0° C., is quenched with 20 ml saturated sodium bicarbonate, and the layers are separated. The aqueous layer is extracted with 4×10 ml dichloromethane and the combined organics are dried over potassium carbonate. The dried organics are concentrated in vacuo to an amber oil. The crude material is chromatographed over 30 g silica gel (230–400 mesh), eluting with 20% acetone/hexane, while collecting 5 ml fractions. Fractions 11–16 are combined and concentrated to afford 339 mg (87%) of 3-(1-chloroethyl)-5,6,7,8-tetrahydroisoquinoline.

H-NMR (CDCl$_3$, TMS): δ 1.81 (m, 4), 1.86 (d, J=7 Hz, 3), 2.75 (m, 4), 5.08 (q, J=7, 14 Hz,1), 7.14 (s, 1), 8.26 (s, 1) ppm. $^{13}$C-NMR (CDCl$_3$): δ 22.3; 22.5; 24.9; 26.1; 28.8; 59.1; 121.2; 132.6; 147.2; 149.7; 157.4 ppm. TLC (silica gel-60, F-254): R$_f$=0.42, 20% acetone/hexane. Infrared (ν max, liquid): 2932, 1599, 1436, 1398, 1238, 1050, 601 cm$^{-1}$. Mass Spectrum: Calculated for C$_{11}$H$_{14}$ClN+H: 196.0893. Found: 196.0896.

4-Amino-6-chloro-2-mercapto-pyrimidine mesylate salt (482 mg, 1.9 mmole) is dissolved in 4 ml dry dimethylformamide in a 25 ml one neck round bottom flask under nitrogen. The solution is treated with 60% sodium hydride (150 mg, 3.74 mmole) (exotherm) and the mixture is stirred 40 min. 3-(1-Chloroethyl)-5,6,7,8-tetrahydroisoquinoline (325 mg, 1.7 mmole) in 2×1 ml dry dimethylformamide, is added to the reaction and the mixture is stirred 3 hours at room temperature. The reaction mixture is poured into 100 ml water and is extracted with 4×25 ml ethyl acetate. The combined organics are backwashed with 4×50 ml 50% saturated sodium chloride. The organics are dried over potassium carbonate and are concentrated in vacuo to a yellow oil. The crude material is chromatographed over 25 g silica gel (230–400 mesh), eluting with 40% acetone/hexane while collecting 5 ml fractions. Fractions 15–21 are combined and concentrated to afford 335 mg of an off-white foam. Crystallization from diethyl ether provided 261 mg (48%) of 4-Amino-6-chloro-2-(1-(3-(5,6,7,8-tetrahydroisoquinolyl))ethyl)thio-pyrimidine as a white solid.

H-NMR (d$_6$DMSO): δ 1.51 (d, J=6.5 Hz, 3), 1.59 (m, 4), 2.54 (m, 4), 4.80 (q, J-6.5, 13 Hz, 1), 6.05 (s, 1), 7.04 (s, 1), 7.21 (bs, 2), 8.08 (s, 1) ppm. $^{13}$C-NMR (d$_6$DMSO): δ 21.4; 21.8; 22.1; 25.3; 28.0; 44.7; 98.6; 121.9; 131.3; 146.2; 149.6; 157.4; 164.3; 170.4 ppm. TLC (silica gel-60, F-254): R$_f$=0.55, 50% acetone/hexane. Melting Point: 155–156° C. Ultraviolet (λ max, Ethanol), nm(ε): 229(25,100); 253(12, 600); 275(8,050); 286(7,260). Infrared (ν max, mineral oil): 3303, 3156, 2925, 1641, 1571, 1535, 1462, 1368, 1283, 1124 cm$^{-1}$. Analysis: Calculated for C$_{15}$H$_{17}$ClN$_4$S: C, 56.15; H,5.34; N,17.46. Found: C, 55.94; H,5.49; N,17.35.

Example 234

4-Amino-6-trifluoromethyl-2-(1-(3-(5,6,7,8-tetrahydro-isoquinolyl))ethyl)thio-pyrimidine (Cpd #234)

The title compound is prepared according to the procedure of Example 233 except that the alkylation of 3-(1-chloroethyl)-5,6,7,8-tetrahydroisoquinoline is performed with 4-amino-6-trifluoromethyl-2-mercapto-pyrimidine mesylate salt. Melting Pt 60–161° C.

Example 235

4-Amino-6-chloro-2-(1-(1-(5,6,7,8-tetrahydroisoquinolyl))-ethyl)thiopyrimidine (Cpd #235)

5,6,7,8-Tetrahydroisoquinoline (13.3 g, 100 mmole) is dissolved in 35 ml glacial acetic acid in a 200 ml one neck round bottom flask. The solution is warmed to 95–100° C. and is treated dropwise with 30% hydrogen peroxide (28 ml). The reaction is stirred at 95–100° C. for 6h, is treated portionwise with paraformaldehyde until negative to starch iodide paper, and the volatiles are removed in vacuo. The residue is azeotroped with 2×100 ml toluene and the crude material is chromatographed over 500 g silica gel (230–400 mesh), eluting with 4 1 6% methanol/dichloromethane followed by 1 1 10% methanol/dichloromethane while collecting 50 ml fractions. Fractions 39–82 are combined and concentrated to afford 12.8 g (86%) of 5,6,7,8-tetrahydroisoquinoline-N-oxide.

H-NMR (CDCl$_3$, TMS): δ 1.77–1.97 (m, 4), 2.70 (m, 4), 6.98 (m, 1), 7.98 (m, 2) ppm. $^{13}$C-NMR (CDCl$_3$): δ 21.4; 21.8; 27.6; 28.3; 125.7; 135.7; 135.9; 137.4; 138.2 ppm. TLC (silica gel-60, F-254): R$_f$=0.39, 10% methanol/dichloromethane. Melting Point: 94–98° C. Infrared (ν max, mineral oil): 2926, 1485, 1450, 1260, 1141, 740 cm$^{-1}$. Mass Spectrum: Calculated for C$_9$H$_{11}$NO+H: 150.0919. Found: 150.0918.

5,6,7,8-Tetrahydroisoquinoline-N-oxide (12.7 g, 85 mmole) is dissolved in 250 ml dichloromethane in a 500 ml one neck round bottom flask under nitrogen. The solution is treated with trimethyloxonium tetrafluoroborate (12.6 g, 85 mmole) and the reaction is stirred 1 h at room temperature. The volatiles are removed in vacuo to a pale oily residue. The residue is dissolved in 225 ml methanol and the solution is heated to reflux. Ammonium persulfate (8 g, 34 mmole), in 34 ml water, is added rapidly dropwise to the refluxing mixture. The reaction is stirred 30 min and is treated with a second lot of ammonium persulfate (8 g, 34 mmole) in 34 ml water. The reaction is stirred an additional hour at reflux, is cooled, and the bulk of the methanol is removed in vacuo. The residue is poured into 100 ml ice containing 100 ml 10% hydrochloric acid. The mixture is washed with 2×50 ml ethyl acetate, the pH is adjusted to 9 with 45% potassium hydroxide, and the mixture is extracted with 4×50 ml dichloromethane. The haloorganics are dried over potassium carbonate and were concentrated in vacuo to a brown solid. The crude material is chromatographed over 350 g silica gel (230–400 mesh), eluting with 3 1 20% acetone/chloroform+ 0.6% conc. ammonium hydroxide followed by 1 1 32% acetone/chloroform+0.6% conc. ammonium hydroxide, while collecting 50 ml fractions. Fractions 19–27 are combined and concentrated to afford 4.3 g (31%) of 1-hydroxymethyl-5,6,7,8-tetrahydroisoquinoline.

H-NMR (CDCl$_3$, TMS): δ 1.83 (m, 4), 2.50 (m, 2), 2.76 (m, 2), 4.60 (s, 1), 4.95 (bs,1), 6.94 (d, J=5 Hz, 1), 8.24 (d, J=5 Hz, 1) ppm. $^{13}$C-NMR (CDCl$_3$): δ 21.8; 22.1; 23.0; 28.9; 60.9; 122.9; 128.7; 143.8; 146.3; 155.6 ppm. TLC (silica gel-60, F-254): R$_f$=0.50, 33% acetone/chloroform+ 0.6% ammonium 100 hydroxide. Melting Point: 81–82° C. Infrared (ν max, mineral oil): 3325, 2925, 1595, 1459, 1426, 1397, 1074, 839 cm$^{-1}$. Mass Spectrum, [M/Z](relative intensity): [163](93). Analysis: Calculated for C$_{10}$H$_{13}$NO: C, 73.59; H,8.03; N,8.58. Found: C, 73.77; H,7.89; N,8.69.

1-Hydroxymethyl-5,6,7,8-tetrahydroisoquinoline (4.14 g, 25.4 mmole) is dissolved in 75 ml dioxane in a 200 ml one neck round bottom flask under nitrogen. The solution is treated with selenium dioxide (1.56 g, 14.0 mmole) and the reaction mixture is warmed to 80–85° C. for 2.5 h. The mixture is cooled to room temperature, is diluted with 125 ml dichloromethane and is filtered through celite. The filter cake is washed well with fresh dichloromethane and the filtrate is concentrated in vacuo to an amber oil. The crude material is chromatographed over 200 g silica gel (230–400 mesh), eluting with 1:5:4 acetone/chloroform/hexane while collecting 50 ml fractions. Fractions 11–18 are combined and concentrated to give 3.69 g (90%) of 5,6,7,8,-tetrahydroisoquinoline-1-carbaldehyde.

H-NMR (CDCl$_3$, TMS): δ 1.81 (m, 4), 2.84 (m, 2), 3.19 (m, 2), 7.18 (d, J=4.7 Hz, 1), 8.49 (d, J=4.7 Hz, 1), 10.18 (s, 1) ppm. $^{13}$C-NMR (CDCl$_3$): δ 21.5; 22.3; 25.3; 29.5; 127.6; 135.9; 146.4; 148.4; 149.6; 195.8 ppm. TLC (silica gel-60, F-254): R$_f$=0.62, 50% acetone/hexane. Infrared (ν max, mineral oil): 2928, 1710, 1581, 1464, 846 cm$^{-1}$. Mass Spectrum: Calculated for C$_{10}$H$_{11}$NO+H: 162.0919. Found: 162.0921.

Methylmagnesium bromide in diethyl ether (9.3 ml, 28 mmole) is dissolved in 10 ml tetrahydrofuran at 0° C. in an oven dried 100 ml two neck round bottom flask under nitrogen. The solution is treated with 5,6,7,8,-Tetrahydroisoquinoline-1-carbaldehyde (3.61 g, 22.4 mmole) followed by 10 ml diethyl ether. The reaction mixture is warmed to room temperature and then to reflux for 1 h. The mixture is cooled, is quenched with 20 ml 10% hydrochloric acid, and the pH is adjusted to 9 with 2N sodium hydroxide. The layers are separated, the aqueous layer is washed with 4×50 ml dichloromethane, and the combined organics are dried over potassium carbonate. The dried organics are concentrated in vacuo to give 3.47 g (87%) of 1-(1-hydroxyethyl)-5,6,7,8-tetrahydroisoquinoline.

H-NMR (CDCl$_3$, TMS): δ 1.38 (d, J=6.5 Hz, 3), 1.73–1.97 (m, 4), 2.52–2.80 (m, 4), 4.92 (q, J=6.5, 13 Hz, 1), 6.92 (bs, 1), 6.91 (d, J=5 Hz, 1), 8.21 (d, J=5 Hz, 1) ppm. $^{13}$C-NMR (CDCl$_3$): δ 22.0; 22.6; 23.7; 24.5; 29.3; 65.4; 123.3; 128.5; 144.4; 147.0; 160.6 ppm. TLC (silica gel-60, F-254): R$_f$=0.54, 50% acetone/hexane. Melting Point: 60–61° C. Infrared (ν max, mineral oil): 3053, 2923, 1590, 1457, 1401, 1118, 838 cm$^{-1}$. Mass Spectrum, [M/Z](relative intensity): [177](26), [162](100). Analysis: Calculated for C$_{11}$H$_{15}$NO: C, 74.54; H,8.53; N,7.90. Found: C, 74.45; H,8.42; N,7.83.

1-(1-Hydroxyethyl)-5,6,7,8-tetrahydroisoquinoline (1.77 g, 10 mmole) is dissolved in 30 ml dichloromethane in a 100 ml one neck round bottom flask under nitrogen. The solution is cooled to 0° C., is treated dropwise with thionyl chloride (1.1 ml, 15 mmole) in 5 ml dichloromethane, and is stirred 2 h at 0° C. followed by 1 h at room temperature. The mixture is recooled to 0° C., is quenched with 50 ml saturated sodium bicarbonate, and the layers are separated. The aqueous layer is extracted with 3×25 ml dichloromethane and the combined organics are dried over potassium carbonate. The dried organics are concentrated in vacuo to a yellow oil. The crude material is chromatographed over 50 g silica gel (230–400 mesh), eluting with 10% acetone/hexane, while collecting 9 ml fractions. Fractions 10–24 are combined and concentrated to afford 1.96 g (100%) of 1-(1-chloroethyl)-5,6,7,8-tetrahydroisoquinoline.

H-NMR (CDCl$_3$, TMS): δ 1.68–1.94 (m, 7), 2.68–3.01 (m, 4), 5.32 (q, J=6.5, 13 Hz, 1), 6.93 (d, J=5 Hz, 1), 8.31 (d, J=5 Hz, 1) ppm. $^{13}$C-NMR (CDCl$_3$): δ 21.8; 22.6; 22.8; 24.6; 29.4; 54.3; 124.1; 130.4; 145.7; 147.2; 157.1 ppm. TLC (silica gel-60, F-254): R$_f$=0.65, 20% acetone/hexane. Infrared (ν max, liquid): 2932, 1586, 1435, 1042, 844, 654 cm$^{-1}$. Mass Spectrum, [M/Z](relative intensity): [160](100). Analysis: Calculated for C$_{11}$H$_{14}$ClN: C, 67.52; H,7.21; N,7.16. Found: C, 67.12; H,7.16; N,6.99.

4-Amino-6-chloro-2-mercapto-pyrimidine mesylate salt (1.29 g, 5 mmole) is dissolved in 8 ml dry dimethylformamide in a 50 ml one neck round bottom flask under nitrogen. The solution is treated with 60% sodium hydride (400 mg, 10 mmole) (exotherm) and the mixture is stirred 1 h. 1-(1-Chloroethyl)-5,6,7,8-tetrahydroisoquinoline (978 mg, 5 mmole) in 2×2 ml dry dimethylformamide, is added to the reaction and the mixture is stirred overnight at room temperature. The reaction mixture is poured into 300 ml water and is extracted with 4×50 ml ethyl acetate. The combined organics are backwashed with 4×50 ml 50% saturated sodium chloride. The organics are dried over potassium carbonate and are concentrated in vacuo to a yellow foam. The crude material is chromatographed over 100 g silica gel (230–400 mesh), eluting with 30% acetone/hexane while collecting 22 ml fractions. Fractions 18–24 are combined and concentrated to afford a white foam.

Crystallization from diethyl ether provided 945 mg (59%) of 4-Amino-6-chloro-2-(1-(1-(5,6,7,8-tetrahydroisoquinolyl))ethyl)thio-pyrimidine as a white solid.

H-NMR (d$_6$DMSO): δ 1.67–1.85 (m, 7), 2.73–2.97 (m, 4), 5.24 (q, J=6.5, 13 Hz, 1), 6.22 (s, 1), 7.01 (d, J=5 Hz, 1), 7.36 (bs, 1), 8.24 (d, J=5 Hz, 1) ppm. $^{13}$C-NMR (d$_6$DMSO): δ 21.4; 21.5; 21.6; 22.5; 24.5; 41.2; 98.9; 123.3; 129.6; 145.5; 146.6; 157.6; 158.6; 164.5; 171.0 ppm. TLC (silica gel-60, F-254): R$_f$=0.46, 50% acetone/hexane. Melting Point: 186–187° C. Ultraviolet (λ max, Ethanol), nm(ε): 229(23,600); 257(11,900); 265(10,800); 273(9,690); 285(7, 840). Infrared (ν max, mineral oil): 3280, 3138, 2931, 1661, 1573, 1532, 1366, 1275, 1113, 829 cm$^{-1}$. Mass Spectrum, [M/Z](relative intensity): [320](18), [283](26), [160](100). Analysis: Calculated for C$_{15}$H$_{17}$ClN$_4$S: C, 56.15; H,5.34; N,17.46. Found: C, 56.30; H,5.65; N,17.09.

Example 236

4-Amino-5-bromo-6-chloro-2-(1-(1-(5,6,7,8-tetrahydroisoquinolyl))ethyl)thio-pyrimidine (Cpd #236)

1-[(4-Amino-6-chloro-pyrimidin-2-yl)]thio-1-(1-(5,6,7, 8-tetrahydroisoquinolyl)-ethane (400 mg, 1.25 mmole) is suspended in 6 ml methanol in a 25 ml one neck round bottom flask under nitrogen at 0° C. The suspension is treated slowly dropwise with bromine (74 μl, 1.44 mmole) and the reaction mixture is stirred 20 min at 0° C. The volatiles are removed in vacuo and the residue is partitioned between 4×25 ml dichloromethane and 1×25 ml saturated sodium carbonate. The organic layer is dried over potassium carbonate and is concentrated in vacuo to a pale yellow foam. The crude material is chromatographed over 25 g silica gel (230–400 mesh) eluting with 30% acetone/hexane while collecting 5 ml fractions. Fractions 17–24 are combined and concentrated to give 379 mg of a pale foam. Crystallization from hexane afforded 325 mg (65%) of 4-Amino-5-bromo-6-chloro-2-(1-(1-(5,6,7,8-terahydroisoquinolyl))ethyl)thio-pyrimidine as an off-white solid.

H-NMR (d$_6$DMSO): δ 1.72–1.91 (m, 7), 2.69–2.77 (m, 3), 3.04–3.14 (m, 1), 5.5 (q, J=6.5, 13 Hz, 1), 5.96 (bs, 2), 6.87 (d, J=5 Hz, 1), 8.27 (d, J=5 Hz, 1) ppm. $^{13}$C-NMR (d$_6$DMSO): δ 20.8; 21.8; 22.8; 24.8; 29.5; 42.0; 96.4; 123.0; 129.9; 145.6; 146.7; 158.0; 158.8; 160.8; 169.5 ppm. TLC (silica gel-60, F-254): R$_f$=0.53, 50% acetone/hexane. Melting Point: 175–176° C. Ultraviolet (λ max, Ethanol), nm(ε): 230(20,700); 265(15,600); 297(9,290). Infrared (ν max, mineral oil): 3482, 3283, 2922, 1632, 1537, 1520, 1459, 1339, 1274, 845 cm$^{-1}$ Mass Spectrum, [M/Z](relative intensity): [398](13). Analysis: Calculated for $C_{15}H_{16}ClBrN_4S$: C, 45.07; H,4.03; N,14.02. Found: C, 45.03; H,4.10; N,19.94.

Example 237

4-Amino-6-chloro-2-(1-(7-chlorofuro[2,3c]pyridine-5-yl)ethyl)thio-pyrimidine (Cpd #237)

2-Chloro-3-pyridinol (60 g, 0.46 mole) is dissolved in 700 ml water containing potassium carbonate (220 g, 1.6 mole) in a 21 one neck round bottom flask. The solution is treated with iodine (141 g, 0.56 mole) and the reaction is stirred 4 h at room temperature. The excess iodine is quenched with saturated sodium thiosulfate and the pH of the mixture is adjusted to 2 with 12 N hydrochloric acid. The mixture is extracted with 3×250 ml ethyl acetate. The combined organics are dried over magnesium sulfate and are concentrated in vacuo to a yellow solid. The crude solid is recrystallized from 150 ml ethyl acetate and 700 ml heptane to give 69 g (58%) of 2-chloro-3-hydroxy-6-iodo-pyridine. The mother liquor is concentrated to a yellow solid which is recrystallized from 60 ml ethyl acetate and 370 ml heptane to provide 15.5 g (13%).

H-NMR (d$_6$DMSO): δ 6.90 (d, J=8 Hz, 1); 7.43 (d, J=8 HZ, 1), 10.87 (bs, 1) ppm. $^{13}$C-NMR (d$_6$DMSO): δ 100.7; 126.5; 134.5; 137.6; 150.2 ppm. Melting Point: 142–143° C. Infrared (ν max, mineral oil): 3056, 2925, 1554, 1457, 1398, 1289, 1226, 1086 cm$^{-1}$. Mass Spectrum, [M/Z](relative intensity): [255](80). Analysis: Calculated for $C_5H_3ClINO$: C, 23.51; H,1.18; N,5.48. Found: C, 23.44; H,1.22; N,5.39. A flame dried 500 ml three neck round bottom flask under nitrogen is charged with 100 ml tetrahydrofuran and butyllithium (82 ml, 132 mmole). The solution is cooled to –78° C., is treated dropwise with 2-chloro-3-hydroxy-6-iodopyridine (15.3 g, 60 mmole) in 100 ml dry tetrahydrofuran, and is stirred 1 h at –78° C. The mixture is treated dropwise with acetaldehyde (7.4 ml, 132 mmole) and is stirred 1 h at –78° C. and then is allowed to slowly ramp to –40° C. The reaction is quenched with 100 ml water and the layers are separated.
The pH of the aqueous layer is adjusted to 3.5 with 10% hydrochloric acid and the mixture is extracted with 4×50 ml ethyl acetate. The combined organics are dried over potassium carbonate and are concentrated in vacuo to a crude white solid. The crude material is adsorbed onto 25 g silica gel (230–400 mesh) and this plug is chromatographed over 500 g silica gel (230–400 mesh), eluting with 50% ethyl acetate/hexane, while collecting 50 ml fractions. Fractions 58–92 are combined and concentrated to give 4.75 g (46%) of 2-chloro-3-hydroxy-6-(1-hydroxyethyl)-pyridine H-NMR (d$_6$DMSO): δ 1.10 (d, J=6.5 Hz, 3), 4.40 (m, 1), 5.10 (d, J=4.5 Hz, 1), 7.12 (s,2), 10.27 (s, 1) ppm. $^{13}$C-NMR (d$_6$DMSO): δ 24.0; 68.4; 119.6; 124.6; 136.2; 147.9; 156.0 ppm. TLC (silica gel-60, F-254): R$_f$=0.26, 50% ethyl acetate/hexane. Melting Point: 89–92° C.,d. Infrared (ν max, mineral oil): 3334, 2925, 2569, 1558, 1090, 840, 761 cm$^{-1}$. Mass Spectrum, [M/Z](relative intensity): [173](12). 2-Chloro-3-hydroxy-6-(1-hydroxyethyl)-pyridine (4.5 g, 23.6 mmole) is suspended in 70 ml water in a 200 ml one neck round bottom flask. The suspension is treated successively with potassium carbonate (6.5 g, 47.2 mmole) and iodine (12.0 g, 47.2 mmole) and the reaction mixture is stirred 4 h at room temperature. The excess iodine is quenched with saturated sodium thiosulfate and the pH of the reaction mixture is adjusted to 3 with 10% hydrochloric acid. The solid is collected, washed with water, and is taken up in ethyl acetate. The organic layer is dried over magnesium sulfate and is concentrated in vacuo to a yellow solid. The solid is washed with chloroform and is dried to provide 4.4 g (62%) of 2-chloro-3-hydroxy-4-iodo-6-(1-hydroxyethyl)-pyridine.

H-NMR (d$_6$DMSO): δ 1.10 (d, J=6.5 Hz, 3), 4.38 (q, J=6.5, 13 Hz, 1), 5.22 (bs 1), 7.59 (s, 1), 10.2 (bs, 1) ppm. $^{13}$C-NMR (d$_6$DMSO): δ 24.0; 68.1; 100.1; 129.6; 136.3; 148.1; 157.7 ppm TLC (silica gel-60, F-254): R$_f$=0.24, 50% ethyl acetate/hexane. Melting Point: 114–116° C.,d. Infrared (ν max, mineral oil): 3078, 2926, 1669, 1537, 1458, 1377, 1256, 1075, 874 cm$^{-1}$. Mass Spectrum, [M/Z](relative intensity): [299](16). Analysis: Calculated for $C_7H_7ClINO_2$: C, 28.07; H,2.36; N,4.68. Found: C, 27.96; H,2.28; N,4.55. 2-Chloro-3-hydtoxy4-iodo-6-(1-hydroxyethyl)-pyridine (6.2 g, 20.7 mmole) is dissolved in 60 ml chloroform in a 250 ml one neck round bottom flask under nitrogen. The solution is diluted with 60 ml triethylamine and is treated with trimethylsilyl acetylene (3.2 ml, 22.8 mmole) followed by bis (triphenylphosphine) palladium dichloride (435 mg, 0.62 mnole) and cuprous iodide (59 mg, 0.31 mmole). The reaction is stirred 4 h at room temperature, the volatiles are removed in vacuo, and the residue is diluted with 50 ml water. The pH of the mixture is adjusted to 2.5 with 5% hydrochloric acid and the mixture is extracted with 4×50 ml ethyl acetate. The combined organics are dried over magnesium sulfate and are concentrated in vacuo to an amber oil. The crude material is chromatographed over 150 g silica gel (230–400 mesh), eluting with 30% ethyl acetatehexane while collecting 22 ml fractions. Fractions 21–44 are combined and concentrated to afford 3.82 g (67%) of 2-chloro-3-hydroxy-6-(1-hydroxyethyl)-4-trimethylsilylethynyl-pyridine.

H-NMR (CDCl$_3$, TMS): δ 0.20 (s, 9), 1.39 (d, J=6.5 Hz, 3), 2.77 (bs, 1), 4.71 (q, J=6.5, 13 Hz, 1), 6.07 (bs, 1), 7.16 (s, 1) ppm. $^{13}$C-NMR (CDCl$_3$TMS): δ-2; 23.8; 68.8; 96.2; 107.0; 119.6; 121.3; 137.1; 147.6; 154.8 ppm. TLC (silica gel-60, F-254): R$_f$=0.49, 50% ethyl acetate/hexane. Melting Point: 97–98° C. Infrared (ν max, mineral oil): 3155, 2924, 2162, 1598, 1461, 1323, 1253, 1198, 1081, 959 cm$^{-1}$. Mass Spectrum, [M/Z](relative intensity): [2693](14). Analysis: Calculated for $C_{12}H_{16}ClNO_2Si$: C, 53.32; H,5.99; N,5.18@ 0.18% water found. Found: C, 52,85; H,6.99; N,5.02.

2-Chloro-3-hydroxy-6-(1-hydroxyethyl)-4-timethylailylethnyl-pyrdine (3.82 g, 14.2 mmole) is dissolved in 125 ml tetrahydrofuran in a 200 ml one neck round bottom flask under nitrogen. The solution is cooled to 0° C. is treated with mercuric trifluoroacetate (8.2 g. 19.1 mnmole), and is stirred 20 min at 0° C. The reaction is stirred 1 h at room temperature, is diluted with 75 ml saturated sodium chloride, and the aixe is stirred vigorously for 1 h. The pH of the mixture is adjusted to 8 with 2N sodiun hydroaxde and the layers are separated. The aqueous layer is extracted with 4×50 ml 10% methanol/dichloromethaune, the combined organics are dried over magnesium sulfate and are concentrated in vacua to a yellow foam. Crystlization from ether provided 5.69 g of crude intermediate mercuriochoride. The crude solid is dissved in 77 ml ethanol in a 200 ml one neck round bottom flask under nitrogen at 50° C. The solution is treated with triethylsilane (4.9 ml, 30.6 mmole) and the reaction mixture is stirred 30 min at room temperature. The reaction is filtered through celite and the filter cake is washed well with 1:1 methanol/dichloromethane. The filtrate is concentrated in vacuo to a yellow oil which is partitioned between 1×75 ml saturated sodium bicarbonate and 4×25 ml dichloromethane. The combined organics are dried over potassium carbonate and concentrated in vacuo to a yellow oil. The crude material is chromatographed over 125 g silica gel (230–400 mesh) eluting with 25% ethyl acetate/hexane while collecting 22 ml fractions. Fractions 18–33 are combined and concentrated to give 1.93 g (50%) of 7-chloro-5-(1-hydroxyethyl)-2-trimethylsilyl-[2,3c]pyridine.

H-NMR (CDCl$_3$, TMS): δ 0.40 (s, 9), 1.53 (d, J=6.5 Hz, 3), 3.45 (bs, 1), 4.9 (q, J=6.5, 13 Hz, 1), 6,98 (s, 1), 7.46 (8.1) ppm. $^{13}$C-NMR (CDCl$_3$): δ-1.6; 24.5; 69.5; 110.8; 115.8; 132.6; 137.3; 149.8; 156,6; 170.1 ppm. TLC (silica gel-60, F-254): R$_f$=0.29, 50% ethyl acetate/hexane. Infrared (ν max, mineral oil): 3319, 2924, 1607, 1566, 1255, 1296, 1143, 1078, 901 cm$^{-1}$. Mass Spectrum, [M/Z](realtive intensity): [269](3). Preparation of 7-chloro-5-(1-hydroxyethyl1-furo[2,3c]pyridine.

Method A:

A solution of 2-chloro-3-hydroxy-6-(-hydroxyethyl) 4trimethylsilylethynyl-pyridine (2.16 g, 8 mmol) in 32 mL of 1:1 triethylamine/ethanol was treated with cuprous iodide (76 mg, 0.4 mmol) and the reaction was stirred for 2 h at 75° C. The mixture was diluted with 32 mL of methanol and treated with 16 mL of 2N sodium hydroxide. The mixture was stirred for 25 min at 75° C., cooled, and the volatiles were removed in vacuo. The residue was dissolve in 50 mL of methanol, treated with DARCO, and was refluxed for 20 min. The mixture was filtered through celite and the cake was washed well with methanol. The filtrate was concentrated in vacuo and the crude material was chromatographed over 150 g of silica gel (230–400 mesh), eluting with 35% ethyl acetate/hexanes to provide 1.33 g (82%) of 7-chloro-5-(1-hydroxyethyl)-furo[2,3c]pyridine.

Method B:

7-Chloro-5-(1-hydroxyethyl)-2-trimethylsilyl-furo[2,3c]pyridine (809 mg, 3.0 mmole) was dissolved in 18 ml absolute ethanol in a 100 ml one neck round bottom flask. The solution is treated with 2N sodium hydroxide (6 ml, 12 mmole) and the reaction mixture is stirred 45 min at room temperature. The bulk of the ethanol is removed under reduced pressure and the residue is partitioned between 1×25 ml 50% saturated sodium chloride and 4×25 ml dichloromethane. The combined organics are dried over potassium carbonate and are concentrated in vacuo to provide 542 mg (92%) of 7-chloro-5-(1-hydroxyethyl)-furo[2,3c]pyridine.

H-NMR (CDCl$_3$, TMS): δ 1.54 (d, J=6.5 Hz, 3), 3.55 (bs, 1), 4.97 (q, J=6.5, 13 Hz, 1), 6.84 (d, J=2 Hz, 1), 7.53 (s, 1), 7.81 (d, J=2 Hz, 1) ppm. $^{13}$C-NMR (CDCl$_3$): δ 24.4; 69.5; 107.2; 111.3; 132.8; 136.8; 146.8; 149.2; 157.3 ppm. TLC (silica gel-60, F-254): R$_f$=0.35, 50% ethyl acetate/hexane. Melting Point: 71–73° C. Infrared (ν max, mineral oil): 3205, 2925, 1611, 1572, 1445, 1342, 1122, 1034, 985 cm$^{-1}$ Mass Spectrum, [M/Z](relative intensity): [197](3). Analysis: Calculated for C$_9$H$_8$ClNO$_2$: C, 54.70; H,4.08; N,7.09. Found: C, 54.46; H,4.01; N,7.04.

7-Chloro-5-(1-hydroxyethyl)-furo[2,3c]pyridine (510 mg, 2.58 mmole) is dissolved in 5 ml dichloromethane in a 25 ml one neck round bottom flask under nitrogen. The solution is cooled to 0° C., is treated with thionyl chloride (281 μl, 3.87 mmole) in 2 ml dichloromethane, and the reaction is stirred 30 min at 0° C. followed by 1 h at room temperature. The reaction is quenched with 1×10 ml saturated sodium bicarbonate, the layers are separated and the aqueous layer is extracted with 3×10 ml dichloromethane. The combined organics are dried over potassium carbonate and are concentrated in vacuo to give 525 mg (94%) of 7-chloro-5-(1-chloroethyl)-furo[2,3c]pyridine.

H-NMR (CDCl$_3$, TMS): δ 1.91 (d, J=6.5 Hz, 3), 5.24 (q, J=6.5, 13 Hz, 1), 6.88 (d, J=2 Hz, 1), 7.70 (s, 1), 7.82 (d, J=2 Hz, 1) ppm. $^{13}$C-NMR (CDCl$_3$): δ 25.4; 58.4; 107.3; 113.2; 133.1; 136.7; 147.2; 149.3; 154.1 ppm. TLC (silica gel-60, F-254): R$_f$=0.65, 50% ethyl acetate/hexane. Infrared (ν max, liquid): 2981, 1610, 1571, 1451, 1316, 1137, 1031, 866 cm$^{-1}$. Mass Spectrum, [M/Z](relative intensity): [215](6). Analysis: Calculated for C$_9$H$_7$Cl$_2$NO: C, 50.03; H,3.27; N,6.48. Found: C, 50.27; H,3.23; N,6.34.

4-Amino-6-chloro-2-mercapto-pyrimidine mesylate salt (565 mg, 2.2 mmole) is dissolved in 4 ml dry dimethylformamide in a 25 ml one neck round bottom flask under nitrogen. The solution is cooled to 0° C., is treated with 60% sodium hydride (175 mg, 4.38 mmole) and the mixture is stirred 1 h at room temperature. 7-Chloro-5-(1-chloroethyl)-furo[2,3c]-pyridine (474 mg, 2.2 mmole) in 2×1 ml dry dimethylformamide, is added to the reaction and the mixture is stirred overnight at room temperature. The reaction mixture is diluted with 1×50 ml diethyl ether and the organic layer is washed with 4×25 ml 50% saturated sodium chloride. The organics are dried over potassium carbonate and are concentrated in vacuo to a yellow oil. The crude material is chromatographed over 30 g silica gel (230–400 mesh), eluting with 35% ethyl acetate/hexane while collecting 9 ml fractions. Fractions 12–24 are combined and concentrated to afford a 484 mg of a pale foam. Crystallization from diethyl ether provided 457 mg (61%) of 4-Amino-6-chloro-2-(1-(7-chlorofuro[2,3c]pyridine-5-yl)ethyl)thio-pyrimidine (Cpd #237) as a white solid.

H-NMR (d$_6$DMSO): δ 1.49 (d, J=6.5 Hz, 3), 4.89 (q, J=6.5, 13 Hz, 1), 5.97 (s, 1), 6.92 (d, J=2 Hz, 1), 7.16 (bs, 2), 7.65 (s, 1), 8.12 (d, J=2 Hz, 1) ppm. $^{13}$C-NMR (d$_6$DMSO): δ 21.5; 44.5; 99.0; 107.8; 115.0; 131.9; 137.0; 146.2; 151.2; 154.6; 157.6; 164.5; 170.2 ppm. TLC (silica gel-60, F-254): R$_f$=0.34, 50% ethyl acetate/hexane Melting Point: 156° C. Ultraviolet (λ max, Ethanol), nm(ε): 212(36, 800); 230(27,000); 249(18,000); 285(12,000). Infrared (ν max, mineral oil): 3471, 3152, 2926, 1649, 1537, 1441, 1365, 1286, 1117, 864 cm$^{-1}$. Mass Spectrum, [M/Z](relative intensity): [340](41). Analysis: Calculated for C$_{13}$H$_{10}$Cl$_2$N$_4$OS: C, 45.76; H,2.95; N,16.42. Found: C, 45.71; H,2.75; N,16.45.

Example 238

4-Amino-6-chloro-2-(1-(furo[2,3-c]pyridin-5-yl) ethyl)thio-pyrimidine (Cpd #238)

7-Chloro-5-(1-hydroxyethyl)-furo[2,3c]pyridine (1.1 g, 4.1 mmole) is dissolved in 10 ml ethanol in a 50 ml one neck round bottom flask under nitrogen. The solution is treated with 20% palladium hydroxide on carbon (820 mg) followed by cyclohexene (4.05 ml, 40.8 mmole) and the reaction mixture is heated to reflux for 3.5 h. The reaction is filtered through celite and the filter cake is washed with 16 ml ethanol. The filtrate is diluted with 2N sodium hydroxide (8 ml, 16 mmole) and the reaction mixture is stirred 1 h at room temperature. The ethanol is removed under reduced pressure and the residue is partitioned between 1×50 ml 50% saturated sodium chloride and 4×25 ml dichloromethane. The combined organics are dried over potassium carbonate and are concentrated in vacuo to a colorless oil. The crude material is chromatographed over 25 g silica gel (230–400 mesh), eluting with 70% ethyl acetate/hexane while collecting 9 ml fractions. Fractions 11024 are combined and concentrated to give 504 mg (76%) of 5-(1-hydroxyethyl)-furo[2,3c]pyridine.

H-NMR (CDCl$_3$, TMS): δ 1.55 (d, J=6.5 Hz, 3), 4.19 (bs, 1), 5.01 (q, J=6.5, 13 Hz, 1), 6.78 (d, J=2 Hz, 1), 7.56 (s, 1), 7.76 (d, J=2 Hz, 1), 8.76 (s, 1) ppm. $^{13}$C-NMR (CDCl$_3$): δ 24.7; 69.6; 106.1; 111.8; 132.0; 135.0; 148.8; 151.4; 156.5 ppm. TLC (silica gel-60, F-254): R$_f$=0.18, 50% ethyl acetate/hexane. Infrared (υ max, liquid): 3355, 2973, 1614, 1465, 1280, 1130, 1096, 1034, 880 cm$^{-1}$. Mass Spectrum, [M/Z](relative intensity): [163](2).

5-(1-Hydroxyethyl)-furo[2,3c]pyridine (450 mg, 2.76 mmole) is dissolved in 6 ml dichloromethane in a 25 ml one neck round bottom flask under nitrogen. The solution is cooled to 0° C., is treated with thionyl chloride (300 μl, 4.14 mmole) in 2 ml dichloromethane, and the reaction is stirred 20 min at 0° C. followed by 1 h at room temperature. The reaction is quenched with 1×10 ml saturated sodium bicarbonate, the layers are separated and the aqueous layer is extracted with 3×10 ml dichloromethane. The combined organics are dried over potassium carbonate and are concentrated in vacuo to give 478 mg (96%) of 5-(1-chloroethyl)-furo[2,3c]pyridine.

H-NMR (CDCl$_3$, TMS): δ 1.94 (d, J=6.5 Hz, 3), 5.30 (q, J=6.5, 13 Hz, 1), 6.81 (d, J=2 Hz, 1), 7.73 (s, 1), 7.78 (d, J=2 Hz, 1), 8.84 (s, 1) ppm. $^{13}$C-NMR (CDCl$_3$): δ 25.4; 59.3; 106.3; 113.6; 133.0; 134.9; 148.8; 151.5; 153.8 ppm. TLC (silica gel-60, F-254): R$_f$=0.55, 50% ethyl acetate/hexane. Infrared (υ max, liquid): 2980, 1610, 1462, 1303, 1127, 1033, 760 cm$^{-1}$. Mass Spectrum, [M/Z](relative intensity): [181](4). Analysis: Calculated for C$_9$H$_8$ClNO: C, 59.32; H,4.46; N,7.69@0.34% water found. Found: C, 59.05; H,4.39; N,7.58.

4-Amino-6-chloro-2-mercapto-pyrimidine mesylate salt (602 mg, 2.3 mmole) is dissolved in 4 ml dry dimethylformamide in a 25 ml one neck round bottom flask under nitrogen. The solution is cooled to 0° C., is treated with 60% sodium hydride (186 mg, 4.66 mmole) and the mixture is stirred 1 h at room temperature. 5-(1-chloroethyl)-furo[2,3c]pyridine (424 mg, 2.3 mmole) in 2×1 ml dry dimethylformamide, is added to the reaction and the mixture is stirred overnight at room temperature. The reaction mixture is diluted with 1×50 ml diethyl ether and the organic layer is washed with 4×25 ml 50% saturated sodium chloride. The organics are dried over potassium carbonate and are concentrated in vacuo to a yellow oil. The crude material is chromatographed over 30 g silica gel (230–400 mesh), eluting with 50% ethyl acetate/hexane while collecting 9 ml fractions. Fractions 14–24 are combined and concentrated to afford a 509 mg of a pale foam. Crystallization from diethyl ether provided 432 mg (60%) of 4-Amino-6-chloro-2-(1-(furo[2,3-c]pyridin-5-yl)ethyl)thio-pyrimidine (Cpd #238) as a white solid.

H-NMR (d$_6$DMSO): δ 1.66 (d, J=6.5 Hz, 3), 5.08 (q, J=6.5, 13 Hz, 1), 6.11 (s, 1) 6.96 (d, J=2 Hz, 1), 7.29 (bs, 2), 7.74 (s, 1), 8.16 (d, J=2 Hz, 1), 8.84 (s, 1) ppm. $^{13}$C-NMR (d$_6$DMSO): δ 21.9; 44.9; 98.6; 106.3; 114.2; 132.9; 134.3; 149.8; 150.7; 153.7; 157.4; 164.2; 170.4 ppm. TLC (silica gel-60, F-254): R$_f$=0.20, 50% ethyl acetate/hexane. Melting Point: 187–188° C. Ultraviolet (λ max, Ethanol), nm(ε): 231(26,000); 248(18,900); 281(10,200); 287(10,300); 296 (6,340). Infrared (υ max, mineral oil): 3453, 2925, 1640, 1567, 1532, 1467, 1370, 1284, 821 cm$^{-1}$. Mass Spectrum, [M/Z](relative intensity): [306](8). Analysis: Calculated for C$_{13}$H$_{11}$ClN$_4$OS: C, 50.90; H,3.61; N,18.26. Found: C, 50.82; H,3.66; N,18.28.

Example 239

4-Amino-6-trifluoromethyl-2-(1-(furo[2,3-c]pyridin-5-yl)ethyl)thio-pyrimidine (Cpd #239)

The title compound is prepared according to the procedure described for 4-amino-6-chloro-2-(1-(furo[2,3c]pyridine-7-yl)ethyl)thio-pyrimidine except that the alkylation of 7-(1-chloroethyl)-furo[2,3c]pyridine is preformed with 4-amino-6-trifluoromethyl-2-mercapto-pyrimidine (Example 238). Melting Pt 180–181.5° C.

Example 242

4-Amino-6-chloro-2-(1-(2-methylfuro[2,3c]pyridine-5-yl)ethyl)thio-pyrimidine (Cpd #242)

2-Chloro-3-hydroxy-4-iodo-6-(1-hydroxyethyl)-pyridine (3.60 g, 12 mmol) and propargyl trimethylsilane (2.5 mL, 16.8 mmol) arecombined with cuprous oxide (930 mg, 6.5 mmol) in 20 mL of pyridine in a screw cap pressure tube. The reactioni as heated to 110° C. for 9 h, cooled to room temperature, and the volatiles are removed in vacuo. The residue is diluted with 50 mL of ethyl acetate, filtered through celite, and the filtrate is concentrated in vacuo. The crude material is chromatographed over 125 g of silica gel (230–400 mesh), eluting with 25% ethyl acetate/hexanes to give 1.21 g (48%) of 7-chloro-5-(1-hydroxyethyl)-2-methyl-furo[2,3c]pyridine (Melting point 77–79° C.).

A solution of 7-chloro-5-(1-hydroxyethyl)-2-methyl-furo[2,3c]pyridine (269 mg, 1.27 mmol) in 4 mL of ethanol is treated successively with 269 mg of 20% palladium on carbon and cyclohexadiene (1.2 mL, 12.7 mmol). The reaction is warmed to 85° C. for 45 min, filtered through celite and the cake is washed well with methanol. The filtrate is concentrated in vacuo to an oil which is partitioned between 25 mL of saturated sodium bicarbonate and 4×15 mL of ethyl acetate. The organics are dried over potassium carbonate and concentrated in vacuo to afford 198 mg (88%) of 5-(1-hydroxyethyl)-2-methyl-furo[2,3c]pyridine.

A solution of 5-(1-hydroxyethyl)-2-methyl-furo[2,3c] pyridine (207 mg, 1.17 mmol) in 5 mL of methylene chloride at 0° C. is treated with thionyl chloride (0.127 mL, 1.75 mmol) and the reaction is stirred at room temperature for 1.5 h. The mixture is quenched with 10 mL of saturated sodium bicarbonate. The aqueous layer is extracted with 3×10 mL of methylene chloride and the combined organics are dried over potassium carbonate. The organics are concentrated in vacuo to provide 215 mg (94%) of 5-(1-chloroethyl)-2-methyl-furo[2,3c]pyridine.

A solution of 4-amino-6-chloro-2-mercapto-pyrimidine mesylate salt (283 mg, 1.1 mmol) in 2 mL of N,N- dimethylformamide at 0° C. is treated with 97 mg (60% in oil, 2.4 mmol) of sodium hydride and warmed to room temperature for 1 h. A solution of 5-(1-chloroethyl)-2-methyl-furo[2,3c]pyridine (211 mg, 1.1 mmol) in 2×1 mL of N,N-dimethylformamide is added to the mixture and the reaction was stirred for 3 days. The reaction is diluted with 25 mL of ethyl acetate, is washed with 3×25 mL of 50% saturated sodium chloride and dried over potassium carbonate. The organics are concentrated in vacuo and the crude material was chromatographed over 20 g of silica gel (230–400 mesh), eluting with 60% ethyl acetate/hexanes to afford 220 g of material which was crystallized from ether to provide 180 mg (52%) of Cpd #242 (Melting Pt. 161–163° C.).

Following the general procedure of Example 242 and including non-critical changes, but utilizing intermediates from this preparation and/or the appropriate pyrimidine precursor, the following compounds are synthesized:

Example 240/Cpd #240

4-Amino-6-chloro-2-(1-(7-chloro-2-methylfuro[2,3c]pyridin-5-yl)ethyl)thio-pyrimidine, Melting Pt. 174–175° C.

7-Chloro-5-(1-hydroxyethyl)-2-methyl-furo[2,3c]pyridine (634 mg, 3.0 mmole) was dissolved in 5 ml of dichloromethane in a 10 ml one neck round bottom flask under nitrogen. The solution was cooled to 0° C., was treated with thionyl chloride (327 μl, 4.5 mmole), and the reaction was stirred for 30 min at 0° C. followed by 1 h at room temperature. The reaction was added to 25 ml of saturated sodium bicarbonate, was diluted with 15 ml of dichloromethane, and the mixture was stirred vigorously. The aqueous layer was washed with 3×10 ml of dichloromethane, and the combined organics were dried over potassium carbonate. The dried organics were concentrated in vacuo to give 640 mg (93%) of 7-chloro-5-(1-chloroethyl)-2-methyl-furo[2,3c]pyridine as a yellow solid (Melting Point: 48–50° C.).

4-Amino-6-chloro-2-mercaptopyrimidine mesylate salt (442 mg, 1.7 mmole) was suspended in 4 ml of dry dimethylformamide in a 10 ml one neck round bottom flask under nitrogen. The suspension was cooled to 0° C., was treated with sodium hydride (137 mg, 3.44 mmole), and the mixture was stirred for 1 h at room temperature. 7-Chloro-5-(1-chloroethyl)-2-methyl-furo[2,3c]pyridine (395 mg, 1.7 mmole), in 1×2 ml of dry dimethylformamide, was added dropwise to the reaction and the mixture was stirred for 60 h. The reaction mixture was diluted with 50 ml of ethyl acetate, was washed with 4×25 ml of 50% saturated sodium chloride, and the organics were dried over anhydrous potassium carbonate. The dried organics were concentrated in vacuo to an amber oil. The crude material was chromatographed over 20 g of silica gel (230–400 mesh), eluting with 30% ethyl acetate/hexane while collecting 9 ml fractions. Fractions 17–30 were combined and concentrated to give 410 mg of an off-white solid which was washed with 20 ml 1:1 hexane/diethyl ether to afford 385 mg (64%) of 4-amino-6-chloro-2-(1-(7-chloro-2-methyl-furo[2,3c]pyridin-5-yl)ethylthio)-pyrimidine Cpd 240 (Melting Point: 174–175° C.).

Example 241/Cpd #241

4-Amino-6-trifluoromethyl-2-(1-(7-chloro-2-methylfuro[2,3c]pyridine-5-yl)ethyl)thio-pyrimidine, Melting Pt. 160–161° C.

4-Amino-2-mercapto-6-trifluoromethyl-pyrimidine mesylate salt (740 mg, 2.5 mmole) was suspended in 8 ml of dry dimethylformamide in a 25 ml one neck round bottom flask under nitrogen. The suspension was cooled to 0° C., was treated with sodium hydride (220 mg, 5.5 mmole), and the mixture was stirred for 1 h at room temperature. 7-Chloro-5-(1-chloroethyl)-2-methyl-furo[2,3c]pyridine (585 mg, 2.5 mmole), in 2×2 ml of dry dimethylformamide, was added dropwise to the reaction and the mixture was stirred 18 h. The reaction mixture was diluted with 60 ml of ethyl acetate, was washed with 4×25 ml of 50% saturated sodium chloride, and the organics were dried over anhydrous potassium carbonate. The dried organics were concentrated in vacuo to a yellow oil. The crude material was chromatographed over 50 g of silica gel (230–400 mesh), eluting with 25% ethyl acetate/hexane while collecting 9 ml fractions. Fractions 19–39 were combined and concentrated to give 410 mg of an off-white solid which was washed with 20 ml 1:1 hexane/diethyl ether to afford 385 mg (63%) of 4-amino-2-(1-(7-chloro-2-methyl-furo[2,3c]pyridin-5-yl) ethylthio)-6-trifluoromethyl-pyrimidine (Cpd 241) as a white solid (Melting Point: 160–161° C.).

Example 243/Cpd #243

4-Amino-6-trifluoromethyl-2-(1-(2-methylfuro[2,3c]pyridine-5-yl)ethyl)thio-pyrimidine, Melting Pt. 180–181° C.

4-Amino-2-mercapto-6-trifluoromethyl-pyrimidine mesylate salt (616 mg, 2.1 mmole) was suspended in 8 ml of dry dimethylformamide in a 50 ml one neck round bottom flask under nitrogen. The suspension was cooled to 0° C., was treated with sodium hydride (176 mg, 4.4 mmole), and the mixture was stirred for 1 h at room temperature. 5-(1-Chloroethyl)-2-methyl-furo[2,3c]pyridine (413 mg, 2.1 mmole), in 2×2 ml of dry dimethylformamide, was added dropwise to the reaction and the mixture was stirred 18 h. The reaction mixture was diluted with 50 ml of ethyl acetate, was washed with 4×25 ml of 50% saturated sodium chloride, and the organics were dried over anhydrous potassium carbonate. The dried organics were concentrated in vacuo to a yellow oil. The crude material was chromatographed over 30 g of silica gel (230–400 mesh), eluting with 30% ethyl acetate/hexane while collecting 9 ml fractions. Fractions 24–48 were combined and concentrated to give 562 mg of an off-white solid which was washed with diethyl ether to afford 478 mg (67%) of 4-amino-2-(1-(2-methyl-furo[2,3c]pyridin-5-yl)ethylthio)-6-trifluoromethyl-pyrimidine (Cpd 243) (Melting Point: 180–181° C.).

Example 244

4-Amino-6-chloro-2-(1-(6-chloro-5-methoxy-4-vinyl-2-pyridyl)ethyl)thio-pyrimidine (Cpd #244)

A solution of 2-chloro-3-hydroxy-4-iodo-6-(1-hydroxyethyl)-pyridine (3.6 g, 12 mmol) in 36 mL of N,N-dimethylformamide is treated with bis (triphenylphosphine)-palladium dichloride (632 mg, 0.9 mmol) and tetravinyltin (2.7 mL, 15 mmol) and heated at 50° C. for 24 h and at room temperature for 40 h. The mixture is poured into 300 mL of ethyl acetate, filtered through a celite pad and the filtrate is washed with 4×50 mL of saturated sodium chloride. The organics are concentrated in vacuo and the crude material is chromatographed over 150 g of silica gel (230–400 mesh), eluting with 25% ethyl acetate/hexanes to provide 1.68 g (70%) of 2-chloro-3-hydroxy-4-vinyl-6-(1-hydroxyethyl)-pyridine.

A solution of 2-chloro-3-hydroxy-4-vinyl-6-(1-hydroxyethyl)-pyridine (1.46 g, 7.31 mmol) in 12 mL of N,N-dimethylformamide is treated with sodium hydride (292 mg, 60% in oil, 7.31 mmol) and stirred at room temperature for 1 h. The mixture is treated with methyl iodide (0.5 mL, 8.04 mmol) and stirred for 2 h. The reaction is diluted with 125 mL of ethyl acetate and washed with 4×50 mL of saturated sodium chloride. The organics are dried over potassium carbonate and concentrated in vacuo. The crude material is chromatographed over 150 g of silica gel (230–400 mesh), eluting with 25% ethyl acetate/hexanes to give 1.09 g (78%) of 2-chloro-3-methoxy-4-vinyl-6-(1-hydroxyethyl)-pyridine.

A solution of 2-chloro-3-methoxy-4-vinyl-6-(1-hydroxyethyl)-pyridine (446 mg, 2.09 mmol) in 10 mL of methylene chloride at 0° C. is treated with thionyl chloride (0.227 mL, 3.13 mmol) and stirred at room temperature for 1 h. The reaction is quenched with 15 mL of saturated sodium bicarbonate. The aqueous layer is extracted with 3×10 mL of methylene chloride. The combined organics are dried over potassium carbonate and concentrated in vacuo to provide 447 mg (92%) of 2-chloro-3-methoxy-4-vinyl-6-(1-chloroethyl)-pyridine.

A solution of 4-amino-6-chloro-2-mercapto-pyrimidine mesylate salt (433 mg, 1.68 mmol) in 4 mL of N,N-dimethylformamide at 0° C. is treated with 141 mg (60% in oil, 3.53 mmol) of sodium hydride and warmed to room temperature for 1 h. A solution of 2-chloro-3-methoxy-4-vinyl-6-(1-chloroethyl)-pyridine (390 mg, 1.68 mmol) in 2×1 mL of N,N-dimethylformamide is added to the mixture and the reaction is stirred for 20 h. The reaction is diluted with 50 mL of ethyl acetate, is washed with 4×25 mL of 50% saturated sodium chloride and dried over potassium carbonate. The organics are concentrated in vacuo and the crude material is chromatographed over 20 g of silica gel (230–400 mesh), eluting with 25% ethyl acetate/hexanes to afford 122 mg (20%) of Cpd #244 (Melting Pt. 157–158° C.).

Example 245

4-Amino-6-chloro-2-(1-(4-ethyl-5-methoxy-2-pyridyl)ethyl)thio-pyrimidine (Cpd #245)

A solution of 2-chloro-3-methoxy-4-vinyl-6-(1-hydroxyethyl)-pyridine (485 mg, 2.27 mmol) in 10 mL of ethanol is treated with 485 mg of 20% palladium on carbon and 1,4-cyclohexadiene (2.0 mL, 21 mmol) and the reaction is refluxed for 4 h. The catalyst is removed by filtration through celite and the filter pad washed well with methanol. The filtrate is concentrated in vacuo and the residue is partitioned between 25 mL of saturated sodium bicarbonate and 4×25 mL of ethyl acetate. The combined organics are dried over potassium carbonate and concentrated in vacuo. The crude material is chromatographed over 20 g of silica gel (230–400 mesh), eluting with 100 mL of 50% ethyl acetate/hexanes followed by 80% ethyl acetate/hexanes to afford 256 mg (63%) of 3-methoxy-4-ethyl-6-(1-hydroxyethyl)-pyridine.

A solution of 3-methoxy-4-ethyl-6-(1-hydroxyethyl)-pyridine (236 mg, 1.3 mmol) in 5 mL of methylene chloride at 0° C. is treated with thionyl chloride (0.141 mL, 1.95 mmol) and stirred at room temperature for 1 h. The reaction is quenched with 12 mL of saturated sodium bicarbonate. The aqueous layer is extracted with 3×10 mL of methylene chloride. The combined organics are dried over potassium carbonate and concentrated in vacuo to provide 249 mg (96%) of 3-methoxy-4-ethyl-6-(1-chloroethyl)-pyridine.

A solution of 4-amino-6-chloro-2-mercapto-pyrimidine mesylate salt (290 mg, 1.1 mmol) in 2 mL of N,N-dimethylformamide at 0° C. is treated with 92 mg (60% in oil, 2.3 mmol) of sodium hydride and warmed to room temperature for 1 h. A solution of 3-methoxy- 4-ethyl-6-(1-chloroethyl)-pyridine (225 mg, 1.1 mmol) in 2×1 mL of N,N-dimethylformamide is added dropwise to the mixture and the reaction was stirred for 18 h. The reaction is diluted with 50 mL of ethyl acetate, was washed with 4×25 mL of 50% saturated sodium chloride and dried over potassium carbonate. The organics are concentrated in vacuo and the crude material is chromatographed over 20 g of silica gel (230–400 mesh), eluting with 50% ethyl acetate/hexanes to afford 256 mg of an oil which upon crystallization from ether gave 188 mg (53%) of Cpd #245 (Melting Pt. 136–137° C.).

Example 246

4-Amino-6-chloro-2-(1-(3-methylfuro[2,3c]pyridine-5-yl)ethyl)thio-pyrimidine (Cpd #246)

A solution of 2-chloro-3-hydroxy-4-iodo-6-(1-hydroxyethyl)-pyridine (3.6 g, 12 mmol) in 24 mL of N,N-dimethylformamide at 0° C. is treated with 480 mg (60% in oil, 12 mmol) of sodium hydride and stirred at room temperature for 1 h. The reaction is treated with 1.14 g (13.2 mmol) of allyl bromide and stirred for 2 h. The mixture is poured into 125 mL of ethyl acetate and washed with 4×50 mL of saturated sodium chloride, 2×25 mL of 50% saturated sodium carbonate and dried over potassium carbonate. The dried organics are concentrated in vacuo, diluted with 20 mL of hexanes, and chilled to −15° C. The solid is filtered to provide 3.61 g (89%) of 2-chloro-3-(1-propen-3-yl)-4-iodo-6-(1-hydroxyethyl)-pyridine.

Method A:

A solution of 2-chloro-3-(1-propen-3-yl)-4-iodo-6-(1-hydroxyethyl)-pyridine (3.50 g, 10.3 mmol) in 30 mL of N,N-dimethylformamide is treated successively with sodium formate (872 mg, 12.8 mmol), sodium carbonate (3.28 g, 30.9 mmol), tetrabutylammonium chloride (3.91 g, 14.1 mmol) and palladium acetate (130 mg, 0.6 mmol). The reaction is warmed to 50° C. for 2 h, was cooled to room temperature, and is diluted with 150 mL of ethyl acetate. The organics are washed with 4×50 mL of 50% saturated sodium chloride, dried over potassium carbonate, and concentrated in vacuo. The crude material is dissolved in 50 mL of methanol, treated with DARCO, and refluxed for 20 min. The mixture is filtered through celite and concentrated in vacuo. The crude material is chromatographed over 50 g of silica gel (230–400 mesh), eluting with 25% ethyl acetate/ hexanes to afford 631 mg (29%) of 7-chloro-5-(1-hydroxyethyl)-3-methyl-furo[2,3c]pyridine (Melting point 67–68° C.), A solution of 7-chloro-5-(1-hydroxyethyl)-3-methyl-furo [2,3c]pyridine (550 mg, 2.6 mmol) in 12 mL of ethanol is treated with 20% palladium hydroxide of carbon (550 mg) and cyclohexadiene (2.6 mL, 28 mmol) and the reactionias heated to reflux for 2 h. The mixture is cooled, filtered through celite, and the filter pad is washed well with methanol. The filtrate is concentrated in vacuo and the residue partioned between 25 mL of saturated sodium bicarbonate and 4×20 mL of methylene chloride. The combined organics ware dried over potassium carbonate and concentrated in vacuo to give 422 mg (92%) of 5-(1-hydroxyethyl)-3-methyl-furo[2,3c]pyridine (Melting point 56–58 ° C.).

Method B:

Part 1: 3-(1-propen-3-yl)-2-chloro-6-(1-hydroxyethyl)-4-iodo-pyridine (40 g, 117.8 mmole) was combined with N,N'-azo-bis(isobutyryl)nitrile (1.94 g, 11.8 mmole) in 260 ml benzene in a flame dried 500 ml one neck round bottom flask under nitrogen. The solution was warmed to reflux and was treated rapidly dropwise with tributyltin hydride (34.2 ml, 127.2 mmole) in 60 ml dry benzene. The reaction was stirred for 1 h at reflux, was cooled, and the benzene was removed in vacuo. The residue was chromatographed over 750 g silica gel (230–400 mesh), eluting with 2 l 10% ethyl acetate/hexane, 2 l 20% ethyl acetate/hexane, followed by 3 l 35% ethyl acetate/hexane, and after a 2 l forerun collecting 50 ml fractions. Fractions 54-102 were combined and concentrated to afford 22.2 g (88%) of 7-chloro-2,3-dihydro-5-(1-hydroxyethyl)-3-methyl-furo[2,3c]-pyridine as a pale yellow oil. $^1$H NMR (CDCl$_3$, TMS): δ 1.37 (d, J=7 Hz, 3), 1.48 (d, J=6.5 Hz, 3), 2.91 (bs, 1), 3.65 (bs, 1), 4.24 (t, J=8.8 Hz, 1), 4.83 (m, 2), 7.12 (m, 1) ppm.

Part 1 (Preferred Alternate):

A solution of 2-chloro-3-(1-propen-3-yl)-4-iodo-6-(1-hydroxyethyl)-pyridine (1.06 g, 3.14 mmol) in THF (5 mL) is treated with 50% hypophosphorous acid (2.13 g, 15.73 mmol), triethylamine (1.75 g, 17.33 mmol), and 2,2'-azobis (2-methylpropino-nitrile) (AIBN; 192 mg, 1.23 mmol). The solution is stirred at reflux for 2 hours. The solution is allowed to cool and concentrated in vacuo. Sat'd NaHCO$_3$ is added, and the mixture is extracted 3× EtOAc. The organics are dried over MgSO$_4$, and concentrated in vacuo. The crude light yellow oil is chromatographed (SiO$_2$, hexane/ethyl acetate, 2:1) to yield 650 mg (97%) of 7-chloro-2,3-dihydro-5-(1-hydroxyethyl)-3-methyl-furo[2, 3-c]pyridine, mp 67–68° C.

Part 2: 7-Chloro-2,3-dihydro-5-(1-hydroxyethyl)-3-methyl-furo[2,3c]-pyridine (26 g, 122 mmole) was dissolved in 200 ml methanol in a 500 ml one neck round bottom was treated with 5.5 g DARCO, and was refluxed for 20 min. The mixture was filtered through celite and the filter cake was washed with methanol. The filtrate was concentrated in vacuo to give 25 g of a pale oil. The oil was dissolved in 160 ml absolute ethanol, was treated with 5.5 g 20% palladium hydroxide on carbon, and was diluted with 60 ml (120 mmole) of 2N aqueous sodium hydroxide. The mixture was hydrogenated at 22 PSI for 20 h. The catalyst was removed by filtration and the filter cake was washed with fresh absolute ethanol. The filtrate was concentrated in vacuo to a pasty residue and was partitioned between 1×200 ml 50% saturated sodium bicarbonate and 4×100 ml dichloromethane. The organics were dried over potassium carbonate and were concentrated in vacuo to provide 20.1 g (93%) of 2,3-dihydro-5-(1-hydroxyethyl)-3-methyl-furo[2,3c]-pyridine as a pale yellow oil. $^1$H NMR (CDCl$_3$, TMS): δ 1.36 (m, 3), 1.48 (m,3), 3.56 (m, 1), 4.05 (bs, 1), 4.13 (m, 1), 4.86 (t, J=9 Hz, 1), 4.87 (q, J=6.4, 12.9 Hz, 1), 7.15 (s, 1), 8.03 (s, 1) ppm.

2,3-Dihydro-5-(1-hydroxyethyl)-3-methyl-furo[2,3c]-pyridine (20.1 g, 112 mmole) was dissolved in 112 ml pyridine in a 200 ml one neck round bottom flask under nitrogen. The solution was treated with acetic anhydride (31.2 ml, 336 mmole) and was stirred overnight at room temperature. The pyridine was removed in vacuo and the residue was taken up in 200 ml ethyl acetate. The solution was stirred vigorously for one hour with 200 ml saturated sodium bicarbonate containing 35 g solid sodium bicarbonate. The layers were separated and the organic layer was extracted with 4×100 ml 50% saturated sodium chloride. The organics were dried over anhydrous magnesium sulfate and were concentrated in vacuo to give 24.8 g (quant) of 5-(1-acetoxyethyl)-2,3-dihydro-3-methyl-furo[2,3c] pyridine as a pale oil. $^1$H NMR (CDCl$_3$, TMS): δ 1.36 (m, 3), 1.58 (m, 3), 2.11 (m, 3), 3.57 (m, 1), 4.14 (t, J=8.4 Hz, 1), 4.75 (t, J=8.4 Hz, 1), 5.89 (q, J=6.5, 13 Hz, 1), 7.18 (m, 1), 8.12 (s, 1) ppm.

5-(1-Acetoxyethyl)-2,3-dihydro-3-methyl-furo[2,3c] pyridine (24.3 g, 110 mmole) was combined with 2,3,5,6-tetrachlorobenzoquinone (29.6 g, 120.4 mmole) in 500 ml dioxane in a 1000 ml one neck round bottom flask under nitrogen. The reaction was warmed to a gentle reflux for 24 h, was cooled to room temperature, was filtered and the filter cake was washed well with ethyl acetate. The filtrate was concentrated in vacuo to a reddish brown slurry which was diluted with 100 ml dioxane, was filtered, and the filter cake was washed with diethyl ether. The filtrate was concentrated to a brown oil, was diluted with 500 ml methanol followed by 185 ml (370 mmole) of 2N sodium hydroxide, and the reaction was stirred 1 h at room temperature. The methanol was removed in vacuo, the aqueous residue was diluted with 300 ml water, and the mixture was extracted with 4×100 ml dichloromethane. The combined organics were backwashed with 2×100 ml 1N sodium hydroxide, were dried over potassium carbonate, and were concentrated in vacuo to a greenish oil. The oil was dissolved in 200 ml methanol and was refluxed with DARCO for 20 min. The mixture was filtered through celite, the filter cake was washed well with methanol, and the filtrate was concentrated in vacuo to provide 18.4 g (94%) of 5-(1-hydroxyethyl)-3-methyl-furo [2,3c]pyridine (Melting Point: 56–58° C.).

A solution of 5-(1-hydroxyethyl)-3-methyl-furo[2,3c] pyridine (436 mg, 2.46 mmol) in 10 mL of methylene chloride at 0° C. is treated with thionyl chloride (0.268 mL, 3.69 mmol) and the reaction is stirred at room temperature for 1.5 h. The mixture is quenched with 15 mL of saturated sodium bicarbonate. The aqueous layer is extracted with 3×10 mL of methylene chloride and the combined organics are dried over potassium carbonate. The organics are concentrated in vacuo to provide 467 mg (97%) of 5-(1-chloroethyl)-3-methyl-15 furo[2,3c]pyridine.

A solution of 4-amino-6-chloro-2-mercapto-pyrimidine mesylate salt (589 mg, 2.28 mmol) in 6 mL of N,N-dimethylformamide at 0° C. is treated with 192 mg (60% in oil, 4.8 mmol) of sodium hydride and warmed to room temperature for 1 h. A solution of 5-(1-chloroethyl)-3-methyl-furo[2,3c]pyridine (447 mg, 2.28 mmol) in 2×2 mL of N,N-dimethylformamide is added to the mixture and the reaction was stirred for 18 h. The reaction is diluted with 70 mL of ethyl acetate, was washed with 4×50 mL of 50% saturated sodium chloride and dried over potassium carbonate. The organics are concentrated in vacuo and the crude material is chromatographed over 25 g of silica gel (230–400 mesh), eluting with 40% ethyl acetate/hexanes to afford 460 mg of material which is washed with ether to provide 369 mg (50%) of Cpd #246 (Melting Pt. 184–185° C.).

Example 247

4-Amino-6-chloro-2-(1-(2,3-dihydrofuro[2,3c] pyridine-5-yl)ethyl)thio-pyrimidine (Cpd #247)

5-(1-Hydroxyethyl)-furo[2,3c]pyridine (489 mg, 3.0 mmol) is dissolved in a small PARR shaker bottle which had been pretreated with 0.239 mL (3.6 mmol) of acetyl chloride. The solution is treated with 210 mg of 20% palladium hydroxide on carbon catalyst and the reaction is shaken under 20 psi (to 14 psi) of hydrogen for 2 h. The catalyst is removed by filtration through celite and the filter pad washed well with methanol. The filtrate is concentrated and partitioned wetween 20 mL of saturated sodium bicarbonate and 4×10 mL of methylene chloride. The combined organics are dried over potassium carbonate and concentrated. The crude material is chromatographed over 20 g of silica gel (230–400 mesh), eluting with 4:2:1 chloroform/ethyl acetate/acetone 5 to afford 495 mg (99%) of 5-(1-hydroxyethyl)-(2,3-dihydro)furo[2,3c]pyridine.

A solution of 5-(1-hydroxyethyl)-(2,3-dihydro)furo[2,3c]pyridine (495 mg, 3.0 mmol) 10 mL of methylene chloride at 0° C. is treated with thionyl chloride and stirred at room temperature for 2 h. The reaction is quenched with 10 mL of saturated sodium bicarbonate and partition between 10 mL of saturated sodium bicarbonate and 4×10 mL of methylene chloride. The combined organics are concentrated in vacuo to give 495 mg (89%) of 5-(1-chloroethyl)-(2,3-dihydro) furo[2,3c]pyridine.

A solution of 4-amino-6-chloro-2-mercapto-pyrimidine mesylate salt (783 mg, 3.0 mmol) in 8 mL of N,N-dimethylformamide at 0° C. is treated with 243 mg (60% in oil, 6.1 mmol) of sodium hydride and warmed to room temperature for 1 h. A solution of 5-(1-chloroethyl)-(2,3-dihydro)furo[2,3c]pyridine (495 mg, 2.7 mmol) in 2×2 mL of N,N-dimethylformamide is added dropwise to the mixture and the reaction is stirred overnight. The mixture is diluted with 60 mL of ethyl acetate, was washed with 4×25 mL of 50% saturated sodium chloride and dried over potassium carbonate. The organics are concentrated in vacuo and the crude material was chromatographed over 50 g of silica gel (230–400 mesh), eluting with 35% ethyl acetate/hexanes to afford 600 mg (66%) of Cpd #247. Melting Pt. 155–156° C.

Example 248

4-Amino-6-chloro-2-(1-(3,3-dimethyl-2,3-dihydrofuro[2,3c]pyridine-5-yl)ethyl)thio-pyrimidine (Cpd #248)

A solution of 2-chloro-3-hydroxy-4-iodo-6-(1-hydroxyethyl)-pyridine (4.49 g, 15 mmol) in 25 mL of N,N-dimethylformamide at 0° C. is treated with 600 mg (60% in oil, 15 mmol) of sodium hydride and stirred at room temperature for 1 h. The reaction is treated with 1.7 mL (16.5 mmol) of 2-methyl-3-bromopropene and stirred for 2 h. The mixture is diluted with 150 mL of ethyl acetate and washed with 4×50 mL of 1:1 50% saturated sodium chloride/sodium bicarbonate, and dried over potassium carbonate. The crude material is chromatographed over 150 g of silica gel (230–400 mesh), eluting with 25% ethyl acetate/hexanes to give 3.94 g (74%) of 2-chloro-3-(2-methyl-1-propen-3-yl)-4-iodo-6-(1-hydroxyethyl)-pyridine.

A solution of 2-chloro-3-(2-methyl-1-propen-3-yl)-4-iodo-6-(1-hydroxyethyl)-pyridine (3.8 g (10.9 mmol) in 18 mL of N,N-dimethylformamide is treated successively with sodium formate (742 mg, 10.9 mmol), triethylamine (4.6 mL, 32.7 mmol), tetrabutylammonium chloride (3.03 g, 10.9 mmol) and palladium acetate (122 mg, 0.54 mmol). The reaction is warmed to 60° C. for 3 h, and was stirred at room temperature overnight. The reaction mixture is diluted with 100 mL of ethyl acetate, washed with 4×50 mL of 50% saturated sodium chloride, dried over potassium carbonate, and concentrated in vacuo. The crude material is dissolved in methanol, treated with DARCO, and refluxed for 20 min. The mixture is filtered through celite and concentrated in vacuo. The crude material is chromatographed over 100 g of silica gel (230–400 mesh), eluting with 25% ethyl acetate/hexanes to afford 1.41 g (55%) of 7-chloro-5-(1-hydroxyethyl)-2,3-dihydro-3,3-dimethyl-furo[2,3c] pyridine.

A solution of 7-chloro-5-(1-hydroxyethyl)-2,3-dihydro-3,3-dimethyl-furo[2,3c]pyridine (425 mg, 1.87 mmol) in 20 mL of ethanol is treated with 20% palladium hydroxide of carbon (200 mg) and shaken under a hydrogen atmosphere (20-14 psi) for 3 h. The mixture is filtered through celite. The filtrate is concentrated in vacuo and the residue partioned between 20 mL of saturated sodium bicarbonate and 4×20 mL of methylene chloride. The combined organics are dried over potassium carbonate and concentrated in vacuo to give 305 mg (85%) of 5-(1-hydroxyethyl)-2,3-dihydro-3,3-dimethyl-furo[2,3c]-pyridine.

A solution of 5-(1-hydroxyethyl)-2,3-dihydro-3,3-dimethyl-furo[2,3c]pyridine (805 mg, 4.17 mmol) in 15 mL of methylene chloride at 0° C. is treated with thionyl chloride (0.439 mL, 6.25 mmol) and the reaction is stirred at room temperature for 2 h. The mixture is quenched with 25 mL of saturated sodium bicarbonate. The aqueous layer is extracted with 3×20 mL of methylene chloride and the combined organics are dried over potassium carbonate/magnesium sulfate. The organics are concentrated in vacuo to provide 880 mg (99%) of 5-(1-chloroethyl)-2,3-dihydro-3,3-dimethyl-furo[2,3c]pyridine.

A solution of 4-amino-6-chloro-2-mercapto-pyrimidine mesylate salt (1.04 g, 4.04 mmol) in 12 mL of N,N-dimethylformamide at 0° C. is treated with 339 mg (60% in oil, 8.5 mmol) of sodium hydride and warmed to room temperature for 1 h. A solution of 5-(1-chloroethyl)-2,3-dihydro-3,3-dimethyl-furo[2,3c]pyridine (856 mg, 4.04 mmol) in 2×3 mL of N,N-dimethylformamide is added to the mixture and the reaction stirred for 24 h. The reaction is diluted with 100 mL of ethyl acetate, washed with 4×50 mL of 50% saturated sodium chloride and dried over potassium carbonate. The organics are concentrated in vacuo and the crude material was chromatographed over 100 g of silica gel (230–400 mesh), eluting with 40% ethyl acetate/hexanes to afford 1 g of material which is crystallized from ether to provide 878 mg (65%) of Cpd #248 (Melting Pt. 169–170° C.).

Example 250/Cpd #250

4-Amino-6-chloro-2-(1-(7-chloro-3,3-dimethyl-2,3-dihydrofuro[2,3c]pyridine-5-yl)ethyl)thio-pyrimidine, Melting Pt. 203–205° C.

7-Chloro-2,3-dihydro-3,3-dimethyl-5-(1-hydroxyethyl)-furo[2,3c]pyridine (1.12 g, 4.9 mmole) was dissolved in 10 ml of dichloromethane in a 50 ml one neck round bottom flask under nitrogen. The solution was cooled to 0° C., was treated with thionyl chloride (520 µl, 7.4 mmole), and the reaction was stirred for 20 min at 0° C. followed by 1 h at room temperature. The reaction was added to 20 ml of saturated sodium bicarbonate, the aqueous layer was washed with 3×10 ml of dichloromethane, and the combined organics were dried over potassium carbonate. The dried organics were concentrated in vacuo to give 1.14 g (94%) of 7-chloro-5-(1-chloroethyl)-2,3-dihydro-3,3-dimethyl-furo[2,3c]pyridine as a pale yellow oil. $^1$H NMR (CDCl$_3$, TMS): δ 1.39 (s, 3), 1.40 (s, 3), 1.85 (d, J=6.6 Hz, 3), 4.40 (s, 2), 5.10 (q, J=6.6, 13.2 Hz, 1), 7.23 (s, 1) ppm.

4-Amino-6-chloro-2-mercaptopyrimidine mesylate salt (541 mg, 2.1 mmole) was dissolved in 8 ml of dry dimethylformamide in an oven dried 50 ml two neck round bottom flask under nitrogen. The solution was cooled to 0° C., was treated with sodium hydride (176 mg, 4.4 mmole), and the mixture was stirred for 1 h at room temperature. 7-Chloro-5-(1-chloroethyl)-2,3-dihydro-3,3-dimethyl-furo[2,3c]pyridine (492 mg, 2.0 mmole), in 2×2 ml of dry dimethylformamide, was added dropwise to the reaction and the mixture was stirred for 24 h. The reaction mixture was diluted with 70 ml of ethyl acetate, was washed with 4×25 ml of 50% saturated sodium chloride followed by 1×25 ml of saturated sodium chloride, and the organics were dried over anhydrous potassium carbonate. The dried organics were concentrated in vacuo to a light amber oil. The crude material was chromatographed over 100 g of silica gel (230–400 mesh), eluting with 35% ethyl acetate/hexane while collecting 9 ml fractions. Fractions 22–33 were combined and concentrated to give an off-white solid. Washing the solid with diethyl ether provided 318 mg (43%) of 4-amino-6-chloro-2-(1-(7-chloro-2,3-dihydro-3,3-dimethyl-furo[2,3c]yl)ethylthio)-pyrimidine as a white solid (Melting Point: 203–205° C.).

Example 249/Cpd #249

4-Amino-6-chloro-2-(1-(3-ethylfuro[2,3c]pyridine-5-yl)ethyl)thio-pyrimidine, Melting Pt. 125–126° C.

2-Chloro-3-hydroxy-6-(1-hydroxyethyl)-4-iodo-pyridine (4.49 g, 15 mmole) was dissolved in 25 ml dry dimethylformamide in an oven dried 50 ml two neck round bottom flask under nitrogen. The solution was cooled to 0° C., was treated with sodium hydride (600 mg, 15 mmole), and the mixture was stirred 1 h at room temperature. The mixture was treated with crotyl chloride (1.6 ml, 16.5 mmole) and one crystal of lithium iodide and the reaction mixture was stirred 20 h at room temperature. The reaction mixture was diluted with 100 ml ethyl acetate, was washed with 4×50 ml 50% saturated 1:1 sodium chloride/sodium bicarbonate, and was dried over anhydrous magnesium sulfate/potassium carbonate. The dried organics were concentrated in vacuo to a yellow oil which was crystallized from hexane to give 4.72 g (89%) of 3-(2-butenyloxy)-2-chloro-6-(1-hydroxyethyl)-4-iodo-pyridine as a white solid (Melting Point: 61–62.50° C.).

2-Chloro-3-(2-butenyloxy)-6-(1-hydroxyethyl)-4-iodo-pyridine (2.12 g, 6 mmole) was combined with tetrabutylammonium chloride (2.28 g, 8.2 mmole), sodium formate (507 mg, 7.5 mmole), sodium carbonate (1.91 g, 18 mmole) and palladium acetate (78 mg, 0.35 mmole) in 18 ml dimethylformamide in an oven dried 50 ml two neck round bottom flask under nitrogen. The reaction was warmed to 80° C. for 2 h, was diluted with 100 ml ethyl acetate, and the mixture was extracted with 4×50 ml 50% saturated 1:1 sodium chloride/sodium bicarbonate. The organics were dried over potassium carbonate and were concentrated in vacuo to a brown oil. The crude oil was taken up in 50 ml methanol, was refluxed with Darco for 20 min, and was filtered through celite. The filtrate was concentrated in vacuo to a crude amber oil which was chromatographed over 50 g silica gel (230–400 mesh) eluting with 37.5% ethyl acetate/hexane while collecting 9 ml fractions. Fractions 26–37 were combined and concentrated to give 484 mg (36%) of 7-chloro-5-(1-hydroxyethyl)-3-ethyl-furo[2,3c]pyridine as a pale oil which crystallized on standing (Melting Point: 43–450° C.).

7-Chloro-5-(1-hydroxyethyl)-3-ethyl-furo[2,3c]pyridine (600 mg, 2.7 mmole) was combined with 20% palladium hydroxide on carbon (600 mg) in 20 ml absolute ethanol in a 100 ml one neck round bottom flask under nitrogen. The mixture was treated with 1,4 cyclohexadiene (2.5 ml, 27 mmole) and the reaction was warmed to reflux (rapid exotherm) for 2.5 h. The mixture was filtered through celite and the cake was washed well with fresh methanol. The filtrate was concentrated in vacuo and the residue was partitioned between 1×25 ml saturated sodium bicarbonate and 4×20 ml dichloromethane. The combined organics were dried over potassium carbonate and were concentrated in vacuo to provide 464 mg (91%) of 5-(1-hydroxyethyl)-3-ethyl-furo[2,3c]pyridine as an off-white solid. $^1$H NMR (CDCl$_3$, TMS): δ 1.19 (t, J=7.5 Hz, 3), 1.51 (d, J=6.9 Hz, 3), 2.75 (m, 2), 4.45 (bs, 1), 4.99 (q, J=6.9, 13.8 Hz, 1), 7.44 (s, 1), 7.51 (s, 1), 8.02 (s, 1) ppm.

5-(1-Hydroxyethyl)-3-ethyl-furo[2,3c]pyridine (434 mg, 2.3 mmole) was dissolved in 10 ml dichloromethane in a 50 ml one neck round bottom flask under nitrogen. The solution was cooled to 0° C., was treated with thionyl chloride (247 µl, 3.4 mmole), and the reaction was stirred 20 min at 0° C. followed by 3 h at room temperature. The reaction was added to 25 ml saturated sodium bicarbonate, the layers were separated, the aqueous layer was washed with 3×10 ml dichloromethane, and the combined organics were dried over potassium carbonate. The dried organics were concentrated in vacuo to give 467 mg (98%) of 5-(1-chloroethyl)-3-ethyl-furo[2,3c]pyridine as a pale yellow oil. $^1$H NMR (CDCl$_3$, TMS): δ 1.34 (t, J=7.5 Hz, 3), 1.95 (d, J=7.0 Hz, 3), 2.72 (m, 2), 5.30 (q, J=7.0, 14 Hz, 1), 7.53 (m, 1), 7.66 (m, 1), 8.77 (m, 1) ppm.

4-Amino-6-chloro-2-mercaptopyrimidine mesylate salt (553 mg, 2.2 mmole) was dissolved in 6 ml dry dimethylformamide in an oven dried 25 ml two neck round bottom flask under nitrogen. The solution was cooled to 0° C., was treated with sodium hydride (180 mg, 4.5 mmole), and the mixture was stirred 1 h at room temperature. 5-(1-Chloroethyl)-3-ethyl-furo[2,3c]pyridine (450 mg, 2.2 mmole), in 2×4 ml dry dimethylformamide, was added dropwise to the reaction and the mixture was stirred 24 h. The reaction mixture was diluted with 75 ml ethyl acetate, was washed with 4×25 ml 50% saturated sodium chloride followed by 1×25 ml saturated sodium chloride, and the organics were dried over anhydrous potassium carbonate. The dried organics were concentrated in vacuo to a yellow oil. The crude material was chromatographed over 50 g silica gel (230–400 mesh), eluting with 35% ethyl acetate/hexane while collecting 9 ml fractions. Fractions 51–84 were combined and concentrated to give a white foam. Crystallization from diethyl ether provided 382 mg (53%) of 4-amino-6-chloro-2-(1-(3-ethyl-furo[2,3c]pyridin-5-pyrimidine as a white solid (Melting Point: 125–126° C.).

Example 251/Cpd #251

4-Amino-6-chloro-2-(1-(7-chloro-3-ethylfuro-[2,3c] pyridine-5yl)ethyl)thio-pyrimidine, Melting Pt. 165–166° C.

7-Chloro-5-(1-Hydroxyethyl)-3-ethyl-furo[2,3c]pyridine (904 mg, 4.0 mmole) was dissolved in 10 ml dichloromethane in a 50 ml one neck round bottom flask under nitrogen. The solution was cooled to 0° C., was treated with thionyl chloride (422 μl, 6.0 mmole), and the reaction was stirred 20 min at 0° C. followed by 1 h at room temperature. The reaction was added to 20 ml saturated sodium bicarbonate, the layers were separated, the aqueous layer was washed with 3×10 ml dichloromethane, and the combined organics were dried over potassium carbonate. The dried organics were concentrated in vacuo to give 965 mg (98%) of 7-chloro-5-(1-chloroethyl)-3-ethyl-furo[2,3c] pyridine as a yellow oil. $^1$H NMR (CDCl$_3$, TMS): δ 1.31 (t, J=7.5 Hz, 3), 1.90 (d, J=6.9 Hz, 3), 2.70 (m, 2), 5.23 (q, J=6.9, 13.8 Hz, 1), 7.58 (m, 1), 7.69 (s, 1) ppm.

4-Amino-6-chloro-2-mercaptopyrimidine mesylate salt (1.03 g, 4.0 mmole) was dissolved in 12 ml dry dimethylformamide in an oven dried 50 ml two neck round bottom flask under nitrogen. The solution was cooled to 0° C., was treated with sodium hydride (336 mg, 8.4 mmole), and the mixture was stirred 1 h at room temperature. 7-Chloro-5-(1-chloroethyl)-3-ethyl-furo[2,3c]pyridine (924 mg, 3.8 mmole), in 2×3 ml dry dimethylformamide, was added dropwise to the reaction and the mixture was stirred 60 h. The reaction mixture was diluted with 100 ml ethyl acetate, was washed with 4×50 ml 50% saturated sodium chloride followed by 1×50 ml saturated sodium chloride, and the organics were dried over anhydrous potassium carbonate. The dried organics were concentrated in vacuo to a yellow oil. The crude material was chromatographed over 50 g silica gel (230–400 mesh), eluting with 30% ethyl acetate/hexane while collecting 9 ml fractions. Fractions 21–33 were combined and concentrated to give a white solid. The solid was washed with diethyl ether to afford 782 mg (56%) of 4-amino-6-chloro-2-(1-(7-chloro-3-ethyl-furo[2,3c] pyridin-5-yl)ethylthio)-pyrimidine (Melting Point: 165–166° C.).

Example 252/Cpd #252

4-Amino-6-chloro-2-(1-(3-(1-methylethyl)furo[2, 3c]-pyridin-5-yl)ethyl)thio-pyrimidine, Melting Pt. 115–117° C.

2-Chloro-3-hydroxy-6-(1-hydroxyethyl)-4-iodo-pyridine (2.99 g, 10 mmole) was dissolved in 15 ml dry dimethylformamide in an oven dried 100 ml two neck round bottom flask under nitrogen. The solution was cooled to 0° C., was treated with sodium hydride (400 mg, 10 mmole), and the mixture was stirred 1 h at room temperature. The mixture was treated with 1-chloro-3-methyl-2-butene (1.2 ml, 11 mmole) and sodium iodide (150 mg, 1 mmole) and the reaction mixture was stirred 18 h at room temperature. The reaction mixture was diluted with 100 ml ethyl acetate, was washed with 4×50 ml 50% saturated 1:1 sodium chloride/sodium bicarbonate, and was dried over anhydrous potassium carbonate. The dried organics were concentrated in vacuo to a yellow oil which was crystallized from 25 ml hexane to give 3.2 g (87%) of 2-chloro-3-(3-methyl-2-butenyloxy)-6-(1-hydroxyethyl)-4-iodo-pyridine as an off-white solid, Melting Point: 80–81° C.

2-Chloro-3-(3-methyl-2-butenyloxy)-6-(1-hydroxyethyl)-4-iodo-pyridine (3.12 g, 8.5 mmole) was combined with tetrabutylammonium chloride (2.36 g, 8.5 mmole), sodium formate (577 mg, 8.5 mmole), triethylamine (3.6 ml, 25 mmole) and palladium acetate (95 mg, 0.42 mmole) in 18 ml dimethylformamide in an oven dried 50 ml two neck round bottom flask under nitrogen. The reaction was warmed to 60° C. for 2 h, was diluted with 125 ml ethyl acetate, and the mixture was extracted with 4×50 ml 50% saturated sodium chloride. The organics were dried over potassium carbonate and were concentrated in vacuo to a brown oil. The crude oil was taken up in 50 ml methanol, was refluxed with Darco for 20 20 min, and was filtered through celite. The filtrate was concentrated in vacuo to a crude amber oil which was chromatographed over 100 g silica gel (230–400 mesh) eluting with 30% ethyl acetate/hexane while collecting 22 ml fractions. Fractions 14–21 were combined and concentrated to give 698 mg (34%) of 7-chloro-5-(1-hydroxyethyl)-3-isopropyl-furo[2,3c] pyridine as a yellow oil which crystallized on standing (Melting Point: 45–46.5° C.).

7-Chloro-5-(1-hydroxyethyl)-3-isopropyl-furo[2,3c] pyridine (678 mg, 2.8 mmole) was combined with 20% palladium hydroxide on carbon (678 mg) in 20 ml absolute ethanol in a 50 ml one neck round bottom flask under nitrogen. The mixture was treated with 1,4 cyclohexadiene (2.7 ml, 28 mmole) and the reaction was warmed to reflux (rapid exotherm) for 2 h. The mixture was filtered through celite and the cake was washed well with fresh methanol. The filtrate was concentrated in vacuo and the residue was partitioned between 1×20 ml saturated sodium bicarbonate and 4×15 ml dichloromethane. The combined organics were dried over potassium carbonate and were concentrated in vacuo to provide 554 mg (96%) of 5-(1-hydroxyethyl)-3-isopropyl-furo[2,3c]pyridine as a pail oil. $^1$H NMR (CDCl$_3$, TMS): δ 1.33 (d, 6), 1.56 (d, J=6.5 Hz, 1), 3.09 (m, 1), 4.16 (bs, 1), 5.02 (q, J=6.5, 13 Hz, 1), 7.50 (m, 1), 7.54 (s, 1), 8.72 (s, 1) ppm.

5-(1-Hydroxyethyl)-3-isopropyl-furo[2,3c]pyridine (544 mg, 2.6 mmole) was dissolved in 10 ml dichloromethane in a 50 ml one neck round bottom flask under nitrogen. The solution was cooled to 0° C., was treated with thionyl chloride (279 μl, 4.0 mmole), and the reaction was stirred 20 min at 0° C. followed by 1 h at room temperature. The reaction was added to 15 ml saturated sodium bicarbonate, the layers were separated, the aqueous layer was washed with 3×10 ml dichloromethane, and the combined organics were dried over potassium carbonate. The dried organics were concentrated in vacuo to give 554 mg (93%) of 5-(1-chloroethyl)-3-isopropyl-furo[2,3c]pyridine as a pale yellow oil. $^1$H NMR (CDCl$_3$, TMS): δ 1.37 (d, 6), 1.96 (d, J=6.5 Hz, 3), 3.10 (m, 1), 5.23 (q, J=6.5, 13 Hz, 1), 7.51 (m, 1), 7.70 (m, 1), 8.78 (m, 1) ppm.

4-Amino-6-chloro-2-mercaptopyrimidine mesylate salt (785 mg, 3.0 mmole) was dissolved in 8 ml dry dimethylformamide in an oven dried 50 ml two neck round bottom flask under nitrogen. The solution was cooled to 0° C., was treated with sodium hydride (267 mg, 6.7 mmole), and the mixture was stirred 1 h at room temperature. 5-(1-Chloroethyl)-3-isopropyl-furo[2,3c]pyridine (524 mg, 2.3 mmole), in 2×3 ml dry dimethylformamide, was added dropwise to the reaction and the mixture was stirred 24 h. The reaction mixture was diluted with 100 ml ethyl acetate, was washed with 3×25 ml 50% saturated sodium chloride followed by 1×25 ml saturated sodium chloride, and the organics were dried over anhydrous potassium carbonate. The dried organics were concentrated in vacuo to a yellow oil. The crude material was chromatographed over 45 g silica gel (230–400 mesh), eluting with 35% ethyl acetate/hexane while collecting 9 ml fractions following a 120 ml forerun. Fractions 16–39 were combined and concentrated to give 631 mg of a pale foam. Crystallization from diethyl ether/hexane (drops) provided 564 mg (69%) of 4-amino-6-chloro-2-(1-(3-isopropyl-furo[2,3c]pyridin-5-yl) ethylthio)-pyrimidine as a white solid (Melting Point: 115–117° C.).

Example 253

Preparation of 4-amino-6-chloro-2-(1-(4-cylcopentyl)-2-pyridyl)-ethyl)thio-pyrimidine (Cpd #253)

Part A: 1-(2-(4-cyclopentyl)pyridyl)ethanol (100 mg, 0.52 mmol) is dissolved in CH$_2$Cl$_2$ (2 ml) at 0° C., then treated with triethylamine (0.1 ml, 0.72 mmol) and MsCl (60 μl, 0.65 mmol). After stirring at 20° C. for 30 minutes, saturated NaHCO$_3$ (1 ml) is added and the aqueous is extracted three times with CH$_2$Cl$_2$. The organics are combined, washed with saturated NaHCO$_3$ and saturated NaCl, dried over MgSO$_4$, and concentrated in vacuo: 120 mg (0.44 mmol, 85%) mp 141–143° C.

Part B: 4-amino-6-chloro-2-thio-pyrimidine mesylate salt (Cpd #110A; 100 mg, 0.39 mmol) in EtOH (0.5 ml) at 40° C. is treated with 3.25M NaOH (0.25 ml, 0.8 mmol) and stirred for 15 minutes. The mesylate of Part A (120 mg, 0.44 mmol) is added and stirred for 1 hour. After cooling to 20° C., water is added and the reaction filtered. The solid is washed with water and ethanol, then dried: 46 mg (0.14 mmol, 35%) of Cpd #253, mp 144–146° C.

Following the general procedure of Example 253 and making non-critcal changes, but beginning with the appropriate alcohol, the following compounds are synthesized:

Example 255

4-amino-6-chloro-2-(1-(4-cylcopropyl)-2-pyridyl)-ethyl)thio-pyrimidine, mp 148–149° C.

Example 256

4-amino-6-chloro-2-(1-(4-(1-methylpropyl)-2-pyridyl)-ethyl)thio-pyrimidine, mp 108–110° C.

Example 257

4-amino-6-chloro-2-(1-(4-cylcohexyl)-2-pyridyl)-ethyl)thio-pyrimidine, mp 62–64° C.

Example 258

4-amino-6-chloro-2-(1-(4-(1-pyrryl))-2-pyridyl)-ethyl)thio-pyrimidine, mp 189° C.

Example 259

4-amino-6-chloro-2-(1-(4-dimethylamino)-2-pyridyl)-ethyl)thio-pyrimidine,

NMR: δ (CDCl$_3$) 8.20–8.21(d, J=5.90, 1H), 6.71 (m, 1H), 6.37–6.39 (m, 1H), 6.10 (s, 1H), 5.00–5.02 (m, 3H), 3.01 (s, 6H), 1.76–1.77 (d, J=7.13, 3H)

Example 260

4-amino-6-chloro-2-(1-(5-(1-methylethyl)-3-pyridyl)-ethyl)thio-pyrimidine, mp 123–124° C.

Example 261

4-amino-6-chloro-2-(1-(4-(1-ethylpropyl)-2-pyridyl)-ethyl)thio-pyrimidine, mp 146–147° C.

Example 262

4-amino-6-chloro-2-(1-(4-methyl-6-(1-pyrryl))-2-pyridyl)-ethyl)thio-pyrimidine, mp 155–157° C.

Example 263

4-amino-6-chloro-2-(1-(4-(2-propyloxy))-2-pyridyl)-ethyl)thio-pyrimidine, NMR: δ (CDCl$_3$) 8.34–8.36 (d, J=5.76, 1H), 6.97 (m, 1H), 6.63–6.65 (m, 1H), 6.11 (s, 1H), 5.10 (s, 2H), 5.03–5.08 (q, J=7.13, 1H), 4.61–4.67 (m, 1H), 1.74–1.76 (d, J=7.18, 3H), 1.34–1.36 (m, 6H)

Example 264

Preparation of 4-hydroxy-6-trifluoromethyl-2-pyrimidinethiol (Cpd #264)

To a solution of 25% NaOMe/MeOH (23 ml, 0.10 mol) and ethanol (27 ml) are added thiourea (5.33 g, 0.70 mol)

and ethyl 4,4,4-trifluoroacetoacetate (7.3 ml, 50 mmol), then the reaction is heated to reflux for 16 hrs. The mixture is cooled to 22° C., concentrated in vacuo, and the residue dissolved in water (50 ml), acidified with HCl (7 ml), and filtered. The solid is collected, washed with water, and dried: 6.58 g (32.5 mmol, 65%).

Example 265

Preparation of 6-trifluoromethyl-2-(4-methoxy-phenylmethyl)thio-4-pyrimidinol (Cpd 265)

4-hydroxy-6-trifluoromethyl-2-pyrimidinethiol (Cpd #264; 4.90 g, 25.0 mmol) in ethanol (8 ml) is treated with 3.25 N NaOH (8 ml, 26.0 mmol) followed by 4-methoxybenzyl chloride (3.5 ml, 25.7 mmol). After refluxing for 1 hr, the reaction is diluted with water and filtered. The solid is recrystallized from ethanol: 4.63 g (14.6 mmol, 58%), mp 169–170° C.

Example 266

Preparation of 4-chloro-6-trifluoromethyl-2-(4-methoxy-phenylmethyl)-thio-pyrimidine 6-trifluoromethyl-2-(4-methoxy-phenylmethyl)thio-4-pyrimidinol (Cpd 265; 7.9 g, mmol), POCl$_3$ (19 ml), and 2-picoline (2.5 ml) are combined and heated to reflux for 18 hrs. The reaction is poured onto ice, extracted thrice with ethyl acetate, dried with MgSO$_4$, and concentrated in vacuo.

Example 267

Preparation of 4-amino-6-trifluoromethyl-2-(4-methoxy-phenylmethyl)-thio-pyrimidine The crude oil of Example 266 (Cpd #266) is dissolved in acetonitrile (75 ml) and ammonium hydroxide (150 ml) then stirred for 18 hrs at 22° C. The reaction is extracted thrice with ethyl acetate, dried with MgSO$_4$, and concentrated in vacuo: 7.20 g (22.8 mmol, 91%).

NMR: δ (CDCl$_3$) 7.35 (d, J=8.5, 1H), 6.83 (d, J=8.5, 1H), 6.41 (s, 1H), 5.2 (s, 2H), 4.33 (s, 2H), 3.79 (s, 3H).

Example 268

Preparation of 4-amino-6-trifluoromethyl-2-pyrimidinethiol mesylate salt (Cpd #268)

4-amino-6-trifluoromethyl-2-(4-methoxy-phenylmethyl) thio-pyrimidine (Cpd #267; 7.20 g, 22.8 mmol) was dissolved in methylene chloride (100 ml) and treated with methane sulfonic acid (14.3 ml, 220 mmol) and stirred for 21 hrs. The solid was filtered, washed with water, and dried under vacuum. Melting point: 222–223° C.

Example 269

Preparation of 4-amino-6-trifluoromethyl-2-(1-(4-(1-dimethylethyl)-2-pyridyl)-ethyl)thio-pyrimidine (Cpd #269)

4-amino-6-trifluoromethyl-2-pyrimidinethiol mesylate salt (Cpd #268; 400 mg, 2.05 mmol) in EtOH (0.63 ml) at 40° C. is treated with 3.25M NaOH (0.63 ml, 2.05 mmol) and stirred for 15 minutes. 1-(4-(1,1-dimethylethyl)-2-pyridyl)ethyl chloride (550 mg, 2.30 mmol) was added and stirred for 1 hour. After cooling to 20° C., water is added and the reaction filtered. The solid is washed with water and ethanol, then dried: 315 mg (0.88 mmol, 43%), mp 162–163° C.

Following the general procedure of Example 269 and making non-critcal changes, but beginning with the appropriate halide, the following compounds are synthesized:

Example 270/Cpd #270

4-amino-6-trifluoromethyl-2-(2-naphthylmethyl) thio-pyrimidine, mp 144–145° C.

Example 271/Cpd #271

4-amino-6-trifluoromethyl-2-((4-(1-methylethyl)2-pyridyl)methyl)thio-pyrimidine, mp 150° C.

Example 272/Cpd #272

4-amino-6-trifluoromethyl-2-(1-(4-(1-methylethyl)2-pyridyl)ethyl)thio-pyrimidine, mp 145° C.

Example 273/Cpd #273

4-amino-6-trifluoromethyl-2-((4-(1, 1-dimethylethyl)2-pyridyl)methyl)-thio-pyrimidine, mp 164° C.

Example 274

Preparation of 4-(Diethoxymethyl)-6-hydroxy-2-(2-naphthylmethyl)-thio-pyrimidine (Cpd #274)

Ethyl (4,4-diethoxy)acetoacetate (12.4 g, 56.8 mmol) and thiourea (4.57 g, 60 mmol) in ethanol (45 ml) are treated with 25% NaOMe/MeOH (13 ml, 56.8 mmol), then heated to reflux for 4 hrs. The reaction is diluted with water (50 ml), then treated with 2-bromomethyl naphthylene (12.00 g, 54.3 mol). After 1 hr, the reaction ss diluted with water and filtered: 11.17 g (30.1 mmol, 55%).

NMR: δ (DMSO) 7.94 (s, 1H), 7.85 (m, 3H), 7.58 (dd, J$_{d1}$=8.4, J$_{d2}$=1.6, 1H), 7.47 (m, 3H), 6.15 (s, 1H), 5.21 (s, 1H), 4.56 (s, 2H), 3.58 (m, 4H), 1.14 (m, 6H).

Example 275

Preparation of 6-hydroxy-2-(2-naphthylmethyl)thio-4-pyrimidine carboxaldehyde oxime (Cpd #275)

4-(Diethoxymethyl)-6-hydroxy-2-(2-naphthylmethyl) thio-pyrimidine (Cpd #274; 1.00 g, 2.7 mmol is suspended in 50% HOAc (20 ml) and refluxed for 2 hrs, then concentrated in vacuo. The residue is suspended in hot ethanol (25 ml), treated with NaOAc (1.5 g), then a solution of hydroxylamine hydrochloride (1.0 g) in water (25 ml). The solution is refluxed for 30 min, then cooled to 0° C. and filtered: 720 mg (2.31 mmol, 86%)

NMR: δ (DMSO) 12.0 (s, 1H), 8.03 (s, 1H), 7.9 (s, 1H), 7.85 (m, 3H), 7.58 (d, J=8.4, 1H), 7.48 (m, 3H), 6.3 (s, 1H), 4.56 (s, 2H).

Example 276

Preparation of 6-chloro-2-(2-naphthylmethyl)thio-4-pyrimidine carbonitrile (Cpd 276)

6-hydroxy-2-(2-naphthylmethyl)thio-4-pyrimidine carboxaldehyde oxime (720 mg, 2.31 mmol), POCl$_3$ (3 ml), and 2-picoline (0.5 ml) are heated to reflux for 2 hrs. The reaction mixture is poured onto ice/water, extracted thrice with ethyl acetate, dried with MgSO$_4$, and concentrated in vacuo. The product is purified by chromatography (SiO$_2$, ethyl acetate/hexane, 5/95): 524 mg (1.67 mmol, 73%), mp 120–121° C.

Example 277

Preparation of 6-amino-2-(2-naphthylmethyl)thio-4-pyrimidine carbonitrile (Cpd 277)

6-chloro-2-(2-naphthylmethyl)thio-4-pyrimidine carbonitrile (Cpd 276; 60 mg, 3.07 mmol) was stirred in THF/NH$_4$OH (1:1, 15 ml) at 22° C. for 6 hrs. The reaction was diluted with ethyl acetate, washed with brine, dried with MgSO$_4$, then concentrated in vacuo: 871 mg (2.97 mmol, 97%), mp 154–155° C.

Example 278

4-amino-6-hydroxy-2-thio-5-pyrimidinyl ethanol (Cpd 278)

Sodium metal (3.91 g, 0.17 mol) is added to absolute ethanol (535 ml) and after complete dissolution of the metal, thiourea (7.74 g, 0.102 mol) and α-cyano-γ-butyrolactone (11.325 g, 0.102 mol)[1] are added together. The reaction mixture is heated to reflux for 18 hours. After cooling and concentrating in vacuo, the residue is dissolved in cold water (75 ml) and the aqueous is washed 2x with diethyl ether. The aqueous layer is neutralized with glacial acetic acid and the resultant precipitate is collected by filtration: 13.08 g (70 mmol, 68%), mp 293–295° C. (dec).

1 Fissekis, Myles and Brown, G. B., J. Org. Chem., 29 2670 (1964) H$_2$O, 2x6% NaHCO$_3$, dried with MgSO$_4$, then concentrated in vacuo. The crude product is then purified by chromatography (SiO$_2$ 1:1 hexane/ethyl acetate): 60 mg (0.18 mmol, 57%), mp 156–158° C.

Example 279

Preparation of 2-(4-amino-6-hydroxy-2-[2-naphthylmethyl]thio-5-pyrimidinyl)-ethanol (Cpd #279)

4-amino-6-hydroxy-2-thio-5-pyrimidinyl ethanol (Cpd 278; 2.33 g, 12.8 mmol) is slurried in ethanol (3.9 ml) and treated with 3.25 M NaOH (3.92 ml, 12.8 mmol). 2-Bromomethylnaphthalene (2.88 g, 13.0 mmol) is added and stirred for 18 hours at 22° C. The solution is cooled to 0° C. and filtered: 3.87 g (11.9 mmol, 93%), mp 192–193° C.

Example #280

Preparation of 2-(4-amino-6-hydroxy-2-(2-naphthylmethyl)thio-5-pyrimidinyl)-1-(dimethyl-tert-butylsilyloxy)ethane (Cpd #280)

2-(4-amino-6-hydroxy-2-[2-naphthylmethyl]thio-5-pyrimidinyl)-ethanol (Cpd #279; 106 mg, 0.32 mmol) is dissolved in pyridine (0.64 ml) and the solution is cooled to 0° C. then treated with t-butyl dimethylsilyl chloride (0.058 g, 0.39 mmol). The solution is stirred at 0° C. for 2 hours and two new spots developed in the mixture. The reaction mixture is poured into methylene chloride and washed 3x with 1 M HCl, 10% HCl, 3x H$_2$O, 2x 6% NaHCO$_3$, dried with MgSO$_4$, then concentrated in vacuo. The crude product is then purified by chromatography (SiO$_2$ 1:1 hexane/ethyl acetate): 60 mg (0.18 mmol, 57%), mp 156–158° C.

Example 281

Preparation of 4-chloro-2-(naphthylmethyl)thio-5,6-dihydro-7H-pyrrolo[2,3-d]pyrimidine (Cpd #281)

2-(4-amino-6-hydroxy-2-(2-naphthylmethyl)thio-5-pyrimidinyl)-1-(dimethyl-tert-butylsilyloxy)ethane (Cpd #280; 104 mg, 0.23 mmol) is treated with 2-picoline (28 μL, 0.28 mmol) and phosphorus oxychloride (0.22 ml, 2.3 mmol). The solution is heated to reflux for 2 hours, stirred overnight at 22° C. then heated again to reflux for an additional hour. The solution was cooled and ice is added. The resultant solid was filtered, washed with cold 50% ethanol, and dried under vacuum. The recovered solids, 81 mg are purified by chromatography (SiO$_2$, 4:1 hexane/ethyl acetate): 64 mg (0.19 mmol, 85%), mp 107–110° C.

Example 282

Preparation of 4-Amino-6-chloro-2-(1-(3-chlorofuro[2,3c]pyridine-5-yl)ethyl)thio-pyrimidine.

A solution of 5-(1-hydroxyethyl)-furo[2,3c]pyridine (2.64 g, 16.2 mmol) in 50 mL of methylene chloride at 0° C. is treated with triethylamine (2.7 mL, 19.4 mmol) followed by acetyl chloride (1.38 mL, 19.4 mmol) and the reaction is stirred at room temperature for 3 h. The mixture is washed with 2x50 mL of saturated sodium bicarbonate, the organics are dried over potassium carbonate and concentrated in vacuo. The crude material iss chromatographed over 150 g of silica gel (230–400 mesh), eluting with 15% ethyl acetate/hexanes to give 2.4 g (72%) of 5-(1-acetyloxyethyl)-furo[2,3c]pyridine.

A solution of 5-(1-acetyloxyethyl)-furo[2,3c]pyridine (616 mg, 3.0 mmol) in 30 mL of methylene chloride at 0° C. is saturated with chlorine (g) and is allowed to slowly warm to room temperature. The reaction is stirred for 2 h, is layered with 30 mL of saturated sodium bicarbonate and is gently stirred for 1.5 h. The mixture is further diluted with 20 mL of saturated sodium bicarbonate and stirred vigorously for 20 min. The aqueous layer is extracted with 3x15 mL of methylene chloride and the combined organics are dried over potassium carbonate and concentrated in vacuo. The crude material (856 mg) is combined with 256 mg of similarly prepared material and chromatographed over 50 g of silica gel (230–400 mesh), eluting with 15% ethyl acetate/hexanes to afford 757 mg (69%) of 5-(1-acetyloxyethyl)-2,3-dichloro-2,3-dihydrofuro[2,3c]pyridine.

A solution of 5-(1-acetyloxyethyl)-2,3-dichloro-2,3-dihydrofuro[2,3c]pyridine (680 mg, 2.46 mmol) in 18 mL of ethanol is treated with 2.04 g (14.8 mmol) of potassium carbonate and stirred vigorously for 2 h. The volatiles are removed in vacuo and the residue is partitioned between 25 mL of 50% saturated sodium chloride and 4x25 mL of methylene chloride. The combined organics are dried over potassium carbonate and concentrated in vacuo. The crude material is chromatographed over 25 g of silica gel (230–400 mesh), elution with 50% ethyl acetate/hexanes to give 395 mg (81%) of 5-(1-hydroxyethyl)-3-chlorofuro[2,3c]pyridine.

Chloronation of 370 mg (1.9 mmol) of 5-(1-hydroxyethyl)-3-chlorofuro[2,3c]pyridine with thionyl chloride as described for Cpd #246 gives 378 mg (92%) of 5-(1-chloroethyl)-3-chlorofuro[2,3c]pyridine.

Alkylation of 365 mg (1.70 mmol) of 5-(1-chloroethyl)-3-chlorofuro[2,3c]pyridine with 657 mg (2.55 mmol) of 4-amino-6-chloro-2-mercapto-pyrimidine mesylate salt (Cpd # 110A) as described for Cpd #246 affords 286 mg (49%) of 4-Amino-6-chloro-2-(1-(3-chlorofuro[2,3c]pyridine-5-yl)ethyl)thio-pyrimidine (Melting Pt. 184–186° C.).

Example 283

Preparation of 4-Amino-6-chloro-2-(1-(3,7-dichlorofuro[2,3c]pyridine-5-yl)ethyl)thio-pyrimidine, Melting Pt. 190–191° C.

7-Chloro-5-(1-hydroxyethyl)-furo[2,3c]pyridine (1.98 g, 10 mmole) was dissolved in 4 ml of pyridine in a 50 ml one neck round bottom flask under nitrogen. The solution was treated with acetic anhydride (2 ml, 22 mmole) and the reaction was stirred for 3 h at room temperature. The bulk of the volatiles were removed in vacuo and the residue was partitioned between 1×50 ml of saturated sodium bicarbonate and 4×25 ml of dichloromethane. The organics were dried over anhydrous potassium carbonate were concentrated in vacuo to a pale oil. The crude material was chromatographed over 40 g of silica gel eluting with 16% ethyl acetate/hexane while collecting 9 ml fractions. Fractions 17–33 were combined and concentrated to give 1.10 g (92%) of 5-(1-acetoxyethyl)-7-chloro-furo[2,3c]pyridine as a colorless oil. $^1$H NMR (CDCl$_3$, TMS): δ 1.63 (d, J=6.6 Hz, 3), 2.13 (s, 3), 5.97 (q, J=6.6, 13.2 Hz, 1), 6.85 (d, J=2, 1), 7.55 (s, 1), 7.81 (d, J=2, 1) ppm.

5-(1-Acetoxyethyl)-7-chloro-furo[2,3c]pyridine (1.05 g, 4.4 mmole) was dissolved in 30 ml of dichloromethane in a 100 ml one neck round bottom flask under nitrogen. The reaction was cooled to 0° C., was saturated with chlorine gas, was allowed to slowly warm to room temperature, and was stirred for 2 h at room temperature. The solution was layered with 40 ml of saturated sodium bicarbonate, was stirred gently for 6 h followed by vigorous stirring for 15 min. The mixture was further diluted with 10 ml of saturated sodium bicarbonate. The aqueous layer was extracted with 2×20 ml of dichloromethane, and the combined organics were dried over potassium carbonate. The dried organics were concentrated in vacuo to afford 1.34 g (98%) of 5-(1-acetoxyethyl)-2,3-dihydro-2,3,7-trichloro-furo[2,3c]pyridine as a pale yellow oil. $^1$H NMR (CDCl$_3$, TMS): δ 1.59 (m, 3), 2.13 (m, 3), 5.44 (m, 1), 5.90 (m, 1), 6.53 (s, 1), 7.43 (m, 1) ppm.

5-(1-Acetoxyethyl)-2,3-dihydro-2,3,7-trichloro-furo[2,3c]pyridine (1.34 g, 4.3 mmole) was dissolved in 18 ml of absolute ethanol in a 100 ml one neck round bottom flask under nitrogen. The solution was treated with potassium carbonate (3.5 g, 25 mmole) and the reaction mixture was stirred vigorously overnight. The suspension was brought to homogeneity with water, was diluted with 5 ml 2N sodium hydroxide, and the volatiles were removed in vacuo. The residue was partitioned between 1×50 ml of 50% saturated sodium chloride and 4×25 ml of dichloromethane. The combined organics were dried over potassium carbonate and were concentrated in vacuo to an yellow paste. The crude material was chromatographed over 50 g of silica gel (230–400 mesh), eluting with 20% ethyl acetate/hexane while collecting 9 ml fractions. Fractions 27–48 were combined and concentrated to afford 857 mg (84%) of 5-(1-acetoxyethyl)-3,7-dichloro-2,3-dihydro-furo[2,3c]pyridine (9) as a white solid (Melting Point: 98–101° C.).

3-Chloro-(1-hydroxyethyl)-furo[2,3c]pyridine (800 mg, 3.5 mmole) was dissolved in 10 ml of dichloromethane in a 50 ml one neck round bottom flask under nitrogen. The solution was cooled to 0° C., was treated with thionyl chloride (375 μl, 5.2 mmole), and the reaction was stirred for 20 min at 0° C. followed by 1 h at room temperature. The reaction was added to 50 ml of saturated sodium bicarbonate, the aqueous layer was washed with 3×10 ml of dichloromethane, and the combined organics were dried over potassium carbonate. The dried organics were concentrated in vacuo to give 847 mg of a yellow oil. The crude material was chromatographed over 40 g of silica gel (230–400 mesh) eluting with 10% ethyl acetate/hexane while collecting 9 ml fractions. Fractions 6–16 were combined and concentrated to give 807 mg (93%) of 5-(1-chloroethyl)-3,7-dichloro-furo[2,3c]pyridine as a colorless oil. $^1$H NMR (CDCl$_3$, TMS): δ 1.93 (d, J=6.7 Hz, 3), 5.23 (q, J=6.7 Hz, 13.4 Hz, 1), 7.72 (s, 1), 7.85 (s, 1) ppm. 4-Amino-6-chloro-2-mercaptopyrimidine mesylate salt (1.12 g, 4.4 mmole) was dissolved in 8 ml of dry dimethylformamide in an oven dried 50 ml two neck round bottom flask under nitrogen. The solution was cooled to 0° C., was treated with sodium hydride (224 mg, 5.6 mmole), and the mixture was stirred for 1 h at room temperature. 5-(1-Chloroethyl)-3,7-dichloro-furo[2,3c]pyridine (780 mg, 3.1 mmole), in 2×2 ml of dry dimethylformamide, was added dropwise to the reaction and the mixture was stirred for 72 h. The reaction mixture was diluted with 100 ml of ethyl acetate, was washed with 4×50 ml of 50% saturated 1:1 sodium chloride/sodium bicarbonate followed by 1×25 ml of saturated sodium chloride, and the organics were dried over anhydrous potassium carbonate. The dried organics were concentrated in vacuo to a yellow paste. The crude material was chromatographed over 60 g of silica gel (230–400 mesh), eluting with 25% ethyl acetate/hexane while collecting 9 ml fractions. Fractions 14–21 were combined and concentrated to give 800 mg of a white solid. Washing with diethyl ether provided 696 mg (60%) of 4-amino-6-chloro-2-(1-(3,7-dichloro-furo[2,3c]pyridin-5-yl)ethylthio)-pyrimidine as a white solid (Melting Point: 190–191° C.).

Example 284

Preparation of 4-Amino-6-chloro-2-(1-(3-bromofuro[2,3c]pyridine-5-yl)ethyl)thio-pyrimidine, Melting Pt. 175–176.5° C.

5-(1-Acetoxyethyl)-furo[2,3c]pyridine (1.32 g, 6.4 mmole) was dissolved in 30 ml of chloromethane in a 100 ml one neck round bottom flask under nitrogen. The solution was layered with 50 ml of saturated sodium bicarbonate and was treated with bromine (1.99 ml, 38.6 mmole) in a single lot. The reaction was stirred gently for 5 h at room temperature, and the aqueous layer was washed with 2×20 ml of dichloromethane. The combined organics were concentrated in vacuo to an amber oil. The oil was partitioned between 1×50 ml of saturated sodium bicarbonate and 4×25 ml of dichloromethane. The organics were dried over potassium carbonate and were concentrated in vacuo to give 2.15 g (93%) of 5-(1-acetoxyethyl)-2,3-dibromo-2,3-dihydro-furo[2,3c]pyridine as a pale yellow oil.

5-(1-Acetoxyethyl)-2,3-dibromo-2,3-dihydro-furo[2,3c] pyridine (2.15 g, 5.9 mmole) was dissolved in 20 ml of absolute ethanol in a 50 ml one neck round bottom flask under nitrogen. The solution was treated with potassium carbonate (4.9 g, 35.6 mmole) and the reaction mixture was stirred vigorously for 18 h. The mixture was filtered, the filtrate was concentrated to a yellow oil and the potassium carbonate filter cake was partitioned between 1×50 ml of water and 4×25 ml of dichloromethane. The organics were combined with the filtrate residue and were dried over potassium carbonate and were concentrated in vacuo to a yellow paste. The crude material was chromatographed over 50 g of silica gel (230–400 mesh), eluting with 40% ethyl acetate/hexane while collecting 9 ml fractions. Fractions 24–51 were combined and concentrated to afford 1.04 g (67% overall) of 3-bromo-5-(1-hydroxyethyl)-furo[2,3c] pyridine as a pale tan solid (Melting Point: 108–110° C.).

3-Bromo-(1-hydroxyethyl)-furo[2,3c]pyridine (1.01 g, 4.2 mmole) was dissolved in 15 ml of dichloromethane in a 50 ml one neck round bottom flask under nitrogen. The solution was cooled to 0° C., was treated with thionyl chloride (454 μl, 6.2 mmole), and the reaction was stirred for 20 min at 0° C. followed by 1.5 h at room temperature. The reaction was added to 25 ml of saturated sodium bicarbonate, the aqueous layer was washed with 3×25 ml of dichloromethane, and the combined organics were dried over potassium carbonate. The dried organics were concentrated in vacuo to give 1.05 g (97%) of 3-bromo-5-(1-chloroethyl)-furo[2,3c]pyridine as a yellow oil. $^1$H NMR (CDCl$_3$, TMS): δ 1.95 (d, J=6.8 Hz, 3), 5.31 (q, J=6.8, 13.7 Hz, 1), 6.68 (m, 1), 7.80 (s, 1), 8.83 (m, 1) ppm.

4-Amino-6-chloro-2-mercaptopyrimidine mesylate salt (1.48 g, 5.7 mmole) was dissolved in 15 ml of dry dimethylformamide in an oven dried 100 ml two neck round bottom flask under nitrogen. The solution was cooled to 0° C., was treated with sodium hydride (505 mg, 12.6 mmole), and the mixture was stirred for 1 h at room temperature. 5-(1-Chloroethyl)-3-bromo-furo[2,3c]pyridine (856 mg, 4.0 mmole), in 2×2 ml of dry dimethylformamide, was added dropwise to the reaction and the mixture was stirred for 68 h. The reaction mixture was diluted with 125 ml of ethyl acetate, was washed with 4×50 ml of 50% saturated sodium chloride followed by 1×25 ml of saturated sodium chloride, and the organics were dried over anhydrous potassium carbonate. The dried organics were concentrated in vacuo to an amber oil. The crude material was chromatographed over 100 g of silica gel (230–400 mesh), eluting with 40% ethyl acetate/hexane while collecting 22 ml fractions. Fractions 14–23 were combined and concentrated to give 978 mg of an off-white solid. Washing with diethyl ether provided 880 mg (58%) of 4-amino-6-chloro-2-(1-(3-bromo-furo[2,3c] pyridin-5-yl)ethylthio)-pyrimidine as a white solid (Melting Point: 175–176.5° C.).

Example 285

Preparation of 4-Amino-6-chloro-2-(1-(3-bromo-7-chlorofuro[2,3c]pyridine-5-yl)ethyl)thio-pyrimidine, Melting Pt. 181–182° C.

5-(1-Acetoxyethyl)-7-chloro-furo[2,3c]pyridine (1.4 g, 5.8 mmole) was dissolved in 35 ml of dichloromethane in a 200 ml one neck round bottom flask under nitrogen. The solution was layered with 75 ml of saturated sodium bicarbonate and was treated with bromine (4.7 ml, 90.6 mmole) in a single lot. The reaction was stirred gently for 24 h at room temperature, was treated with solid sodium bicarbonate (3 g, 36 mmole), and was stirred vigorously for 6 h. The aqueous layer was washed with 3×30 ml of dichloromethane. The combined organics were concentrated in vacuo to an amber oil. The oil was partitioned between 1×50 ml of saturated sodium bicarbonate and 4×25 ml of dichloromethane. The organics were dried over potassium carbonate and were concentrated in vacuo to give 1.66 g (71%) of 5-(1-acetoxyethyl)-7-chloro-2,3-dibromo-2,3-dihydro-furo [2,3c]pyridine as a pale oil. $^1$H NMR (CDCl$_3$, TMS): δ 1.60 (m, 3), 2.15 (m, 3), 5.67 (m, 1), 5.90 (m, 1), 6.94 (s, 1), 7.43 (m, 1) ppm. 5-(1-Acetoxyethyl)-7-chloro-2,3-dibromo-2,3-dihydro-furo[2,3c]pyridine (1.66 g, 4.2 mmole) was dissolved in 20 ml of 95% ethanol in a 100 ml one neck round bottom flask under nitrogen. The solution was treated with potassium carbonate (4.9 g, 35.6 mmole) and the reaction mixture was stirred vigorously for 18 h. The mixture was filtered, the filtrate was concentrated to a yellow oil and the potassium carbonate filter cake was partitioned between 1×50 ml of water and 4×25 ml of dichloromethane. The organics were combined with the filtrate residue and were dried over potassium carbonate and were concentrated in vacuo to a yellow paste. The crude material was adsorbed onto 2 g of silica gel (230–400 mesh) which was chromatographed over 50 g of silica gel (230–400 mesh), eluting with 20% ethyl acetate/hexane while collecting 9 ml fractions. Fractions 27–60 were combined and concentrated to afford 806 mg (70% overall) of 3-bromo-7-chloro-5-(1-hydroxyethyl)-furo[2,3c]pyridine as a white solid (Melting Point: 125–126° C.).

3-Bromo-(1-hydroxyethyl)-furo[2,3c]pyridine (430 mg, 1.6 mmole) was dissolved in 5 ml of dichloromethane in a 25 ml one neck round bottom flask under nitrogen. The solution was cooled to 0° C., was treated with thionyl chloride (169 μl, 2.3 mmole), and the reaction was stirred for 20 min at 0° C. followed by 3 h at room temperature. The reaction was added to 20 ml of saturated sodium bicarbonate, and the organic layer was anhydrous potassium carbonate. The dried organics were concentrated in vacuo to a pale oil. The crude material was chromatographed over 25 g of silica gel (230–400 mesh) eluting with 20% ethyl acetate/hexane while collecting 5 ml fractions. Fractions 6–12 were combined and concentrated to afford 406 mg (88%) of 3-bromo-7-chloro-5-(1-chloroethyl)-furo[2,3c] pyridine as colorless oil which crystallized on standing (Melting Point: 62–64° C.).

4-Amino-6-chloro-2-mercaptopyrimidine mesylate salt (437 mg, 1.7 mmole) was dissolved in 6 ml of dry dimethylformamide in an oven dried 50 ml two neck round bottom flask under nitrogen. The solution was cooled to 0° C., was treated with sodium hydride (142 mg, 3.6 mmole), and the mixture was stirred for 1 h at room temperature. 5-(1-Chloroethyl)-3-bromo-7-chloro-furo[2,3c]pyridine (385 mg, 1.3 mmole), in 2×2 ml of dry dimethylformamide, was added dropwise to the reaction and the mixture was stirred for 48 h. The reaction mixture was diluted with 75 ml of ethyl acetate, was washed with 4×25 ml of 50% saturated sodium chloride followed by 1×25 ml of saturated sodium chloride, and the organics were dried over anhydrous potassium carbonate. The dried organics were concentrated in vacuo to a yellow paste. The crude material was chromatographed over 40 g of silica gel (230–400 mesh), eluting with 25% ethyl acetate/hexane while collecting 9 ml fractions. Fractions 26–39 were combined and concentrated to give 347 mg of an off-white solid. Washing with diethyl ether provided 267 mg (49%) of 4-amino-6-chloro-2-(1-(3-bromo-7-chloro-furo[2,3c]pyridin-5-yl) pyrimidine as a white solid (Melting Point: 181–182° C.).

Example 286

Preparation of 4-Amino-6-chloro-2-(1-(7-chloro-3-methylfuro[2,3c]pyridine-5-yl)ethyl)thio-pyrimidine, Melting Pt. 198–199.5° C.

7-Chloro-5-(1-Hydroxyethyl)-3-methyl-furo[2,3c]pyridine (2.3 g, 10.9 mmole) was dissolved in 100 ml dichloromethane in a 200 ml one neck round bottom flask under nitrogen. The solution was cooled to O° C., was treated with thionyl chloride (1.2 ml, 16.3 mmole), and the reaction was stirred 20 min at 0° C. followed by 3 h at room temperature. The reaction was added to 85 ml saturated sodium bicarbonate, the layers were separated, the aqueous layer was washed with 3×25 ml dichloromethane, and the combined organics were dried over potassium carbonate. The dried organics were concentrated in vacuo to give 2.36 g (94%) of 7-chloro-5-(1-chloroethyl)-3-methyl-furo[2,3c]pyridine as a pale yellow oil which crystallized on standing (Melting Point: 49–51° C.).

4-Amino-6-chloro-2-mercaptopyrimidine mesylate salt (1.29 g, 5.0 mmole) was suspended in 20 ml dry dimethylformamide in a 100 ml one neck round bottom flask under nitrogen. The suspension was cooled to 0° C., was treated with sodium hydride (430 mg, 10.8 mmole), and the mixture was stirred 1 h at room temperature. 7-Chloro-5-(1-chloroethyl)-3-methyl-furo[2,3c]pyridine (920 mg, 4.0 mmole), in 2×4 ml dry dimethylformamide, was added dropwise to the reaction and the mixture was stirred 48 h. The reaction mixture was diluted with 125 ml ethyl acetate, was washed with 4×50 ml 50% saturated sodium chloride followed by 1×25 ml saturated sodium chloride, and the organics were dried over anhydrous potassium carbonate. The dried organics were concentrated in vacuo to a yellow oil. The crude material was chromatographed over 100 g silica gel (230–400 mesh), eluting with 30% ethyl acetate/hexane while collecting 22 ml fractions. Fractions 25–36 were combined and concentrated to give 1.04 g of a white solid which was washed with 10 ml 20% diethyl ether/hexane to afford 1.02 g of 4-amino-6-chloro-2-(1-(7-chloro-3-methyl-furo[2,3c]pyridin-5-yl)ethylthio)-pyrimidine as a white solid (Melting Point: 198–199.5° C.).

Example 287

Preparation of 4-Amino-6-trifluoromethyl-2-(1-(7-chloro-3,3-dimethyl-2,3-dihydrofuro[2,3c]pyridine-5-yl)ethyl)thio-pyrimidine, Melting Pt. 170–172° C.

4-Amino-2-mercapto-6-trifluoromethyl-pyrimidine mesylate salt (742 mg, 2.5 mmole) was dissolved in 8 ml of dry dimethylformamide in an oven dried 50 ml two neck round bottom flask under nitrogen. The solution was cooled to 0° C., was treated with sodium hydride (210 mg, 5.3 mmole), and the mixture was stirred for 1 h at room temperature. 7-Chloro-5-(1-chloroethyl)-2,3-dihydro-3,3-dimethyl-furo[2,3c]pyridine (569 mg, 2.3 mmole), in 2×2 ml of dry dimethylformamide, was added dropwise to the reaction and the mixture was stirred for 24 h. The reaction mixture was diluted with 75 ml of ethyl acetate, was washed with 4×25 ml of 50% saturated sodium chloride followed by 1×25 ml of saturated sodium chloride, and the organics were dried over anhydrous potassium carbonate. The dried organics were concentrated in vacuo to a yellow oil. The crude material was chromatographed over 50 g of silica gel (230–400 mesh), eluting with 30% ethyl acetate/hexane while collecting 9 ml fractions. Fractions 13–30 were combined and concentrated to give a white foam. Crystallization from hexane/diethyl ether provided 786 mg (84%) of 4-amino-2-(1-(7-chloro-2,3-dihydro-3,3-dimethyl-furo[2,3c]pyridin-5-yl)ethylthio)-6-trifluoromethyl-pyrimidine as an off-white solid (Melting Point: 170–172° C.).

Example 288

Following the general procedure of Example 277 and including non-critical changes, but employing the appropriate amine, the following compound is prepared:
Cpd #288 6-methylamino-2-(2-naphthylmethyl)thio-4-pyrimidine carbonitrile, mp 169–171 C.

When R12 and R13 are different, the compounds of Formula I (as well as IA and IB) are drawn as the racemic mixture and include the R and S isomers, which can be resolved from the racemic mixture by HPLC using a chiral column, such as Chiralcel OD-H, eluting with an appropriate solvent mixture, such as isopropanol/hexane (see e.g. PROCEDURE A). The R and S isomers of Formula I (when R12 and R13 are different) can be prepared from an appropriate chiral halide (or mesylate) II (see chart I). The appropriate chiral halide (or mesylate) II is prepared from a chiral alcohol IV. The appropriate chiral alcohol IV can be prepared from the appropriate ketone V using a chiral reducing agent, such as (+) or (–)-diisopinocampheylchloroborane or other chiral reducing agents known in the art. The appropriate chiral alcohol IV is also obtained from the resolution of the racemic alcohol IV via the enzymatic hydrolysis of the appropriate racemic acetate VI with the appropriate enzyme, such as PS-30 amano lipase or L1754 Type VII from candidae cylindracea or other enzymes known in the art. The appropriate chiral alcohol IV is also obtained from the resolution of the racemic alcohol IV via the enzymatic esterification (such as acetylation or butyration) of the racemic alcohol using the appropriate enzyme, such as porcine pancreatic lipase type II, or other enzymes known in the art.

Example 289 and 290

(R)-(+)-4-Amino-6-chloro-2-(1-(3-methylfuro[2,3c] pyridine-5-yl)ethyl)thio-pyrimidine (Cpd #289) and (S)-(–)-4-Amino-6-chloro-2-(1-(3-methylfuro[2,3c] pyridine-5-yl)ethyl)thio-pyrimidine (Cpd #290)

Method A: Cpd #246 is separated into its (+) and (–) enantiomers using HPLC with the chiral column, Chiralcel OD-H, eluting with 20% isopropanol/hexane, with a flow rate of 0.5 mL/minute. Cpd #289 [a]$_D$+278° (c 0.91, chloroform); Cpd #290 [a]$_D$-276° (c 0.91, chloroform).

Method B:

Part 1:

A solution of racemic 5-(1-hydroxyethyl)-3-methyl-furano[2,3c]pyridine (15.3 g, 0.0864 mol) in 200 ml of ether at room temperature was treated with 2,2,2-trifluoroethylbutyrate (58.8 g, 0.3458 mol, 4.0 eq.) and PPL (porcine pancreatic lipase, type II, Sigma Chemical Co., 22.3 g) and stirred for 7 days in a stoppered flask. The contents were diluted with 150 ml of ether plus 10 g of celite, filtered through a pad of celite (50 g) and washed the pad thoroughly with ether. The filtrate was concentrated at reduced pressure and pumped overnight under high vacuum. Chromatography with 400 g of silica gel, packed and eluted with acetone-methylene chloride (1:6), (1:5) and finally (1:4), yielded 10.8 g (50.6%) of the (R)-(+)-5-(1-butyryloxyethyl)-3-methyl-furano[2,3c]pyridine (rotation: [α]$_D$=+76.5° (c=1.50, CHCl$_3$); 99.9% ee; $^1$H NMR (CDCl$_3$, TMS): δ 8.78 (s, 1 H), 7.50 (s, 2 H), 6.04 (q, 1 H, 6.62 Hz), 2.35 (t, 2 H, J=7.45 Hz), 2.23 (s, 3 H), 1.72-1.57 (m, 2 H), 1.64 (d, 3 H, J=4.65 Hz), 0.92 (t, 3 H, J=7.42 Hz) ppm) and 7.51 g (49.1%) of (S)-(-)-5-(1-hydroxyethyl)-3-methyl-furano[2,3c]pyridine (rotation: [α]$_D$=-38.6° (c=0.725, CHCl$_3$); 99% ee; $^1$H NMR (CDCl$_3$,TMS): δ 8.69 (s, 1 H), 7.51 (s, 1 H), 7.46 (s, 1 H), 5.00 (q, 1 H, J=6.46 Hz), 2.23 (s, 3 H), 1.55 (d, 3 H, J=6.49 Hz) ppm).

Part 2: (R)-(+)-5-(1-Butyryloxyethyl)-3-methyl-furano[2,3c]pyridine (1.75 g, 7.085 mmol) in 100 ml of methanol, cooled at 0–5 ° C., was treated with K$_2$CO$_3$ (1.955 g, 14.17 mmol, 2.0 eq.) in 25 ml of water. The cooling bath was removed after 30 min and the reaction mixture was allowed to stir at ambient temperature for 4 h. The addition of 120 ml of crushed ice was followed by acidification with 2N NaHSO$_4$ (14.17 ml, 28.34 mmol) to pH 5. The contents were poured into 125 ml of saturated NaHCO$_3$, extracted three times with ethylacetate, the combined organic extracts dried with anhydrous Na$_2$SO$_4$ and concentrated in vacuo. Chromatography using 50 g of silica gel, packed and eluted with acetone-methylene chloride (1:6), gave 1.12 g (89%) of (R)-(+)-5-(1-hydroxyethyl)-3-methyl-furano[2,3c]pyridine as a white solid (rotation: [α]$_D$=+42.4° (c=0.870, CHCl$_3$); $^1$H NMR (CDCl$_3$,TMS): δ 8.66 (s, 1 H), 7.47 (s, 1 H), 7.40 (s, 1 H), 4.95 (q, 1 H, J=6.45 Hz), 3.77 (brs, 1 H), 2.19 (s, 3 H), 1.50 (d, 3 H, J=6.43 Hz) ppm).

A solution of (R)-(+)-5-(1-hydroxyethyl)-3-methyl-furano[2,3c]pyridine (0.100 g, 0.565 mmol) in 2 ml of dry tetrahydrofuran was treated with triphenylphosphine (0.148 g, 0.565 mmol, 1.0 eq.), benzoic acid (0.069 g, 0.565 mmol, 1.0 eq.). In a dropwise fashion, diethylazodicarboxylate (0.098 g, 0.656 mmol, 1.0 eq.) over a 30 sec period. After stirring for 2 h at room temperature an additional 20% more of each reagent was added. After 30 min longer, the contents were concentrated at reduced pressure, dissolved in ethylacetate, treated with 600 mg of silica gel and reconcentrated in vacuo. The free flowing powder was applied to a silica gel column, packed and eluted with ethylacetate-hexane (1:9), to yield 136 mg (85%) of (S)-(+)-5-(1-benzoyloxyethyl)-3-methyl-furano[2,3c]pyridine (rotation: [α]$_D$ =+56.80° (c=1.05, CHCl$_3$); $^1$H NMR (CDCl$_3$,TMS): δ 8.79 (s, 1 H), 8.13 (s, 1 H), 8.11 (s, 1 H), 7.63-7.38 (m, 5 H), 6.30 (q, 1 H, J=6.59 Hz), 2.22 (s, 3 H), 1.78 (d, 3 H, J=6.58 Hz) ppm.

A solution of (S)-(+)-5-(1-benzoyloxyethyl)-3-methyl-furano[2,3c]pyridine (0.134 g, 0.477 mmol) in 9 ml of methanol at 0–5° C. was treated with K$_2$CO$_3$ (0.132 g, 0.954 mmol, 2.0 eq.) in 2.2 ml of water. After 5 min, the cooling bath was removed and the reaction mixture was stirred for 4 h. The contents were cooled in an ice bath, treated with 2N NaHSO$_4$ (0.954 ml, 1.91 mmol), poured into 20 ml of saturated NaHCO$_3$, extracted twice with ethylacetate and the combined organic extracts dried with anhydrous Na$_2$SO$_4$. The filtrate was concentrated in vacuo and chromatographed with 10 g of silica gel, packed and eluted with acetone-methylene chloride (1:6), to give 83 mg (99%) of (S)-(-)-5-(1-hydroxyethyl)-3-methyl-furano[2,3c]pyridine (rotation: [α]$_D$=-40.60° (c=0.675, CHCl$_3$)).

Part 3: Oxalyl chloride (1.01 ml, 11.5 mmole) was dissolved in 40 ml dry dichloromethane in an oven dried 100 ml two neck round bottom flask under nitrogen. The solution was cooled to -60° C., was treated dropwise with dimethyl sulfoxide (1.63 ml, 23 mmole) in 1×5 ml dichloromethane, and was stirred for 20 min. The mixture was treated with 7-chloro-2,3-dihydro-5-(1-hydroxyethyl)-3-methyl-furano[2,3c]-pyridine (2.14 g, 10 mmole) in 1×5 ml dichloromethane and the reaction was stirred for 20 min at -60° C. The reaction mixture was treated dropwise with triethylamine (7.0 ml, 50 mmole), was stirred for 20 min at -60° C., followed by 1 h at room temperature. The mixture was diluted with 125 ml ethyl acetate, was washed with 2×50 ml 1:1 5% hydrochloric acid/saturated sodium chloride, and the organics were dried over anhydrous magnesium sulfate. The organics were concentrated in vacuo to a dark yellow oil. The crude material was chromatographed over 75 g silica gel (230–400 mesh), eluting with 12% ethyl acetate/hexane while collecting 9 ml fractions. Fractions 41–72 were combined and concentrated to give 1.80 g (85%) of 5-Acetyl-7-chloro-2,3-dihydro-3-methyl-furano[2,3c]pyridine as a white solid. $^1$H NMR (CDCl$_3$, TMS): δ 1.38 (d, J=7 Hz, 3), 2.65 (s, 3), 3.70 (m, 10, 4.31 (dd, J=7.5, 9 Hz, 1), 4.91 (t, J=9.2 Hz, 1), 7.88 (s, 5-Acetyl-7-chloro-2,3-dihydro-3-methyl-furano[2,3c]pyridine (1.8 g, 8.5 mmole) was dissolved in 15 ml dry tetrahydrofuran in an oven dried 100 ml two neck round bottom flask under nitrogen. The solution was cooled to -30° C. and the resultant suspension was treated slowly dropwise with (-) diisopinocampheyl borane chloride (5.9 g, 18.3 mmole) in 1×16 ml dry tetrahydrofuran. The reaction was placed in an ice/acetone bath (-18° C.) and was allowed to stir overnight as the cooling bath expired. The reaction was recooled to -18° C., was treated dropwise with a solution containing 15 ml saturated sodium bicarbonate and 4.5 ml 30% hydrogen peroxide, and the mixture was stirred for 1 h at room temperature. The mixture was diluted with 120 ml of ethyl acetate, the layers were separated, and the organic layer was washed with 2×50 ml saturated sodium bicarbonate, 1×50 ml water, and 1×50 ml saturated sodium chloride. The organics were dried over 1:1 anhydrous potassium carbonate/anhydrous magnesium sulfate and were concentrated in vacuo to a yellow oil. The crude material was chromatographed over 125 g silica gel (230–400 mesh), eluting with 1 1 20% ethyl acetate/hexane followed by 1 l 33% ethyl acetate/hexane, while collecting 22 ml fractions. Fractions 47–77 were combined and concentrated to give 1.73 g (95%) of (S)-7-chloro-2,3-dihydro-5-(1-hydroxyethyl)-3-methyl-furano[2,3c]pyridine as a pale oil. $^1$H NMR (CDCl$_3$, TMS): δ 1.36 (m, 3), 1.47 (d, J=6.4 Hz, 3), 2.86 (bs, 1), 3.65 (m, 1), 4.22 (t, J=8.0 Hz, 1), 4.82 (m, 2), 7.09 (m, 1) ppm.

7-Chloro-2,3-dihydro-5-(1-(S)-hydroxyethyl)-3-methyl-furano[2,3c]pyridine (1.61 g, 7.5 mmole) was dissolved in 25 ml absolute ethanol containing 20% palladium hydroxide on carbon (400 mg) in a 250 ml PARR shaker bottle. The reaction mixture was hydrogenated at 25 PSI for 4 h, was filtered through celite, and the filter cake was washed well with absolute ethanol. The filtrate was concentrated in vacuo to a pale paste which was partitioned between 1×50 ml saturated sodium bicarbonate and 4×20 ml dichloromethane. The combined organics were dried over anhydrous potassium carbonate and were concentrated in vacuo to afford 1.24 g (92%) of (S)-2,3-dihydro-5-(1-hydroxyethyl)-3-methyl-furano[2,3c]pyridine as a pale oil. $^1$H NMR (CDCl$_3$, TMS): δ 1.31 (m, 3), 1.44 (d, J=6.4 Hz, 3), 3.54 (m, 1), 4.09 (t, J=8.4 Hz, 1), 4.28 (bs, 1), 4.70 (t, J=8.8 Hz, 1), 4.81 (q, J=6.3, 12.8 Hz, 1), 7.11 (s, 1), 7.97 (s, 1) ppm.

(S)-2,3-Dihydro-5-(1-hydroxyethyl)-3-methyl-furano[2,3c]pyridine (1.2 g, 6.7 mmole) was dissolved in 7 ml pyridine in a 25 ml one neck round bottom flask under nitrogen. The solution was treated with acetic anhydride (1.4 ml, 14.7 mmole) and was stirred overnight at room temperature. The volatiles were removed under a stream of nitrogen and the residue was partitioned between 1×40 ml ethyl acetate and 1×40 ml saturated sodium bicarbonate. The organics were dried over anhydrous magnesium sulfate and were concentrated in vacuo to give 1.43 g (96%) of (S)-5-(1-acetoxyethyl)-2,3-dihydro-3-methyl-furano[2,3c]pyridine as a pale oil. $^1$H NMR (CDCl$_3$, TMS): δ 1.35 (m, 3), 1.56 (m, 3), 2.08 (m, 3), 3.54 (m, 1), 4.12 (t, J=8.2 Hz, 1), 4.73 (t, J=9 HZ, 1), 5.88 (q, J=6.6, 13.2 Hz, 1), 7.16 (m, 1), 8.10 (s, 1) ppm.

(S)-2,3-Dihydro-5-(1-acetoxyethyl)-3-methyl-furano[2,3c]pyridine (1.4 g, 6.3 mmole) was combined with 2,3,4,5-tetrachlorobenzoquinone (1.7 g, 6.8 mmole) in 25 ml dioxane in a 100 ml one neck round bottom flask under nitrogen. The reaction was warmed to reflux for 28 h, was cooled to room temperature, and the bulk of the dioxane was removed in vacuo. The hydroquinone was removed by filtration and the filter cake was washed with 1:1 ethyl acetate/diethyl ether and the filtrate was concentrated to a brown oil. The crude material was dissolved in 25 ml methanol in a 100 ml one neck round bottom flask and the solution was treated with 2N sodium hydroxide (10 ml, 20 mmole). The mixture was stirred 1 h at room temperature, the methanol was removed in vacuo, and the residue was partitioned between 1×50 ml saturated sodium bicarbonate and 4×20 ml dichloromethane. The organics were dried over anhydrous potassium carbonate and were concentrated in vacuo to a tan solid. The crude material was chromatographed over 50 g silica gel (230–400 mesh) eluting with 32% ethyl acetate/hexane followed by 40% ethyl acetate/hexane while collecting 125 ml fractions. Fractions 6–12 were combined and concentrated to afford 1.01 g (90%) of (S)-5-(1-hydroxyethyl)-3-methyl-furano[2,3c]pyridine as a white solid. An aliquot was converted to the corresponding acetate which was determined to be 92% ee by chiral HPLC. $^1$H NMR (CDCl$_3$, TMS): δ 1.57 (d, J=6.5 Hz, 3), 2.26 (d, J=1.3 Hz, 3), 4.04 (bs, 1), 5.05 (q, J=6.5, 13 Hz, 1), 7.50 (s, 1), 8.74 (d, J=0.6 Hz, 1) ppm.

Part 4: A solution of (S)-(−)-5-(1-hydroxyethyl)-3-methyl-furano[2,3c]pyridine (0.0691 g, 0.390 mmol; Method B, Part 1) in carbon tetrachloride (0.601 g, 3.90 mmol, 10 eq.) at 0–5° C. was treated with chloroform (0.150 ml) and triphenylphosphine (0.205 g, 0.781 mmol, 2.0 eq.) and the reaction mixture was stirred for 20 min. The cooling bath was removed and the reaction mixture was stirred at room temperature overnight. The contents were poured into 25 ml of water, extracted two times with ethylacetate-hexane (1:1), the combined organic extracts dried with anhydrous Na$_2$SO$_4$ and concentrated at reduced pressure. Trituration of the residue four times with ethylacetate-hexane (1:6) was followed by hromatography with 15 g of silica gel, packed and eluted with acetone-methylene chloride-hexane (0.5:2:7.5) to provide 57.4 mg (75%) of (R)-(+)-5-(1-chloroethyl)-3-methyl-furano[2,3c]pyridine (Optical rotation: [α]$_D$=+68.40 (c=1.53, CHCl$_3$).

A magnetically stirred suspension of sodium hydride (1.25 g, 0.0522 mol, 2.10 eq., 60% oil dispersion) in 80 ml of dimethylformamide cooled at 16° C. was treated with 4-amino-6-chloro-2-mercaptopyrimidine mesylate salt (6.71 g, 0.0261 mol, 1.05 eq.) and the reaction mixture stirred for 15 min. The cooling bath was removed and the contents stirred at ambient temperature for 1.5 h. (R)-(+)-5-(1-Chloroethyl)-3-methyl-furano[2,3c]pyridine (4.86 g, 0.0249 mol, 1.0 eq.) in 15 ml of dimethylformamide was added at once with a 10 ml and a 2 ml rinse with same solvent. The reaction mixture was allowed to stir at room temperature for 5 days. The contents were poured into ice water, extracted two times with ether, the combined organic extracts dried with anhydrous Na$_2$SO$_4$ and concentrated at reduced pressure. Chromatography with 350 g of silica gel, packed and eluted with ethylacetate-hexane (2:3), then (1:1), provided 6.55 g (82%) of (S)-(−)-4-amino-6-chloro-2-(1-(3-methylfurano[2,3c]pyridin-5-yl)ethylthio)-pyrimidine. The filtrate obtained after two crystallizations from methyl-t-butylether-methylene chloride-ethylacetate was concentrated in vacuo to provide 4.83 g (61%) of (S)-(−)-4-amino-6-chloro-2-(1-(3-methylfurano[2,3c]pyridin-5-yl)ethylthio)-pyrimidine (Melting Point: 156–157° C.; Optical rotation: [α]$_D$=−270.30 (c=0.620, CHCl$_3$). Cpd #291 R-(+)-4-Amino-6-chloro-2-(1-(4-ethyl-2-pyridyl)ethyl)thio-pyrimidine, Cpd #292 (−)-4-Amino-6-chloro-2-(1-(4-ethyl-2-pyridyl)ethyl)thio-pyrimidine Procedure A: Cpd #216 is separated into its (+) and (−) enantiomers using HPLC with the chiral column, Chiralcel OD-H, eluting with 20% isopropanol/hexane +0.05% acetic acid, with a flow rate of 0.5 mL/minute. [a]$_D$+276.4° (c 1.21, chloroform); [a]$_D$−288.60 (c 1.28, chloroform).

Procedure B: A solution of racemic 2-(1-hydroxyethyl)-4-ethylpyridine (1.0 g, 6.62 mmol) in 10 mL of ether at room temperature is treated with 2,2,2-trifluoroethylbutyrate (1.0 mL, 6.62 mmol) and 1.0 g of porcine pancreatic lipase type II and stirred under nitrogen for 3 days. Celite is added to the mixture and after 15 min the reaction is filtered through celite, washed with ether and concentrated to afford 1.38 g of material. The material is chromatographed on 70 g of silica gel, eluting with (1:9) acetone/methylene chloride to give 0.456 g of (+)-1-(4-ethylpyridin-2-yl)ethyl butyrate, $[\alpha]_D$+84.0° (c 1.325, chloroform) (99% ee).

A solution of (+)-1-(4-ethylpyridin-2-yl)ethyl butyrate (0.059 g, 0.27 mmol) in 6 mL of methanol is treated with 0.0737 g (0.534 mmol) of potassium carbonate in 2 mL of water at 0° C. After 30 min, the mixture is stirred at room temperature for 2 h. To the mixture is added 57 mg of ammonium chloride in 4 mL of water along with enough 2N potassium hydrogen sulfate to bring the pH of the solution to 7. The mixture is extracted twice with ethyl acetate after pouring it into 20 mL of saturated brine and 10 mL of water. The combined organics are dried over sodium sulfate and concentrated. The material is chromatographed over 10 g of silica gel, eluting with (1:5) acetone/methylene chloride to afford 30.5 mg (76%) of R-(+)-2-(1-hydroxyethyl)-4-ethylpyridine, $[a]_D$+33.0° (c 1.525, chloroform).

Conversion of R-(+)-2-(1-hydroxyethyl)-4-ethylpyridine to Cpd #291 ($[\alpha]_D$+273.7°) is accomplished as described for Cpd #216.

Example 293

4-Amino-6-chloro-2-(1-(7-chloro-3-trifluoromethyl)-furo[2,3c]pyridin-5-yl)ethylthio)-pyrimidine (Cpd #293)

2-Chloro-3-hydroxy-6-(1-hydroxyethyl)pyridine (7.19 g, 41.4 mmole) was dissolved in 80 ml of water containing potassium carbonate (17.2 g, 124 mmole) in a 200 ml one neck round bottom flask. The solution was treated with iodine (31.5 g, 124 mmole) and was stirred for 6 h at room temperature. The mixture was quenched with saturated sodium thiosulfate and the pH was adjusted to 2 with 12 N hydrochloric acid. The precipitate was collected, was washed with water, and was dried. The yellow solid was further washed with diethyl ether to provide 4.68 g (38%) of 6-acetyl-2-chloro-3-hydroxy-4-iodo-pyridine as a pale tan solid (Melting Point: 223–224° C.).

6-Acetyl-2-chloro-3-hydroxy-4-iodo-pyridine (6.12 g, 20.6 mmole) was combined with trimethylsilyl acetylene (3.5 ml, 24.7 mmole), bis (triphenylphosphine) palladium dichloride (730 mg, 10 mmole) and cuprous iodide (99 mg, 0.52 mmole) in 37 ml of 2:1 chloroform/tetrahydrofuran in a 100 ml one neck round bottom flask under nitrogen. The suspension was treated with triethylamine (6 ml, 43 mmole) and the reaction was stirred for 2 h at room temperature. The mixture was diluted with 150 ml of ethyl acetate and was washed with 2×50 ml of 5% hydrochloric acid. The organics were dried over anhydrous magnesium sulfate, treated with 10 g of silica gel (230–400 mesh), and concentrated to dryness. The plug was chromatographed over 200 g of silica gel (230–400 mesh), eluting with 25% ethyl acetate/hexane+0.1% acetic acid, while collecting 50 ml fractions. Fractions 10–18 were combined and concentrated to give 4.88 g (88%) of 6-acetyl-2-chloro-3-hydroxy-4-(2-trimethylsilylethynyl) pyridine as a pale tan solid. $^1$H NMR (d$_6$DMSO): δ 8 0.26 (s, 9), 2.51 (s, 3), 7.78 (s, 1) ppm.

6-Acetyl-2-chloro-3-hydroxy-4-(2-trimethylsilylethynyl) pyridine (4.8 g, 18.2 mmole) was dissolved in 50 ml of dry tetrahydrofuran in an oven dried 100 ml two neck round bottom flask under nitrogen. The solution was cooled to 0° C., was treated with mercuric trifluoroacetate (8.54 g, 20.0 mmole), and was stirred for 2 h at room temperature. The reaction was diluted with 40 ml of saturated sodium chloride and the mixture was stirred for 1 h at room temperature. The pH was adjusted to 8 with 2 N sodium hydroxide and the mixture was diluted with 150 ml of ethyl acetate. The aqueous layer was washed with 50 ml of ethyl acetate. The combined organics were dried over anhydrous magnesium sulfate and were concentrated in vacuo to a yellow solid. The crude material was dissolved in acetone and was adsorbed onto 20 g of silica gel (230–400 mesh) by concentration to dryness. The plug was chromatographed over 200 g of silica gel (230-400 mesh), eluting with 2 1 30% ethyl acetate/hexane followed by 2 1 50% ethyl acetate/hexane while collecting 50 ml fractions. Fractions 8-48 were combined and concentrated to give a yellow solid which was washed with 100 ml 25% diethyl ether/hexane to provide 8.47 g (93%) of 5-acetyl-7-chloro-3-chloromercurio-2-trimethylsilyl-furo[2,3c]pyridine as an off-white solid. $^1$H NMR (d$_6$DMSO): δ 8 0.42 (s, 9), 2.65 (s, 3), 8.80 (s, 1) ppm.

5-Acetyl-7-chloro-3-chloromercurio-2-trimethylsilyl-furo[2,3c]pyridine (7.0 g, 14 mmole) was suspended in 190 ml of 1:1 water/acetonitrile in a 500 ml one neck round bottom flask under nitrogen. The suspension was treated dropwise 60 ml of water containing potassium iodide (5.1 g, 30.8 mmole) and iodine (3.91 g, 15.4 mmole) and the reaction was stirred for 2 h at room temperature. The mixture was diluted with 95 ml water and was cooled to −15° C. for 1 h. The precipitate was collected, was washed with water, and was dried in vacuo to afford 5.38 g (98%) of 5-acetyl-7-chloro-3-iodo-2-trimethylsilyl-furo[2,3c]pyridine as a tan solid (Melting Point: 92–93° C.).

5-Acetyl-7-chloro-3-iodo-2-trimethylsilyl-furo[2,3c] pyridine (1.51 g, 3.8 mmole) was dissolved in 15 ml of methanol in a 100 ml one neck round bottom flask under nitrogen. The solution was cooled to 0° C. (suspension), was treated with sodium borohydride (135 mg, 3.6 mmole), and was stirred for 20 min at 0° C. followed by 30 min at room temperature. The mixture was diluted with 15 ml of methanol followed by 15 ml of saturated sodium bicarbonate and the suspension was stirred for 3 h at room temperature. The methanol was removed in vacuo, the residual slurry was diluted with 15 ml of water, and the precipitate was collected. The filter cake was washed with water and was dried to give 1.16 g (92%) of 7-chloro-5-(1-hydroxyethyl)-3-iodo-furo[2,3c]pyridine as a pale grey solid. $^1$H NMR (CDCl$_3$, TMS): δ 6 1.58 (d, J=6.6 Hz, 3), 5.01 (q, J=6.6, 13.2 Hz, (s, 1), 7.84 (s, 1) ppm.

7-Chloro-3-iodo-5-(1-hydroxyethyl)-furo[2,3c]pyridine (4.2 g, 13 mmole) was dissolved in 20 ml of pyridine in a 200 ml one neck round bottom flask under nitrogen. The solution was treated with acetic anhydride (7 ml, 62 mmole) and the reaction was stirred 4 h at room temperature. The volatiles were removed in vacuo (toluene, 100 ml, azeotrope) and the residue was partitioned between 1×100 ml of saturated sodium bicarbonate and 3×40 ml of ethyl acetate. The combined organics were dried over anhydrous potassium carbonate/magnesium sulfate to afford 4.74 g (quant) of 5-(1-acetoxyethyl)-7-chloro-3-iodo-furo[2,3c] pyridine as an off-white solid (Melting Point: 102–104° C.).

5-(1-Acetoxyethyl)-7-chloro-3-iodo-furo[2,3c]pyridine (4.37 g, 12 mmole) was combined with cuprous iodide (3.41 g, 18 mmole), spray dried potassium fluoride (834 mg, 14.4 mmole), and triethylsilyl-trifluoromethane (2.65 ml, 14.4 mmole) in 35 ml of dimethylformamide in a screw cap pressure tube under nitrogen. The reaction was warmed to 85° C. for 5.5 h, was cooled, and was diluted with 500 ml of ethyl acetate. The mixture was washed with 3×200 ml of 50% saturated sodium chloride, 1×100 ml of 50% saturated disodium EDTA, and 1×100 ml of saturated sodium chloride. The organics were dried over anhydrous potassium carbonate and were concentrated in vacuo to a black oil. The crude material was chromatographed over 300 g of silica gel (230–400 mesh), eluting with 10% ethyl acetate/hexane while collecting 50 ml fractions. Fractions 17–23 were combined and concentrated to give 1.7 g (46%) of 5-(1-acetoxyethyl)-7-chloro-3-trifluoromethyl-furo[2,3c]pyridine as an off-white solid (Melting Point: 98–99° C.).

5-(1-Acetoxyethyl)-7-chloro-3-trifluoromethyl-furo[2,3c]pyridine (1.21 g, 3.9 mmole) was dissolved in 40 ml of dichloromethane in an oven dried 250 ml three neck round bottom flask under nitrogen. The solution was cooled to −78° C., was treated dropwise with diisobutylaluminum hydride (9.8 ml, 9.8 mmole), and the reaction mixture was stirred for 1 h at −78° C. The mixture was carefully quenched with 60 ml of 0.5 M sodium potassium tartrate at −78° C. and was stirred vigorously at room temperature for 2 h. The layers were separated and the aqueous layer was extracted with 3×20 ml of dichloromethane. The combined organics were dried over anhydrous potassium carbonate and were concentrated in vacuo to give 1.04 g of a white solid. The crude material was chromatographed over 50 g of silica gel (230–400 mesh) eluting with 20% ethyl acetate/hexane while collecting 9 ml fractions. Fractions 20–32 were combined and concentrated to give 1.0 g (96%) of 7-chloro-5-(1-hydroxyethyl)-3-trifluoromethyl-furo[2,3c]pyridine as a white solid (Melting Point: 90–91° C.).

7-chloro-5-(1-hydroxyethyl)-3-trifluoromethyl-furo[2,3c]pyridine (282 mg, 1.1 mmole) was dissolved in 5 ml of dichloromethane in a 25 ml one neck round bottom flask under nitrogen. The solution was cooled to 0° C., was treated with thionyl chloride (116 μl, 1.6 mmole), and the reaction was stirred for 20 min at 0° C. followed by 2 h at room temperature. The reaction was added to 10 ml of saturated sodium bicarbonate, and the aqueous layer was washed with 3×10 ml of dichloromethane. The combined organics were dried over anhydrous potassium carbonate and were concentrated in vacuo to provide 280 mg (93%) of 7-chloro-5-(1-chloroethyl)-3-trifluoromethyl-furo[2,3c]pyridine as a pale yellow oil. $^1$H NMR (CDCl$_3$, TMS): 8 1.93 (d, J =6.6 Hz, 3), 5.23 (q, J=6.5, 13 Hz, 1) 7.77 (s, 1), 8.17 (m, 1) ppm.

4-Amino-6-chloro-2-mercaptopyrimidine mesylate salt (300 mg, 1.1 mmole) was dissolved in 4 ml of dry dimethylformamide in an oven dried 50 ml two neck round bottom flask under nitrogen. The solution was cooled to 0° C., was treated with sodium hydride (102 mg, 2.6 mmole), and the mixture was stirred for 1 h at room temperature. 5-(1-Chloroethyl)-7-chloro-3-trifluoromethyl-furo[2,3c]pyridine (300 mg, 1.1 mmole), in 2 x 1 ml of dry dimethylformamide, was added dropwise to the reaction and the mixture was stirred for 24 h. The reaction mixture was diluted with 70 ml of ethyl acetate, was washed with 4×25 ml of 50% saturated sodium chloride followed by 1×25 ml of saturated sodium chloride, and the organics were dried over anhydrous potassium carbonate. The dried organics were concentrated in vacuo to a yellow paste. The crude material was chromatographed over 30 g of silica gel (230–400 mesh), eluting with 20% ethyl acetate/hexane while collecting 9 ml fractions. Fractions 21–36 were combined and concentrated to give 299 mg of an off-white solid. Washing with 10% diethyl ether/hexane provided 284 mg (66%) of 4-amino-6-chloro-2-(1-(7-chloro-3-trifluoromethyl)-furo[2,3c]pyridin-5-yl)ethylthio)-pyrimidine as a white solid (Melting Point: 169–170° C.).

Example 294

4-Amino-6-chloro-2-(1-(3-trifluoromethyl)-furo[2,3c]pyridin-5-yl)ethylthio)-pyrimidine (Cpd #294)

7-chloro-5-(1-hydroxyethyl)-3-trifluoromethyl-furo[2,3c]pyridine (647 mg, 2.4 mmole) was combined with 20% palladium hydroxide on carbon (647 mg) in 20 ml of absolute ethanol in a 100 ml one neck round bottom flask. The suspension was treated with 1,4-cyclohexadiene (2.3 ml, 24.4 mmole) and was warmed to reflux for 4 h. The mixture was filtered through celite and the cake was washed with ethanol. The filtrate was concentrated in vacuo to an orange paste. The crude material was partitioned between 1×25 ml of saturated sodium bicarbonate and 4×20 ml of dichloromethane. The combined organics were dried over potassium carbonate and were concentrated in vacuo to a pale amber oil. The crude material was chromatographed over 30 g of silica gel (230–400 mesh) eluting with 35% ethyl acetate/hexane while collecting 9 ml fractions. Fractions 8–11 were combined and concentrated to give 188 mg (29%) of recovered 7-chloro-5-(1-hydroxyethyl)-3-trifluoromethyl-furo[2,3c]pyridine as a white solid. Fractions 17–28 were combined and concentrated to provide 339 mg (60%) of 5-(1-hydroxyethyl)-3-trifluoromethyl-furo[2,3c]pyridine as a white solid (Melting Point: 88–90° C.).

5-(1-Hydroxyethyl)-3-trifluoromethyl-furo[2,3c]pyridine (324 mg, 1.4 mmole) was dissolved in 10 ml of dichloromethane in a 50 ml one neck round bottom flask under nitrogen. The solution was cooled to 0° C., was treated with thionyl chloride (153 μl, 2.1 mmole), and the reaction was stirred for 20 min at 0° C. followed by 2 h at room temperature. The reaction was added to 20 ml saturated sodium bicarbonate, and the aqueous layer was washed with 3×10 ml of dichloromethane. The combined organics were dried over anhydrous potassium carbonate and were concentrated in vacuo to provide 327 mg (94%) of 5-(1-chloroethyl)-3-trifluoromethyl-furo[2,3c]pyridine as a pale yellow oil. $^1$H NMR (CDCl$_3$, TMS): δ 8 1.95 (d, J =6.5 Hz, 3), 5.30 (q, J=6.5, 13 Hz, 1), 7.81 (s, 1), 8.13 (m, 1), 8.93 (m, 1) ppm.

4-Amino-6-chloro-2-mercaptopyrimidine mesylate salt (346 mg, 1.3 mmole) was dissolved in 4 ml of dry dimethylformamide in an oven dried 50 ml two neck round bottom flask under nitrogen. The solution was cooled to 0° C., was treated with sodium hydride (118 mg, 2.9 mmole), and the mixture was stirred for 1 h at room temperature. 5-(1-Chloroethyl)-3-trifluoromethyl-furo[2,3c]pyridine (305 mg, 1.2 mmole), in 2×1 ml of dry dimethylformamide, was added dropwise to the reaction and the mixture was stirred for 72 h. The reaction mixture was diluted with 70 ml of ethyl acetate, was washed with 4×25 ml of 50% saturated sodium chloride followed by 1×25 ml of saturated sodium chloride, and the organics were dried over anhydrous potassium carbonate. The dried organics were concentrated in vacuo to a yellow oil. The crude material was chromatographed over 30 g of silica gel (230–400 mesh), eluting with 30% ethyl acetatelhexane while collecting 9 ml fractions. Fractions 22–42 were combined and concentrated to give 325 mg of a yellow foam. Crystallization from 10% diethyl etherlhexane provided 253 mg (56%) of 4-amino-6-chloro-2-(1-(3-trifluoromethyl)-furo[2,3c]pyridin-5-yl)ethylthio)-pyrimidine as an off-white solid (Melting Point: 91–93° C.).

Example 295

4-Amino-2-(1-(7-chloro-3-methyl-furo[2,3c]pyridin-5-yl)ethylthio)-6-trifluoromethyl-pyrimidine (Cpd #295)

4-Amino-2-mercapto-6-trifluoromethyl-pyrimidine mesylate salt (1.12 g, 3.85 mmole) was suspended in 12 ml dry dimethylformamide in an oven dried 100 ml one neck round bottom flask under nitrogen. The suspension was cooled to 0° C., was treated with sodium hydride (331 mg, 8.3 mmole), and the mixture was stirred 1 h at room temperature. 7-Chloro-5-(1-chloroethyl)-3-methyl-furo[2,3c]pyridine (805 mg, 3.5 mmole), in 2×3 ml dry dimethylformamide, was added dropwise to the reaction and the mixture was stirred 48 h. The reaction mixture was diluted with 120 ml ethyl acetate, was washed with 4×50 ml 50% saturated sodium chloride followed by 1×25 ml saturated sodium chloride, and the organics were dried over anhydrous potassium carbonate. The dried organics were concentrated in vacuo to a pale yellow solid. The crude material was chromatographed over 100 g silica gel (230–400 mesh), eluting with 25% ethyl acetate/hexane while collecting 22 ml fractions. Fractions 21–45 were combined and concentrated to give 1.09 g of a white solid which was washed with 10 ml 20% diethyl ether/hexane to afford 997 mg of 4-amino-2-(1-(7-chloro-3-methyl-furo[2,3c]pyridin-5-yl)ethylthio)-6-trifluoromethyl-pyrimidine as a white solid (Melting Point: 172–173° C.).

Example 296

4-Amino-6-trifluoromethyl-2-(1-(3-methyl-furo[2,3c]pyridin-5-yl)ethylthio)-pyrimidine (Cpd #296)

4-Amino-6-trifluoromethyl-2-mercaptopyrimidine mesylate salt (561 mg, 1.93 mnole) was suspended in 6 ml dry dimethylformamide in an oven dried 50 ml two neck round bottom flask under nitrogen. The suspension was cooled to 0° C., was treated with sodium hydride (162 mg, 4.04 mmole), and the mixture was stirred 1 h at room temperature. 5-(1-chloroethyl)-3-methyl-furo[2,3c]pyridine (350 mg, 1.75 mmole), in 2×2 ml dry dimethylforomamide, was added dropwise to the reaction and the mixture was stirred 24 h. The reaction mixture w as diluted with 75 ml ethyl acetate, was washed with 4×25 ml 50% saturated sodium chloride followed by 1×25 ml saturated sodium chloride, and the organics were dried over anhydrous potassium carbonate. The dried organics were concentrated in vacuo to a yellow oil. The crude material was chromatographed over 50 g silca gel (230–400 mesh), eluting with 35% ethyl acetatelhexane while collecting 9 ml fractions. Fractions 40–80 were combined and concentrated to give 290 mg (79%) of 4-amino-6-trifluoromethyl-2-(1-(3-methyl-furo[2,3c]pyridin-5-yl)ethylthio)-pyrimidine as an off-white solid (Melting Point: 198–200° C.).

Example 297 and 298

(S)-(−)-4-Amino-6-trifluoromethyl-2-(l1-(3-methylfuro[2,3c]pyridin-5-yl)ethylthio)-pyrimidine (Cpd #297) and (R)-(+)-4-Amino-6-trifluoromethyl-2-(1-(3-methylfuro[2,3c]pyridin-5-yl)ethylthio)-pyrimidine (Cpd #298)

Method A : A sample of 4-amino-6-trifluoromethyl-2-(1-(3-methylfuro[2,3c]pyridin-5-yl)ethylthio)-pyrimidine (Cpd #296; 1.20 g) was resolved using chiral HPLC (Chiralcel OD-H; 46×25 cm; 0.5 mL/min; 20% isopropanol/hexane) to provide (475.5 mg) of (S)-(−)-4-amino-6-trifluoromethyl-2-(1-(3-methylfuro[2,3c]pyridin-5-yl)ethylthio)-pyrimidine (13.6 min) and 478.2 mg of (R)-(+)-4-amino-6-trifluoromethyl-2-(1-(3-methylfuro[2,3c]pyridin-5-yl)ethylthio)-pyrimidine (21.1 min). The (S)-(−)-4-amino-6-trifluoromethyl-2-(1-(3-methylfuro[2,3c]pyridin-5-yl)ethylthio)-pyrimidine was dissolved in acetone-methylene chloride-methanol solvent mixture, treated with 2.3 g of silica gel and concentrated at reduced pressure. The free flowing powder was applied to a 25 g column of silca gel, packed and eluted with acetone-methylene chloride-methanol (5:93:2), to yield 367 mg of pure product. The (R)-(+)-4-amino-6-trifluoromethyl-2-(1-(3-methylfuro[2,3c]pyridin-5-yl)ethylthio)-pyrimidine was chromatographed in the same fashion to provide 352 mg of pure enantiomer. Cpd 297, Melting Point: 179–181° C.; Optical rotation: $[\alpha]_D 32$ 132.50° (c=0.495, CHCl$_3$); >99% ee. Cpd 298, Melting Point: 179–181° C.; Optical rotation: $[\alpha]_D$=+129.8° (c=0.645, CHCl$_3$); 98% ee.

Method B: A magnetically stirred suspension of sodium hydride (2.55 g, 63.5 mmol, 60% oil dispersion) in 110 ml of dimethylformamide cooled at 0° C. was treated with 4-amino-6-trifluoromethyl-2-mercaptopyrimidine mesylate salt (8.86 g, 30.4 mmol) and the reaction mixture stirred for 1 h at ambient temperature. (R)-(+)-5-(1-Chloroethyl)-3-methyl-furano[2,3c]pyridine (5.4 g, 27.6 mmol) in 2×10 ml of dimethylformamide was added and the reaction mixture was allowed to stir at room temperature for 3.5 days. The contents were poured into 800 ml of ice water, extracted with 4×100 ml of ethyl acetate. The combined organic extracts were washed with 4×100 ml of 50% saturated NaCl and dried with 1:1 potassium carbonate/anhydrous MgSO$_4$ and concentrated at reduced pressure. Chromatography with 300 g of silica gel, packed and eluted with 38% ethylacetate-hexane provided 9.3 g (95%, 94 % ee) of (S)-(−)-4-amino-6-chloro-2-(1-(3-methylfurano[2,3c] pyridin-5-yl)ethylthio)-pyrimidine. Recrystallization of the solid with ethyl acetate afforded 6.5 g (66%, 97 % ee) of (S)-(−)-4-amino-6-chloro-2-(1-(3-methylfurano[2,3c]pyridin-5-yl)ethylthio)-pyrimidine (Melting Point: 180.5–181.5° C.; Optical rotation: $[\alpha]_D$=−131.6° (c=0.525, CHCl$_3$)).

Example 299 and 300

(S)-(−)-4-Amino-6-chloro-2-(1-(furo[2,3c]pyridin-5-yl)ethylthio)-pyrimidine (Cpd #299) and (R)-(+)-4-Amino-6-chloro-2-(1-(furo[2,3c]pyridin-5-yl) ethylthio)-pyrimidine (Cpd #300)

Method A: A 200 mg sample of 4-amino-6-chloro-2-(1-(furo[2,3c]pyridin-5-yl)ethylthio)-pyrimidine (Cpd #238; racemate) was resolved using a Chiralcel OD-H column, eluting with 20% isopropanol/hexane at a flow rate of 0.5 ml/min. Two pools of material were isolated with Retention Times of 15.6 min (Cpd 299, 74 mg) and 26.1 min (Cpd 300, 97 mg).

The column isolates were chromatographed independently over 10 g silica gel (230–400 mesh) eluting with 45% ethyl acetate/hexane while collecting 5 ml fractions. Crystallization from hexane/diethyl ether afforded either 55 mg (Cpd 299, Melting Point: 144–145° C., Rotation: $[\alpha]_d^{25}$=−301.80°) or 59 mg (Cpd 300, Melting Point: 144–145° C., Rotation: $[\alpha]_d^{25}$=+299.60°) of the enantiomers as white solids.

Method B: 7-Chloro-5-(1-hydroxyethyl)-furo[2,3c]pyridine(3.95 g, 20 mmole) was dissolved in 110 ml methanol containing 20% palladium hydroxide on carbon (1g) in a 200 ml one neck round bottom flask under nitrogen. The suspension was treated with cyclohexene (19.8 ml, 200 mmole) followed by sodium hydroxide (15 ml, 30 mmole) and the reaction was refluxed for 3.5 h. The mixture was cooled, filtered through celite, and the filter cake was washed well with fresh methanol. The filtrate was concentrated in vacuo to a yellow paste. The residue was partitioned between 1×50 ml water and 4×25 ml dichloromethane, the organics were dried over potassium carbonate and were concentrated in vacuo to a pale oil (3.16 g). The crude material was chromatographed over 125 g silica gel (230–400 mesh), eluting with 60% ethyl acetatelhexane while collecting 22 ml fractions. Fractions 32–72 were combined and concentrated to give 2.52 g (77%) of the title compound 5-(1-hydroxyethyl)-furo[2,3c]pyridine as a pale oil. $^1$H-NMR (CDCl$_3$, TMS): δ1.55 (d, J=6.5 Hz, 3), 4.19 (bs, 1), 5.01 (q, J=6.5, 13 Hz, 1), 6.78 (d, J=2 Hz, 1), 7.56 (s, 1), 7.76 (d, J=2 Hz, 1), 8.76 (s, 1) ppm.

Part 1:5-(1-Hydroxyethyl)-furo[2,3c]pyridine (11.3 g, 69.4 mmole) was combined with porcine pancreatic lipase type (II) (16.5 g) and 2,2,2 trifluoroethyl butyrate (41.8 ml, 227 mmole) in 226 ml diethyl ether in a 500 ml one neck round bottom flask under nitrogen. The reaction was stirred 9 days at room temperature, was filtered to removed the enzyme, and the filter cake was washed well with diethyl ether. The filtrate was concentrated in vacuo to a pale oil. The residue was azeotroped with 3×200 ml toluene and was pumped at hi vac at 40° C. for 3h. The crude material was chromatographed over 300 g silica gel (230–400 mesh), eluting with 60% ethyl acetated/hexane while collecting 50 ml fractions. Fractions 10–18 were combined and concentrated to provide 7.53 g (46.5%) of (R)-(+)-5-(1-butyryloxy)-furo[2,3c]pyridine ($^1$H NMR (CDCl$_3$, TMS): δ 0.94 (t, J=7.4 Hz, 3), 1.61–1.74 (m, 5), 2.36 (m, 2), 6.04 (q, J=6.6 Hz, 13.2 Hz, 1), 6.79 (m, 1), 7.75 (d, J=2.1 Hz, 1), 8.85 (s, 1) ppm; Rotation (c=1): $[\alpha]_d^{25}$=+84.0°; 99% ee) as a pale oil. Fractions 27–63 were combined and concentrated to give 5.03 g, (44.50%) of (S)-(−)-5-(1-hydroxyethyl)-furo[2,3c]pyridine (Melting Point: 59–61° C.; Rotation (c=1): $[\alpha]_d^{25}$ =−35.8°) as an off-white solid.

Part 2: (R)-(+)-5-(4-butyryloxy)-furo[2,3c]pyridine (7.5 g, 3 2.2 mmole) was dissolved in 88 ml methanol in a 200 ml one neck round bottom flask under nitrogen. The solution was treated with 2N sodium hydroxide (35.4 ml, 70.8 mmole), the reaction was stirred for 1 h, and the volatiles were removed in vacuo. The residue was partitioned between 1×25 dichloromethane and 1×100 ml water. The insoluble material was removed by filtration through celite. The layers were separated and the aqueous layer was further extracted with 3×25 ml dichloromethane. The combined organics were dried over potassium carbonate and were concentrated in vacuo to give 4.68 g (89%) of the title compound (R)-(+)-5-(1-hydroxyethyl)-furo[2,3c]pyridine as a white solid (Melting Point: 60–61° C.; Rotation (c=1): $[\alpha]_d^{25}$=+37.0°).

(R)-(+)-5-(1-Hydroxyethyl)-furo[2,3c]pyridine (6.87 g, 25.7 mmole) was combined with benzoic acid (3.86g, 31.6 mmole), and triphenylphosphine (8.29 g, 31.6 mmole) in 125 ml dry tetrahydrofuran in a 200 ml one neck round bottom flask under nitrogen. The solution was treated dropwise with diethyl-azidodicarboxylate (moderate add rate, allow some exotherm) and the reaction was stirred for 1.5 h at room temperature. The volatiles were removed in vacuo and the oily residue was diluted successively with equal volumes of diethyl ether and hexane and the white solid was collected by filtration. The filtrate was concentrated in vacuo to an amber oil. The crude material was chromatographed over 250 g silica gel (230–400 mesh), eluting with 20% ethyl acetate/hexane while collecting 22 ml fractions. Fractions 48–95 were combined and concentrated to give 6.87 g (90%) of the title compound (S)-(+)-5-(1-benzoyloxyethyl)-furo[2,3c]pyridine as a pale oil (Rotation: $[\alpha]_d^{25}$=+52.70); $^1$H NMR (CDCl$_3$, TMS): δ 1.79 (d, J=6.7 Hz, 3), 6.32 (q, J=6.7, 13.4 Hz,1), 6.80 (m, 1), 7.41–7.48 (m, 2), 7.52–7.60 (m, 1), 7.71 (s, 1), 7.76 (d, J=2.1 Hz, 1), 8.12 (m, 2), 8.95 (s, 1) ppm.

Part 3: (S)-(+)-5-(1-benzoyloxyethyl)-furo[2,3c]pyridine (6.87 g, 25.7 mmole) was dissolved in 88 ml methanol in a 200 ml one neck round bottom flask under nitrogen. The solution was treated with 2N sodium hydroxide (28.3 ml, 56.6 mmole), the reaction was stirred for 2 h at room temperature, and the volatiles were removed in vacuo. The residue was partitioned between 1×50 ml water and 4×25 ml dichloromethane. The organics were dried over anhydrous potassium carbonate and were concentrated in vacuo to an amber oil. The crude material was chromatographed over 150 g silica gel (230–400 mesh), eluting with 65% ethyl acetate/hexane while collecting 22 ml fractions. Fractions 25–70 were combined and concentrated to afford 3.96 g (94%) of the title compound (S)-(−)-5-(1-hydroxyethyl)-furo[2,3c]pyridine as a white solid (Melting Point: 60–61° C.; Rotation: $[\alpha]_d^{25}$=35=3+)

(S)-(−)-5-(1-Hydroxyethyl)-furo[2,3c]pyridine (9.0 g, 55.2 mmole) was dissolved in 35 ml chloroform in a 200 ml one neck round bottom flask under nitrogen. The solution was treated with triphenylphosphine (28.9 g, 110.3 mmole) followed by carbon tetrachloride (106 ml, 1.10 mole) and the reaction was stirred for 24 h at room temperature. The solution was diluted with 35 ml hexane, was stirred for 30 min, and the white precipitate was removed by filtration. The filter cake was washed with 100 ml 20% diethyl ether/hexane and the filtrate was concentrated to a small volume (cold bath, not to dryness). The residue was chromatographed over 350 g silica gel (230–400 mesh), eluting with 15% ethyl acetate/hexane while collecting 50 ml fractions. Fractions 23–48 were combined and concentrated to afford 8.48 g (83%) of the title compound (R)-(+)-5-(1-chloroethyl)-furo[2,3c]pyridine as a low melting off-white solid (Melting Point: 36–38° C.; 97% ee; Rotation: $[\alpha]_d^{25}$=+ 73.0°).

An oven dried 250 ml three neck round bottom flask under nitrogen was charged with 60% sodium hydride (3.5 g, 87.5 mmole). The hydride was washed with 3×7 ml hexane, was suspended in 75 ml dry dimethylformamide, and the mixture was cooled to 0° C. The suspension was treated portionwise with 4-amino-6-chloro-2-mercaptopyrimidine mesylate salt (10.9 g, 42.3 mmole) and was stirred for 1 h at room temperature. The reaction mixture was treated dropwise with (R)-(+)-5-(1-chloroethyl)-furo[2,3c]pyridine (7.4 g, 40.6 mmole) in 1×20 ml dimethylformamide (5 ml rinse) and the mixture was stirred 5 days at room temperature. The mixture was poured into 400 ml ethyl acetate, was extracted with 4×100 ml 50% saturated sodium chloride, and was dried over anhydrous potassium carbonate/magnesium sulfate. The dried organics were concentrated in vacuo to an amber oil. The crude material was diluted with acetone/dichloromethane and was chromatographed over 450 g silica gel (230–400 mesh), eluting with 45% ethyl acetate/hexane, and after a 1,000 ml forerun collecting 50 ml fractions. Fractions 21–63 were combined and concentrated to give 11.05 g (89%, 97.6% ee) of (S)-(–)-4-amino-6-chloro-2-(1-(furo[2,3c]pyridin-5-yl)ethylthio)-pyrimidine as a white solid. Recrystallization from ethyl acetate gave 7.92 g (64%, 99% ee) of (S)-(–)-4-amino-6-chloro-2-(1-(furo[2,3c] pyridin-5-yl)ethylthio)-pyrimidine (Melting Point: 169–170.5° C.; Rotation: $[\alpha]_d^{25}$=–334°). $^1$H NMR (d$_6$DMSO): δ 1.70 (d, J=7 Hz, 3), 5.11 (q, J=6.9, 13.8, Hz, 1), 6.15 (s, 1), 7.00 (m, 1), 7.30 (bs, 2), 7.78 (d, J=1 Hz, 1), 8.20 (d, J=2.1 Hz, 1), 8.88 (s, 1) ppm.

Example 301

(S)-(–)-4-Amino-6-chloro-2-(1-(furo[2,3c]pyridin-5-yl)ethylthio)-pyrimidine mesylate salt (Cpd #301)

(S)-(–)-4-Amino-6-chloro-2-(1-(furo[2,3c]pyridin-5-yl) ethylthio)-pyrimidine (Cpd 299; 2.0 g, 6.52 mmole) was dissolved in 62 ml ethyl acetate in a 200 ml one neck round bottom flask under nitrogen. The solution was seeded with previously prepared material, was treated slowly dropwise with methane sulfonic acid (423 μl, 6.52 mmole) in 62 ml diethyl ether, and was stirred for 2 h at room temperature. The solid was collected, washed with diethyl ether, and was dried in vacuo at 50° C. to afford 2.57 g (98%) of the title compound (S)-(–)-4-amino-6-chloro-2-(1-(furo[2,3c] pyridin-5-yl)ethylthio)-pyrimidine mesylate salt as a fine white solid (Melting Point: 201–202° C.).

Example 302

(S)-(–)-4-Amino-6-chloro-2-(1-(3-methylfuro[2,3c] pyridin-5-yl)ethylthio)-pyrimidine, esylate salt (Cpd #302)

To a solution of (S)-(–)-4-amino-6-chloro-2-(1-(3-methylfuro[2,3c]pyridin-5-yl)ethylthio)-pyrimidine (Cpd #290; 1.45 g, 4.53 mmol) in 36 ml of methylene chloride plus 9 ml of methanol was added 154 ml of diethylether at room temperature. A solution of ethanesulfonic acid (0.525 g, 95%, 4.53 mmol, 1.0 eq.) in 54 ml of diethylether was added dropwise at room temperature over a 17 min period. After the addition was complete, the reaction mixture was seeded with the crystalline salt and stirred overnight at room temperature. The gummy insoluble residue which formed initially became a pure white crystalline solid which was collected by filtration and dried to provide 1.87 g (96%) of (S)-(–)-4-amino-6-chloro-2-(1-(3-methylfuro[2,3c]pyridin-5-yl)ethylthio)-pyrimidine, esylate salt (Mp. 203–204 ° C.).

Example 303

4-amino-6-chloro-2-(((5-benzyloxy-6-chloro)-2-pyridyl)-ethyl)thio-pyrimidine

Step 1: To a solution of 2-chloro-6-iodo-3-pyridinol (500 mg, 1.96 mmol), and K$_2$CO$_3$ (690 mg, 5.0 mmol) in methanol (5 mL) was added benzyl bromide (510 mg, 3.0 mmol). The reaction was refluxed for 60 minutes and was allowed to cool to 22° C. The mixture was then concentrated in vacuo. The remaining solids were slurried in ethyl acetate and filtered. The filtrate was dried over MgSO$_4$ and concentrated in vacuo to yield 416 mg (61%) of 2-chloro-3-benzyloxy-6-iodo-pyridine.

Step 2: 2-Chloro-3-benzyloxy-6-iodo-pyridine (416 mg, 1.2 mmol) in THF (4 mL) was cooled to –78° C. and treated with n-butyllithium (1.2 mL of 1.6M in hexanes, 1.92 mmol). After 60 minutes, acetaldehyde (237 mg, 5.4 mmol) was added and the reaction was allowed to warm to 22° C. over 2 hours. The reaction was quenched with water (5 mL) and concentrated in vacuo. The remaining solution was extracted several times with ethyl acetate, dried over MgSO$_4$, and concentrated in vacuo to yield an oil. The oil was chromatographed 1:1 hexane/ethyl acetate to yield 220 mg (70%) of 2-chloro-3-benzyloxy-6-(1-hydroxyethyl)-pyridine.

Following the general procedure of Example 253 and making non-critical changes, but beginning with 2-chloro-3-benzyloxy-6-(1-hydroxyethyl)-pyridine, the title compound is prepared 98 mg (65%) mp 70–72° C.

Example 304

4-amino-6-chloro-2-(furo[2,3-b]pyridin-5-yl-methylthio)-pyrimidine; (Cpd 304)

5-(Chloromethyl)-furo[2,3-b]pyridine was prepared according to the procedures outlined in I. N. Houpis, W. B. Choi, P. J. Reider, A. Molina, H. Churchill, J. Lynch, R. P. Volante Tetrahedron Lett. 9355–9358 (1994).

The title compound (Cpd #304; mp 124–126° C.) is prepared according to the procedure described for Example 253, part B except that the alkylation is performed with 5-(chloromethyl)-furo[2,3-b]pyridine.

Example 305

6-amino-2-(2-naphthylmethylthio)-pyrimidine-4-carboxylic acid ethyl ester; (Cpd #305)

Step 1: Thioorotic acid (1.72 g, 10.0 mmol) was suspended in 50% EtOH (30 ml), treated with sodium hydroxide (880 mg, 22 mmol), then stirred for 5 min at rt. 2-Bromomethyl-naphthalene (2.21 g, 10 mmol) was added and the reaction heated to reflux for 2 hrs. The warm reaction was acidified with 1N HCl (11 ml) and after cooling, the precipitate was collected and dried to give 3.03 g (97%) of 6-hydroxy-2-(2-naphthylmethylthio)-pyrlmidine-4-carboxylic acid.

Step 2: A solution of 6-hydroxy-2-(2-naphthylmethylthio)-pyrimidine-4-carboxylic acid (2.50 g, 8.0 mmol) and 1,1-carbonyldiimidazole (1.94 g, 12 mmol) in DMF (30 ml) were stirred for 30 min, then treated with abs ethanol (8.0 ml). After 1.5 hrs of stirring, the reaction was poured onto water, stirred for 20 min, then filtered and dried to give 2.371 g (88%) of 6-hydroxy-2-(2-naphthylmethylthio)-pyrimidine-4-carboxylic acid ethyl ester.

Step 3: A solution of 6-hydroxy-2-(2-naphthylmethylthio)-pyrimidine-4-carboxylic acid ethyl ester (2.32 g, 6.81 mmol) and 2-picoline (0.7 ml) in $POCl_3$ (7 ml) were stirred at rt for 3 hrs, then poured onto ice. The solid was collected by filtration then heated briefly with $NH_4OH$ for 15 min. The solid was collected and recrystallized from methanol to yield 1.72 g (70%) of 6-chloro-2-(2-naphthylmethylthio)-pyrimidine-4-carboxylic acid ethyl ester, mp 95–96° C.

Step 4: 6-Chloro-2-(2-naphthylmethylthio)-pyrimidine-4-carboxylic acid ethyl ester (1.107 g, 2.08 mmol) was dissolved in DMF (9.0 ml), then treated with sodium azide (600 mg, 9.23 mmol) and stirred for 24 hrs. The yellow solution was concentrated in vacuo, then diluted with ethyl acetate. The organics were filtered through celite, washed with water and brine, then dried with $MgSO_4$, and concentrated in vacuo to give 1.20 g (100%+) of 6-azo-2-(2-naphthylmethylthio)-pyrimidine-4-carboxylic acid ethyl ester.

Step 5: A solution of 6-azo-2-(2-naphthylmethylthio)-pyrimidine-4-carboxylic acid ethyl ester (1.20 g) in ethyl acetate (45 ml) and ethanol (20 ml) was treated with tin(II) chloride (3.80 g, 16.9 mmol) and stirred at rt for 15 min. The reaction was poured onto ice/$NaHCO_3$, filtered through celite, and the filtrate extracted 2× ethyl acetate. The organics were washed with brine, dried with $MgSO_4$, and concentrated in vacuo: 646 mg (62%) of 6-amino-2-(2-naphthylmethylthio)-pyrimidine-4-carboxylic acid ethyl ester (Cpd #305), mp 188–189° C.

Example 306

(S)-(−)4-Amino-2-(3-methyl-furano[2,3c]pyridin-5-yl)ethylthio-6-trifluoromethyl-pyrimidine mesylate salt (Cpd #306)

(S)-(−)4-Amino-2-(3-methyl-furano[2,3c]pyridin-5-yl) ethylthio-6-trifluoromethyl-pyrimidine (354 mg, 1.0 mmole) was dissolved in 25 ml diethyl ether in a 50 ml one neck round bottom flask. The solution was treated slowly dropwise with methane sulfonic acid (64 µl, 1.0 mmole) in 5 ml diethyl ether. The flocculant suspension was allowed to stir for 20 h at room temperature. The fine white solid was collected, was washed with diethyl ether, and was dried in vacuo at 50° C. to afford 422 mg (94%) of (S)-(−)4-amino-2-(3-methyl-furano[2,3c]pyridin-5-yl)ethylthio-6-trifluoromethyl-pyrimidine mesylate salt. (Melting Point: 161–163° C.).

Example 307

4-amino-6-chloro-2-(((5-isobutoxy-6-chloro)-2-pyridyl)-ethyl)thio-pyrimidine (Cpd #307)

Following the general procedure of Example 303 and making non-critical changes, but beginning with isobutyryl chloride, the title compound 4-amino-6-chloro-2-(((5-isopropoxy-6-chloro)-2-pyridyl)-ethyl)thio-pyrimidine is synthesized, $^1H$ NMR ($CDCl_3$) δ 7.37 (d, J=6.2 Hz, 1 H), 7.10 (d, J=6.2 Hz, 1 H), 6.12 (s, 1 H), 5.06 (q, 1 H), 4.96 (s, 2 H), 3.77 (d, J=4.8 Hz, 2 H), 2.15 (m, 1 H), 1.73 (d, J=5.4 Hz, 3 H), 1.06 (d, J=5.0 Hz, 6 H).

Following the above procedures and making non-critical variations, the following compounds are prepared:

4-Amino-6-chloro-2-(1-(3-trifluoromethylfuro[2,3-c]pyridin-5-yl)ethyl)thio-pyrimidine, Mp 91–93° C.
4-Amino-6-chloro-2-(1-(7-chloro-3-trifluoromethylfuro[2,3-c]pyridin-5-yl)ethyl)thio-pyrimidine, Mp 169–170° C.
4-Amino-6-chloro-2-(1-(3-fluorofuro[2,3-c]pyridin-5-yl)ethyl)thio-pyrimidine,
4-Amino-6-chloro-2-(1-(3-((2,2,2-trifluoro)ethyl)furo[2,3-c]pyridin-5-yl)ethyl)thio-pyrimidine,
4-Amino-6-chloro-2-(1-(3-((1-trifluoromethyl-2,2,2-trifluoro)ethyl)furo[2,3-c]pyridin-5-yl)ethyl)thio-pyrimidine,
4-Amino-6-chloro-2-(1-(3-cyanofuro[2,3-c]pyridin-5-yl)ethyl)thio-pyrimidine,
4-Amino-6-chloro-2-(1-(3-carbomethoxyfuro[2,3-c]pyridin-5-yl)ethyl)thio-pyrimidine,
4-Amino-6-chloro-2-(1-(3-aminocarbinylfuro[2,3-c]pyridin-5-yl)ethyl)thio-pyrimidine,
4-Amino-6-chloro-2-(1-(3-(N,N-dimethylaminocarbinyl)furo[2,3-c]pyridin-5-yl)ethyl)thio-pyrimidine,
4-Amino-6-chloro-2-(1-(3-(methylsulfonylamino)furo[2,3-c]pyridin-5-yl)ethyl)thio-pyrimidine,
4-Amino-6-chloro-2-(1-(3-(methylcarboxyamino)furo[2,3-c]pyridin-5-yl)ethyl)thio-pyrimidine,
4-Amino-6-chloro-2-(1-(3-phenylfuro[2,3-c]pyridin-5-yl)ethyl)thio-pyrimidine,
4-Amino-6-chloro-2-(1-(3-(tert-butyl)furo[2,3-c]pyridin-5-yl)ethyl)thio-pyrimidine,
4-Amino-6-chloro-2-(1-(3-cyclopropylfuro[2,3-c]pyridin-5-yl)ethyl)thio-pyrimidine,
4-Amino-6-trifluoromethyl-2-(1-(3-fluorofuro[2,3-c]pyridin-5-yl)ethyl)thio-pyrimidine,
4-Amino-6-trifluoromethyl-2-(1-(3-((2,2,2-trifluoro)ethyl)furo[2,3-c]pyridin-5-yl)ethyl)thio-pyrimidine,
4-Amino-6-trifluoromethyl-2-(1-(3-((1-trifluoromethyl-2,2,2-trifluoro)ethyl)furo[2,3-c]pyridin-5-yl)ethyl)thio-pyrimidine,
4-Amino-6-trifluoromethyl-2-(1-(3-cyanofuro[2,3-c]pyridin-5-yl)ethyl)thio-pyrimidine,
4-Amino-6-trifluoromethyl-2-(1-(3-carbomethoxyfuro[2,3-c]pyridin-5-yl)ethyl)thio-pyrimidine,
4-Amino-6-trifluoromethyl-2-(1-(3-aminocarbinylfuro[2,3-c]pyridin-5-yl)ethyl)thio-pyrimidine,
4-Amino-6-trifluoromethyl-2-(1-(3-(N,N-dimethylaminocarbinyl)furo[2,3-c]pyridin-5-yl)ethyl)thio-pyrimidine,
4-Amino-6-trifluoromethyl-2-(1-(3-(methylsulfonylamino)furo[2,3-c]pyridin-5-yl)ethyl)thio-pyrimidine,
4-Amino-6-trifluoromethyl-2-(1-(3-(methylcarboxyamino)furo[2,3-c]pyridin-5-yl)ethyl)thio-pyrimidine,
4-Amino-6-trifluoromethyl-2-(1-(3-phenylfuro[2,3-c]pyridin-5-yl)ethyl)thio-pyrimidine,
4-Amino-6-trifluoromethyl-2-(1-(3-(tert-butyl)furo[2,3-c]pyridin-5-yl)ethyl)thio-pyrimidine, 4-Amino-6-trifluoromethyl-2-(1-(3-cyclopropylfuro[2,3-c]pyridin-5-yl)ethyl)thio-pyrimidine,
4-Amino-6-cyano-2-(1-(3-fluorofuro[2,3-c]pyridin-5-yl)ethyl)thio-pyrimidine,
4-Amino-6-cyano-2-(1-(3-((2,2,2-trifluoro)ethyl)furo[2,3-c]pyridin-5-yl)ethyl)thio-pyrimidine,
4-Amino-6-cyano-2-(1-(3-((1-trifluoromethyl-2,2,2-trifluoro)ethyl)furo[2,3-c]pyridin-5-yl)ethyl)thio-pyrimidine,
4-Amino-6-cyano-2-(1-(3-cyanofuro[2,3-c]pyridin-5-yl)ethyl)thio-pyrimidine,
4-Amino-6-cyano-2-(1-(3-carbomethoxyfuro[2,3-c]pyridin-5-yl)ethyl)thio-pyrimidine,
4-Amino-6-cyano-2-(1-(3-aminocarbinylfuro[2,3-c]pyridin-5-yl) ethyl)thio-pyrimidine,
4-Amino-6-cyano-2-(l1-(3-(N,N-dimethylaminocarbinyl)furo[2,3-c]pyridin-5-yl)ethyl)thio-pyrimidine,
4-Amino-6-cyano-2-(1-(3-(methylsulfonylamino)furo[2,3-c]pyridin-5-yl)ethyl)thio-pyrimidine,
4-Amino-6-cyano-2-(1-(3-(methylcarboxyamino)furo[2,3-c]pyridin-5-yl)ethyl)thio-pyrimidine,
4-Amino-6-cyano-2-(1-(3-phenylfuro[2,3-c]pyridin-5-yl)ethyl)thio-pyrimidine,
4-Amino-6-cyano-2-(1-(3-(tert-butyl)furo[2,3-c]pyridin-5-yl)ethyl)thio-pyrimidine,
4-Amino-6-cyano-2-(1-(3-cyclopropylfuro[2,3-c]pyridin-5-yl)ethyl)thio-pyrimidine,
4-Amino-6-chloro-2-(1-(3-fluorothieno[2,3-c]pyridin-5-yl)ethyl)thio-pyrimidine,
4-Amino-6-chloro-2-(1-(3-((2,2,2-trifluoro)ethyl)thieno[2,3-c]pyridin-5-yl)ethyl)thio-pyrimidine,
4-Amino-6-chloro-2-(1-(3-((1-trifluoromethyl-2,2,2-trifluoro)ethyl)thieno[2,3-c]pyridin-5-yl)ethyl)thio-pyrimidine,
4-Amino-6-chloro-2-(1-(3-cyanothieno[2,3-c]pyridin-5-yl)ethyl)thio-pyrimidine,
4-Amino-6-chloro-2-(1-(3-carbomethoxythieno[2,3-c]pyridin-5-yl)ethyl)thio-pyrimidine,
4-Amino-6-chloro-2-(1-(3-aminocarbinylthieno[2,3-c]pyridin-5-yl)ethyl)thio-pyrimidine,
4-Amino-6-chloro-2-(1-(3-(N,N-dimethylaminocarbinyl)thieno[2,3-c]pyridin-5-yl)ethyl)thio-pyrimidine,
4-Amino-6-chloro-2-(1-(3-(methylsulfonylamino)thieno[2,3-c]pyridin-5-yl)ethyl)thio-pyrimidine,
4-Amino-6-chloro-2-(1-(3-(methylcarboxyamino)thieno[2,3-c]pyridin-5-yl)ethyl)thio-pyrimidine,
4-Amino-6-chloro-2-(1-(3-phenylthieno[2,3-c]pyridin-5-yl)ethyl)thio-pyrimidine,
4-Amino-6-chloro-2-(1-(3-(tert-butyl)thieno[2,3-c]pyridin-5-yl)ethyl)thio-pyrimidine,
4-Amino-6-chloro-2-(1-(3-cyclopropylthieno[2,3-c]pyridin-5-yl)ethyl)thio-pyrimidine,
4-Amino-6-trifluoromethyl-2-(1-(3-fluorothieno[2,3-c]pyridin-5-yl)ethyl)thio-pyrimidine,
4-Amino-6-trifluoromethyl-2-(1-(3-((2,2,2-trifluoro)ethyl)thieno[2,3-c]pyridin-5-yl)ethyl)thio-pyrimidine,
4-Amino-6-trifluoromethyl-2-(1-(3-((1-trifluoromethyl-2,2,2-trifluoro)ethyl)thieno[2,3-c]pyridin-5-yl)ethyl)thio-pyrimidine,
4-Amino-6-trifluoromethyl-2-(1-(3-cyanothieno[2,3-c]pyridin-5-yl)ethyl)thio-pyrimidine,
4-Amino-6-trifluoromethyl-2-(1-(3-carbomethoxythieno[2,3-c]pyridin-5-yl)ethyl)thio-pyrimidine,
4-Amino-6-trifluoromethyl-2-(1-(3-aminocarbinylthieno[2,3-c]pyridin-5-yl)ethyl)thio-pyrimidine,
4-Amino-6-trifluoromethyl-2-(1-(3-(N,N-dimethylaminocarbinyl)thieno[2,3-c]pyridin-5-yl)ethyl)thio-pyrimidine,
4-Amino-6-trifluoromethyl-2-(1-(3-(methylsulfonylamino)thieno[2,3-c]pyridin-5-yl)ethyl)thio-pyrimidine,
4-Amino-6-trifluoromethyl-2-(1-(3-(methylcarboxyamino)thieno[2,3-c]pyridin-5-yl)ethyl)thio-pyrimidine,
4-Amino-6-trifluoromethyl-2-(1-(3-phenylthieno[2,3-c]pyridin-5-yl)ethyl)thio-pyrimidine,
4-Amino-6-trifluoromethyl-2-(1-(3-(tert-butyl)thieno[2,3-c]pyridin-5-yl)ethyl)thio-pyrimidine,
4-Amino-6-trifluoromethyl-2-(1-(3-cyclopropylthieno[2,3-c]pyridin-5-yl)ethyl)thio-pyrimidine,
4-Amino-6-cyano-2-(1-(3-fluorothieno[2,3-c]pyridin-5-yl)ethyl)thio-pyrimidine,
4-Amino-6-cyano-2-(1-(3-((2,2,2-trifluoro)ethyl)thieno[2,3-c]pyridin-5-yl)ethyl)thio-pyrimidine,
4-Amino-6-cyano-2-(1-(3-((1-trifluoromethyl-2,2,2-trifluoro)ethyl)thieno[2,3-c]pyridin-5-yl)ethyl)thio-pyrimidine,
4-Amino-6-cyano-2-(1-(3-cyanothieno[2,3-c]pyridin-5-yl)ethyl)thio-pyrimidine,
4-Amino-6-cyano-2-(1-(3-carbomethoxythieno[2,3-c]pyridin-5-yl)ethyl)thio-pyrimidine,
4-Amino-6-cyano-2-(1-(3-aminocarbinylthieno[2,3-c]pyridin-5-yl)ethyl)thio-pyrimidine,
4-Amino-6-cyano-2-(1-(3-(N,N-dimethylaminocarbinyl)thieno[2,3-c]pyridin-5-yl)ethyl)thio-pyrimidine,
4-Amino-6-cyano-2-(1-(3-(methylsulfonylamino)thieno[2,3-c]pyridin-5-yl)ethyl)thio-pyrimidine,
4-Amino-6-cyano-2-(1-(3-(methylcarboxyamino)thieno[2,3-c]pyridin-5-yl)ethyl)thio-pyrimidine,
4-Amino-6-cyano-2-(1-(3-phenylthieno[2,3-c]pyridin-5-yl)ethyl)thio-pyrimidine,
4-Amino-6-cyano-2-(1-(3-(tert-butyl)thieno[2,3-c]pyridin-5-yl)ethyl)thio-pyrimidine,
4-Amino-6-cyano-2-(1-(3-cyclopropylthieno[2,3-c]pyridin-5-yl)ethyl)thio-pyrimidine,
4-Amino-6-chloro-2-(1-(3-fluoro-1H-pyrrolo[2,3-c]pyridin-5-yl)ethyl)thio-pyrimidine,
4-Amino-6-chloro-2-(1-(3-((2,2,2-trifluoro)ethyl)-1H-pyrrolo[2,3-c]pyridin-5-yl)ethyl)thio-pyrimidine,
4-Amino-6-chloro-2-(1-(3-((1-trifluoromethyl-2,2,2-trifluoro)ethyl)-1H-pyrrolo[2,3-c]pyridin-5-yl)ethyl)thio-pyrimidine,
4-Amino-6-chloro-2-(1-(3-cyano-1H-pyrrolo[2,3-c]pyridin-5-yl)ethyl)thio-pyrimidine,
4-Amino-6-chloro-2-(1-(3-carbomethoxy-1H-pyrrolo[2,3-c]pyridin-5-yl)ethyl)thio-pyrimidine,
4-Amino-6-chloro-2-(1-(3-aminocarbinyl-1H-pyrrolo[2,3-c]pyridin-5-yl)ethyl)thio-pyrimidine,
4-Amino-6-chloro-2-(1-(3-(N,N-dimethylaminocarbinyl)-1H-pyrrolo[2,3-c]pyridin-5-yl)ethyl)thio-pyrimidine,
4-Amino-6-chloro-2-(1-(3-(methylsulfonylamino)-1H-pyrrolo[2,3-c]pyridin-5-yl)ethyl)thio-pyrimidine,
4-Amino-6-chloro-2-(1-(3-(methylcarboxyamino)-1H-pyrrolo[2,3-c]pyridin-5-yl)ethyl)thio-pyrimidine,
4-Amino-6-chloro-2-(1-(3-phenyl-1H-pyrrolo[2,3-c]pyridin-5-yl)ethyl)thio-pyrimidine,
4-Amino-6-chloro-2-(1-(3-(tert-butyl)-1H-pyrrolo[2,3-c]pyridin-5-yl)ethyl)thio-pyrimidine,
4-Amino-6-chloro-2-(1-(3-cyclopropyl-1H-pyrrolo[2,3-c]pyridin-5-yl)ethyl)thio-pyrimidine,
4-Amino-6-trifluoromethyl-2-(1-(3-fluoro-1H-pyrrolo[2,3-c]pyridin-5-yl)ethyl)thio-pyrimidine,
4-Amino-6-trifluoromethyl-2-(1-(3-((2,2,2-trifluoro)ethyl)-1H-pyrrolo[2,3-c]pyridin-5-yl)ethyl)thio-pyrimidine,
4-Amino-6-trifluoromethyl-2-(1-(3-((1-trifluoromethyl-2,2,2-trifluoro)ethyl)-1H-pyrrolo[2,3c]pyridin-5-yl)ethyl)thio-pyrimidine, 4-Amino-6-trifluoromethyl-2-(1-(3-cyano-1H-pyrrolo[2,3-c]pyridin-5-yl)ethyl)thio-pyrimidine,
4-Amino-6-trifluoromethyl-2-(1-(3-carbomethoxy-1H-pyrrolo[2,3-c]pyridin-5-yl)ethyl)thio-pyrimidine,
4-Amino-6-trifluoromethyl-2-(1-(3-aminocarbinyl-1H-pyrrolo[2,3-c]pyridin-5-yl)ethyl)thio-pyrimidine,
4-Amino-6-trifluoromethyl-2-(1-(3-(N,N-dimethylaminocarbinyl)-1H-pyrrolo[2,3-c]pyridin-5-yl)ethyl)thio-pyrimidine,
4-Amino-6-trifluoromethyl-2-(1-(3-(methylsulfonylamino)-1H-pyrrolo[2,3-c]pyridin-5-yl)ethyl)thio-pyrimidine,
4-Amino-6-trifluoromethyl-2-(1-(3-(methylcarboxyamino)-1H-pyrrolo[2,3-c]pyridin-5-yl)ethyl)thio-pyrimidine,
4-Amino-6-trifluoromethyl-2-(1-(3-phenyl-1H-pyrrolo[2,3-c]pyridin-5-yl)ethyl)thio-pyrimidine,
4-Amino-6-trifluoromethyl-2-(1-(3-(tert-butyl)-1H-pyrrolo[2,3-c]pyridin-5-yl)ethyl)thio-pyrimidine,
4-Amino-6-trifluoromethyl-2-(1-(3-cyclopropyl-1H-pyrrolo[2,3-c]pyridin-5-yl)ethyl)thio-pyrimidine,
4-Amino-6-cyano-2-(1-(3-fluoro-1H-pyrrolo[2,3-c]pyridin-5-yl)ethyl)thio-pyrimidine,
4-Amino-6-cyano-2-(1-(3-((2,2,2-trifluoro)ethyly)-1H-pyrrolo[2,3-c]pyridin-5-yl)ethyl)thio-pyrimidine,
4-Amino-6-cyano-2-(1-(3-((1-trifluoromethyl-2,2,2-trifluoro)ethyl)-1H-pyrrolo[2,3-c]pyridin-5-yl)ethyl)thio-pyrimidine,
4-Amino-6-cyano-2-(1-(3-cyano-1H-pyrrolo[2,3-c]pyridin-5-yl)ethyl)thio-pyrimidine,
4-Amino-6-cyano-2-(1-(3-carbomethoxy-1H-pyrrolo[2,3-c]pyridin-5-yl)ethyl)thio-pyrimidine,
4-Amino-6-cyano-2-(1-(3-aminocarbinyl-1H-pyrrolo[2,3-c]pyridin-5-yl)ethyl)thio-pyrimidine,
4-Amino-6-cyano-2-(1-(3-(N,N-dimethylaminocarbinyl)-1H-pyrrolo[2,3-c]pyridin-5-yl)ethyl)thio-pyrimidine,
4-Amino-6-cyano-2-(1-(3-(methylsulfonylamino)-1H-pyrrolo[2,3-c]pyridin-5-yl)ethyl)thio-pyrimidine,
4-Amino-6-cyano-2-(1-(3-(methylcarboxyamino)-1H-pyrrolo[2,3-c]pyridin-5-yl)ethyl)thio-pyrimidine,
4-Amino-6-cyano-2-(1-(3-phenyl-1H-pyrrolo[2,3-c]pyridin-5-yl)ethyl)thio-pyrimidine,
4-Amino-6-cyano-2-(1-(3-(tert-butyl)-1H-pyrrolo[2,3-c]pyridin-5-yl)ethyl)thio-pyrimidine,
4-Amino-6-cyano-2-(1-(3-cyclopropyl-1H-pyrrolo[2,3-c]pyridin-5-yl)ethyl)thio-pyrimidine,
4-Amino-6-chloro-2-(1-(3-fluoro-1-methyl-1H-pyrrolo[2,3-c]pyridin-5-yl)ethyl)thio-pyrimidine,
4-Amino-6-chloro-2-(1-(3-((2,2,2-trifluoro)ethyl)-1-methyl-1H-pyrrolo[2,3-c]pyridin-5-yl)ethyl)thio-pyrimidine,
4-Amino-6-chloro-2-(1-(3-((1-trifluoromethyl-2,2,2-trifluoro)ethyl)-1-methyl-1H-pyrrolo[2,3-c]pyridin-5-yl)ethyl)thio-pyrimidine,
4-Amino-6-chloro-2-(1-(3-cyano-1-methyl-1H-pyrrolo[2,3-c]pyridin-5-yl)ethyl)thio-pyrimidine,
4-Amino-6-chloro-2-(1-(3-carbomethoxy-1-methyl-1H-pyrrolo[2,3-c]pyridin-5-yl)ethyl)thio-pyrimidine,
4-Amino-6-chloro-2-(1-(3-aminocarbinyl-1-methyl-1H-pyrrolo[2,3-c]pyridin-5-yl)ethyl)thio-pyrimidine,
4-Amino-6-chloro-2-(1-(3-(N,N-dimethylaminocarbinyl)-1-methyl-1H-pyrrolo[2,3-c]pyridin-5-yl)ethyl)thio-pyrimidine,
4-Amino-6-chloro-2-(1-(3-(methylsulfonylamino)-1-methyl-1H-pyrrolo[2,3-c]pyridin-5-yl)ethyl)thio-pyrimidine,
4-Amino-6-chloro-2-(1-(3-(methylcarboxyamino)-1-methyl-1H-pyrrolo[2,3-c]pyridin-5-yl)ethyl)thio-pyrimidine,
4-Amino-6-chloro-2-(1-(3-phenyl-1-methyl-1H-pyrrolo[2,3-c]pyridin-5-yl)ethyl)thio-pyrimidine,
4-Amino-6-chloro-2-(1-(3-(tert-butyl)-1-methyl-1H-pyrrolo[2,3-c]pyridin-5-yl)ethyl)thio-pyrimidine,
4-Amino-6-chloro-2-(1-(3-cyclopropyl-1-methyl-1H-pyrrolo[2,3-c]pyridin-5-yl)ethyl)thio-pyrimidine,
4-Amino-6-trifluoromethyl-2-(1-(3-fluoro-1-methyl-1H-pyrrolo[2,3-c]pyridin-5-yl)ethyl)thio-pyrimidine,
4-Amino-6-trifluoromethyl-2-(1-(3-((2,2,2-trifluoro)ethyl)-1-methyl-1H-pyrrolo[2,3-c]pyridin-5-yl)ethyl)thio-pyrimidine,
4-Amino-6-trifluoromethyl-2-(1-(3-((1-trifluoromethyl-2,2,2-trifluoro)ethyl)-1-methyl-1H-pyrrolo[2,3-c]pyridin-5-yl)ethyl)thio-pyrimidine,
4-Amino-6-trifluoromethyl-2-(1-(3-cyano-1-methyl-1H-pyrrolo[2,3-c]pyridin-5-yl)ethyl)thio-pyrimidine,
4-Amino-6-trifluoromethyl-2-(1-(3-carbomethoxy-1-methyl-1H-pyrrolo[2,3-c]pyridin-5-yl)ethyl)thio-pyrimidine,
4-Amino-6-trifluoromethyl-2-(1-(3-aminocarbinyl-1-methyl-1H-pyrrolo[2,3-c]pyridin-5-yl)ethyl)thio-pyrimidine,
4-Amino-6-trifluoromethyl-2-(1-(3-(N,N-dimethylaminocarbinyl)-1-methyl-1H-pyrrolo[2,3-c]pyridin-5-yl)ethyl)thio-pyrimidine,
4-Amino-6-trifluoromethyl-2-(1-(3-(methylsulfonylamino)-1-methyl-1H-pyrrolo[2,3-c]pyridin-5-yl)ethyl)thio-pyrimidine,
4-Amino-6-trifluoromethyl-2-(1-(3-(methylcarboxyamino)-1-methyl-1H-pyrrolo[2,3-c]pyridin-5-yl)ethyl)thio-pyrimidine,
4-Amino-6-trifluoromethyl-2-(1-(3-phenyl-1-methyl-1H-pyrrolo[2,3-c]pyridin-5-yl)ethyl)thio-pyrimidine,
4-Amino-6-trifluoromethyl-2-(1-(3-(tert-butyl)-1-methyl-1H-pyrrolo[2,3-c]pyridin-5-yl)ethyl)thio-pyrimidine,
4-Amino-6-trifluoromethyl-2-(1-(3-cyclopropyl-1-methyl-1H-pyrrolo[2,3-c]pyridin-5-yl)ethyl)thio-pyrimidine,
4-Amino-6-cyano-2-(1-(3-fluoro-1-methyl-1H-pyrrolo[2,3-c]pyridin-5-yl)ethyl)thio-pyrimidine,
4-Amino-6-cyano-2-(1-(3-((2,2,2-trifluoro)ethyl)-1-methyl-1H-pyrrolo[2,3-c]pyridin-5-yl)ethyl)thio-pyrimidine,
4-Amino-6-cyano-2-(1-(3-((1-trifluoromethyl-2,2,2-trifluoro)ethyl)-1-methyl-1H-pyrrolo[2,3-c]pyridin-5-yl)ethyl)thio-pyrimidine,
4-Amino-6-cyano-2-(1-(3-cyano-1-methyl-1H-pyrrolo[2,3-c]pyridin-5-yl)ethyl)thio-pyrimidine,
4-Amino-6-cyano-2-(1-(3-carbomethoxy-1-methyl-1H-pyrrolo[2,3-c]pyridin-5-yl)ethyl)thio-pyrimidine,
4-Amino-6-cyano-2-(1-(3-aminocarbinyl-1-methyl-1H-pyrrolo[2,3-c]pyridin-5-yl)ethyl)thio-pyrimidine,
4-Amino-6-cyano-2-(1-(3-(N,N-dimethylaminocarbinyl)-1-methyl-1H-pyrrolo[2,3-c]pyridin-5-yl)ethyl)thio-pyrimidine,
4-Amino-6-cyano-2-(1-(3-(methylsulfonylamino)-1-methyl-1H-pyrrolo[2,3-c]pyridin-5-yl)ethyl)thio-pyrimidine,
4-Amino-6-cyano-2-(1-(3-(methylcarboxyamino)-1-methyl-1H-pyrrolo[2,3-c]pyridin-5-yl)ethyl)thio-pyrimidine,
4-Amino-6-cyano-2-(1-(3-phenyl-1-methyl-1H-pyrrolo[2,3-c]pyridin-5-yl)ethyl)thio-pyrimidine,
4-Amino-6-cyano-2-(1-(3-(tert-butyl)-1-methyl-1H-pyrrolo[2,3-c]pyridin-5-yl)ethyl)thio-pyrimidine,
4-Amino-6-cyano-2-(1-(3-cyclopropyl-1-methyl-1H-pyrrolo[2,3-c]pyridin-5-yl)ethyl)thio-pyrimidine,
4-Amino-6-trifluoromethyl-2-(1-(7-chlorofuro[2,3-c]pyridin-5-yl)ethyl)thio-pyrimidine, 4-Amino-6-trifluoromethyl-2-(1-(3-methylfuro[2,3-c]pyridin-5-yl)ethyl)thio-pyrimidine,
4-Amino-6-trifluoromethyl-2-(1-(2,3-dihydrofuro[2,3-c]pyridin-5-yl)ethyl)thio-pyrimidine,
4-Amino-6-trifluoromethyl-2-(1-(3,3-dimethyl-2,3-dihydrofuro[2,3-c]pyridin-5-yl)ethyl)thio-pyrimidine,
4-Amino-6-trifluoromethyl-2-(1-(3-ethylfuro[2,3-c]pyridin-5-yl)ethyl)thio-pyrimidine,
4-Amino-6-trifluoromethyl-2-(1-(7-chloro-3-ethylfuro[2,3-c]pyridin-5-yl)ethyl)thio-pyrimidine,
4-Amino-6-trifluoromethyl-2-(1-(3-(1-methylethyl)furo[2,3-c]pyridin-5-yl)ethyl)thio-pyrimidine,
4-Amino-6-cyano-2-(1-(7-chlorofuro[2,3-c]pyridin-5-yl)ethyl)thio-pyrimidine,
4-Amino-6-cyano-2-(1-(furo[2,3-c]pyridin-5-yl)ethyl)thio-pyrimidine,
4-Amino-6-cyano-2-(1-(7-chloro-2-methylfuro[2,3-c]pyridin-5-yl)ethyl)thio-pyrimidine,
4-Amino-6-cyano-2-(1-(2-methylfuro[2,3-c]pyridin-5-yl)ethyl)thio-pyrimidine,
4-Amino-6-cyano-2-(1-(3-methylfuro[2,3-c]pyridin-5-yl)ethyl)thio-pyrimidine,
4-Amino-6-cyano-2-(1-(2,3-dihydrofuro[2,3-c]pyridin-5-yl)ethyl)thio-pyrimidine,
4-Amino-6-cyano-2-(1-(3,3-dimethyl-2,3-dihydrofuro[2,3-c]pyridin-5-yl)ethyl)thio-pyrimidine,
4-Amino-6-cyano-2-(1-(3-ethylfuro[2,3-c]pyridin-5-yl)ethyl)thio-pyrimidine,
4-Amino-6-cyano-2-(1-(7-chloro-3,3-dimethyl-2,3-dihydrofuro[2,3-c]pyridin-5-yl)ethyl)thio-pyrimidine,
4-Amino-6-cyano-2-(1-(7-chloro-3-ethylfuro[2,3-c]pyridin-5-yl)ethyl)thio-pyrimidine,
4-Amino-6-cyano-2-(1-(3-(1-methylethyl)furo[2,3-c]pyridin-5-yl)ethyl)thio-pyrimidine,
4-Amino-6-cyano-2-(1-(7-chlorothieno[2,3-c]pyridin-5-yl)ethyl)thio-pyrimidine,
4-Amino-6-cyano-2-(1-(thieno[2,3-c]pyridin-5-yl)ethyl)thio-pyrimidine,
4-Amino-6-cyano-2-(1-(7-chloro-2-methylthieno[2,3-c]pyridin-5-yl)ethyl)thio-pyrimidine,
4-Amino-6-cyano-2-(1-(2-methylthieno[2,3-c]pyridin-5-yl)ethyl)thio-pyrimidine,
4-Amino-6-cyano-2-(1-(3-methylthieno[2,3-c]pyridin-5-yl)ethyl)thio-pyrimidine,
4-Amino-6-cyano-2-(1-(2,3-dihydrothieno[2,3-c]pyridin-5-yl)ethyl)thio-pyrimidine,
4-Amino-6-cyano-2-(1-(3,3-dimethyl-2,3-dihydrothieno[2,3-c]pyridin-5-yl)ethyl)thio-pyrimidine,
4-Amino-6-cyano-2-(1-(3-ethylthieno[2,3-c]pyridin-5-yl)ethyl)thio-pyrimidine,
4-Amino-6-cyano-2-(1-(7-chloro-3,3-dimethyl-2,3-dihydrothieno[2,3-c]pyridin-5-yl)ethyl)thio-pyrimidine,
4-Amino-6-cyano-2-(1-(7-chloro-3-ethylthieno[2,3-c]pyridin-5-yl)ethyl)thio-pyrimidine,
4-Amino-6-cyano-2-(1-(3-(1-methylethyl)thieno[2,3-c]pyridin-5-yl)ethyl)thio-pyrimidine,
4-Amino-6-cyano-2-(1-(7-chloro-1H-pyrrolo[2,3-c]pyridin-5-yl)ethyl)thio-pyrimidine,
4-Amino-6-cyano-2-(1-(1H-pyrrolo[2,3-c]pyridin-5-yl)ethyl)thio-pyrimidine,
4-Amino-6-cyano-2-(1-(7-chloro-2-methyl-1H-pyrrolo[2,3-c]pyridin-5-yl)ethyl)thio-pyrimidine,
4-Amino-6-cyano-2-(1-(2-methyl-1H-pyrrolo[2,3-c]pyridin-5-yl)ethyl)thio-pyrimidine,
4-Amino-6-cyano-2-(1-(3-methyl-1H-pyrrolo[2,3-c]pyridin-5-yl)ethyl)thio-pyrimidine,
4-Amino-6-cyano-2-(1-(2,3-dihydro-1H-pyrrolo[2,3-c]pyridin-5-yl)ethyl)thio-pyrimidine, 4-Amino-6-cyano-2-(1-(3,3-dimethyl-2,3-dihydro-1H-pyrrolo[2,3-c]pyridin-5-yl)ethyl)thio-pyrimidine,
4-Amino-6-cyano-2-(1-(3-ethyl-1H-pyrrolo[2,3-c]pyridin-5-yl)ethyl)thio-pyrimidine,
4-Amino-6-cyano-2-(1-(7-chloro-3,3-dimethyl-2,3-dihydro-1H-pyrrolo[2,3-c]pyridin-5-yl)ethyl)thio-pyrimidine,
4-Amino-6-cyano-2-(1-(7-chloro-3-ethyl-1H-pyrrolo[2,3-c]pyridin-5-yl)ethyl)thio-pyrimidine,
4-Amino-6-cyano-2-(1-(3-(1-methylethyl)-1H-pyrrolo[2,3-c]pyridin-5-yl)ethyl)thio-pyrimidine,
4-Amino-6-cyano-2-(1-(7-chloro-1-methyl-1H-pyrrolo[2,3-c]pyridin-5-yl)ethyl)thio-pyrimidine,
4-Amino-6-cyano-2-(1-(-1-methyl-1H-pyrrolo[2,3-c]pyridin-5-yl)ethyl)thio-pyrimidine,
4-Amino-6-cyano-2-(1-(7-chloro-2-methyl-1-methyl-1H-pyrrolo[2,3-c]pyridin-5-yl)ethyl)thio-pyrimidine,
4-Amino-6-cyano-2-(1-(2-methyl-1-methyl-1H-pyrrolo[2,3-c]pyridin-5-yl)ethyl)thio-pyrimidine,
4-Amino-6-cyano-2-(1-(3-methyl-1-methyl-1H-pyrrolo[2,3-c]pyridin-5-yl)ethyl)thio-pyrimidine,
4-Amino-6-cyano-2-(1-(2,3-dihydro-1-methyl-1H-pyrrolo[2,3-c]pyridin-5-yl)ethyl)thio-pyrimidine,
4-Amino-6-cyano-2-(1-(3,3-dimethyl-2,3-dihydro-1-methyl-1H-pyrrolo[2,3-c]pyridin-5-yl)ethyl)thio-pyrimidine,
4-Amino-6-cyano-2-(1-(3-ethyl-1-methyl-1H-pyrrolo[2,3-c]pyridin-5-yl)ethyl)thio-pyrimidine,
4-Amino-6-cyano-2-(1-(7-chloro-3,3-dimethyl-2,3-dihydro-1-methyl-1H-pyrrolo[2,3-c]pyridin-5-yl)ethyl)thio-pyrimidine,
4-Amino-6-cyano-2-(1-(7-chloro-3-ethyl-1-methyl-1H-pyrrolo[2,3-c]pyridin-5-yl)ethyl)thio-pyrimidine,
4-Amino-6-cyano-2-(1-(3-(1-methylethyl)-1-methyl-1H-pyrrolo[2,3-c]pyridin-5-yl)ethyl)thio-pyrimidine,
4-Amino-6-chloro-2-(1-(7-chlorothieno[2,3-c]pyridin-5-yl)ethyl)thio-pyrimidine,
4-Amino-6-chloro-2-(1-(thieno[2,3-c]pyridin-5-yl)ethyl)thio-pyrimidine,
4-Amino-6-chloro-2-(1-(7-chloro-2-methylthieno[2,3-c]pyridin-5-yl)ethyl)thio-pyrimidine,
4-Amino-6-chloro-2-(1-(2-methylthieno[2,3-c]pyridin-5-yl)ethyl)thio-pyrimidine,
4-Amino-6-chloro-2-(1-(3-methylthieno[2,3-c]pyridin-5-yl)ethyl)thio-pyrimidine
4-Amino-6-chloro-2-(1-(2,3-dihydrothieno[2,3-c]pyridin-5-yl)ethyl)thio-pyrimidine,
4-Amino-6-chloro-2-(1-(3,3-dimethyl-2,3-dihydrothieno[2,3-c]pyridin-5-yl)ethyl)thio-pyrimidine,
4-Amino-6-chloro-2-(1-(3-ethylthieno[2,3-c]pyridin-5-yl)ethyl)thio-pyrimidine,
4-Amino-6-chloro-2-(1-(7-chloro-3,3-dimethyl-2,3-dihydrothieno[2,3-c]pyridin-5-yl)ethyl)thio-pyrimidine,
4-Amino-6-chloro-2-(1-(7-chloro-3-ethylthieno[2,3-c]pyridin-5-yl)ethyl)thio-pyrimidine,
4-Amino-6-chloro-2-(1-(3-(1-methylethyl)thieno[2,3-c]pyridin-5-yl)ethyl)thio-pyrimidine,
4-Amino-6-chloro-2-(1-(7-chloro-1H-pyrrolo[2,3-c]pyridin-5-yl)ethyl)thio-pyrimidine,
4-Amino-6-chloro-2-(1-(1H-pyrrolo[2,3-c]pyridin-5-yl)ethyl)thio-pyrimidine,
4-Amino-6-chloro-2-(1-(7-chloro-2-methyl-1H-pyrrolo[2,3-c]pyridin-5-yl)ethyl)thio-pyrimidine,
4-Amino-6-chloro-2-(1-(2-methyl-1H-pyrrolo[2,3-c]pyridin-5-yl)ethyl)thio-pyrimidine,
4-Amino-6-chloro-2-(1-(3-methyl-1H-pyrrolo[2,3-c]pyridin-5-yl)ethyl)thio-pyrimidine, 4-Amino-6-chloro-2-(1-(2,3-dihydro-1H-pyrrolo[2,3-c]pyridin-5-yl)ethyl)thio-pyrimidine,
4-Amino-6-chloro-2-(1-(3,3-dimethyl-2,3-dihydro-1H-pyrrolo[2,3-c]pyridin-5-yl)ethyl)thio-pyrimidine,
4-Amino-6-chloro-2-(1-(3-ethyl-1H-pyrrolo[2,3-c]pyridin-5-yl)ethyl)thio-pyrimidine,
4-Amino-6-chloro-2-(1-(7-chloro-3,3-dimethyl-2,3-dihydro-1H-pyrrolo[2,3-c]pyridin-5-yl)ethyl)thio-pyrimidine,
4-Amino-6-chloro-2-(1-(7-chloro-3-ethyl-1H-pyrrolo[2,3-c]pyridin-5-yl)ethyl)thio-pyrimidine,
4-Amino-6-chloro-2-(1-(3-(1-methylethyl)-1H-pyrrolo[2,3-c]pyridin-5-yl)ethyl)thio-pyrimidine,
4-Amino-6-chloro-2-(1-(7-chloro-1-methyl-1H-pyrrolo[2,3-c]pyridin-5-yl)ethyl)thio-pyrimidine,
4-Amino-6-chloro-2-(1-(1-methyl-1H-pyrrolo[2 ,3-c]pyridin-5-yl)ethyl)thio-pyrimidine,
4-Amino-6-chloro-2-(1-(7-chloro-2-methyl-1-methyl-1H-pyrrolo[2,3-c]pyridin-5-yl)ethyl)thio-pyrimidine,
4-Amino-6-chloro-2-(1-(2-methyl-1-methyl-1H-pyrrolo[2,3-c]pyridin-5-yl)ethyl)thio-pyrimidine,
4-Amino-6-chloro-2-(1-(3-methyl-1-methyl-1H-pyrrolo[2,3-c]pyridin-5-yl)ethyl)thio-pyrimidine,
4-Amino-6-chloro-2-(1-(2,3-dihydro-1-methyl-1H-pyrrolo[2,3-c]pyridin-5-yl)ethyl)thio-pyrimidine,
4-Amino-6-chloro-2-(1-(3,3-dimethyl-2,3-dihydro-1-methyl-1H-pyrrolo[2,3-c]pyridin-5-yl)ethyl)thio-pyrimidine,
4-Amino-6-chloro-2-(1-(3-ethyl-1-methyl-1H-pyrrolo[2,3-c]pyridin-5-yl)ethyl)thio-pyrimidine,
4-Amino-6-chloro-2-(1-(7-chloro-3,3-dimethyl-2,3-dihydro-1-methyl-1H-pyrrolo[2,3-c]pyridin-5-yl)ethyl)thio-pyrimidine,
4-Amino-6-chloro-2-(1-(7-chloro-3-ethyl-1-methyl-1H-pyrrolo[2,3-c]pyridin-5-yl)ethyl)thio-pyrimidine,
4-Amino-6-chloro-2-(1-(3-(1-methylethyl)-1-methyl-1H-pyrrolo[2,3-c]pyridin-5-yl)ethyl)thio-pyrimidine,
4-Amino-6-trifluoromethyl-2-(1-(7-chlorothieno[2,3-c]pyridin-5-yl)ethyl)thio-pyrimidine,
4-Amino-6-trifluoromethyl-2-(1-(thieno[2,3-c]pyridin-5-yl)ethyl)thio-pyrimidine,
4-Amino-6-trifluoromethyl-2-(1-(7-chloro-2-methylthieno[2,3-c]pyridin-5-yl)ethyl)thio-pyrimidine,
4-Amino-6-trifluoromethyl-2-(1-(2-methylthieno[2,3-c]pyridin-5-yl)ethyl)thio-pyrimidine,
4-Amino-6-trifluoromethyl-2-(1-(3-methylthieno[2,3-c]pyridin-5-yl)ethyl)thio-pyrimidine,
4-Amino-6-trifluoromethyl-2-(1-(2,3-dihydrothieno[2,3-c]pyridin-5-yl)ethyl)thio-pyrimidine,
4-Amino-6-trifluoromethyl-2-(1-(3,3-dimethyl-2,3-dihydrothieno[2,3-c]pyridin-5-yl)ethyl)thio-pyrimidine,
4-Amino-6-trifluoromethyl-2-(1-(3-ethylthieno[2,3-c]pyridin-5-yl)ethyl)thio-pyrimidine,
4-Amino-6-trifluoromethyl-2-(1-(7-chloro-3,3-dimethyl-2,3-dihydrothieno[2,3-c]pyridin-5-yl)ethyl)thio-pyrimidine,
4-Amino-6-trifluoromethyl-2-(1-(7-chloro-3-ethylthieno[2,3-c]pyridin-5-yl)ethyl)thio-pyrimidine,
4-Amino-6-trifluoromethyl-2-(1-(3-(1-methylethyl)thieno[2,3-c]pyridin-5-yl)ethyl)thio-pyrimidine,
4-Amino-6-trifluoromethyl-2-(1-(7-chloro-1H-pyrrolo[2,3-c]pyridin-5-yl)ethyl)thio-pyrimidine,
4-Amino-6-trifluoromethyl-2-(1-(-1H-pyrrolo[2,3-c]pyridin-5-yl)ethyl)thio-pyrimidine,
4-Amino-6-trifluoromethyl-2-(1-(7-chloro-2-methyl-1H-pyrrolo[2,3-c]pyridin-5-yl)ethyl)thio-pyrimidine,
4-Amino-6-trifluoromethyl-2-(1-(2-methyl-1H-pyrrolo[2,3-c]pyridin-5-yl)ethyl)thio-pyrimidine,
4-Amino-6-trifluoromethyl-2-(1-(3-methyl-1H-pyrrolo[2,3-c]pyridin- 5-yl)ethyl)thio-pyrimidine,
4-Amino-6-trifluoromethyl-2-(1-(2,3-dihydro-1H-pyrrolo[2,3-c]pyridin-5-yl)ethyl)thio-pyrimidine,
4-Amino-6-trifluoromethyl-2-(1-(3,3-dimethyl-2,3-dihydro-1H-pyrrolo[2,3-c]pyridin-5-yl)ethyl)thio-pyrimidine,
4-Amino-6-trifluoromethyl-2-(1-(3-ethyl-1H-pyrrolo[2,3-c]pyridin-5-yl)ethyl)thio-pyrimidine,
4-Amino-6-trifluoromethyl-2-(1-(7-chloro-3,3-dimethyl-2,3-dihydro-1H-pyrrolo[2,3-c]pyridin-5-yl)ethyl)thio-pyrimidine,
4-Amino-6-trifluoromethyl-2-(1-(7-chloro-3-ethyl-1H-pyrrolo[2,3-c]pyridin-5-yl)ethyl)thio-pyrimidine,
4-Amino-6-trifluoromethyl-2-(1-(3-(1-methylethyl)-1H-pyrrolo[2,3-c]pyridin-5-yl)ethyl)thio-pyrimidine,
4-Amino-6-trifluoromethyl-2-(1-(7-chloro-1-methyl-1H-pyrrolo[2,3-c]pyridin-5-yl)ethyl)thio-pyrimidine,
4-Amino-6-trifluoromethyl-2-(1-(-1-methyl-1H-pyrrolo[2,3-c]pyridin-5-yl)ethyl)thio-pyrimidine,
4-Amino-6-trifluoromethyl-2-(1-(7-chloro-2-methyl-1-methyl-1H-pyrrolo[2,3-c]pyridin-5-yl)ethyl)thio-pyrimidine,
4-Amino-6-trifluoromethyl-2-(1-(2-methyl-1-methyl-1H-pyrrolo[2,3-c]pyridin-5-yl)ethyl)thio-pyrimidine,
4-Amino-6-trifluoromethyl-2-(1-(3-methyl-1-methyl-1H-pyrrolo[2,3-c]pyridin-5-yl)ethyl)thio-pyrimidine,
4-Amino-6-trifluoromethyl-2-(1-(2,3-dihydro-1-methyl-1H-pyrrolo[2,3-c]pyridin- 5-yl)ethyl)thio-pyrimidine,
4-Amino-6-trifluoromethyl-2-(1-(3,3-dimethyl-2,3-dihydro-1-methyl-1H-pyrrolo[2,3-c]pyridin-5-yl)ethyl)thio-pyrimidine,
4-Amino-6-trifluoromethyl-2-(1-(3-ethyl-1-methyl-1H-pyrrolo[2,3-c]pyridin-5-yl)ethyl)thio-pyrimidine,
4-Amino-6-trifluoromethyl-2-(1-(7-chloro-3,3-dimethyl-2,3-dihydro-1-methyl-1H-pyrrolo[2,3-c]pyridin-5-yl)ethyl)thio-pyrimidine,
4-Amino-6-trifluoromethyl-2-(1-(7-chloro-3-ethyl-1-methyl-1H-pyrrolo[2,3-c]pyridin-5-yl)ethyl)thio-pyrimidine,
4-Amino-6-trifluoromethyl-2-(1-(3-(1-methylethyl)-1-methyl-1H-pyrrolo[2,3-c]pyridin-5-yl)ethyl)thio-pyrimidine,
4-Amino-6-trifluoromethyl-2-(1-(3-chlorofuro[2,3-c]pyridin-5-yl)ethyl)thio-pyrimidine,
4-Amino-6-trifluoromethyl-2-(1-(3,7-dichlorofuro[2,3-c]pyridin-5-yl)ethyl)thio-pyrimidine,
4-Amino-6-trifluoromethyl-2-(1-(3-bromofuro[2,3-c]pyridin-5-yl)ethyl)thio-pyrimidine,
4-Amino-6-trifluoromethyl-2-(1-(3-bromo-7-chlorofuro[2,3-c]pyridin-5-yl)ethyl)thio-pyrimidine,
4-Amino-6-trifluoromethyl-2-(1-(7-chloro-3-methylfuro[2,3-c]pyridin-5-yl)ethyl)thio-pyrimidine,
4-Amino-6-cyano-2-(1-(3-chlorofuro[2,3-c]pyridin-5-yl)ethyl)thio-pyrimidine,
4-Amino-6-cyano-2-(1-(3,7-dichlorofuro[2,3-c]pyridin-5-yl)ethyl)thio-pyrimidine,
4-Amino-6-cyano-2-(1-(3-bromofuro[2,3-c]pyridin-5-yl)ethyl)thio-pyrimidine,
4-Amino-6-cyano-2-(1-(3-bromo-7-chlorofuro[2,3-c]pyridin-5-yl)ethyl)thio-pyrimidine,
4-Amino-6-cyano-2-(1-(7-chloro-3-methylfuro[2,3-c]pyridin-5-yl)ethyl)thio-pyrimidine,
4-Amino-6-chloro-2-(1-(3-chlorothieno[2,3-c]pyridin-5-yl)ethyl)thio-pyrimidine,
4-Amino-6-chloro-2-(1-(3,7-dichlorothieno[2,3-c]pyridin-5-yl)ethyl)thio-pyrimidine, 4-Amino-6-chloro-2-(1-(3-bromothieno[2,3-c]pyridin-5-yl)ethyl)thio-pyrimidine,
4-Amino-6-chloro-2-(1-(3-bromo-7-chlorothieno[2,3-c]pyridin-5-yl)ethyl)thio-pyrimidine,
4-Amino-6-chloro-2-(1-(7-chloro-3-methylthieno[2,3-c]pyridin-5-yl)ethyl)thio-pyrimidine,
4-Amino-6-trifluoromethyl-2-(1-(3-chlorothieno[2,3-c]pyridin-5-yl)ethyl)thio-pyrimidine,
4-Amino-6-trifluoromethyl-2-(1-(3,7-dichlorothieno[2,3-c]pyridin-5-yl)ethyl)thio-pyrimidine,
4-Amino-6-trifluoromethyl-2-(1-(3-bromothieno[2,3-c]pyridin-5-yl)ethyl)thio-pyrimidine,
4-Amino-6-trifluoromethyl-2-(1-(3-bromo-7-chlorothieno[2,3-c]pyridin-5-yl)ethyl)thio-pyrimidine,
4-Amino-6-trifluoromethyl-2-(1-(7-chloro-3-methylthieno[2,3-c]pyridin-5-yl)ethyl)thio-pyrimidine,
4-Amino-6-cyano-2-(1-(3-chlorothieno[2,3-c]pyridin-5-yl)ethyl)thio-pyrimidine,
4-Amino-6-cyano-2-(1-(3,7-dichlorothieno[2,3-c]pyridin-5-yl)ethyl)thio-pyrimidine,
4-Amino-6-cyano-2-(1-(3-bromothieno[2,3-c]pyridin-5-yl)ethyl)thio-pyrimidine,
4-Amino-6-cyano-2-(1-(3-bromo-7-chlorothieno[2,3-c]pyridin-5-yl)ethyl)thio-pyrimidine,
4-Amino-6-cyano-2-(1-(7-chloro-3-methylthieno[2,3-c]pyridin-5-yl)ethyl)thio-pyrimidine,
4-Amino-6-chloro-2-(1-(3-chloro-1H-pyrrolo[2,3-c]pyridin-5-yl)ethyl)thio-pyrimidine,
4-Amino-6-chloro-2-(1-(3,7-dichloro-1H-pyrrolo[2,3-c]pyridin-5-yl)ethyl)thio-pyrimidine,
4-Amino-6-chloro-2-(1-(3-bromo-1H-pyrrolo[2,3-c]pyridin-5-yl)ethyl)thio-pyrimidine,
4-Amino-6-chloro-2-(1-(3-bromo-7-chloro-1H-pyrrolo[2,3-c]pyridin-5-yl)ethyl)thio-pyrimidine,
4-Amino-6-chloro-2-(1-(7-chloro-3-methyl-1H-pyrrolo[2,3-c]pyridin-5-yl)ethyl)thio-pyrimidine,
4-Amino-6-trifluoromethyl-2-(1-(3-chloro-1H-pyrrolo[2,3-c]pyridin-5-yl)ethyl)thio-pyrimidine,
4-Amino-6-trifluoromethyl-2-(1-(3,7-dichloro-1H-pyrrolo[2,3-c]pyridin-5-yl)ethyl)thio-pyrimidine,
4-Amino-6-trifluoromethyl-2-(1-(3-bromo-1H-pyrrolo[2,3-c]pyridin-5-yl)ethyl)thio-pyrimidine,
4-Amino-6-trifluoromethyl-2-(1-(3-bromo-7-chloro-1H-pyrrolo[2,3-c]pyridin-5-yl)ethyl)thio-pyrimidine,
4-Amino-6-trifluoromethyl-2-(1-(7-chloro-3-methyl-1H-pyrrolo[2,3-c]pyridin-5-yl)ethyl)thio-pyrimidine,
4-Amino-6-cyano-2-(1-(3-chloro-1H-pyrrolo[2,3-c]pyridin-5-yl)ethyl)thio-pyrimidine,
4-Amino-6-cyano-2-(1-(3,7-dichloro-1H-pyrrolo[2,3-c]pyridin-5-yl)ethyl)thio-pyrimidine,
4-Amino-6-cyano-2-(1-(3-bromo-1H-pyrrolo[2,3-c]pyridin-5-yl)ethyl)thio-pyrimidine,
4-Amino-6-cyano-2-(1-(3-bromo-7-chloro-1H-pyrrolo[2,3-c]pyridin-5-yl)ethyl)thio-pyrimidine,
4-Amino-6-cyano-2-(1-(7-chloro-3-methyl-1H-pyrrolo[2,3-c]pyridin-5-yl)ethyl)thio-pyrimidine,
4-Amino-6-chloro-2-(1-(3-chloro-1-methyl-1H-pyrrolo[2,3-c]pyridin-5-yl)ethyl)thio-pyrimidine,
4-Amino-6-chloro-2-(1-(3,7-dichloro-1-methyl-1H-pyrrolo[2,3-c]pyridin-5-yl)ethyl)thio-pyrimidine,
4-Amino-6-chloro-2-(1-(3-bromo-1-methyl-1H-pyrrolo[2,3-c]pyridin-5-yl)ethyl)thio-pyrimidine,
4-Amino-6-chloro-2-(1-(3-bromo-7-chloro-1-methyl-1H-pyrrolo[2,3-c]pyridin-5-yl)ethyl)thio-pyrimidine,
4-Amino-6-chloro-2-(1-(7-chloro-3-methyl-1-methyl-1H-pyrrolo[2,3-c]pyridin-5-yl)ethyl)thio-pyrimidine,
4-Amino-6-trifluoromethyl-2-(1-(3-chloro-1-methyl-1H-pyrrolo[2,3-c]pyridin-5-yl)ethyl)thio-pyrimidine,
4-Amino-6-trifluoromethyl-2-(1-(3,7-dichloro-1-methyl-1H-pyrrolo[2,3-c]pyridin-5-yl)ethyl)thio-pyrimidine,
4-Amino-6-trifluoromethyl-2-(1-(3-bromo-1-methyl-1H-pyrrolo[2,3-c]pyridin-5-yl)ethyl)thio-pyrimidine,
4-Amino-6-trifluoromethyl-2-(1-(3-bromo-7-chloro-1-methyl-1H-pyrrolo[2,3-c]pyridin-5-yl)ethyl)thio-pyrimidine,
4-Amino-6-trifluoromethyl-2-(1-(7-chloro-3-methyl-1-methyl-1H-pyrrolo[2,3-c]pyridin-5-yl)ethyl)thio-pyrimidine,
4-Amino-6-cyano-2-(1-(3-chloro-1-methyl-1H-pyrrolo[2,3-c]pyridin-5-yl)ethyl)thio-pyrimidine,
4-Amino-6-cyano-2-(1-(3,7-dichloro-1-methyl-1H-pyrrolo[2,3-c]pyridin-5-yl)ethyl)thio-pyrimidine,
4-Amino-6-cyano-2-(1-(3-bromo-1-methyl-1H-pyrrolo[2,3-c]pyridin-5-yl)ethyl)thio-pyrimidine,
4-Amino-6-cyano-2-(1-(3-bromo-7-chloro-1-methyl-1H-pyrrolo[2,3-c]pyridin-5-yl)ethyl)thio-pyrimidine,
4-Amino-6-cyano-2-(1-(7-chloro-3-methyl-1-methyl-1H-pyrrolo[2,3-c]pyridin-5-yl)ethyl)thio-pyrimidine,
4-Amino-6-trifluoromethyl-2-(1-(3-trifluoromethylfuro[2,3-c]pyridin-5-yl)ethyl)thio-pyrimidine,
4-Amino-6-cyano-2-(1-(3-trifluoromethylfuro[2,3-c]pyridin-5-yl)ethyl)thio-pyrimidine,
4-Amino-6-trifluoromethyl-2-(1-(7-chloro-3-trifluoromethylfuro[2,3-c]pyridin-5-yl)ethyl)thio-pyrimidine,
4-Amino-6-cyano-2-(1-(7-chloro-3-trifluoromethylfuro[2,3-c]pyridin-5-yl)ethyl)thio-pyrimidine,
4-Amino-6-chloro-2-(1-(3-trifluoromethylthieno[2,3-c]pyridin-5-yl)ethyl)thio-pyrimidine,
4-Amino-6-trifluoromethyl-2-(1-(3-trifluoromethylthieno[2,3-c]pyridin-5-yl)ethyl)thio-pyrimidine,
4-Amino-6-cyano-2-(1-(3-trifluoromethylthieno[2,3-cpyridin-5-yl)ethyl)thio-pyrimidine,
4-Amino-6-chloro-2-(1-(7-chloro-3-trifluoromethylthieno[2,3-c]pyridin-5-yl)ethyl)thio-pyrimidine,
4-Amino-6-trifluoromethyl-2-(1-(7-chloro-3-trifluoromethylthieno[2,3-c]pyridin-5-yl)ethyl)thio-pyrimidine,
4-Amino-6-cyano-2-(1-(7-chloro-3-trifluoromethylthieno[2,3-c]pyridin-5-yl)ethyl)thio-pyrimidine,
4-Amino-6-chloro-2-(1-(3-trifluoromethyl-1H-pyrrolo[2,3-c]pyridin-5-yl)ethyl)thio-pyrimidine,
4-Amino-6-trifluoromethyl-2-(1-(3-trifluoromethyl-1H-pyrrolo[2,3-c]pyridin-5-yl)ethyl)thio-pyrimidine,
4-Amino-6-cyano-2-(1-(3-trifluoromethyl-1H-pyrrolo[2,3-c]pyridin-5-yl)ethyl)thio-pyrimidine,
4-Amino-6-chloro-2-(1-(7-chloro-3-trifluoromethyl-1H-pyrrolo[2,3-c]pyridin-5-yl)ethyl)thio-pyrimidine,
4-Amino-6-trifluoromethyl-2-(1-(7-chloro-3-trifluoromethyl-1H-pyrrolo[2,3-c]pyridin-5-yl)ethyl)thio-pyrimidine,
4-Amino-6-cyano-2-(1-(7-chloro-3-trifluoromethyl-1H-pyrrolo[2,3-c]pyridin-5-yl)ethyl)thio-pyrimidine,
4-Amino-6-chloro-2-(1-(3-trifluoromethyl-1-methyl-1H-pyrrolo[2,3-c]pyridin-5-yl)ethyl)thio-pyrimidine,
4-Amino-6-trifluoromethyl-2-(1-(3-trifluoromethyl-1-methyl-1H-pyrrolo[2,3-c]pyridin-5-yl)ethyl)thio-pyrimidine,
4-Amino-6-cyano-2-(1-(3-trifluoromethyl-1-methyl-1H-pyrrolo[2,3-c]pyridin-5-yl)ethyl)thio-pyrimidine,
4-Amino-6-chloro-2-(1-(7-chloro-3-trifluoromethyl-1-methyl-1H-pyrrolo[2,3-c]pyridin-5-yl)ethyl)thio-pyrimidine,
4-Amino-6-trifluoromethyl-2-(1-(7-chloro-3-trifluoromethyl-1-methyl-1H-pyrrolo[2,3-c]pyridin-5-yl)ethyl)thio-pyrimidine, 4-Amino-6-cyano-2-(1-(7-chloro-3-trifluoromethyl-1-methyl-1H-pyrrolo[2,3-c]pyridin-5-yl)ethyl)thiopyrimidine,

TABLE I

| Example | IC50 | Example | IC50 | Example | IC50 |
|---|---|---|---|---|---|
| 34 | 10 | 50 | 0.33 | 85 | 30 |
| 34A | 2 | 51 | 1 | 86 | 40 |
| 35 | 0.3 | 52 | 0.2 | 87 | 100 |
| 36 | 0.05 | 53 | 15 | 88 | 5 |
| 37 | 0.33 | 55 | 0.002 | 89 | 5 |
| 38 | 1 | 57 | 10 | 90 | 5 |
| 39 | 0.16 | 58 | 0.03 | 91 | 2.5 |
| 41 | 0.2 | 59 | 0.036 | 92 | 1 |
| 42 | 0.5 | 60 | 10 | 95 | 1 |
| 43 | 0.14 | 61 | 5 | 96 | 50 |
| 44 | 0.6 | 62 | 0.02 | 98 | 5 |
| 45 | 0.11 | 64 | 0.066 | 99 | 0.5 |
| 46 | 0.1 | 67 | 25 | 100 | 2 |
| 47 | 1 | 68 | 5 | 109 | 2 |
| 48 | 0.5 | 69 | 20 | | |
| 49 | 0.06 | 84 | 10 | | |
| 111 | 0.03 | 128 | 1.00 | 149 | 0.05 |
| 112 | 0.07 | 130 | 0.8 | 151 | 0.06 |
| 113 | 0.09 | 131 | 0.05 | 152 | — |
| 114 | 0.01 | 132 | 0.02 | 153 | 10.00 |
| 115 | 0.05 | 133 | 1.00 | 154 | 0.05 |
| 116 | 10.00 | 134 | 0.05 | 155 | 5.00 |
| 117 | 1.05 | 135 | 0.1 | 156 | 0.1 |
| 118 | 0.07 | 137 | 0.01 | 157 | 10.00 |
| 119 | 0.04 | 138 | 0.12 | 158 | 1.00 |
| 120 | 0.02 | 140 | 0.02 | 159 | 0.5 |
| 121 | 0.01 | 142 | 0.5 | 163 | 20.00 |
| 122 | 0.01 | 143 | 0.05 | 164 | 1.00 |
| 123 | 0.05 | 144 | 5.00 | 165 | 0.05 |
| 124 | 40.00 | 145 | 0.01 | | |
| 125 | 0.05 | 146 | 0.01 | | |
| 126 | 0.05 | 147 | 5.00 | | |
| 127 | 1.0 | 148 | 10.00 | | |
| 166 | 0.02 | 185 | 1.0 | 204 | 95 @ 1 µM |
| 167 | 5.00 | 186 | 0.5 | 207 | 0.068 |
| 168 | 0.05 | 187 | 0.6 | 208 | 1 |
| 169 | 30 @ 50 µM | 188 | 50.00 | 209 | 63 @ 1 µM |
| 170 | 32 @ 50 µM | 189 | 1.00 | 210 | 0.099 |
| 171 | 1.0 | | | 211 | 0.046 |
| 172 | 50.0 | | | 212 | 60 @ 1 µM |
| 173 | 10.0 | 192 | 0.02 | 213 | 92% @ 1 µM |
| 174 | 0.5 | 193 | 0.93 | 214 | 0.178 |
| 175 | 8.0 | 194 | 0.034 | 215 | 0.033 |
| 176 | 25.0 | 195 | 50 | 216 | 0.03 |
| 177 | 37 @ 50 µM | 196 | 10 | 217 | 95% @ 1 µM |
| 178 | 0.5 | 197 | 71 @ 1 µM | 218 | 92% @ 1 µM |
| 179 | 0.5 | 198 | 10 | 219 | 93% @ 1 µM |
| 180 | .05 | 199 | 94 @ 1 µM | 220 | 50 |
| 181 | 1.0 | 200 | 1 | 221 | 0.039 |
| 182 | 0.02 | 201 | 90 @ 1 µM | | |
| 183 | 0.04 | 202 | 85 @ 1 µM | | |
| 184 | 3.0 | 203 | 98 @ 1 µM | | |
| 223 | 0.068 | 242 | 0.118 | 261 | 0.07 |
| 224 | 26% @ 50 µM | 243 | 0.188 | 262 | 0.5 |
| 225 | 0.067 | 244 | 0.186 | 263 | 0.1 |
| 226 | 76% @ 1 µM | 245 | 0.191 | | |
| 227 | 81% @ 50 µM | 246 | 0.031 | | |

TABLE I-continued

| Example | IC50 | Example | IC50 | Example | IC50 |
|---|---|---|---|---|---|
| 228 | 53% @ 1 µM | 247 | 0.061 | | |
| 229 | 69% @ 1 µM | 248 | 0.018 | | |
| 230 | 0.039 | 249 | 0.01 | | |
| 231 | 92% @ 1 µM | 250 | 82% @ 1 µM | 269 | 0.20 |
| 232 | 92% @ 1 µM | 251 | 86% @ 1 µM | 270 | 0.29 |
| 233 | 0.068 | 252 | 83% @ 1 µM | 271 | 0.05 |
| 234 | 0.17 | 253 | 0.2 | 272 | 0.16 |
| 235 | 91% @ 1 µM | | | 273 | 0.1 |
| 236 | 79% @ 1 µM | 255 | 0.1 | | |
| 237 | 0.026 | 256 | 0.1 | | |
| 238 | 0.011 | 257 | 0.5 | 276 | 50 |
| 239 | 0.088 | 258 | 0.03 | 277 | 0.5 |
| 240 | 0.116 | 259 | 0.03 | | |
| 241 | 0.334 | 260 | 0.03 | | |
| 281 | 1 | 289 | 0.014 | 298 | 0.079 |
| | | 290 | 0.014 | 299 | 0.022 |
| | | 291 | 0.08 | 303 | 5.0 |
| | | 292 | 0.017 | 304 | 95% @ 1 |
| | | 293 | 0.19 | 305 | 40% @ 50 |
| | | 294 | 0.104 | | |
| | | 295 | 0.249 | 307 | 1.0 |
| | | 296 | 0.079 | | |
| | | | 0.083 | | |
| | | | 0.075 | | |
| 288 | 50 | 297 | 0.064 | | |

TABLE II

| Example | IC50 | Example | IC50 | Example | IC50 |
|---|---|---|---|---|---|
| 193 | 5.25 | 214 | 0.487 | 233 | 0.067 |
| 194 | 0.049 | 215 | 0.017 | 234 | 0.131 |
| 195 | 40% @ 50 µM | 216 | 0.027 | 235 | 90% @ 1 µM |
| 196 | 71% @ 50 µM | 217 | 58% @ 1 µM | 236 | 58% @ 1 µM |
| 197 | 83% @ 10 µM | 218 | 84% @ 1 µM | 237 | 0.015 |
| 198 | 69% @ 50 µM | 219 | 84% @ 1 µM | 238 | 0.007 |
| 199 | 93% @ 1 µM | 220 | 19% @ 50 µM | 239 | 0.05 |
| 200 | 57% @ 10 µM | 221 | 0.019 | 240 | 0.381 |
| 201 | 80% @ 1 µM | | | 241 | 0.082 |
| 202 | 62% @ 1 µM | 223 | 0.06 | 242 | 0.282 |
| 203 | 96% @ 1 µM | 224 | INACTIVE | 243 | 0.495 |
| 204 | 78% @ 1 µM | 225 | 0.101 | 244 | 0.141 |
| 207 | 0.049 | 226 | 79% @ 50 µM | 245 | 0.343 |
| 208 | 79% @ 10 µM | 227 | 49% @ 50 µM | 246 | 0.024 |
| 209 | 67% @ 10 µM | 228 | 84% @ 10 µM | 247 | 0.072 |
| 210 | 0.08 | 229 | 90% @ 10 µM | 248 | 0.072 |
| 211 | 0.19 | 230 | 0.019 | 249 | 0.023 |
| 212 | 57% @ 10 µM | 231 | 78% @ 1 µM | 250 | 0.153 |
| 213 | 72% @ 1 µM | 232 | 90% @ 1 µM | 251 | 0.144 |
| 252 | 0.175 | | | | |

TABLE II-continued
| Example | IC50 | Example | IC50 | Example | IC50 |
|---|---|---|---|---|---|
| 253 | 0.203 | 289 | 0.029 | | |
| | | 290 | 0.025 | | |
| 255 | 96% @ 1 μM | 291 | 0.187 | | |
| 256 | 0.093 | 292 | 0.007 | | |
| | | 293 | 0.345 | | |
| | | 294 | 0.233 | | |
| | | 295 | 0.212 | | |
| 257 | 78% @ 10 μM | 296 | 0.054 | | |
| | | | 0.111 | | |
| 258 | 0.1 | 297 | 0.078 | | |
| 259 | 0.087 | 298 | 0.113 | | |
| 260 | 0.07 | 299 | 0.02 | | |
| 261 | 0.059 | 303 | 50 | | |
| 262 | 90% @ 10 μM | 304 | 94% @ 1 μM | | |
| 263 | 86% @ 1 μM | 305 | 21% @ 50 μM | | |
| 269 | 0.441 | | | | |
| 270 | 0.434 | 307 | 5.0 | | |
| 271 | 0.031 | | | | |
| 272 | 0.112 | | | | |
| 273 | 75% @ 1 μM | | | | |
| 276 | INACTIVE | | | | |
| 277 | 84% @ 10 μM | | | | |
| 281 | 56% @ 50 μM | | | | |
FORMULAE
Cpd #2
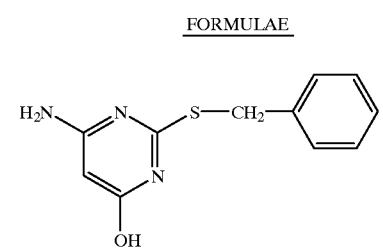
Cpd #3
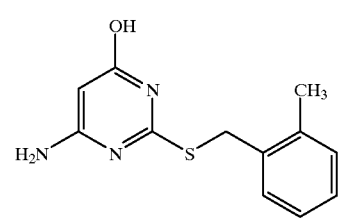
Cpd #4
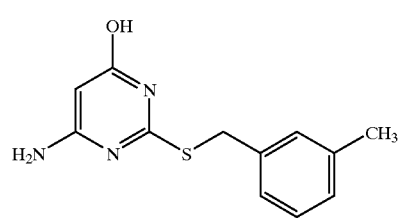
Cpd #5
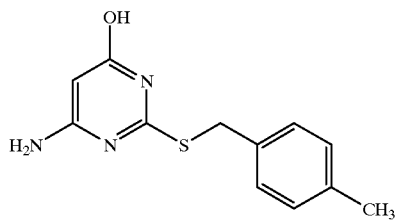
Cpd #6
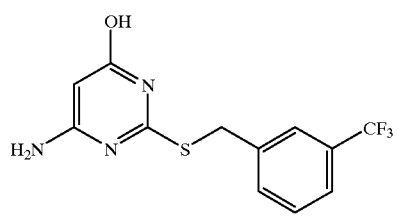
Cpd #7
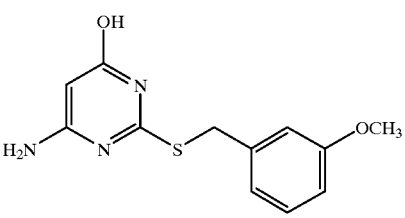
Cpd #8
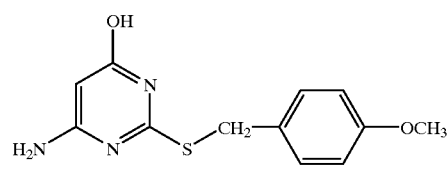
Cpd #9
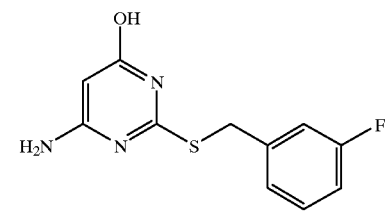
Cpd #10
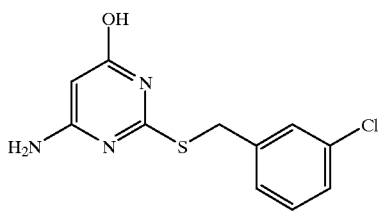
Cpd #11
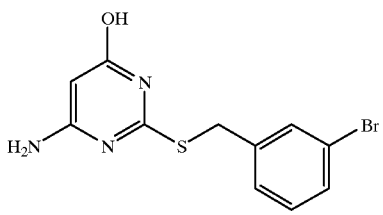

Cpd #12
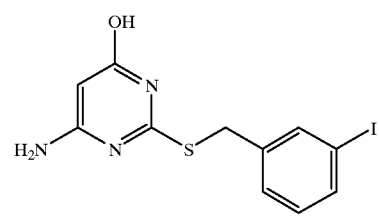
Cpd #13
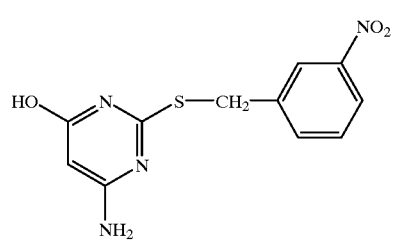
Cpd #14
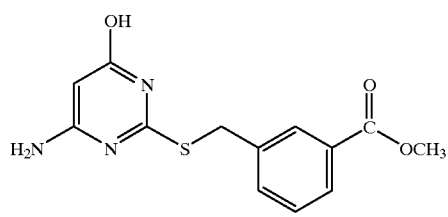
Cpd #15
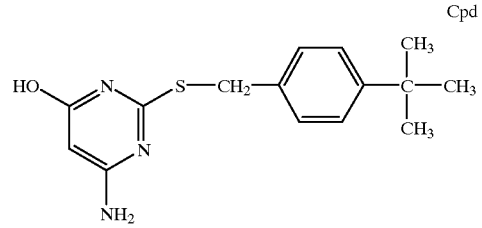
Cpd #16
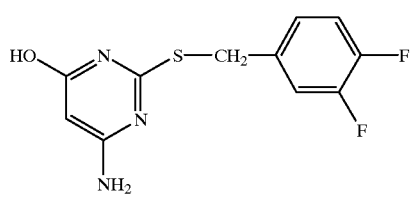
Cpd #17
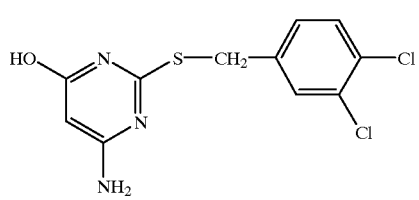
Cpd #18
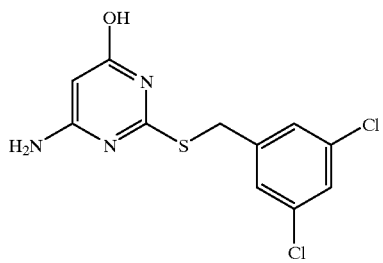
Cpd #19
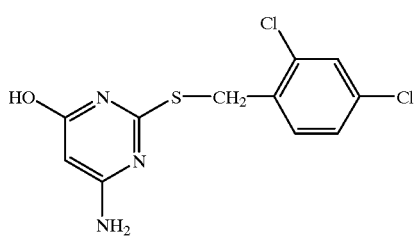
Cpd #20
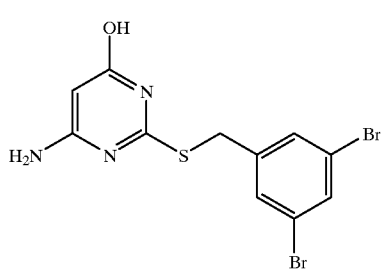
Cpd #21
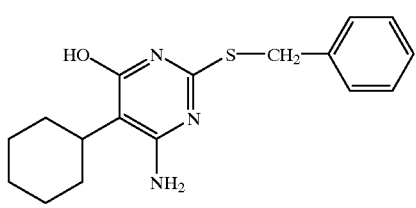
Cpd #22
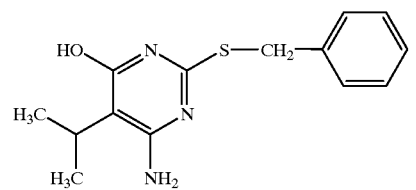
Cpd #23
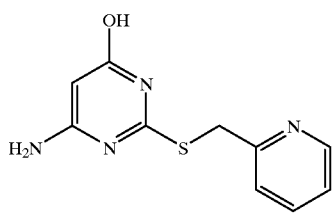

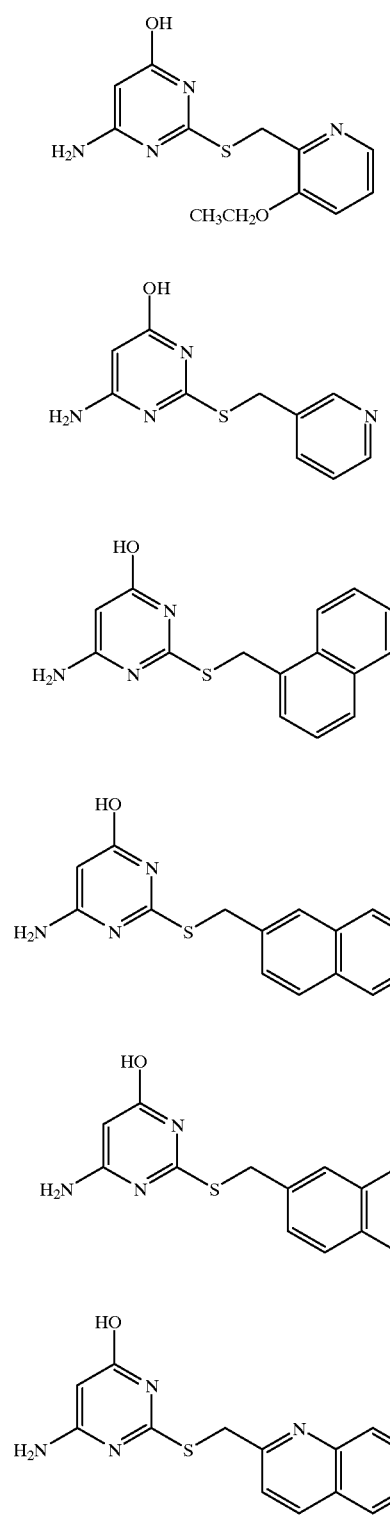
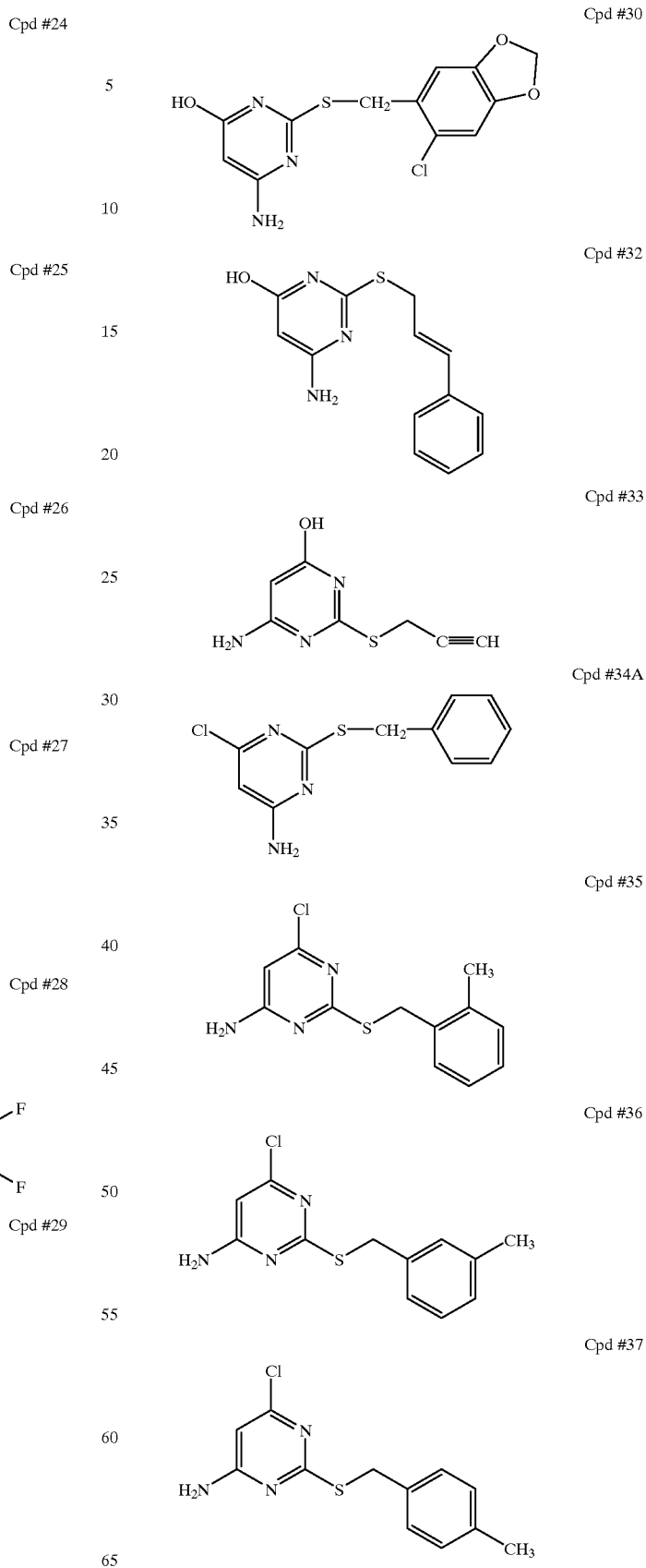

Cpd #38
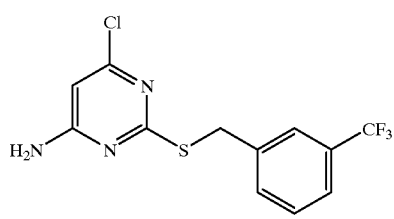
Cpd #39
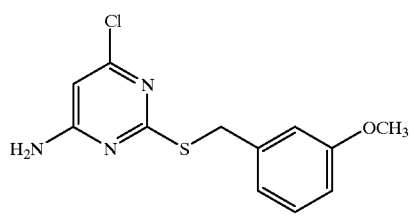
Cpd #40
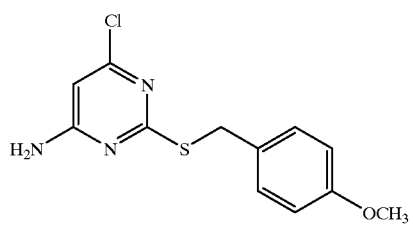
Cpd #41
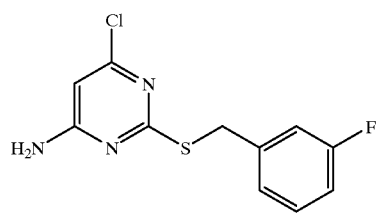
Cpd #42
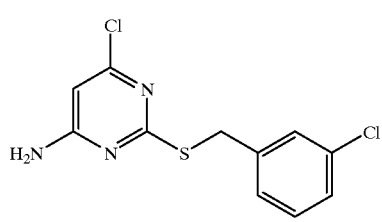
Cpd #43
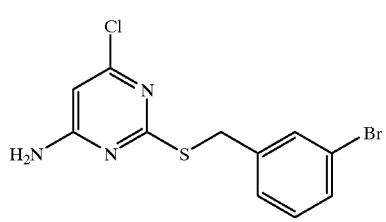
Cpd #44
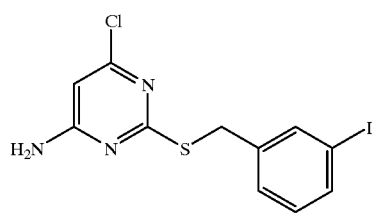
Cpd #45
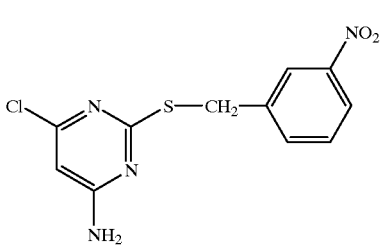
Cpd #46
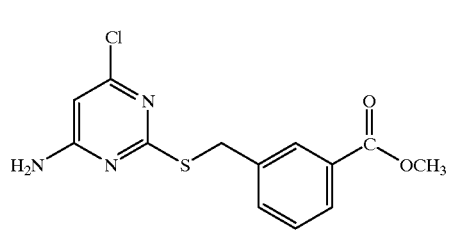
Cpd #47
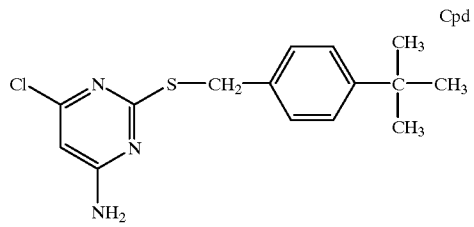
Cpd #48
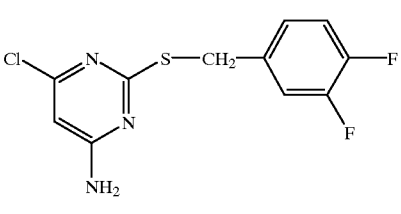
Cpd #49
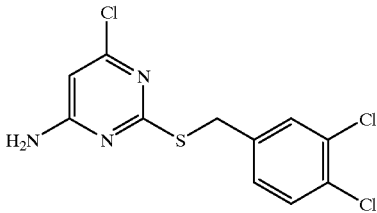

Cpd #50
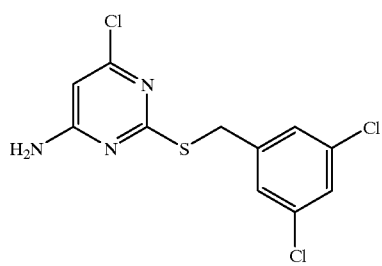
Cpd #51
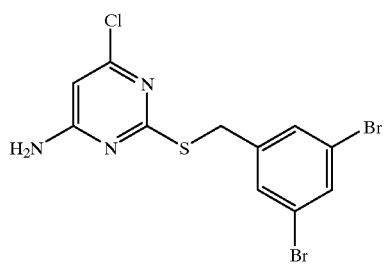
Cpd #52
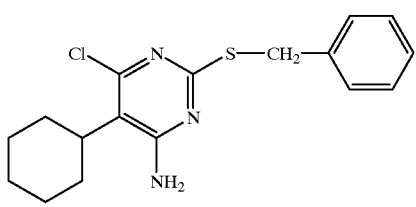
Cpd #53
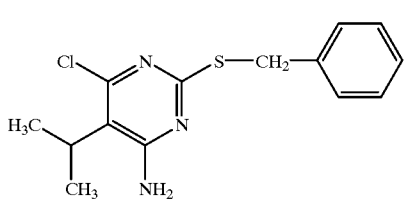
Cpd #54
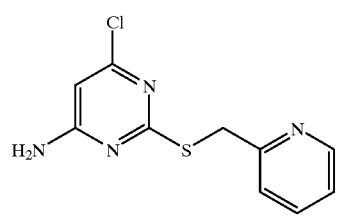
Cpd #55
Cpd #56
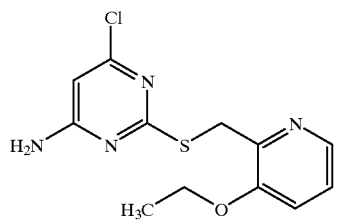
Cpd #57
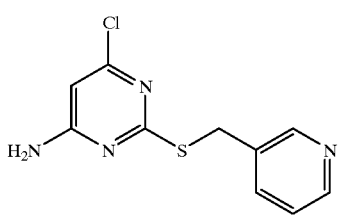
Cpd #58
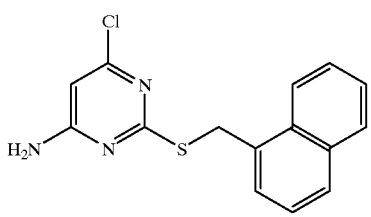
Cpd #59
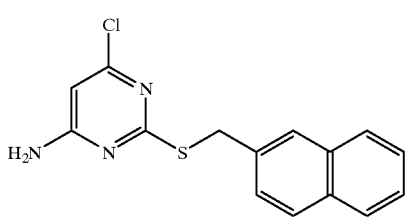
Cpd #60
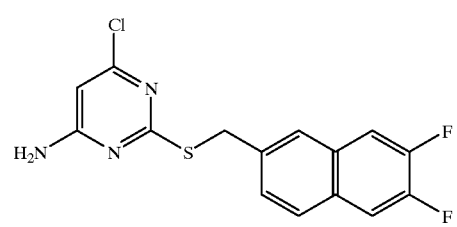
Cpd #61
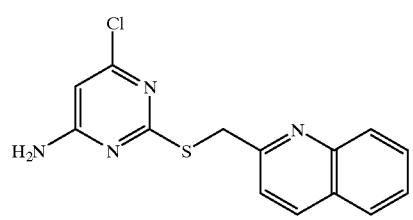

Cpd #62
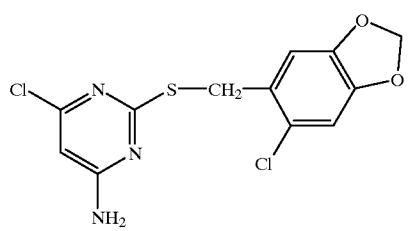
Cpd #64
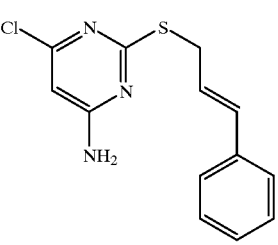
Cpd #65
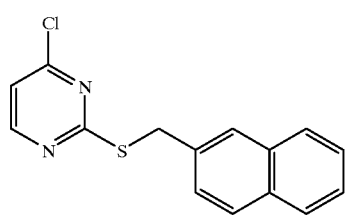
Cpd #66
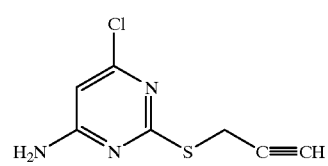
Cpd #67
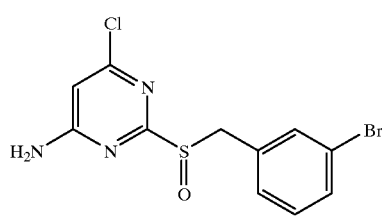
Cpd #68
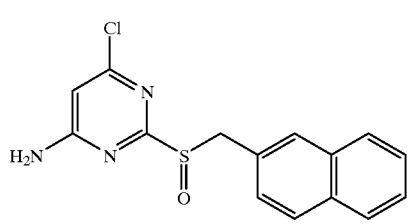
Cpd #69
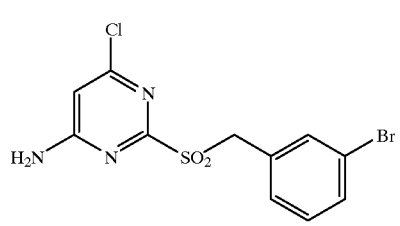
Cpd #70
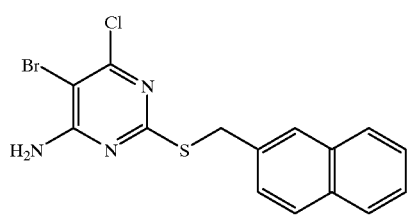
Cpd #71
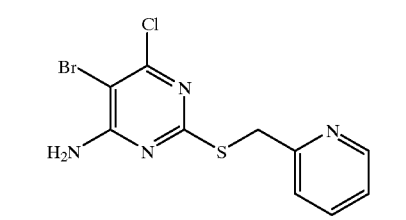
Cpd #72
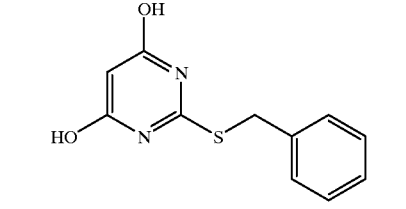
Cpd #73
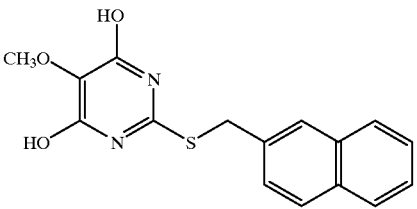
Cpd #74
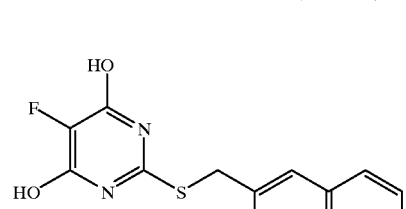
Cpd #75
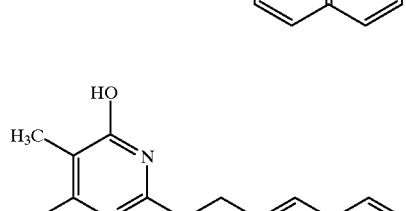

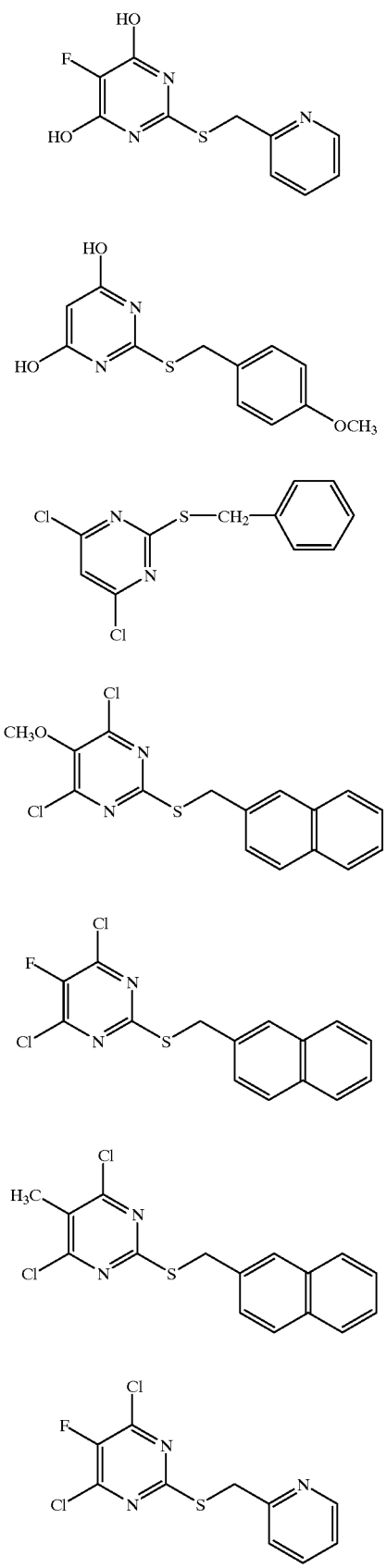
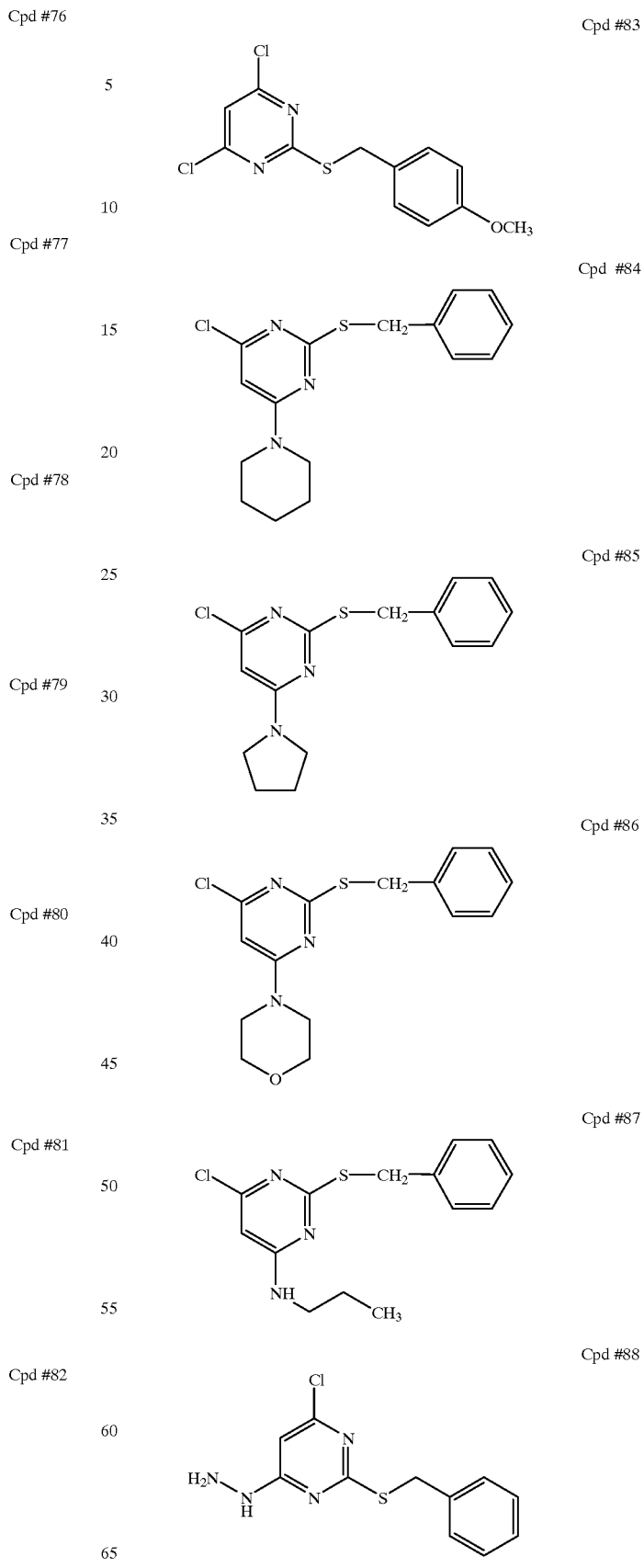

Cpd #89
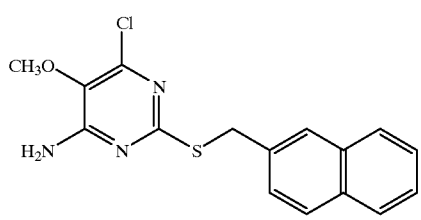
Cpd #90
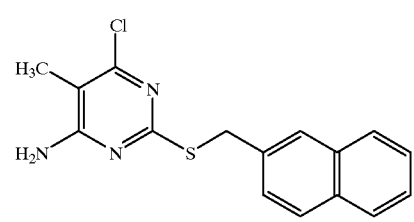
Cpd #91
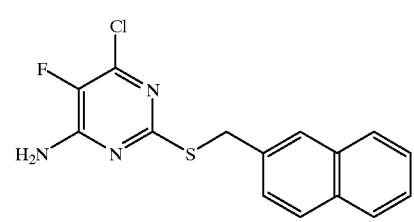
Cpd #92
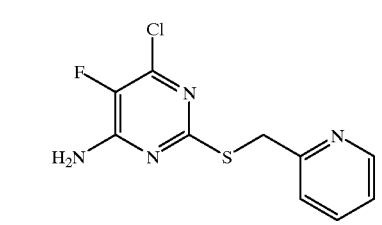
Cpd #93
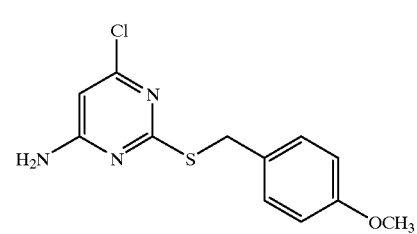
Cpd #94
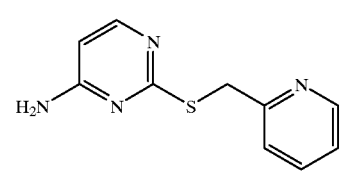
Cpd #95
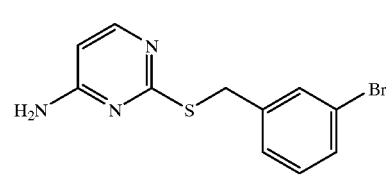
Cpd #96
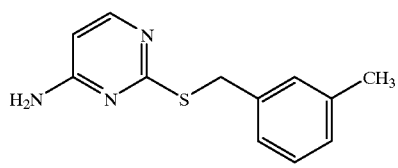
Cpd #97
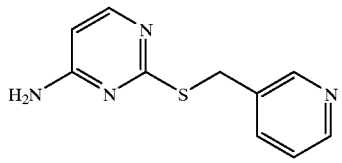
Cpd #98
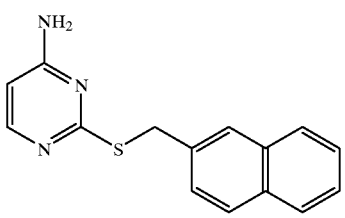
Cpd #99
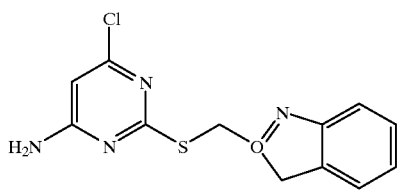
Cpd #100
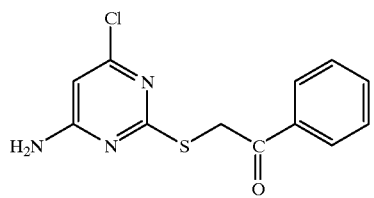
Cpd #101
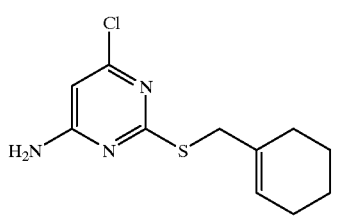
Cpd #102
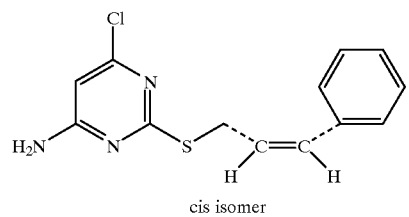
cis isomer Cpd #103
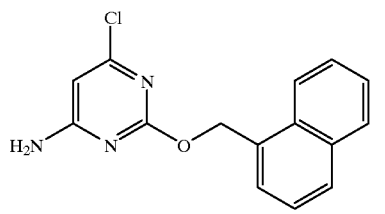
Cpd #104
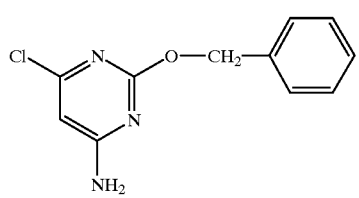
Cpd #105
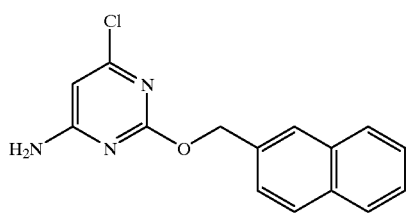
Cpd #106
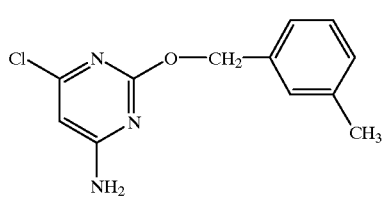
Cpd #107
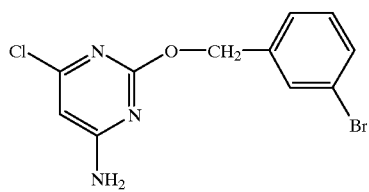
Cpd #108
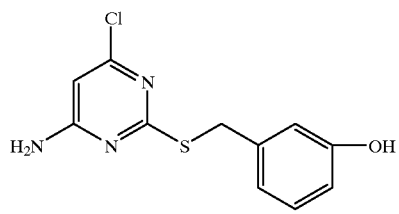
Cpd #109
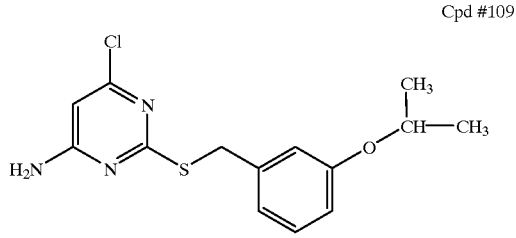
Cpd #110
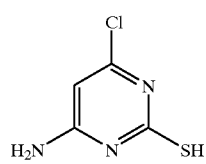
Cpd #111
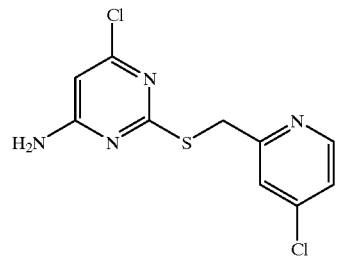
Cpd #112
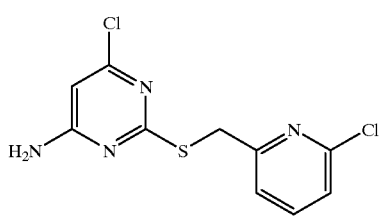
Cpd #113
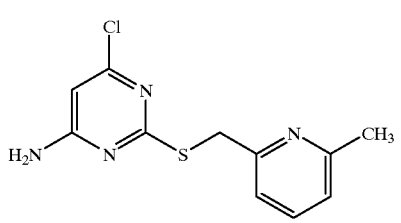
Cpd #114
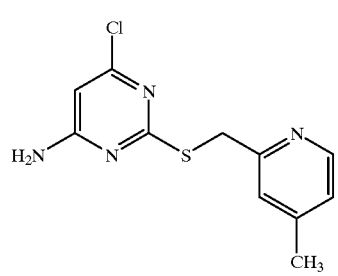
Cpd #115
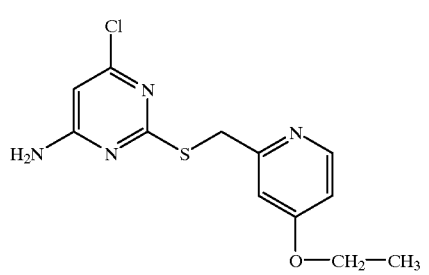

Cpd #116
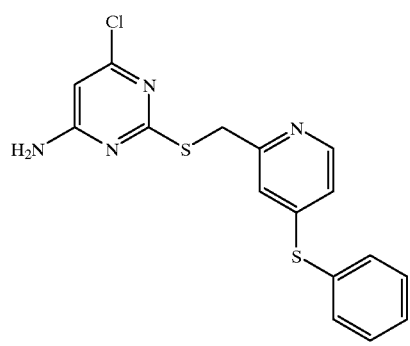
Cpd #117
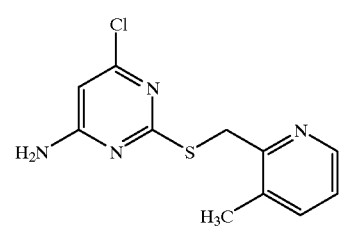
Cpd #118
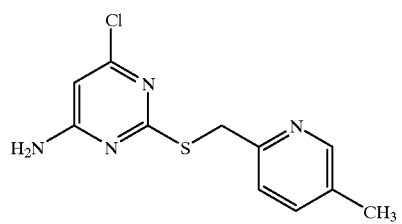
Cpd #119
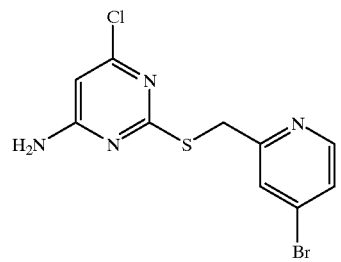
Cpd #120
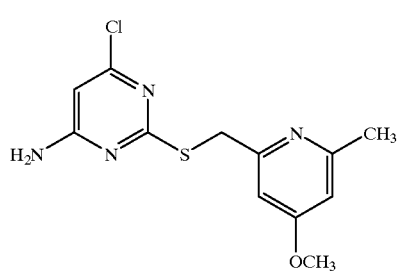
Cpd #121
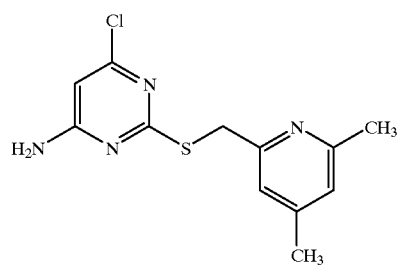
Cpd #122
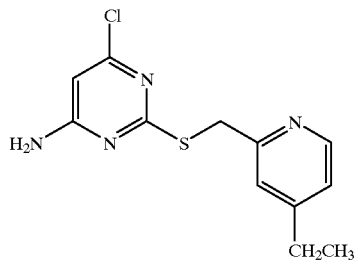
Cpd #123
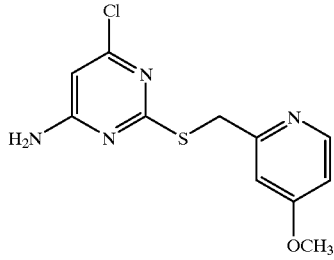
Cpd #124
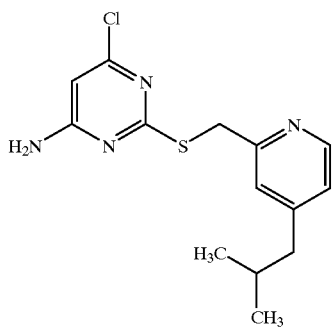
Cpd #125
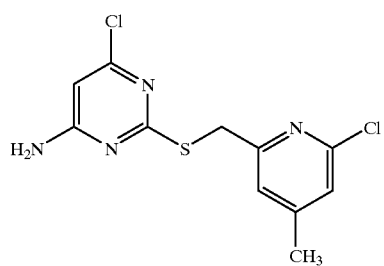

-continued
Cpd #126
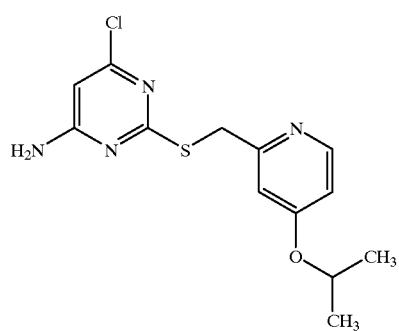
Cpd #127
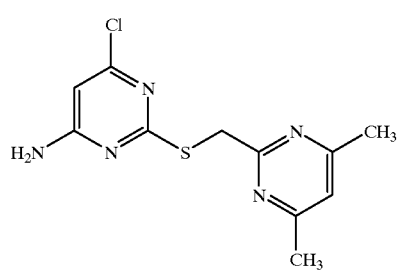
Cpd #128
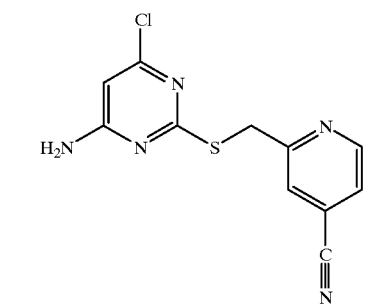
Cpd #130
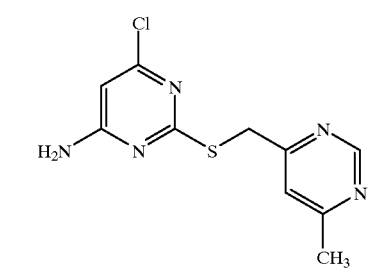
Cpd #131
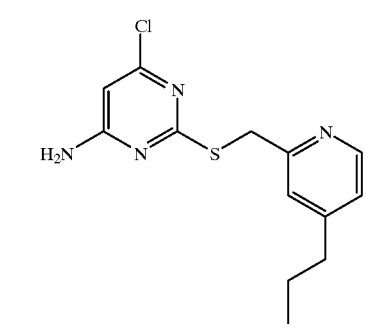
-continued
Cpd #132
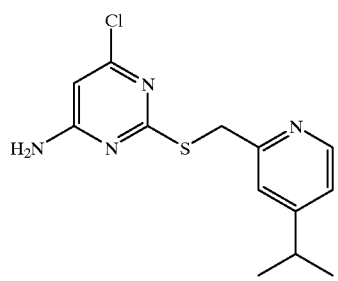
Cpd #133
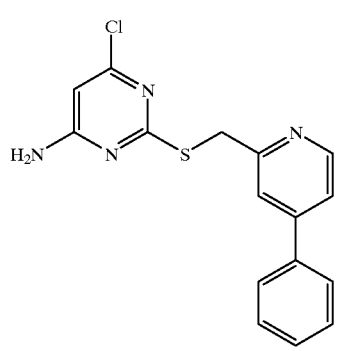
Cpd #134
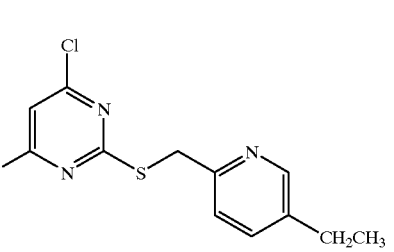
Cpd #135
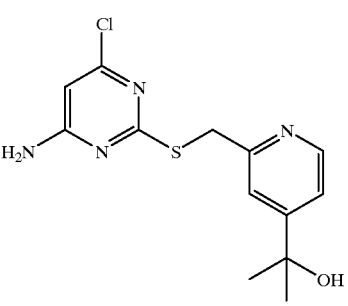
Cpd #137
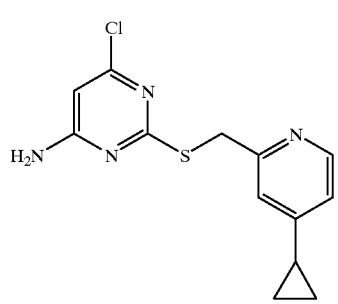

Cpd #138
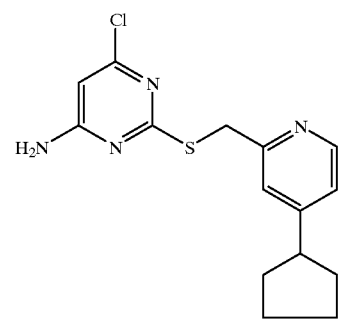
Cpd #145
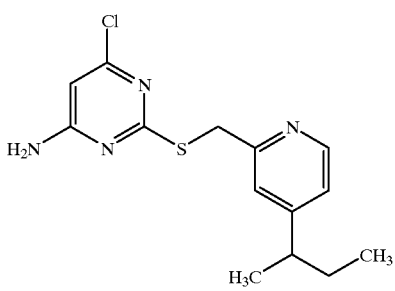
Cpd #140
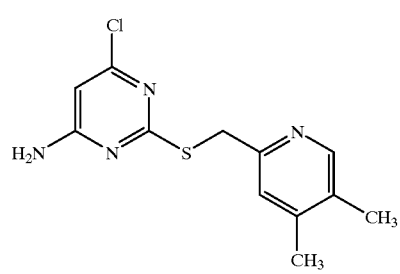
Cpd #146
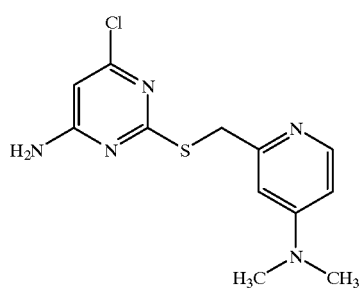
Cpd #142
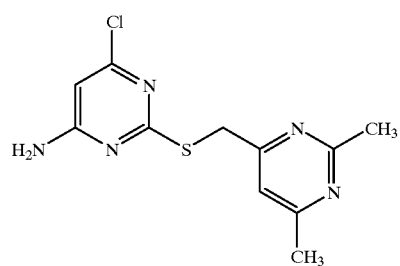
Cpd #147
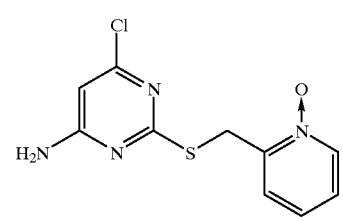
Cpd #143
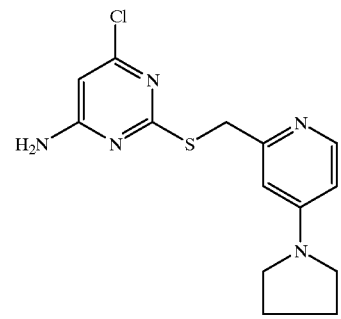
Cpd #148
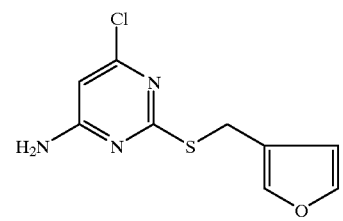
Cpd #144
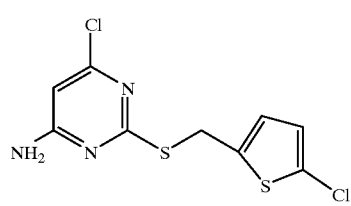
Cpd #149
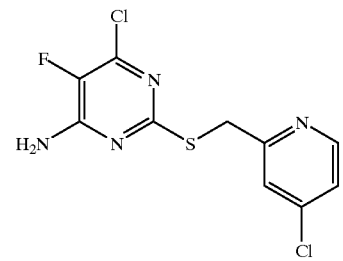

Cpd #151
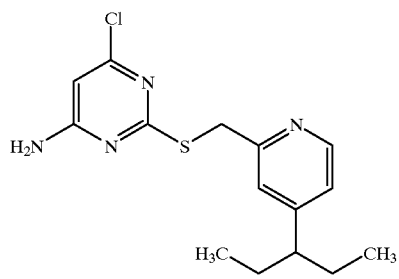
Cpd #152
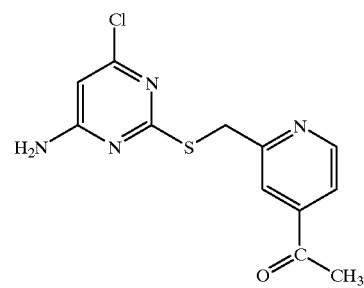
Cpd #153
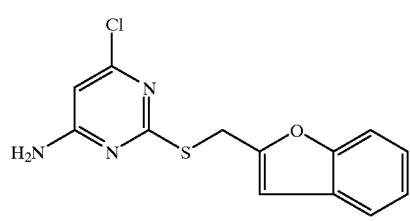
Cpd #154
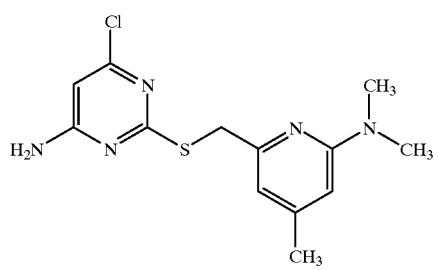
Cpd #155
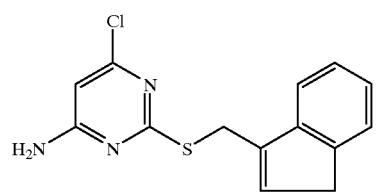
Cpd #156
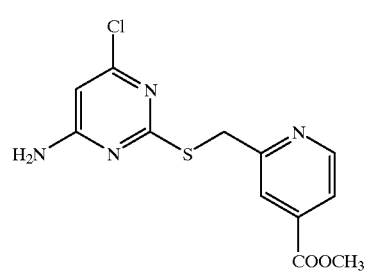
Cpd #157
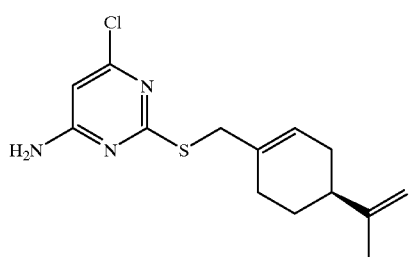
Cpd #158
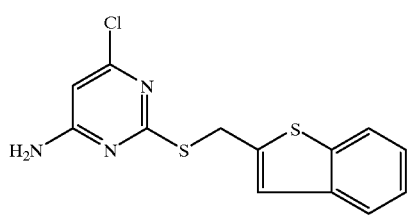
Cpd #159
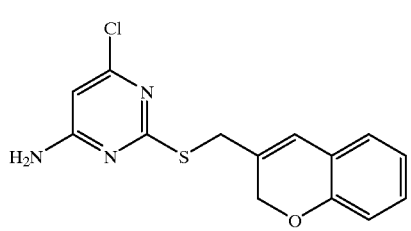
Cpd #163
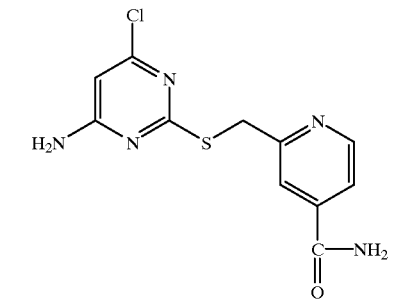
Cpd #164
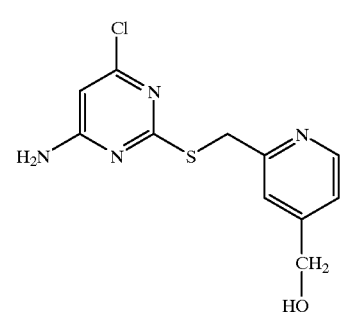

Cpd #165
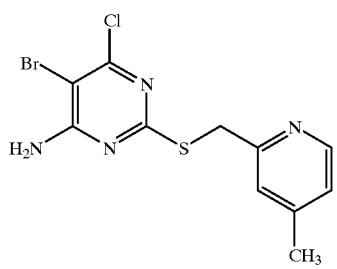
Cpd #166
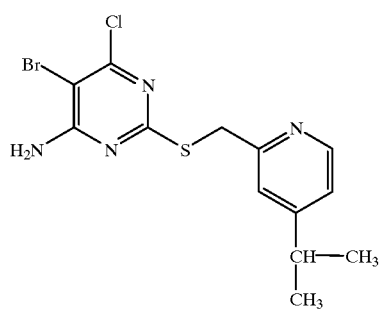
Cpd #167
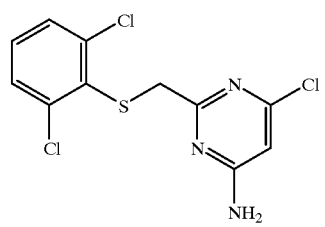
Cpd #168
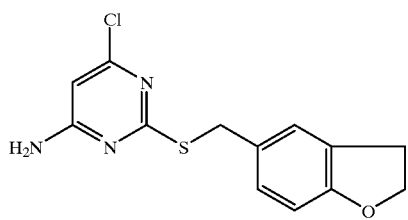
Cpd #169
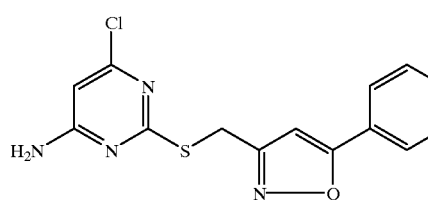
Cpd #170
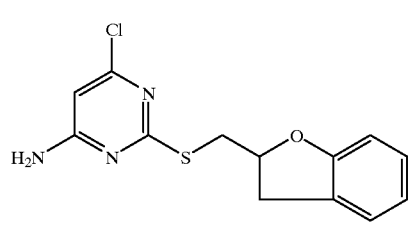
Cpd #171
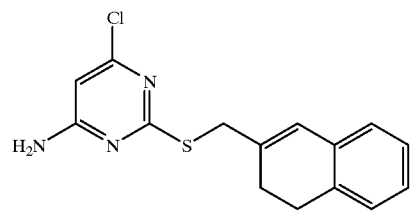
Cpd #172
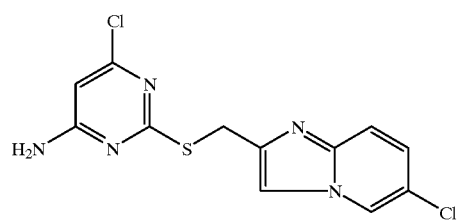
Cpd #173
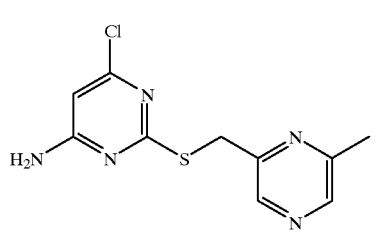
Cpd #174
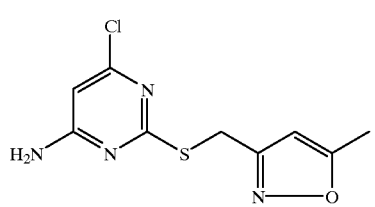
Cpd #175
Cpd #176
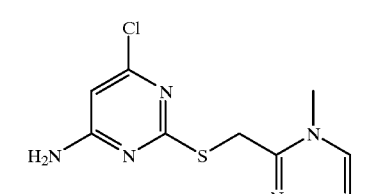
Cpd #177
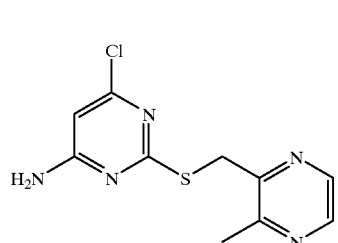

Cpd #178
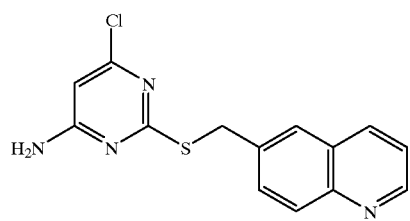
Cpd #179
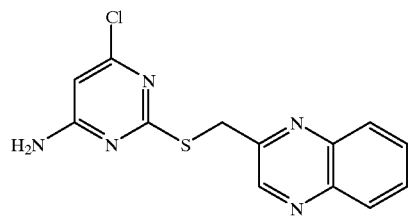
Cpd #180
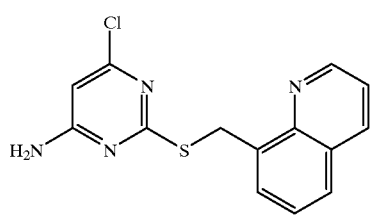
Cpd #181
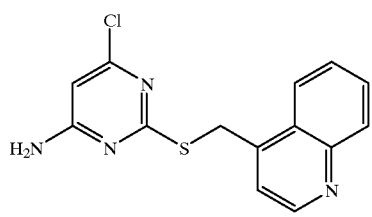
Cpd #182
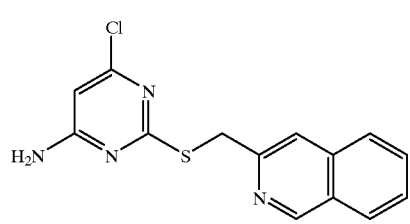
Cpd #183
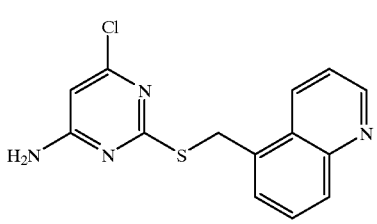
Cpd #184
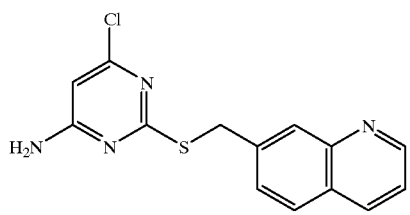
Cpd #186
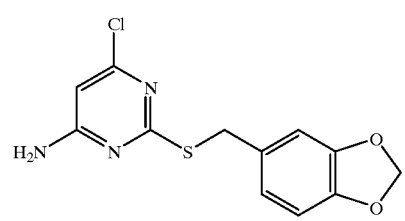
Cpd #187
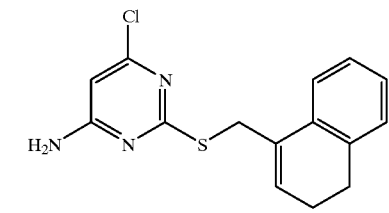
Cpd #188
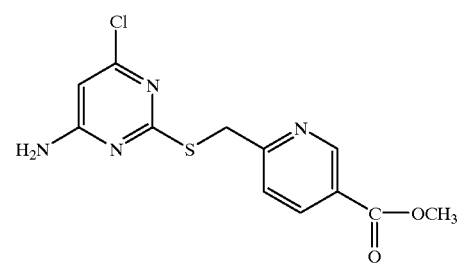
Cpd #189
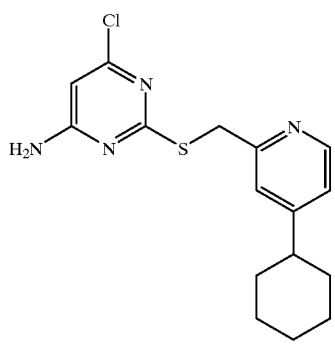
Cpd #190
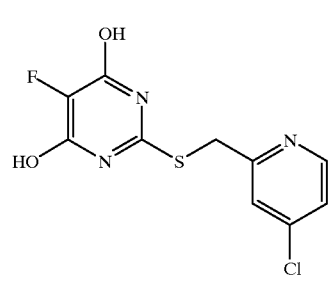

Cpd #191
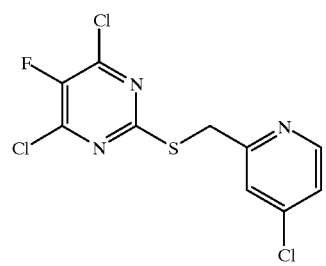
Cpd #192
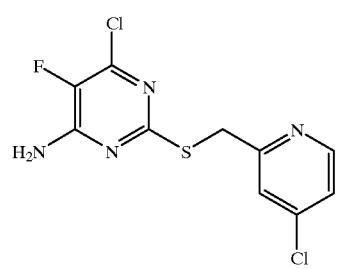
Cpd #193
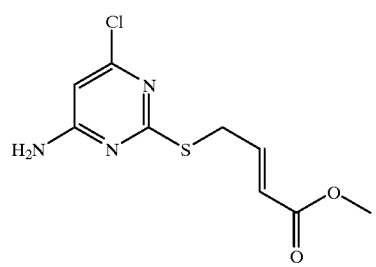
Cpd #194
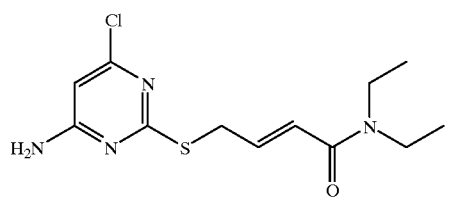
Cpd #195
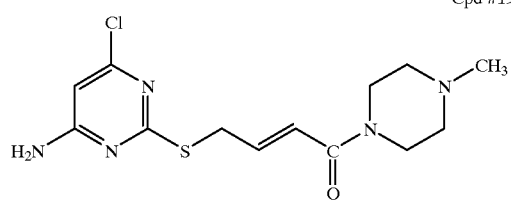
Cpd #196
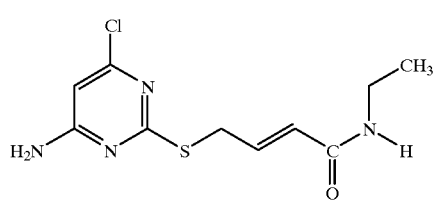
Cpd #197
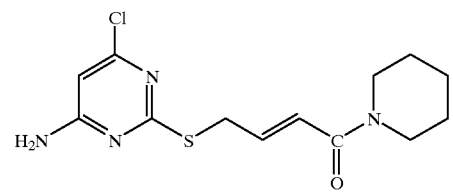
Cpd #198
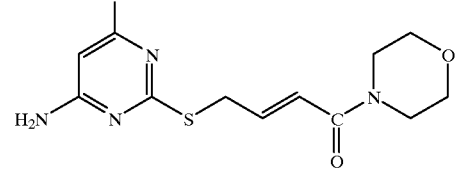
Cpd #199
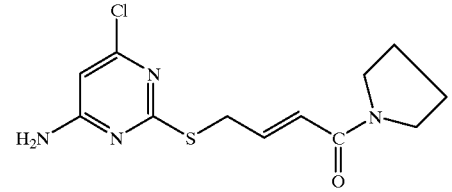
Cpd #200
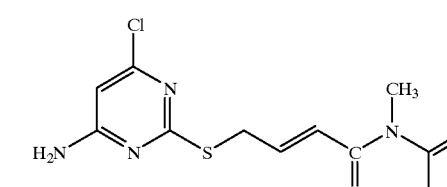
Cpd #201
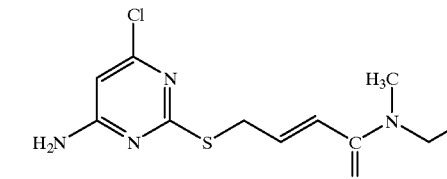
Cpd #202
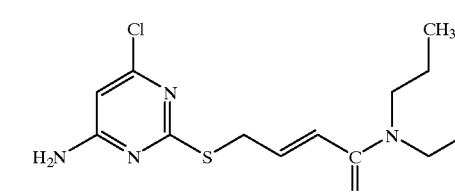
Cpd #203
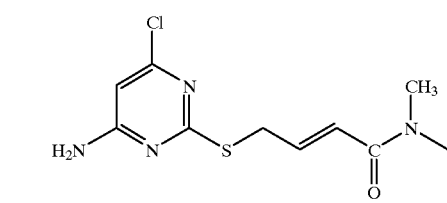

-continued
Cpd #204
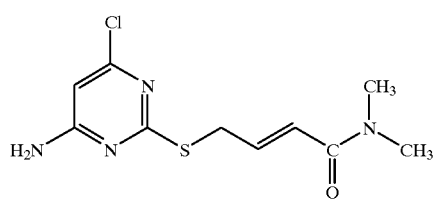
Cpd #207
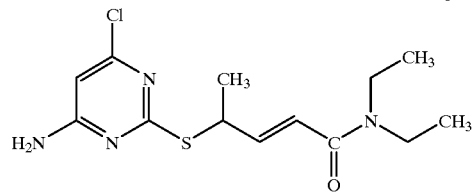
Cpd #208
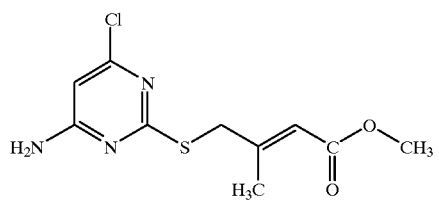
Cpd #209
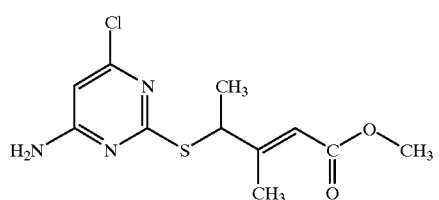
Cpd #210
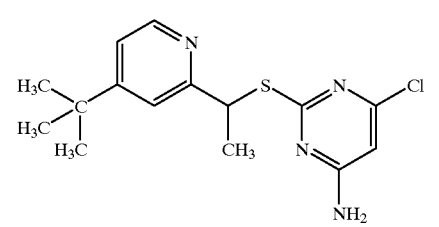
Cpd #211
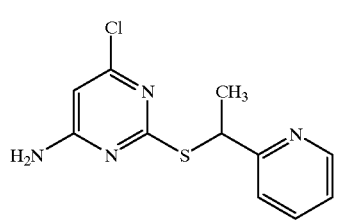
Cpd #212
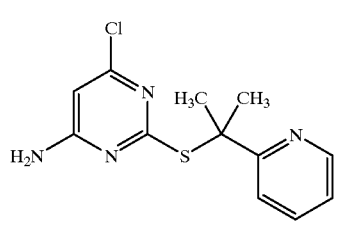
-continued
Cpd #213
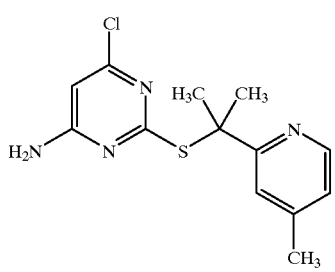
Cpd #214
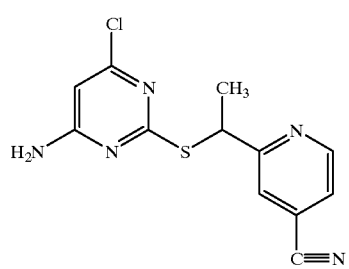
Cpd #215
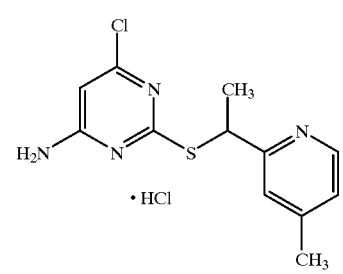
Cpd #216
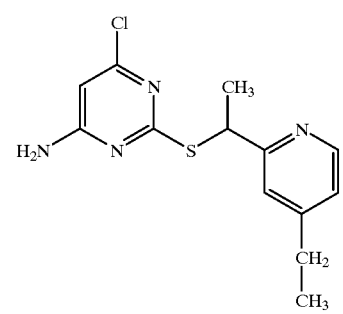
Cpd #217
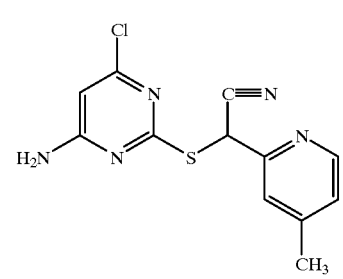

Cpd #218
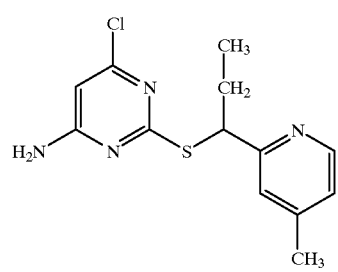
Cpd #219
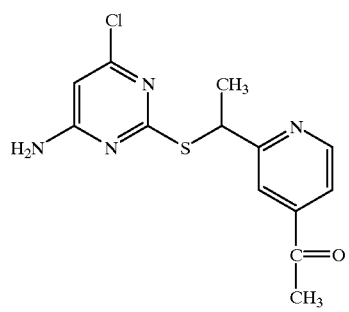
Cpd #220
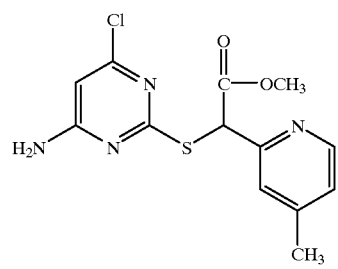
Cpd #221
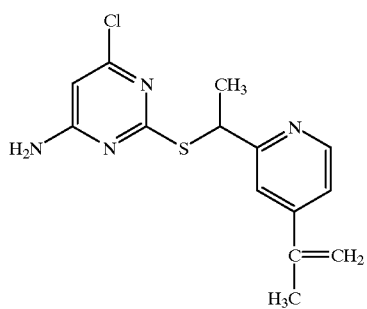
Cpd #223
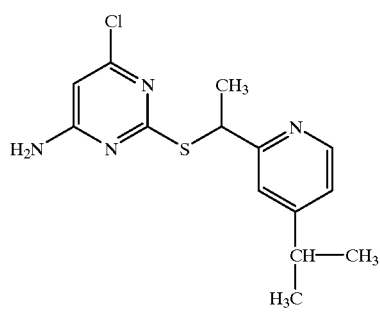
Cpd #224
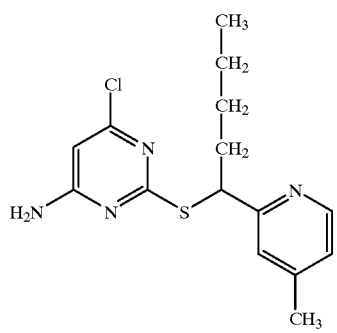
Cpd #225
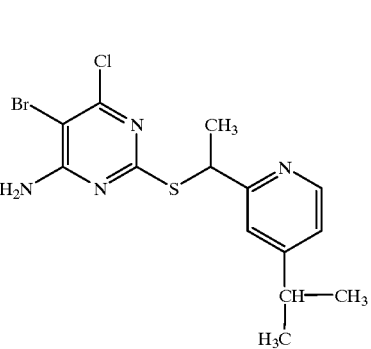
Cpd #226
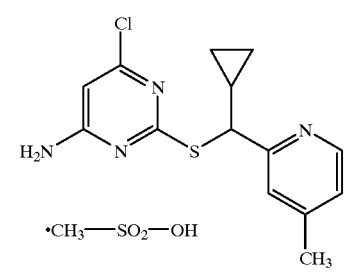
Cpd #227
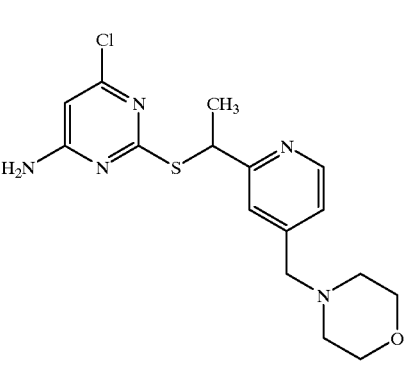

-continued
Cpd #228
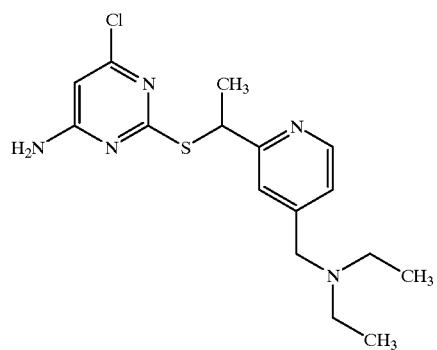
Cpd #229
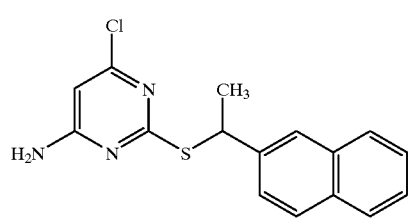
Cpd #230
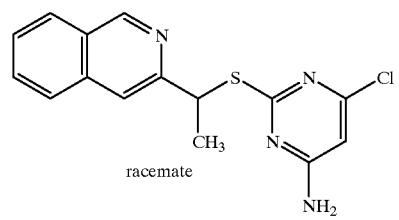
racemate
Cpd #231
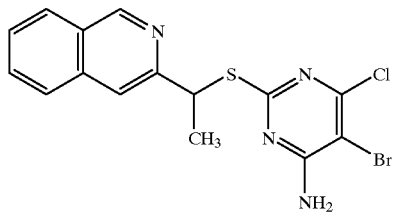
Cpd #232
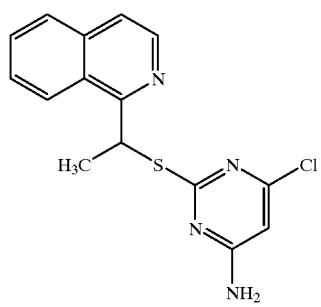
-continued
Cpd #233
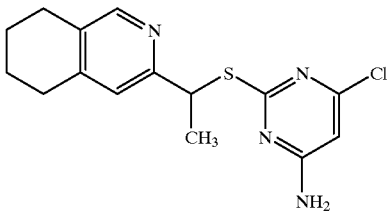
Cpd #234
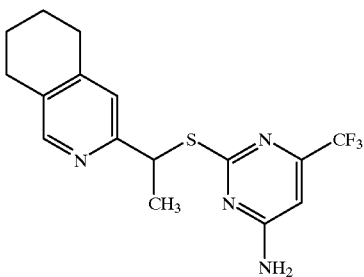
Cpd #235
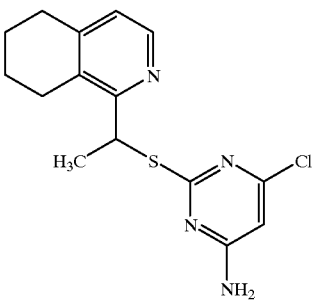
Cpd #236
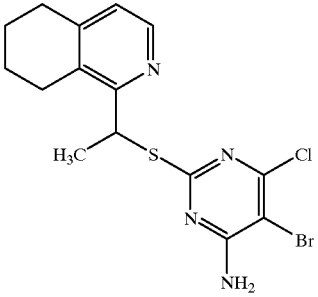
Cpd #237
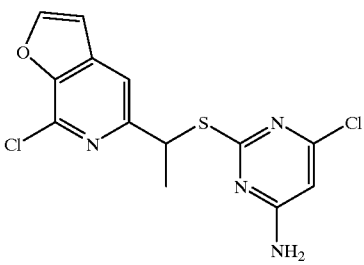

6,043,248
163
-continued
Cpd #238
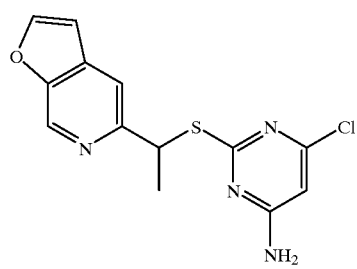
Cpd #239
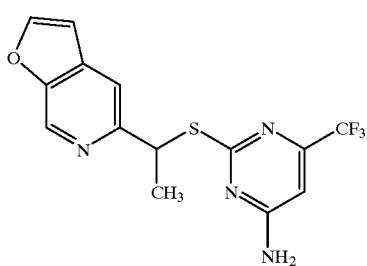
Cpd #240
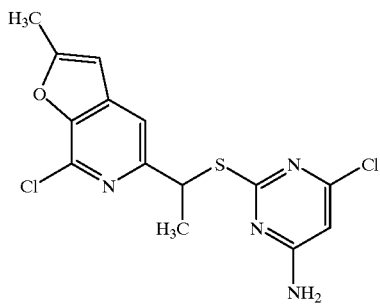
Cpd #241
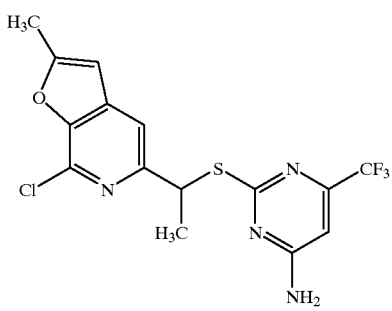
Cpd #242
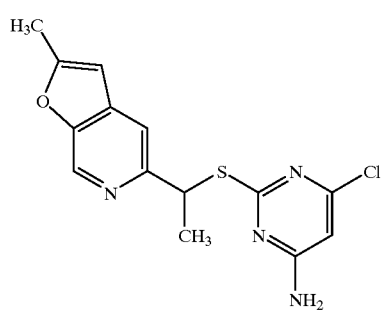
164
-continued
Cpd #243
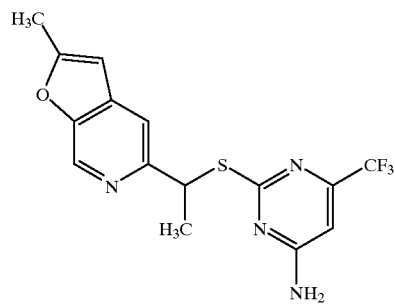
Cpd #244
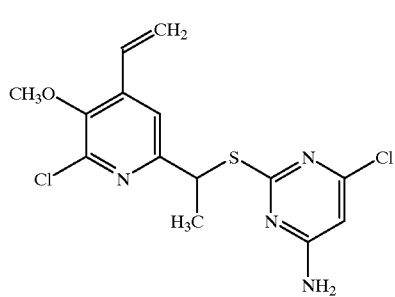
Cpd #245
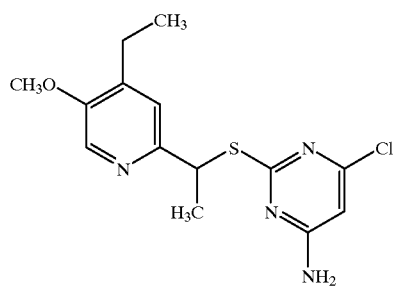
Cpd #246
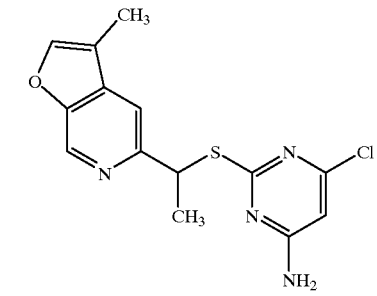
Cpd #247
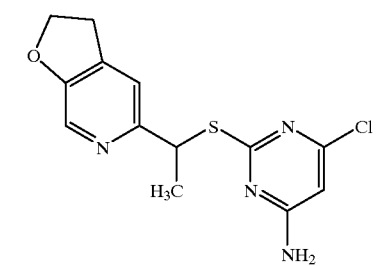

Cpd #248
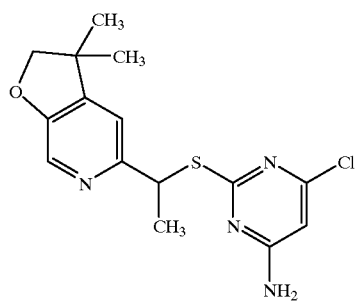
Cpd #249
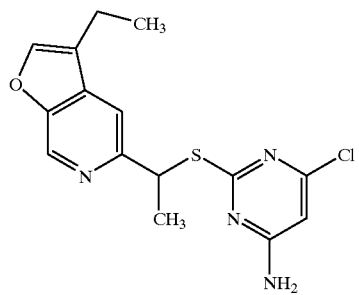
Cpd #250
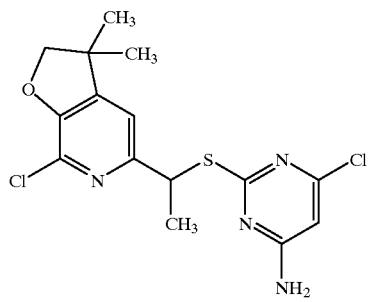
Cpd #251
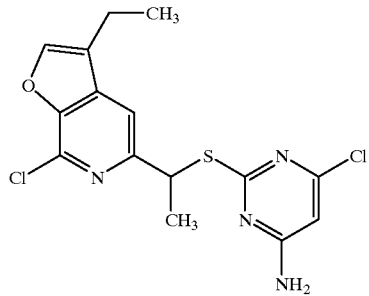
Cpd #252
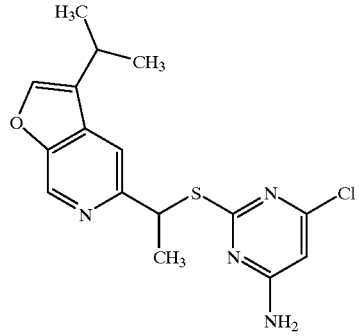
Cpd #253
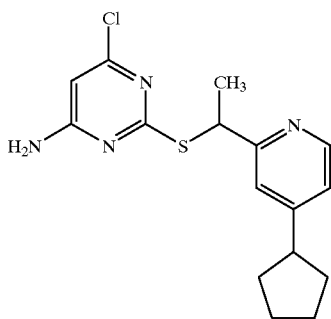
Cpd #255
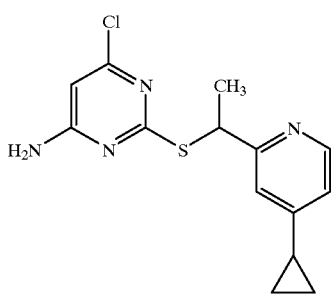
Cpd #256
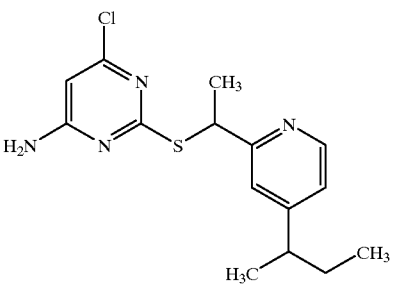
Cpd #257
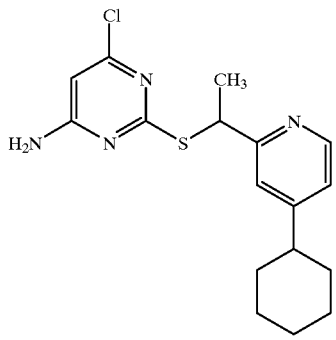

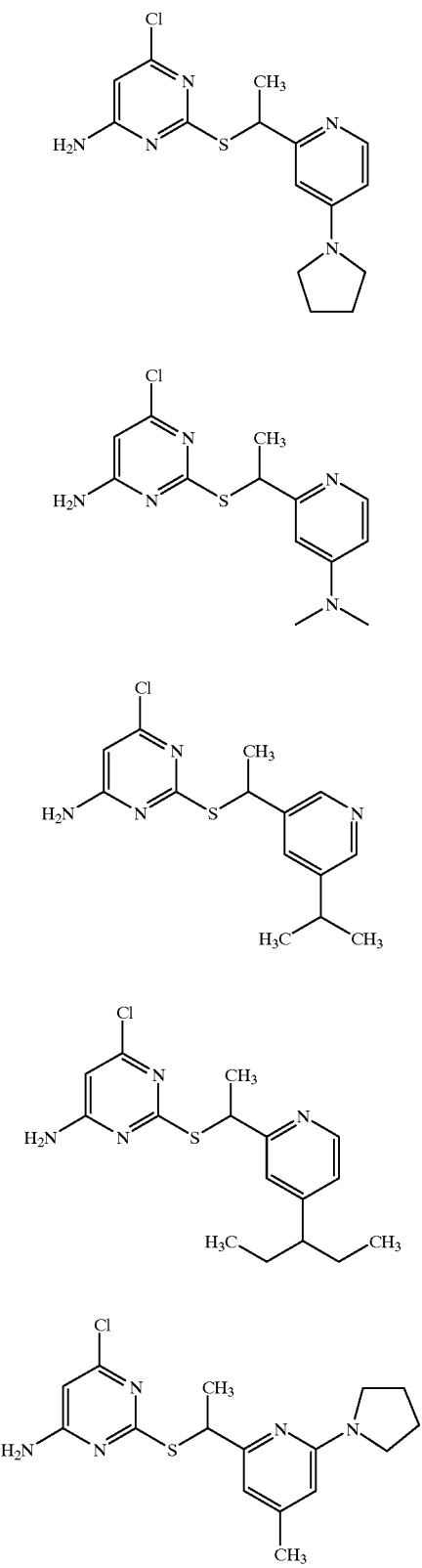
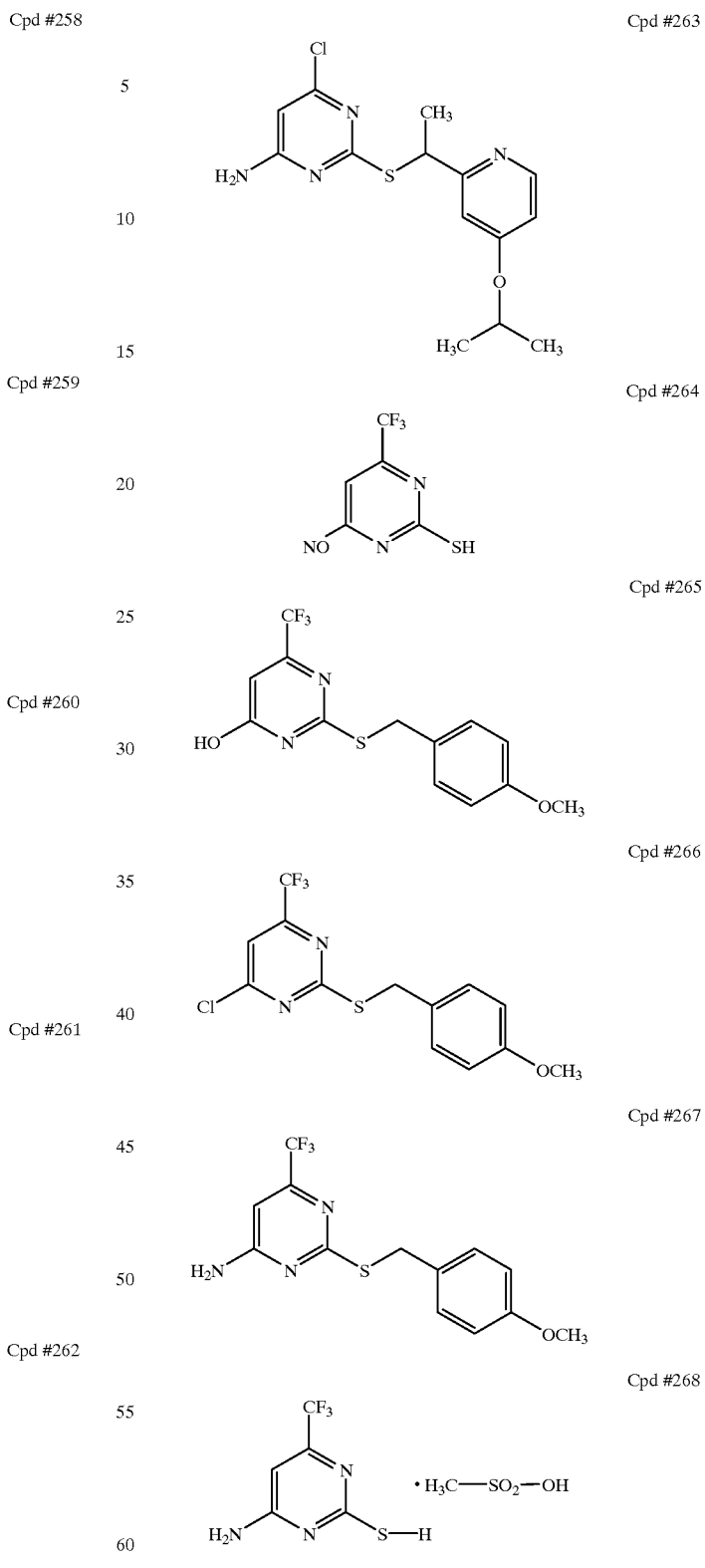

Cpd #269
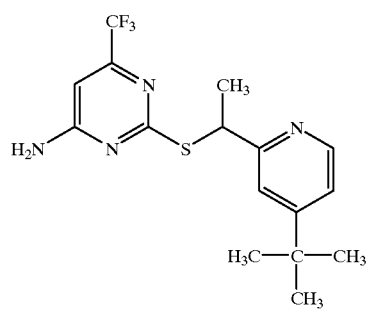
Cpd #270
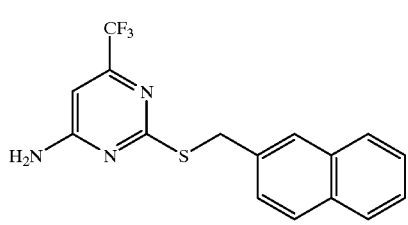
Cpd #271
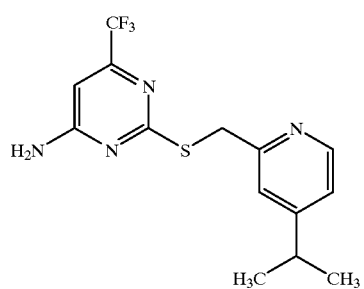
Cpd #272
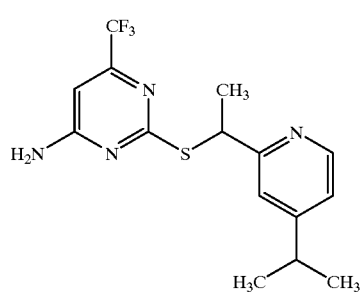
Cpd #273
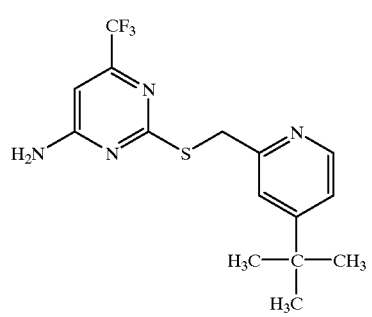
Cpd #274
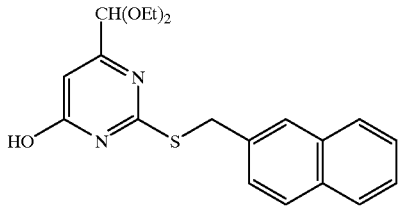
Cpd #275
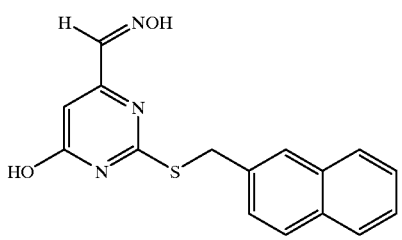
Cpd #276
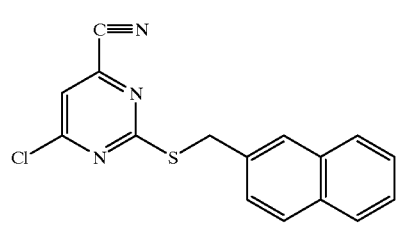
Cpd #277
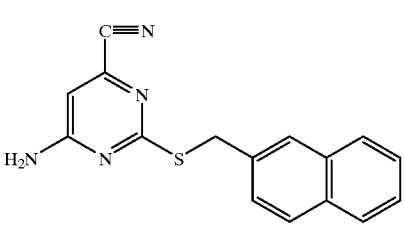
Cpd #278
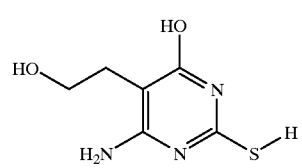
Cpd #279
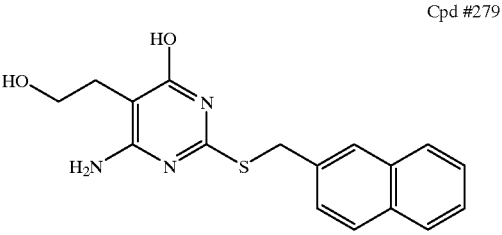
Cpd #280
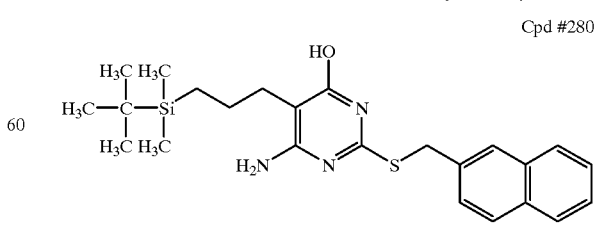

Cpd #281
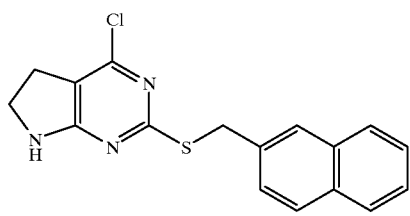
Cpd #282
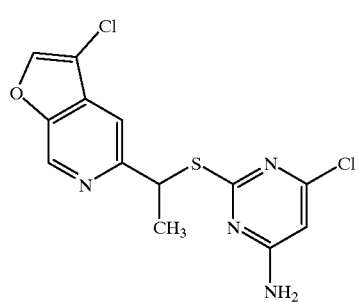
Cpd #283
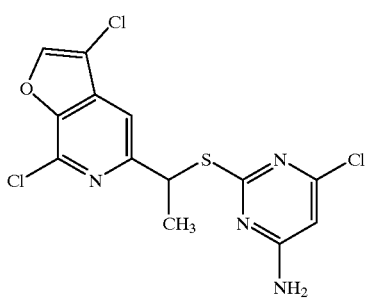
Cpd #284
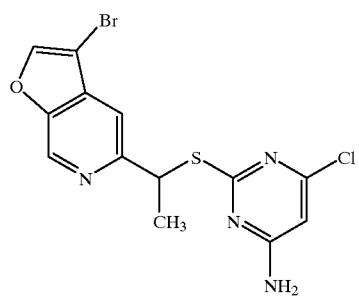
Cpd #285
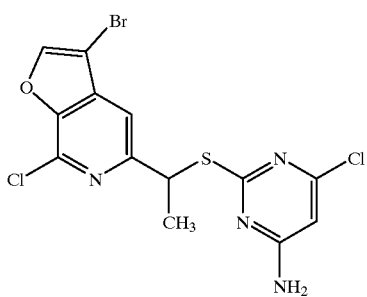
Cpd #286
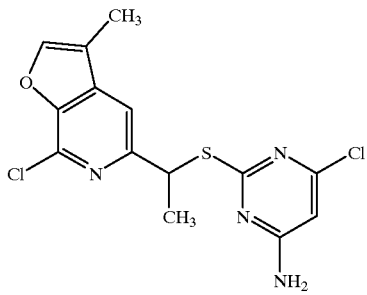
Cpd #287
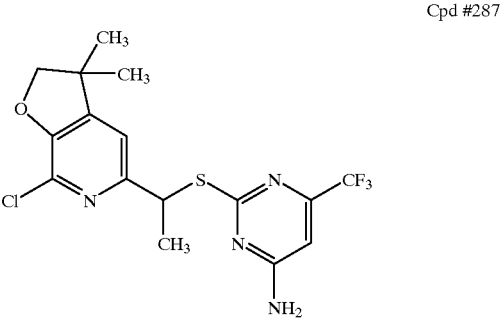
Cpd #288
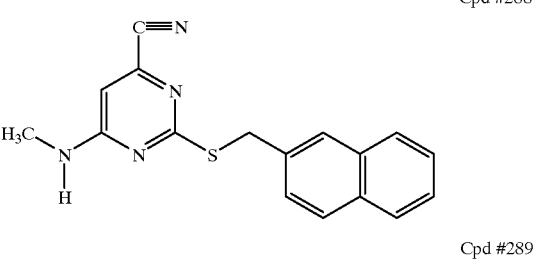
Cpd #289
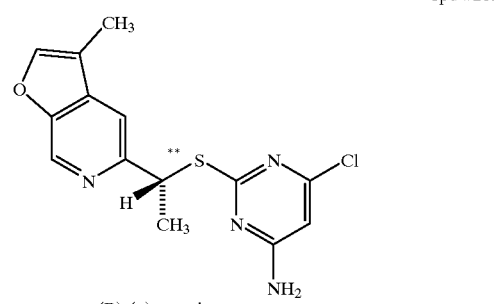
(R)-(+) enantiomer
Cpd #290
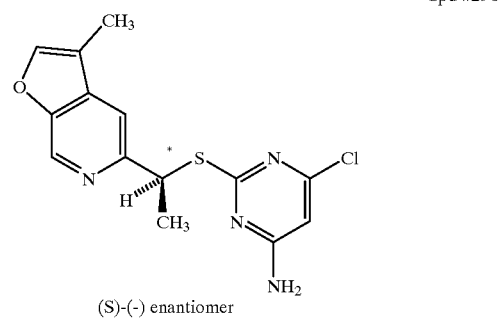
(S)-(-) enantiomer

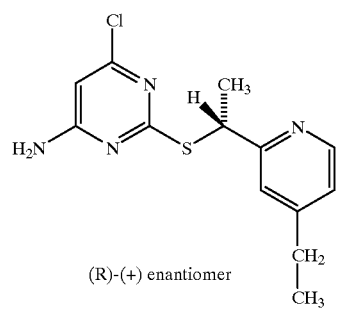
Cpd #291
(R)-(+) enantiomer
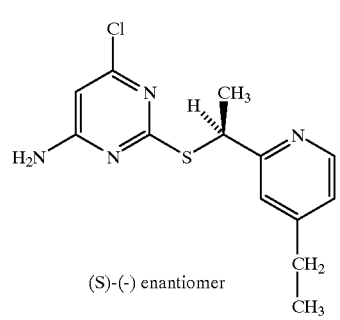
Cpd #292
(S)-(-) enantiomer
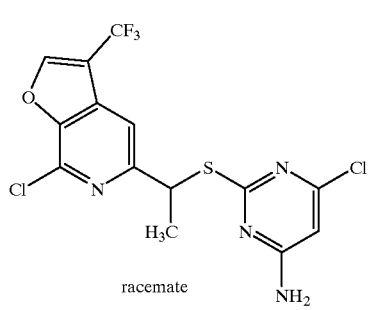
Cpd #293
racemate
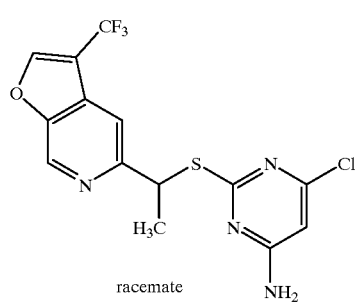
Cpd #294
racemate
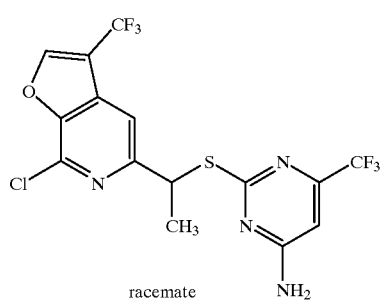
Cpd #295
racemate
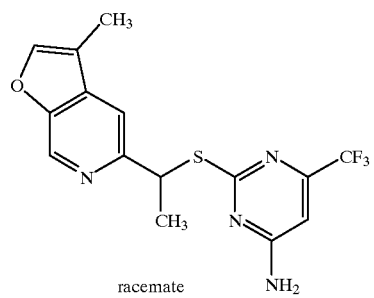
Cpd #296
racemate
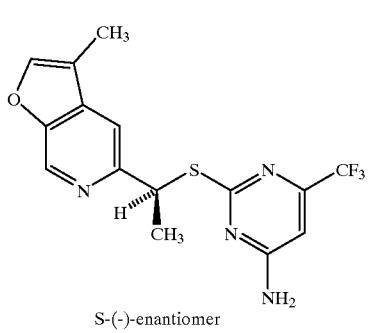
Cpd #297
S-(-)-enantiomer
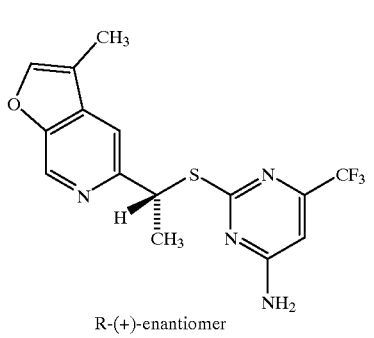
Cpd #298
R-(+)-enantiomer
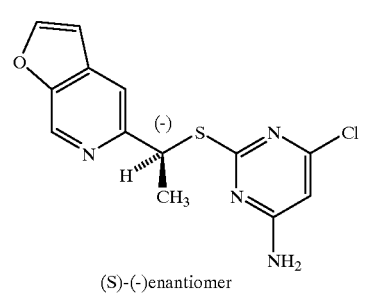
Cpd #299
(S)-(-)enantiomer
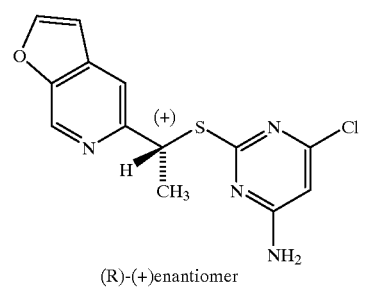
Cpd #300
(R)-(+)enantiomer Cpd #301
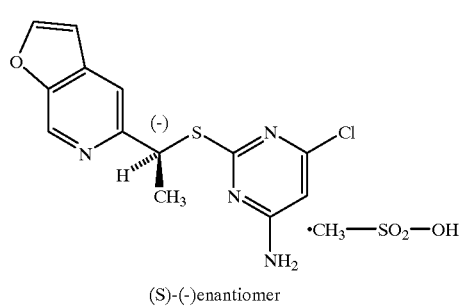
(S)-(-)enantiomer
Cpd #302
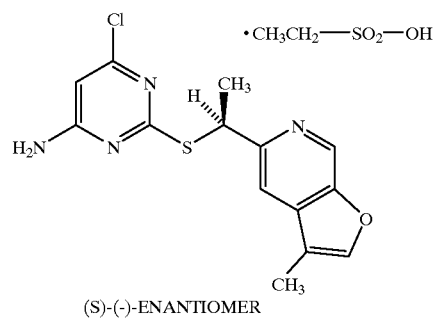
(S)-(-)-ENANTIOMER
Cpd #303
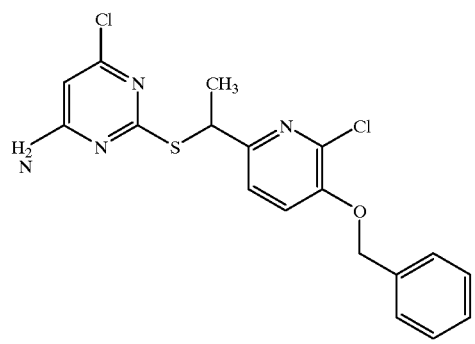
Cpd #304
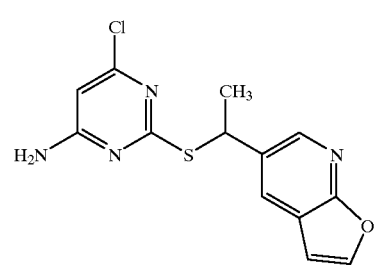
Cpd #305
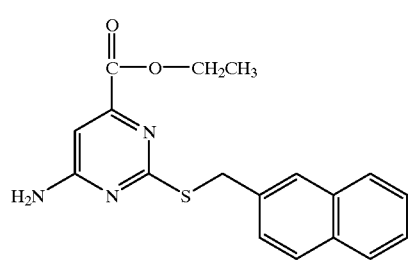
Cpd #306
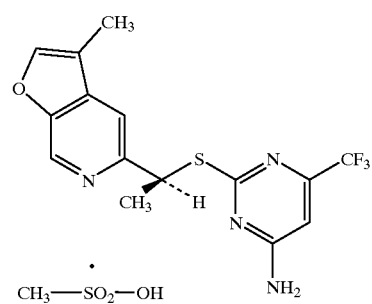
(S)-(-)-enantiomer
Chart A
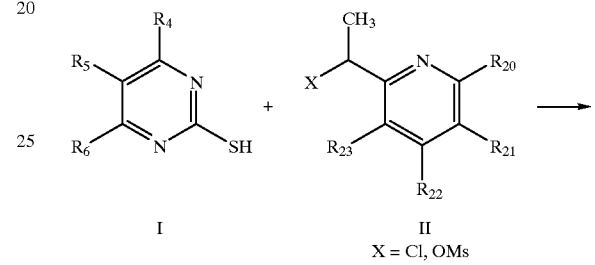
X = Cl, OMs
Chart B
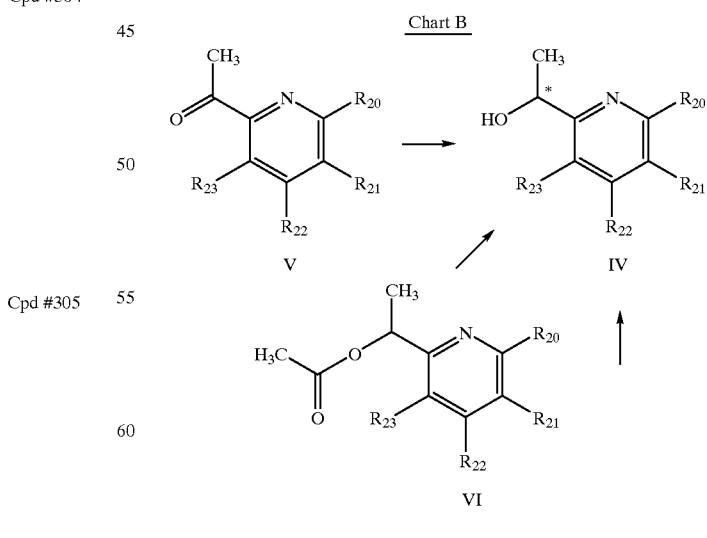

-continued

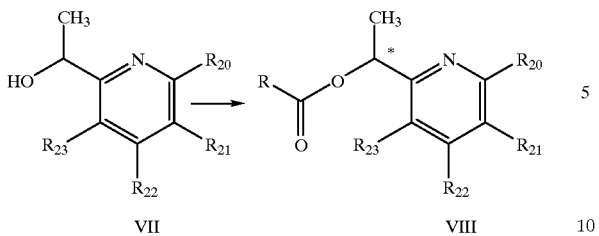

We claim:
1. A compound of the following formula:

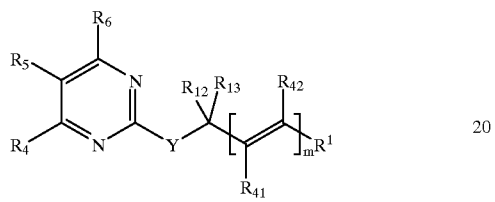

where m is 0 or 1;

$R^1$ is selected from the group consisting of —C≡CH, —CO$_2$R$_{53}$, —CONR$_{54}$R$_{55}$,

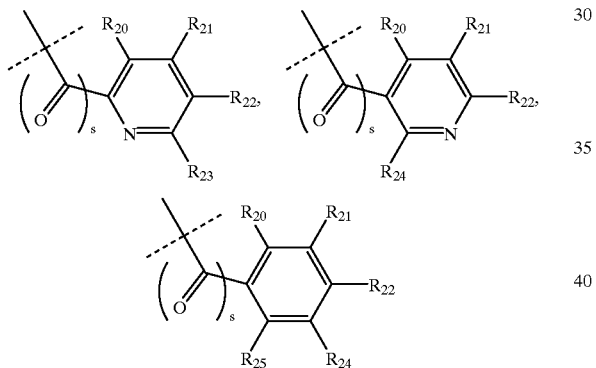

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —CF$_3$, —NO$_2$, -halo, —OH, —CN, phenyl, phenylthio, -styryl, —CO$_2$(R$_{31}$), —CON(R$_{31}$)(R$_{32}$), —CO(R$_{31}$), —(CH$_2$)$_n$—N(R$_{31}$)(R$_{32}$), —C(OH)(R$_{31}$)(R$_{33}$), —(CH$_2$)$_n$N(R$_{31}$)(CO(R$_{33}$)), (CH$_2$)$_n$N(R$_{31}$)(SO$_2$(R$_{33}$)), or $R_{20}$ and $R_{21}$, $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or —(CH$_2$)$_n$—N(R$_{31}$)(R$_{32}$) or one oxo (=O);

where n is 0–3 and $R_{31}$, $R_{32}$, and $R_{33}$ are the same or different and are selected from
—H,
$C_1$–$C_6$ alkyl,
phenyl optionally substituted with 1, 2, or 3 -halo, $C_1$–$C_6$ alkyl, $C_1$–$C_6$ alkoxy, —CF$_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl, or a member selected from the group consisting of: 1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1H-inden-3-yl, 1-H-2-methyl-inden-2-yl, 3,4-dihydronaphth-1-yl, S-4-isopropenylcyclohexen-1-yl or 4-dihydronaphth-2-yl;

where $R_{53}$ is selected from the group consisting of —H, $C_1$–$C_6$alkyl, $C_3$–$C_6$cycloalkyl, phenyl (optionally substituted with 1, 2, or 3 -halo, $C_1$–$C_6$ alkyl, $C_1$–$C_6$ alkoxy, —CF$_3$, —OH, —CN), or a five or six-membered unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —CH$_2$OH, or —(CH$_2$)$_n$—N(R$_{31}$)(R$_{32}$);

where $R_{54}$ and $R_{55}$ being the same or different are selected from —H, $C_1$–$C_6$ alkyl, allyl, or phenyl (optionally substituted with 1, 2, or 3 -halo, $C_1$–$C_6$ alkyl, $C_1$–$C_6$ alkoxy or —CF$_3$), or taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl;

$R_{41}$ and $R_{42}$, being the same or different, are selected from the group consisting of —H and $C_1$–$C_4$ alkyl;

$R_{12}$ is selected from the group consisting of —H, $C_1$–$C_6$ alkyl, —$C_3$–$C_6$ cycloalkyl, —CN, —C(O)NH$_2$, —C(O)N($C_1$–$C_6$alkyl)($C_1$–$C_6$alkyl), —CO$_2$H, —CO$_2$($C_1$–$C_6$alkyl), —CH$_2$OH, —CH$_2$NH$_2$ or —CF$_3$;

$R_{13}$ is selected from the group consisting of —H, $C_1$–$C_6$ alkyl or —CF$_3$;

Y is selected from —S—, —S(O)—, —S(O)$_2$, or —O—;

$R_4$ is selected from the group consisting of —H, —OH, halo or —NR$_{15}$R$_{16}$ where $R_{15}$ is —H and $R_{16}$ is —H, $C_1$–$C_6$ alkyl, —NH$_2$ or $R_{15}$ and $R_{16}$ taken together with the —N form 1-pyrrolidino, 4-morpholino or 1-piperidino;

$R_5$ is selected from the group consisting of —H, —C$_2$H$_4$OH, —C$_2$H$_4$—O—TBDMS, halo, —C$_3$—C$_6$ cycloalkyl, $C_1$–$C_4$ alkyl or $C_1$–$C_3$ alkoxy;

$R_6$ is selected from the group consisting of —H, —OH, halo, —CN, —CF$_3$, —CO$_2$(R$_{61}$), —C(O)R$_{61}$ or —C(O)N(R$_{61}$)(R$_{62}$) where $R_{61}$ and $R_{62}$ are the same or different and are selected from —H, $C_1$–$C_6$ alkyl, phenyl optionally substituted with 1, 2, or 3-halo, $C_1-C_6$ alkyl, $C_1-C_6$ alkoxy, —$CF_3$, —OH, —CN, or where $R_{61}$ and $R_{62}$ taken together with the attached nitrogen to form a ring selected from -pyrrolidinyl, -piperidinyl, -4-morpholinyl, -4-thiomorpholinyl, -4-piperazinyl, or -4-($C_1-C_6$ alkyl)piperazinyl; and pharmaceutically acceptable salts, hydrates, N-oxides and solvates thereof;

with the following provisos:

(1) that $R_4$ and $R_6$ are not both —H;

(2) that $R_{12}$ and $R_{13}$ are not both —H except when $R_6$ is selected from —CN, —$CF_3$, —$CO_2(R_{61})$, —C(O)$R_{61}$ or —C(O)N($R_{61}$)($R_{62}$), or $R_1$ is selected from —$CO_2R_{53}$ or C(O)N($R_{54}$)($R_{55}$);

(3) that when m is 0, Y is —S— or —S(O)—, $R_{13}$ is —H, $R_{12}$ is —H or $C_1-C_4$alkyl, $R_4$ is —H, —OH, halo or $NH_2$, $R_5$ is —H, halo or $C_1-C_4$ alkyl and $R_6$ is from the group consisting of —H, halo or —OH, then $R^1$ is not 2- or 3-pyridinyl optionally substituted with $C_1-C_4$ alkyl, a halogen atom, $NH_2$ or —OH, and;

(4) that $R_1$ is not —$CONR_{54}R_{55}$ when m is 0 and $R_6$ is H; and (5) the compounds are other than
4-amino-6-chloro-2-(1-(4-(4-morpholinylcarbinyl)-2-pyridinyl)-ethyl)thio-pyrimidine and
4-amino-6-chloro-2-(1-(4-methyl-2-pyridyl)pentyl)thio-pyrimidine.

2. A compound according to claim 1 where m is 0, s is 0 and Y is S—.

3. A compound according to claim 2 where $R_{12}$ is $CH_3$ and $R_{13}$ is —H.

4. A compound according to claim 3 where $R_4$ is $NH_2$, $R_5$ is —H, and $R_6$ is Cl, $CF_3$ or CN.

5. A compound according to claim 3 where $R^1$ is

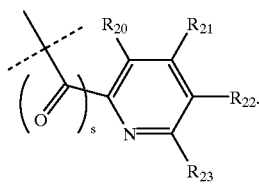

6. A compound according to claim 5 wherein $R_4$ is $NH_2$, $R_5$ is —H, and $R_6$ is Cl, $CF_3$ or CN.

7. A compound according to claim 3 wherein $R^1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)- thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, or 8-(3,4-dihydro)-2H-1-benzothiopyranyl; or such five or six membered ring substituted with 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —C$_3$–C$_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —C$_1$–C$_6$ alkyl, —C$_1$–C$_6$ alkoxy, —OH, —CH$_2$OH or —(CH$_2$)$_n$—N(R$_{31}$)(R$_{32}$) or one oxo (═O).

8. A compound according to claim 7 wherein R$_4$ is NH$_2$, R$_5$ is —H, and R$_6$ is Cl, CF$_3$ or CN.

9. A compound according to claim 8 wherein R$^1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo [3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl and 6-(3,4-dihydro)-2H-pyrano[3,2-b]pyridinyl or such five or six membered ring substituted 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —C$_3$–C$_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —C$_1$–C$_6$ alkyl, —C$_1$–C$_6$ alkoxy, —OH, —CH$_2$OH or —(CH$_2$)$_n$—N(R$_{31}$)(R$_{32}$) or one oxo (═O).

10. A compound according to claim 1 is selected from the group consisting of:

- (E)-N,N-Diethyl-4-[(4-amino-6-chloro-2-pyrimidinyl)thio]-2-butenamide;
- (E)-1-[4-[(4-amino-6-chloro-2-pyrimidinyl)thio]-1-oxo-2-butenyl]pyrrolidine;
- (E)-N-ethyl-N-methyl-4-[(4-amino-6-chloro-2-pyrimidinyl)thio]-2-butenamide;
- (E)-N,N-Diethyl-4-[(4-amino-6-chloro-2-pyrimidinyl)thio]-2-pentenamide;
- 4-Amino-6-chloro-2-(1-(3-isoquinolyl)ethyl)thio-pyrimidine;
- 4-Amino-5-bromo-6-chloro-2-(1-(3-isoquinolyl)ethyl)thio-pyrimidine;
- 4-Amino-6-chloro-2-(1-(3-(5,6,7,8-tetrahydroisoquinolyl))ethyl)thio-pyrimidine;
- 4-Amino-6-trifluoromethyl-2-(1-(3-(5,6,7,8-tetrahydro-isoquinolyl))ethyl)thio-pyrimidine;
- 4-Amino-6-chloro-2-(1-(7-chlorofuro[2,3c]pyridine-5-yl)ethyl)thio-pyrimidine;
- 4-Amino-6-chloro-2-(1-(furo[2,3-c]pyridin-5-yl)ethyl)thio-pyrimidine;
- 4-Amino-6-trifluoromethyl-2-(1-(furo[2,3-c]pyridin-5-yl)ethyl)thio-pyrimidine;
- 4-Amino-6-chloro-2-(1-(7-chloro-2-methylfuro[2,3c]pyridine-5-yl)ethyl)thio-pyrimidine;
- 4-Amino-6-trifluoromethyl-2-(1-(7-chloro-2-methylfuro[2,3c]pyridine-5-yl)ethyl)thio-pyrimidine;
- 4-Amino-6-chloro-2-(1-(2-methylfuro[2,3c]pyridine-5-yl)ethyl)thio-pyrimidine;
- 4-Amino-6-trifluoromethyl-2-(1-(2-methylfuro[2,3c]pyridine-5-yl)ethyl)thio-pyrimidine;
- 4-Amino-6-chloro-2-(1-(3-methylfuro[2,3c]pyridine-5-yl)ethyl)thio-pyrimidine;
- 4-Amino-6-chloro-2-(1-(2,3-dihydrofuro[2,3c]pyridine-5-yl)ethyl)thio-pyrimidine;
- 4-Amino-6-chloro-2-(1-(3,3-dimethyl-2,3-dihydrofuro[2,3c]pyridine-5-yl)ethyl)thio-pyrimidine;
- 4-Amino-6-chloro-2-(1-(3-ethylfuro[2,3c]pyridine-5-yl)ethyl)thio-pyrimidine;
- 4-Amino-6-chloro-2-(1-(7-chloro-3,3-dimethyl-2,3-dihydrofuro[2,3c]pyridine-5-yl)ethyl)thio-pyrimidine;
- 4-Amino-6-chloro-2-(1-(7-chloro-3-ethylfuro-[2,3c]pyridine-5-yl)ethyl)thio-pyrimidine;
- 4-Amino-6-chloro-2-(1-(3-(1-methylethyl)furo[2,3c]-pyridin-5-yl)ethyl)thio-pyrimidine;
- 4-amino-6-trifluoromethyl-2-(1-(4-(1-dimethylethyl)-2-pyridyl)-ethyl)thio-pyrimidine;
- 4-amino-6-trifluoromethyl-2-(2-naphthylmethyl)thio-pyrimidine;
- 4-amino-6-trifluoromethyl-2-((4-(1-methylethyl)-2-pyridyl)methyl)-thio-pyrimidine;
- 4-amino-6-trifluoromethyl-2-(1-(4-(1-methylethyl)-2-pyridyl)ethyl)thio-pyrimidine;
- 4-amino-6-trifluoromethyl-2-((4-(1,1-dimethylethyl)-2-pyridyl)methyl)-thio-pyrimidine;

6-amino-2-(2-naphthylmethyl)thio-4-pyrimidine carbonitrile;

4-Amino-6-chloro-2-(1-(3-chlorofuro[2,3c]pyridine-5-yl)ethyl)thio-pyrimidine;

4-Amino-6-chloro-2-(1-(3,7-dichlorofuro[2,3c]pyridine-5-yl)ethyl)thio-pyrimidine;

4-Amino-6-chloro-2-(1-(3-bromofuro[2,3c]pyridine-5-yl)ethyl)thio-pyrimidine;

4-Amino-6-chloro-2-(1-(3-bromo-7-chlorofuro[2,3c]pyridine-5-yl)ethyl)thio-pyrimidine;

4-Amino-6-chloro-2-(1-(7-chloro-3-methylfuro[2,3c]pyridine-5-yl)ethyl)thio-pyrimidine;

4-Amino-6-trifluoromethyl-2-(1-(7-chloro-3,3-dimethyl-2,3-dihydrofuro[2,3c]pyridine-5-yl)ethyl)thiopyrimidine;

(R)-(+)-4-Amino-6-chloro-2-(1-(3-methylfuro[2,3c]pyridine-5-yl)ethyl)thio-pyrimidine;

(S)-(-)-4-Amino-6-chloro-2-(1-(3-methylfuro[2,3c]pyridine-5-yl)ethyl)thio-pyrimidine;

(S)-(-)-4-Amino-6-trifluoromethyl-2-(1-(3-methylfuro[2,3c]pyridin-5-yl)ethylthio)-pyrimidine;

(S)-(-)-4-Amino-6-chloro-2-(1-(furo[2,3c]pyridin-5-yl)ethylthio)-pyrimidine;

and pharmaceutically acceptable salts, hydrates, N-oxides and solvates thereof.

11. A compound according to claim 1 and selected from the group consisting of (S)-(-)-4-Amino-6-chloro-2-(1-(3-methylfuro[2,3c]pyridine-5-yl)ethyl)thio-pyrimidine;

(S)-(-)-4-Amino-6-chloro-2-(1-(3-methylfuro[2,3c]pyridin-5-yl)ethylthio)-pyrimidine esylate salt;

(S)-(-)-4-Amino-6-trifluoromethyl-2-(1-(3-methylfuro[2,3c]pyridin-5-yl)ethylthio)-pyrimidine;

(S)-(-)4-Amino-2-(3-methyl-furano[2,3c]pyridin-5-yl)ethylthio-6-trifluoromethyl-pyrimidine mesylate salt;

(S)-(-)-4-Amino-6-chloro-2-(1-(furo[2,3c]pyridin-5-yl)ethylthio)-pyrimidine and (S)-(-)-4-Amino-6-chloro-2-(1-(furo[2,3c]pyridin-5-yl)ethylthio)-pyrimidine mesylate salt.

12. A method of treating an individual infected with the human immunodeficiency virus (HIV) which comprises administering an effective amount of an anti-AIDS compound of Formula IA

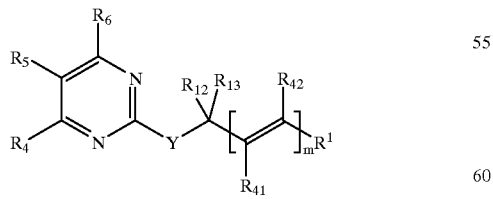

where m is 0 or 1;

$R^1$ is selected from the group consisting of —C≡CH, —CO$_2$R$_{53}$, —CONR$_{54}$R$_{55}$,

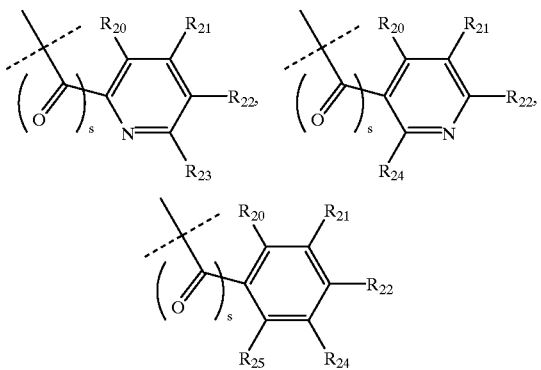

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —CF$_3$, —NO$_2$, -halo, —OH, —CN, phenyl, phenylthio, -styryl, —CO$_2$(R$_{31}$), —CON(R$_{31}$)(R$_{32}$), —CO(R$_{31}$), —(CH$_2$)$_n$—N(R$_{31}$)(R$_{32}$), —C(OH)(R$_{31}$)(R$_{33}$), —(CH$_2$)$_n$N(R$_{31}$)(CO(R$_{33}$)), (CH$_2$)$_n$N(R$_{31}$)(SO$_2$(R$_{33}$)), or where R$_{20}$ and R$_{21}$, or R$_{21}$ and R$_{22}$, or R$_{22}$ and R$_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, CH$_2$CF$_3$ or —CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or —(CH$_2$)$_n$—N(R$_{31}$)(R$_{32}$) or one oxo (=O);

where n is 0–3 and R$_{31}$, R$_{32}$, and R$_{33}$ are the same or different and are selected from
—H,
$C_1$–$C_6$ alkyl,
phenyl optionally substituted with 1, 2, or 3 -halo, $C_1$–$C_6$ alkyl, $C_1$–$C_6$ alkoxy, —CF$_3$, —OH or —CN,
or where R$_{31}$ and R$_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl, or a member selected from the group consisting of:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl;

where R$_{53}$ is selected from the group consisting of —H, C$_1$–C$_6$alkyl, C$_3$–C$_6$cycloalkyl, phenyl (optionally substituted with 1, 2, or 3 -halo, C$_1$–C$_6$ alkyl, C$_1$–C$_6$ alkoxy, —CF$_3$, —OH, —CN), or a five or six-membered unsaturated ring containing 0 or 1 oxygen, nitrogen or sulfur, where the unsaturated ring may be optionally substituted with —H, C$_1$–C$_6$ alkyl, C$_1$–C$_6$ alkoxy, —OH, —CH$_2$OH, or —(CH$_2$)$_n$—N(R$_{31}$)(R$_{32}$);

where R$_{54}$ and R$_{55}$ being the same or different are selected from —H, C$_1$–C$_6$ alkyl, allyl, or phenyl (optionally substituted with 1, 2, or 3-halo, C$_1$–C$_6$ alkyl, C$_1$–C$_6$ alkoxy or —CF$_3$), or taken together with the attached nitrogen to form a ring selected from -pyrrolidinyl, -piperidinyl, -4-morpholinyl, -4-thiomorpholinyl, -4-piperazinyl, -4-(1-C$_1$–C$_6$alkyl)piperazinyl;

R$_{41}$ and R$_{42}$, being the same or different, are selected from the group consisting of —H and C$_1$–C$_4$ alkyl;

R$_{12}$ is selected from the group consisting of —H, C$_1$–C$_6$ alkyl, —C$_3$–C$_6$ cycloalkyl, —CN, —C(O)NH$_2$, —C(O)N(C$_1$–C$_6$alkyl)(C$_1$–C$_6$alkyl), —CO$_2$H, —CO$_2$(C$_1$–C$_6$alkyl), —CH$_2$OH, —CH$_2$NH$_2$ or —CF$_3$;

R$_{13}$ is selected from the group consisting of —H, C$_1$–C$_6$ alkyl or —CF$_3$;

Y is selected from —S—, —S(O)—, —S(O)$_2$, or —O—;

R$_4$ is selected from the group consisting of —H, —OH, halo or —NR$_{15}$R$_{16}$ where R$_{15}$ is —H and R$_{16}$ is —H, C$_1$–C$_6$ alkyl, —NH$_2$ or R$_{15}$ and R$_{16}$ taken together with the —N form 1-pyrrolidino, 4-morpholino or 1-piperidino;

R$_5$ is selected from the group consisting of —H, —C$_2$H$_4$OH, —C$_2$H$_4$-0-TBDMS, halo, —C$_3$–C$_6$ cycloalkyl, C$_1$–C$_4$ alkyl or C$_1$–C$_3$ alkoxy; and R$_6$ is selected from the group consisting of —H, —OH, halo, —CN, —CF$_3$, —CO$_2$(R$_{61}$), —C(O)R$_{61}$ or —C(O)N(R$_{61}$)(R$_{62}$) where R$_{61}$ and R$_{62}$ are the same or different and are selected from

—H,

C$_1$–C$_6$ alkyl, phenyl optionally substituted with 1, 2, or 3 -halo, C$_1$–C$_6$ alkyl, C$_1$–C$_6$ alkoxy,

—CF$_3$, —OH, —CN, or where R$_{61}$ and R$_{62}$ taken together with the attached nitrogen to form a ring selected from -pyrrolidinyl, -piperidinyl, -4-morpholinyl, -4-thiomorpholinyl, -4-piperazinyl, or -4-(C$_1$–C$_6$ alkyl)piperazinyl; and pharmaceutically acceptable salts, hydrates, N-oxides and solvates thereof;

with the provisos:

(1) that R$_4$ and R$_6$ are not both —H;
(2) that R$_{12}$ and R$_{13}$ are not both —H except when R$_6$ is selected from —CN, —CF$_3$, —CO$_2$(R$_{61}$), —C(O)R$_{61}$ or —C(O)N(R$_{61}$)(R$_{62}$), or R$_1$ is selected from —CO$_2$R$_{53}$ or C(O)N(R$_{54}$)(R$_{55}$); and other than 4-amino-6-chloro-2-(1-(4-(4-morpholinylcarbinyl)-2-pyridinyl)ethyl)thio-pyrimidine 4-Amino-6-chloro-2-(1-(4-methyl-2-pyridyl)pentyl)thio-pyrimidine.

13. A method according to claim 12 where m is 0, s is 0 and Y S—.

14. A method according to claim 13 where R$_{12}$ is CH$_3$ and R$_{13}$ is —H.

15. A method according to claim 14 where R$_4$ is NH$_2$, R$_5$ is —H, and R$_6$ is Cl, CF$_3$ or CN.

16. A method according to claim 13 where R$_1$ is

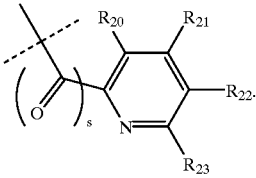

17. A method according to claim 16 wherein R$_4$ is NH$_2$, R$_5$ is —H, and R$_6$ is Cl, CF$_3$ or CN.

18. A method according to claim 15 wherein R$^1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4- tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro )-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, or 8-(3,4-dihydro)-2H-1-benzothiopyranyl; or such five or six membered ring substituted with 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or —(CH$_2$)$_n$—N(R$_{31}$)(R$_{32}$) or one oxo (=O).

19. A method according to claim 18 wherein R$_4$ is NH$_2$, R$_5$ is —H, and R$_6$ is Cl, CF$_3$ or CN.

20. A method according to claim 19 wherein R$^1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo [3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl and 6-(3,4-dihydro)-2H-pyrano[3,2-b]pyridinyl or such five or six membered ring substituted 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or —(CH$_2$)$_n$—N(R$_{31}$)(R$_{32}$) or one oxo (=O).

21. A method of treating an individual infected with the human immunodeficiency virus (HIV) according to claim 12 where the (1) infected individual is asymptomatic but tests positive for the HIV antigen, (2) infected individual is symptomatically sick but does not have "full blown AIDS", (3) individual infected with the human immunodeficiency virus (HIV) has "full blown AIDS".

22. A method of treating an individual infected with the human immunodeficiency virus (HIV) according to claim 12 where the administration is oral and the effective dose is from about 0.10 mg/kg/day to about 500 mg/kg/day.

23. A method of treating an individual infected with the human immunodeficiency virus (HIV) according to claim 12 where the compound is selected from the group consisting of (E)-N,N-Diethyl-4-[(4-amino-6-chloro-2-pyrimidinyl)thio]-2-butenamide;

(E)-1-[4-[(4-amino-6-chloro-2-pyrimidinyl)thio]-1-oxo-2-butenyl]pyrrolidine;

(E)-N-ethyl-N-methyl-4-[(4-amino-6-chloro-2-pyrimidinyl)thio]-2-butenamide;

(E)-N,N-Diethyl-4-[(4-amino-6-chloro-2-pyrimidinyl)thio]-2-pentenamide;
4-Amino-6-chloro-2-(1-(3-isoquinolyl)ethyl)thio-pyrimidine;
4-Amino-5-bromo-6-chloro-2-(1-(3-isoquinolyl)ethyl)thio-pyrimidine;
4-Amino-6-chloro-2-(1-(3-(5,6,7,8-tetrahydroisoquinolyl))ethyl)thio-pyrimidine;
4-Amino-6-trifluoromethyl-2-(1-(3-(5,6,7,8-tetrahydroisoquinolyl))ethyl)thio-pyrimidine;
4-Amino-6-chloro-2-(1-(7-chlorofuro[2,3c]pyridine-5-yl)ethyl)thio-pyrimidine;
4-Amino-6-chloro-2-(1-(furo[2,3-c]pyridin-5-yl)ethyl)thio-pyrimidine;
4-Amino-6-trifluoromethyl-2-(1-(furo[2,3-c]pyridin-5-yl)ethyl)thio-pyrimidine;
4-Amino-6-chloro-2-(1-(7-chloro-2-methylfuro[2,3c]pyridine-5-yl)ethyl)thio-pyrimidine;
4-Amino-6-trifluoromethyl-2-(1-(7-chloro-2-methylfuro[2,3c]pyridine-5-yl)ethyl)thio-pyrimidine;
4-Amino-6-chloro-2-(1-(2-methylfuro[2,3c]pyridine-5-yl)ethyl)thio-pyrimidine;
4-Amino-6-trifluoromethyl-2-(1-(2-methylfuro[2,3c]pyridine-5-yl)ethyl)thio-pyrimidine;
4-Amino-6-chloro-2-(1-(3-methylfuro[2,3c]pyridine-5-yl)ethyl)thio-pyrimidine;
4-Amino-6-chloro-2-(1-(2,3-dihydrofuro[2,3c]pyridine-5-yl)ethyl)thio-pyrimidine;
4-Amino-6-chloro-2-(1-(3,3-dimethyl-2,3-dihydrofuro[2,3c]pyridine-5-yl)ethyl)thio-pyrimidine;
4-Amino-6-chloro-2-(1-(3-ethylfuro[2,3c]pyridine-5-yl)ethyl)thio-pyrimidine;
4-Amino-6-chloro-2-(1-(7-chloro-3,3-dimethyl-2,3-dihydrofuro[2,3c]pyridine-5-yl)ethyl)thio-pyrimidine;
4-Amino-6-chloro-2-(1-(7-chloro-3-ethylfuro-[2,3c]pyridine-5-yl)ethyl)thio-pyrimidine;
4-Amino-6-chloro-2-(1-(3-(1-methylethyl)furo[2,3c]-pyridin-5-yl)ethyl)thio-pyrimidine;
4-amino-6-trifluoromethyl-2-(1-(4-(1-dimethylethyl)-2-pyridyl)-ethyl)thio-pyrimidine;
4-amino-6-trifluoromethyl-2-(2-naphthylmethyl)thio-pyrimidine;
4-amino-6-trifluoromethyl-2-((4-(1-methylethyl)-2-pyridyl)methyl)-thio-pyrimidine;
4-amino-6-trifluoromethyl-2-(1-(4-(1-methylethyl)-2-pyridyl)ethyl)thio-pyrimidine;
4-amino-6-trifluoromethyl-2-((4-(1,1-dimethylethyl)-2-pyridyl)methyl)-thio-pyrimidine;
6-amino-2-(2-naphthylmethyl)thio-4-pyrimidine carbonitrile;
4-Amino-6-chloro-2-(1-(3-chlorofuro[2,3c]pyridine-5-yl)ethyl)thio-pyrimidine;
4-Amino-6-chloro-2-(1-(3,7-dichlorofuro[2,3c]pyridine-5-yl)ethyl)thio-pyrimidine;
4-Amino-6-chloro-2-(1-(3-bromofuro[2,3c]pyridine-5-yl)ethyl)thio-pyrimidine;
4-Amino-6-chloro-2-(1-(3-bromo-7-chlorofuro[2,3c]pyridine-5-yl)ethyl)thio-pyrimidine;
4-Amino-6-chloro-2-(1-(7-chloro-3-methylfuro[2,3c]pyridine-5-yl)ethyl)thio-pyrimidine;
4-Amino-6-trifluoromethyl-2-(1-(7-chloro-3,3-dimethyl-2,3-dihydrofuro[2,3c]pyridine-5-yl)ethyl)thio-pyrimidine;
(R)-(+)-4-Amino-6-chloro-2-(1-(3-methylfuro[2,3c]pyridine-5-yl)ethyl)thio-pyrimidine;
(S)-(−)-4-Amino-6-chloro-2-(1-(3-methylfuro[2,3c]pyridine-5-yl)ethyl)thio-pyrimidine;
(S)-(−)-4-Amino-6-trifluoromethyl-2-(1-(3-methylfuro[2,3c]pyridin-5-yl)ethylthio)-pyrimidine;
(S)-(−)-4-Amino-6-chloro-2-(1-(furo[2,3c]pyridin-5-yl)ethylthio)-pyrimidine;
(S)-(−)-4-Amino-6-chloro-2-(1-(furo[2,3c]pyridin-5-yl)ethylthio)-pyrimidine; and pharmaceutically acceptable salts, hydrates and solvents thereof.

24. A method according to claim 23 where the compound is selected from the group consisting of (S)-(−)-4-Amino-6-chloro-2-(1-(3-methylfuro[2,3c]pyridine-5-yl)ethyl)thio-pyrimidine;
(S)-(−)-4-Amino-6-chloro-2-(1-(3-methylfuro[2,3c]pyridin-5-yl)ethylthio)-pyrimidine esylate salt;
(S)-(−)-4-Amino-6-trifluoromethyl-2-(1-(3-methylfuro[2,3c]pyridin-5-yl)ethylthio)-pyrimidine;
(S)-(−)4-Amino-2-(3-methyl-furano[2,3c]pyridin-5-yl)ethylthio-6-trifluoromethyl-pyrimidine mesylate salt;
(S)-(−)-4-Amino-6-chloro-2-(1-(furo[2,3c]pyridin-5-yl)ethylthio)-pyrimidine and
(S)-(−)-4-Amino-6-chloro-2-(1-(furo[2,3c]pyridin-5-yl)ethylthio)-pyrimidine mesylate salt.

* * * * *